US008546540B2

(12) United States Patent
Hiruma et al.

(10) Patent No.: US 8,546,540 B2
(45) Date of Patent: Oct. 1, 2013

(54) ANTIBODY TARGETING OSTEOCLAST-RELATED PROTEIN SIGLEC-15

(75) Inventors: Yoshiharu Hiruma, Tokyo (JP); Eisuke Tsuda, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 12/677,621

(22) PCT Filed: Oct. 8, 2008

(86) PCT No.: PCT/JP2008/068287
§ 371 (c)(1),
(2), (4) Date: Mar. 11, 2010

(87) PCT Pub. No.: WO2009/048072
PCT Pub. Date: Apr. 16, 2009

(65) Prior Publication Data
US 2010/0209428 A1    Aug. 19, 2010

(30) Foreign Application Priority Data

Oct. 11, 2007  (JP) .................. 2007-265420

(51) Int. Cl.
*C07K 16/00*    (2006.01)
*C07K 16/46*    (2006.01)
*C07K 16/28*    (2006.01)
*C12N 5/20*     (2006.01)

(52) U.S. Cl.
USPC ................ 530/387.1; 530/387.3; 530/388.22; 435/326

(58) Field of Classification Search
None
See application file for complete search history.

(56) References Cited

U.S. PATENT DOCUMENTS

| | | | |
|---|---|---|---|
| 6,855,808 B2 | 2/2005 | Goto et al. | |
| 7,125,686 B1 | 10/2006 | Goto et al. | |
| 7,205,397 B2 | 4/2007 | Goto et al. | |
| 7,276,344 B2 | 10/2007 | Goto et al. | |
| 7,468,268 B2 | 12/2008 | Goto et al. | |
| 7,608,704 B2 * | 10/2009 | Yue et al. ..................... | 536/23.7 |
| 7,989,160 B2 | 8/2011 | Sooknanan et al. | |
| 2004/0023313 A1 | 2/2004 | Boyle et al. | |
| 2004/0033535 A1 | 2/2004 | Boyle et al. | |
| 2004/0076992 A1 * | 4/2004 | Nakamura et al. ................ | 435/6 |
| 2009/0298763 A1 | 12/2009 | Sooknanan et al. | |
| 2010/0104575 A1 | 4/2010 | Sooknanan et al. | |
| 2011/0268733 A1 * | 11/2011 | Hiruma et al. ............. | 424/133.1 |

FOREIGN PATENT DOCUMENTS

| | | |
|---|---|---|
| CA | 2 225 366 C | 10/2006 |
| EP | 1 580 263 A1 | 9/2005 |
| EP | 1 715 038 | 10/2006 |
| JP | 2007-20403 | 2/2007 |
| RU | 2 228 335 C2 | 8/1999 |
| RU | 2 238 948 C2 | 3/2004 |
| WO | WO-0238602 | 5/2002 |
| WO | WO-02064771 | 8/2002 |
| WO | WO-03048305 | 6/2003 |
| WO | WO-2007093042 | 8/2007 |
| WO | WO 2011/041894 A1 | 4/2011 |

OTHER PUBLICATIONS

Harlow E, Lane D.. Antibodies a laboratory manual. Cold Spring Harbor, New York: Cold Spring Harbor Laboratory Press, pp. 141-155, 1989.*
Bird RE, Hardman KD, Jacobson JW, Johnson S, Kaufman BM, Lee SM, Lee T, Pope SH, Riordan GS, Whitlow M. Single-chain antigen-binding proteins. Science. 242(4877):423-426, 1988.*
Owens RJ, Young RJ. The genetic engineering of monoclonal antibodies. J Immunol Methods. 168(2):149-165, 1994.*
Colman PM. Effects of amino acid sequence changes on antibody-antigen interactions. Res Immunol. 145(1):33-36, 1994.*
Ngo J.T, Marks J., Karplus M., Computational complexity, protein structure prediction, and the Levinthal paradox in The Protein Folding Problem, ch.14, pp. 491-494, Birkhauser, 1994.*
Lederman S, et al. A single amino acid substitution in a common African allele of the CD4 molecule ablates binding of the monoclonal antibody, OKT4. Mol Immunol. 28(11):1171-81, 1991.*
Li CH, Yamashiro D, Tseng LF, Chang WC, Ferrara P. beta-Endorphin omission analogs: dissociation of immunoreactivity from other biological activities. Proc Natl Acad Sci U S A. 77(6):3211-3214, 1980.*
Abaza MS, Atassi MZ. Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992;11(5):433-44.*
Nagakawa, Nobuaki et al. "RANK is the Essential Signaling Receptor for Osteoclast Differentiation Factor in Osteoclastogenesis," Biochemical and Biophysical Research Communications, vol. 253, pp. 395-400 (1998).
Angata, T. et al., "Siglec-15: an immune system Siglec conserved throughout vertebrate evolution", *Glycobiology*, vol. 17, No. 8 Aug. 2007, 838-846.
Tsuda, Eisuke , "Hone Kyushu Yokuseiyaku Koho to shite no Hakotsu Saibo Keisei Yokusei Inshi OCIF/OPG, Ko-RANKL Kotai, Oyobi sono hoka no RANKL/RANK System Modulator", *J. Jpn. Orthop. Assoc.*, vol. 79, No. 8 2005 , S753 (1-4-S6-3).
Akatsu, T. et al. "Osteoclastogenesis inhibitory factor suppresses osteoclast survival by interfering in the interaction of stromal cells with osteoclast." Biochemical and Biophysical Research Communications, vol. 250, No. 2, pp. 229-234 (Sep. 18, 1998).
U.S. Appl. No. 13/152,205, Sooknanan et al.

* cited by examiner

*Primary Examiner* — Maher Haddad
(74) *Attorney, Agent, or Firm* — Foley & Lardner LLP

(57) ABSTRACT

To provide a method of detecting abnormal bone metabolism by using a gene strongly expressed in an osteoclast; a method of screening a compound having a therapeutic and/or preventive effect on abnormal bone metabolism; and a pharmaceutical composition for treating and/or preventing abnormal bone metabolism. Provision of a method of detecting abnormal bone metabolism by using the expression of human Siglec-15 gene as an index; a pharmaceutical composition containing an antibody which specifically recognizes human Siglec-15 and has an activity of inhibiting osteoclast formation; and the like.

6 Claims, 40 Drawing Sheets

(A) Control (B) Pre-immune IgG 3,333 ng/ml (C) Anti-Siglec-15 Antibody 370 ng/ml (D) Anti-Siglec-15 Antibody 3,333 ng/ml (A) Anti-Siglec-15 Antibody 1 μg/ml (0) Control

ANTIBODY TARGETING OSTEOCLAST-RELATED PROTEIN SIGLEC-15

This application is a 35 U.S.C. §371 National Stage application of International Application No. PCT/JP2008/068287, filed Oct. 8, 2008, which claims priority to Japanese Application No. 2007-265420, filed Oct. 11, 2007, the contents of all of which are hereby incorporated herein by reference in their entirety.

TECHNICAL FIELD

The present invention relates to a substance useful as a therapeutic and/or preventive agent for abnormal bone metabolism, a method of screening a substance useful as a therapeutic and/or preventive agent for abnormal bone metabolism, a method of detecting abnormal bone metabolism, and a method of treating and/or preventing abnormal bone metabolism.

BACKGROUND

Bone is known to be a dynamic organ which is continuously remodelled by repeated formation and resorption so as to change its own morphology and maintain blood calcium levels. Healthy bone maintains an equilibrium between bone formation by osteoblasts and bone resorption by osteoclasts, and the bone mass is maintained constant. In contrast, when the equilibrium between bone formation and bone resorption is lost, abnormal bone metabolism such as osteoporosis occurs (Endocrinological Review, (1992) 13, pp. 66-80, Principles of Bone Biology, Academic Press, New York, (1996) pp. 87-102,).

As factors which regulate bone metabolism, many systemic hormones and local cytokines have been reported, and these factors collaborate with one another to form and maintain bone (Endocrinological Review, (1992) 13, pp. 66-80, Endocrinological Review, (1996) 17, pp. 308-332). As a change in bone tissue due to aging, the occurrence of osteoporosis is widely known, but the mechanism of its occurrence encompasses various factors such as a decrease in secretion of sex hormones and an abnormality in the receptors for the hormones, variation in cytokine expression locally in bone, expression of aging genes, and osteoclast or osteoblast differentiation failure or dysfunction, and thus, it is difficult to consider it as a simple age-related physiological phenomenon. Primary osteoporosis is largely divided into postmenopausal osteoporosis due to a decrease in secretion of estrogen and senile osteoporosis due to aging, but advancement of basic research on the mechanisms of regulation of bone formation and bone resorption is essential to elucidate the mechanism of its occurrence and to develop a therapeutic agent therefor.

Osteoclasts are multinucleated cells derived from hematopoietic stem cells, and by releasing chloride ions and hydrogen ions on a bone surface to which osteoclasts adhere, osteoclasts acidify a gap between the bone surface and the osteoclasts and also secrete cathepsin K which is an acid protease or the like (American Journal of Physiology, (1991) 260, C1315-C1324). This causes degradation of calcium phosphate, activation of acid proteases and degradation of bone matrix proteins, resulting in bone resorption.

Osteoclast precursor cells have been found to be differentiated into osteoclasts by stimulation with RANKL (receptor activator of NF-κB ligand) expressed on the cell membrane of osteoblasts/stromal cells present on the surface of bone (Proceedings of the National Academy of Science of the United States of America, (1998) 95, pp. 3597-3602, Cell, (1998) 93, pp. 165-176). It has been revealed that RANKL is a membrane protein produced by osteoblasts/stromal cells, its expression being regulated by a bone resorption factor, RANKL induces differentiation of osteoclast precursor cells into multinucleated osteoclasts, and the like (Proceedings of the National Academy of Science of the United States of America, (1998) 95, pp. 3597-3602, Journal of Bone and Mineral Research, (1998) 23, S222). Further, knockout mice devoid of RANKL have been found to develop an osteopetrosis-like disease, and therefore, RANKL has been proved to be a physiological osteoclast differentiation-inducing factor (Nature, (1999) 397, pp. 315-323).

As drugs for treating bone metabolism diseases or shortening the duration of treatment, bisphosphonates, active vitamin $D_3$, calcitonin and derivatives thereof, hormone preparations such as estradiol, SERMs (selective estrogen receptor modulators), ipriflavone, vitamin $K_2$ (menatetrenone), PTH (parathyroid hormone) preparations, calcium preparations and the like are used. However, these drugs do not always exhibit a satisfactory therapeutic effect and the development of an agent with a more potent therapeutic effect has been demanded.

The cell membranes of immune cells are covered with a dense coating of various glycans, such as sialic acid, which are recognized by various glycan-binding proteins. Sialic-acid-binding immunoglobulin-like lectins (hereinafter referred to as "siglecs") are a family of type I membrane proteins which recognize sialylated glycans and bind thereto. Many siglecs are expressed on the cell membranes of immune cells and recognize sialic acid similarly present on the cell membranes of immune cells and regulate cell interaction or cell function and are considered to be involved in the immune response (Nature Reviews Immunology, (2007) 7, pp. 255-266). However, there are also a lot of siglec molecules whose physiological functions have not been elucidated yet. Siglec-15 (Sialic-acid binding immunoglobulin-like lectin 15) is a molecule which has been newly reported to belong to the Siglecs (Glycobiology, (2007) 17, pp. 838-846) and is identical to a molecule called CD33L3 (CD33 molecule-like 3). This molecule is highly evolutionarily conserved from fish to humans and has been found to be strongly expressed in dendritic cells and/or macrophages of human spleen and lymph nodes. Further, as a result of a binding test using a sialic acid probe, it has also been found that human Siglec-15 binds to Neu5Acα2-6GalNAc, and that mouse Siglec-15 binds to Neu5Acα2-3Galβ1-4Glc in addition to Neu5Acα2-6GalNAc (Glycobiology, (2007) 17, pp. 838-846). Until recently, the physiological role of Siglec-15 was not revealed, however, it has been reported that the expression of Siglec-15 increases with the differentiation and maturation of osteoclasts, and the differentiation of osteoclasts is inhibited by decreasing the expression of Siglec-15 by RNA interference (WO 2007/093042). However, the effect of an anti-Siglec-15 antibody on osteoclast differentiation has not been elucidated yet.

DISCLOSURE OF THE INVENTION

Problems that the Invention is to Solve

An object of the invention is to provide: a gene which is specifically expressed in various forms of abnormal bone metabolism such as bone destruction which are seen in osteoporosis, rheumatoid arthritis, cancer metastasis to bone or the like; a substance which inhibits the differentiation and maturation of osteoclasts and the activity thereof; a novel method for screening a therapeutic and/or preventive agent for abnormal bone metabolism; a substance which inhibits the differentiation and maturation of osteoclasts and the activity thereof; and a therapeutic and/or preventive agent for abnormal bone metabolism.

Means for Solving the Problems

The present inventors studied to elucidate the mechanism of osteoclast differentiation, maturation and activation in order to find a substance having a therapeutic and/or preventive effect on abnormal bone metabolism. As a result, they found that the expression of the Siglec-15 gene increases with the differentiation and maturation of osteoclasts and also found that the differentiation of osteoclasts is inhibited by an antibody which specifically binds to Siglec-15, and thus, the invention has been completed.

That is, the invention includes the following inventions.

(1) An antibody which specifically recognizes one or more polypeptides comprising an amino acid sequence described in any one of the following (a) to (i) and inhibits osteoclast formation and/or osteoclastic bone resorption, or a functional fragment of the antibody:

(a) an amino acid sequence represented by SEQ ID NO: 2 in the Sequence Listing;

(b) an amino acid sequence comprising amino acid residues 21 to 328 of the amino acid sequence represented by SEQ ID NO: 2 in the Sequence Listing;

(c) an amino acid sequence comprising amino acid residues 1 to 260 of the amino acid sequence represented by SEQ ID NO: 2 in the Sequence Listing;

(d) an amino acid sequence comprising amino acid residues 21 to 260 of the amino acid sequence represented by SEQ ID NO: 2 in the Sequence Listing;

(e) an amino acid sequence represented by SEQ ID NO: 4 in the Sequence Listing;

(f) an amino acid sequence comprising amino acid residues 21 to 341 of the amino acid sequence represented by SEQ ID NO: 4 in the Sequence Listing;

(g) an amino acid sequence comprising amino acid residues 1 to 258 of the amino acid sequence represented by SEQ ID NO: 4 in the Sequence Listing;

(h) an amino acid sequence comprising amino acid residues 21 to 258 of the amino acid sequence represented by SEQ ID NO: 4 in the Sequence Listing; and (i) an amino acid sequence including substitution, deletion or addition of one or several amino acid residues in the amino acid sequence described in (a) to (h).

(2) An antibody which specifically recognizes one or more polypeptides comprising an amino acid sequence encoded by a nucleotide sequence described in any one of the following (j) to (n) and inhibits osteoclast formation and/or osteoclastic bone resorption, or a functional fragment of the antibody:

(j) a nucleotide sequence represented by SEQ ID NO: 1;

(k) a nucleotide sequence represented by SEQ ID NO: 3;

(l) a nucleotide sequence represented by SEQ ID NO: 19;

(m) a nucleotide sequence represented by SEQ ID NO: 43; and (n) a nucleotide sequence of a polynucleotide which hybridizes to a polynucleotide comprising a nucleotide sequence complementary to the nucleotide sequence described in (j) to (m) under stringent conditions.

(3) The antibody or a functional fragment of the antibody according to (1) or (2) which inhibits the process of cell fusion of osteoclasts.

(4) The antibody or a functional fragment of the antibody according to any one of (1) to (3) which inhibits osteoclast formation induced by TNF-α.

(5) The antibody or a functional fragment of the antibody according to any one of (1) to (4) which inhibits in vitro osteoclast formation at a concentration of 30 μg/ml or less.

(6) The antibody or a functional fragment of the antibody according to (5) which inhibits in vitro osteoclast formation at a concentration of 3 μg/ml or less.

(7) The antibody or a functional fragment of the antibody according to (6) which inhibits in vitro osteoclast formation at a concentration of 1 μg/ml or less.

(8) The antibody or a functional fragment of the antibody according to (7) which inhibits in vitro osteoclast formation at a concentration of from 63 ng/ml to 1 μg/ml.

(9) The antibody or a functional fragment of the antibody according to any one of (1) to (4) which inhibits osteoclastic bone resorption.

(10) The antibody or a functional fragment of the antibody according to (9) which inhibits in vitro osteoclastic bone resorption at a concentration of 3 μg/ml or less.

(11) The antibody or a functional fragment of the antibody according to (10) which inhibits in vitro osteoclastic bone resorption at a concentration of from 0.3 μg/ml to 3 μg/ml.

(12) The antibody or a functional fragment of the antibody according to any one of (1) to (11) which is obtained by a method comprising the following steps 1) and 2):

1) a step of producing an antibody which specifically recognizes any one or more sequences of the amino acid sequences described in any one of the following (a) to (i):

(a) an amino acid sequence represented by SEQ ID NO: 2 in the Sequence Listing;

(b) an amino acid sequence comprising amino acid residues 21 to 328 of the amino acid sequence represented by SEQ ID NO: 2 in the Sequence Listing;

(c) an amino acid sequence comprising amino acid residues 1 to 260 of the amino acid sequence represented by SEQ ID NO: 2 in the Sequence Listing;

(d) an amino acid sequence comprising amino acid residues 21 to 260 of the amino acid sequence represented by SEQ ID NO: 2 in the Sequence Listing;

(e) an amino acid sequence represented by SEQ ID NO: 4 in the Sequence Listing;

(f) an amino acid sequence comprising amino acid residues 21 to 341 of the amino acid sequence represented by SEQ ID NO: 4 in the Sequence Listing;

(g) an amino acid sequence comprising amino acid residues 1 to 258 of the amino acid sequence represented by SEQ ID NO: 4 in the Sequence Listing;

(h) an amino acid sequence comprising amino acid residues 21 to 258 of the amino acid sequence represented by SEQ ID NO: 4 in the Sequence Listing; and (i) an amino acid sequence including substitution, deletion or addition of one or several amino acid residues in the amino acid sequence described in (a) to (h); and 2) a step of screening an antibody which exhibits an inhibitory activity against osteoclast formation and/or an inhibitory activity against bone resorption.

(13) The antibody or a functional fragment of the antibody according to any one of (1) to (11) which is obtained by a method comprising the following steps 1) and 2):

1) a step of producing an antibody which specifically recognizes one or more polypeptides comprising an amino acid sequence encoded by a nucleotide sequence described in any one of the following (j) to (n):

(j) a nucleotide sequence represented by SEQ ID NO: 1;

(k) a nucleotide sequence represented by SEQ ID NO: 3;

(l) a nucleotide sequence represented by SEQ ID NO: 19;

(m) a nucleotide sequence represented by SEQ ID NO: 43; and (n) a nucleotide sequence of a polynucleotide which hybridizes to a polynucleotide comprising a nucleotide sequence complementary to the nucleotide sequence described in (j) to (m) under stringent conditions; and 2) a step of screening an antibody which exhibits an inhibitory activity against osteoclast formation and/or an inhibitory activity against bone resorption.

(14) The antibody or a functional fragment of the antibody according to any one of (1) to (13), characterized in that the antibody is a monoclonal antibody.

(15) The antibody or a functional fragment of the antibody according to (14), characterized by having the same epitope specificity as an antibody produced by hybridoma #32A1 (FERM BP-10999).

(16) The antibody or a functional fragment of the antibody according to (14), characterized by competing with an antibody produced by hybridoma #32A1 (FERM BP-10999).

(17) The antibody or a functional fragment of the antibody according to (14), characterized in that the antibody is an antibody produced by hybridoma #32A1 (FERM BP-10999).

(18) The antibody or a functional fragment of the antibody according to (14), characterized by having the same epitope specificity as an antibody produced by hybridoma #41B1 (FERM BP-11000).

(19) The antibody or a functional fragment of the antibody according to (14), characterized by competing with an antibody produced by hybridoma #41B1 (FERM BP-11000).

(20) The antibody or a functional fragment of the antibody according to (14), characterized in that the antibody is an antibody produced by hybridoma #41B1 (FERM BP-11000).

(21) The antibody or a functional fragment of the antibody according to any one of (1) to (20), characterized in that the antibody is a chimeric antibody.

(22) The antibody or a functional fragment of the antibody according to any one of (1) to (21), characterized in that the antibody is humanized.

(23) The antibody or a functional fragment of the antibody according to any one of (1) to (16), (18) and (19), characterized in that the antibody is a human antibody.

(24) The antibody or a functional fragment of the antibody according to any one of (1) to (23), characterized in that the antibody is an IgG antibody.

(25) The functional fragment of the antibody according to any one of (1) to (24) which is selected from the group consisting of Fab, F(ab')2, Fab' and Fv.

(26) The antibody according to any one of (1) to (16), (18) and (19), characterized by being an scFv.

(27) A pharmaceutical composition characterized by comprising at least one of the antibodies or functional fragments of the antibodies according to (1) to (26).

(28) The pharmaceutical composition according to (27), characterized by being a therapeutic and/or preventive agent for abnormal bone metabolism.

(29) A pharmaceutical composition for treating and/or preventing abnormal bone metabolism characterized by comprising at least one of the antibodies or functional fragments of the antibodies according to (1) to (26) and at least one member selected from the group consisting of bisphosphonates, active vitamin $D_3$, calcitonin and derivatives thereof, hormone preparations such as estradiol, SERMs (selective estrogen receptor modulators), ipriflavone, vitamin $K_2$ (menatetrenone), calcium preparations, PTH (parathyroid hormone) preparations, nonsteroidal anti-inflammatory agents, soluble TNF receptor preparations, anti-TNF-α antibodies or functional fragments of the antibodies, anti-PTHrP (parathyroid hormone-related protein) antibodies or functional fragments of the antibodies, IL-1 receptor antagonists, anti-IL-6 receptor antibodies or functional fragments of the antibodies, anti-RANKL antibodies or functional fragments of the antibodies and OCIF (osteoclastogenesis inhibitory factor).

(30) The pharmaceutical composition according to (28) or (29), wherein the abnormal bone metabolism is selected from the group consisting of osteoporosis, bone destruction accompanying rheumatoid arthritis, cancerous hypercalcemia, bone destruction accompanying multiple myeloma or cancer metastasis to bone, giant cell tumor, tooth loss due to periodontitis, osteolysis around a prosthetic joint, bone destruction in chronic osteomyelitis, Paget's disease of bone, renal osteodystrophy and osteogenesis imperfecta.

(31) The pharmaceutical composition according to (28), characterized in that the abnormal bone metabolism is osteoporosis, bone destruction accompanying rheumatoid arthritis or bone destruction accompanying cancer metastasis to bone.

(32) The pharmaceutical composition according to (29), characterized in that the osteoporosis is postmenopausal osteoporosis, senile osteoporosis, secondary osteoporosis due to the use of a therapeutic agent such as a steroid or an immunosuppressant, or osteoporosis accompanying rheumatoid arthritis.

(33) A method of treating and/or preventing abnormal bone metabolism characterized by administering at least one of the antibodies or functional fragments of the antibodies according to (1) to (26).

(34) A method of treating and/or preventing abnormal bone metabolism characterized by simultaneously or successively administering at least one of the antibodies or functional fragments of the antibodies according to (1) to (26) and at least one member selected from the group consisting of bisphosphonates, active vitamin $D_3$, calcitonin and derivatives thereof, hormone preparations such as estradiol, SERMs (selective estrogen receptor modulators), ipriflavone, vitamin $K_2$ (menatetrenone), calcium preparations, PTH (parathyroid hormone) preparations, nonsteroidal anti-inflammatory agents, soluble TNF receptor preparations, anti-TNF-α antibodies or functional fragments of the antibodies, anti-PTHrP (parathyroid hormone-related protein) antibodies or functional fragments of the antibodies, IL-1 receptor antagonists, anti-IL-6 receptor antibodies or functional fragments of the antibodies, anti-RANKL antibodies or functional fragments of the antibodies and OCIF (osteoclastogenesis inhibitory factor).

(35) The treatment and/or prevention method according to (33) or (34), characterized in that the abnormal bone metabolism is osteoporosis, bone destruction accompanying rheumatoid arthritis or bone destruction accompanying cancer metastasis to bone.

(36) The treatment and/or prevention method according to (35), characterized in that the osteoporosis is postmenopausal osteoporosis, senile osteoporosis, secondary osteoporosis due to the use of a therapeutic agent such as a steroid or an immunosuppressant, or osteoporosis accompanying rheumatoid arthritis.

(37) Hybridoma #32A1 (FERM BP-10999).

(38) Hybridoma #41B1 (FERM BP-11000).

Advantage of the Invention

According to the invention, a therapeutic and/or preventive agent for abnormal bone metabolism whose mechanism of action is to inhibit the differentiation and maturation of osteoclasts and the activity thereof can be obtained.

BEST MODE FOR CARRYING OUT THE INVENTION

Figure 1:
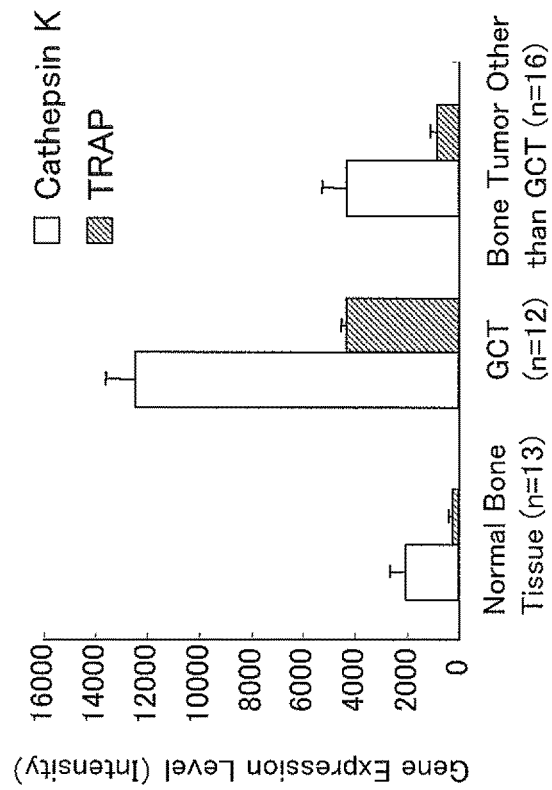
FIG. 1 shows graphs depicting an expression profile analysis for RANK, RANKL, cathepsin K, and TRAP genes in human giant cell tumor tissues.
Figure 1:
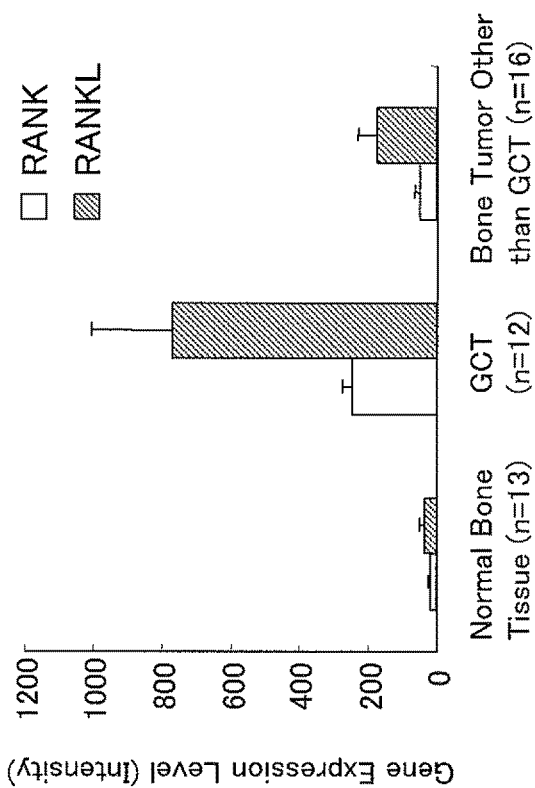

The term "gene" as used herein includes not only DNA, but also mRNA, cDNA and cRNA.

The term "polynucleotide" as used herein is used in the same meaning as a nucleic acid and also includes DNA, RNA, probes, oligonucleotides and primers.

The terms "polypeptide" and "protein" as used herein are used without distinction.

The term "RNA fraction" as used herein refers to a fraction containing RNA.

The term "cell" as used herein also includes cells in an animal individual and cultured cells.

The term "Siglec-15" as used herein is used in the same meaning as Siglec-15 protein.

The term "osteoclast formation" as used herein is used in the same meaning as "osteoclast differentiation" or "osteoclast maturation".

The term "functional fragment of an antibody" as used herein refers to a partial fragment of an antibody having an antigen-binding activity and includes Fab, F(ab')2, scFv and the like. The term also encompasses Fab' which is a monovalent fragment in a variable region of an antibody obtained by treating F(ab')2 under reducing conditions. However, the term is not limited to these molecules as long as the fragment has a binding affinity for an antigen. Further, these functional fragments include not only a fragment obtained by treating a full-length molecule of an antibody protein with an appropriate enzyme, but also a protein produced in an appropriate host cell using a genetically modified antibody gene.

The term "epitope" as used herein refers to a partial peptide of Siglec-15 to which a specific anti-Siglec-15 antibody binds. The above-mentioned epitope which is a partial peptide of Siglec-15 can be determined by methods well known to those skilled in the art such as an immunoassay. Alternatively, for example, the following method can be employed. Various partial structures of Siglec-15 are produced. In the production of the partial structures, a known oligopeptide synthesis technique can be used. For example, a series of polypeptides having appropriately reduced lengths obtained by sequentially shortening Siglec-15 from the C terminus or N terminus are produced using a genetic recombination technique known to those skilled in the art. Thereafter, the reactivity of an antibody against these polypeptides is examined and a recognition site is roughly determined. Then, peptides having shorter lengths are synthesized and the reactivity with these peptides is examined, whereby the epitope can be determined. If a second anti-Siglec-15 antibody binds to a partial peptide to which a first anti-Siglec-15 antibody binds, it can be determined that the first antibody and the second antibody share the same epitope. Further, by confirming that the second anti-Siglec-15 antibody competes with the first anti-Siglec-15 antibody for the binding to Siglec-15 (that is, the second antibody inhibits the binding between Siglec-15 and the first antibody), it can be determined that the first antibody and the second antibody share the same epitope even if the specific epitope sequence has not been determined. Further, when the first antibody and the second antibody bind to the same epitope and also the first antibody has a special effect such as an antigen-neutralizing activity, the second antibody can be expected to have the same activity.

The phrase "hybridization is performed under stringent conditions" as used herein refers to hybridization being performed under the conditions under which identification can be effected by performing hybridization at 68° C. in a commercially available hybridization solution, ExpressHyb Hybridization Solution (manufactured by Clontech, Inc.) or performing hybridization at 68° C. in the presence of 0.7 to 1.0 M NaCl using a filter having DNA immobilized thereon, followed by performing washing at 68° C. using 0.1 to 2×SSC solution (1×SSC solution is composed of 150 mM NaCl and 15 mM sodium citrate) or under conditions equivalent thereto.

1. Siglec-15

The present inventors found that the Siglec-15 gene is specifically expressed in giant cell tumors and also found that the expression level of the Siglec-15 gene increases when a monocyte-derived cell line differentiates into osteoclasts.

As for Siglec-15 to be used in the invention, Siglec-15 is directly purified from monocytes or bone marrow cells of human, non-human mammal (such as guinea pig, rat, mouse, rabbit, pig, sheep, cattle or monkey) or chicken and used, or a cell membrane fraction of the above-mentioned cells is prepared and can be used. Further, Siglec-15 can be obtained by in vitro synthesis thereof or production thereof in a host cell through genetic engineering. In the genetic engineering, specifically, Siglec-15 cDNA is integrated into a vector capable of expressing Siglec-15 cDNA, and Siglec-15 is synthesized in a solution containing enzymes, substrates, and energy substances required for transcription and translation, or another prokaryotic or eucaryotic host cell is transformed to express Siglec-15, whereby the protein can be obtained.

The nucleotide sequence of human Siglec-15 cDNA has been registered in GenBank with an accession number of NM 213602 and is represented by SEQ ID NO: 1 in the Sequence Listing, and its amino acid sequence is represented by SEQ ID NO: 2 in the Sequence Listing. The nucleotide sequence of mouse Siglec-15 cDNA has been registered in GenBank with an accession number of XM 884636 and is represented by SEQ ID NO: 3 in the Sequence Listing, and its amino acid sequence is represented by SEQ ID NO: 4 in the Sequence Listing. Mature human Siglec-15 from which the signal sequence has been removed corresponds to an amino acid sequence composed of amino acid residues 21 to 328 of the amino acid sequence represented by SEQ ID NO: 2. Further, mouse Siglec-15 from which the signal sequence has been removed corresponds to an amino acid sequence composed of amino acid residues 21 to 341 of the amino acid sequence represented by SEQ ID NO: 4. Incidentally, Siglec-15 is sometimes called CD33 antigen-like 3, CD33 molecule-like 3, CD33-like 3 or CD33L3, and all of these represent the same molecule. Siglec-15 cDNA can be obtained by, for example, a so-called PCR method in which a polymerase chain reaction (hereinafter referred to as "PCR") is performed using a cDNA library expressing Siglec-15 cDNA as a template and primers which specifically amplify Siglec-15 cDNA (Saiki, R. K., et al., Science, (1988) 239, 487-49).

Further, a polynucleotide which hybridizes to a polynucleotide composed of a nucleotide sequence complementary to at least one nucleotide sequence selected from the nucleotide sequences represented by SEQ ID NOS: 1 and 3 in the Sequence listing under stringent conditions and which encodes a protein having a biological activity comparable to that of Siglec-15 is also included in Siglec-15 cDNA. Further, a polynucleotide which is a splicing variant transcribed from the human or mouse Siglec-15 locus or a polynucleotide which hybridizes thereto under stringent conditions and encodes a protein having a biological activity comparable to that of Siglec-15 is also included in Siglec-15 cDNA.

Further, a protein which is composed of an amino acid sequence including substitution, deletion or addition of one or several amino acids in at least one amino acid sequence selected from the amino acid sequences represented by SEQ ID NOS: 2 and 4 in the Sequence Listing or the amino acid sequence from which the signal sequence has been removed and has a biological activity comparable to that of Siglec-15 is also included in Siglec-15. Further, a protein which is composed of an amino acid sequence encoded by a splicing variant transcribed from the human or mouse Siglec-15 locus or an amino acid sequence including substitution, deletion or addition of one or several amino acids therein and has a biological activity comparable to that of Siglec-15 is also included in Siglec-15.

2. Detection of Abnormal Bone Metabolism

An analysis of the expression level of the Siglec-15 gene in a group of test samples from various human bone tissues showed that the expression level of the gene significantly increases in giant cell tumor (GCT) which is a bone tumor with a large number of osteoclast-like multinucleated giant cells arising and is characterized by clinical findings of osteolytic bone destruction (Bullough et al., Atlas of Orthopedic Pathology 2nd edition, pp. 17.6-17.8, Lippincott Williams & Wilkins Publishers (1992)).

It was also found that the expression level of the Siglec-15 gene increases when a monocyte-derived cell line is differentiated into osteoclasts.

Accordingly, Siglec-15 is considered to be associated with human pathology such as GCT in which bone resorption is increased. In other words, measurement of the expression level of the Siglec-15 gene and/or Siglec-15 in each cell and/or each tissue enables determination of the state of abnormal bone metabolism accompanied by overexpression of Siglec-15. Examples of the abnormal bone metabolism as used herein include, but are not limited to, osteoporosis (postmenopausal osteoporosis, senile osteoporosis, secondary osteoporosis due to the use of a therapeutic agent such as a steroid or an immunosuppressant, or osteoporosis accompanying rheumatoid arthritis), bone destruction accompanying rheumatoid arthritis, cancerous hypercalcemia, bone destruction accompanying multiple myeloma or cancer metastasis to bone, giant cell tumor, tooth loss due to periodontitis, osteolysis around a prosthetic joint, bone destruction in chronic osteomyelitis, Paget's disease of bone, renal osteodystrophy and osteogenesis imperfecta.

In the invention, the "test sample" to be used for examining the expression level of the Siglec-15 gene and/or Siglec-15 refers to a sample from a tissue of bone marrow, bone, prostate, testis, penis, bladder, kidney, oral cavity, pharynx, lip, tongue, gingiva, nasopharynx, esophagus, stomach, small intestine, large intestine, colon, liver, gallbladder, pancreas, nose, lung, soft tissue, skin, breast, uterus, ovary, brain, thyroid, lymph node, muscle, fat tissue or the like, or blood, a body fluid or an excretion or the like, however, in the invention, blood or bone marrow is more preferred.

3. Method of Screening Substance Which Inhibits Differentiation into Osteoclasts As one embodiment of the invention, a method of screening a substance which inhibits differentiation into osteoclasts by measuring the expression level of the Siglec-15 gene and/ or Siglec-15 can be exemplified.

As another embodiment of the invention, a method of screening a substance which has a therapeutic effect and/or preventive effect on abnormal bone metabolism by identifying a substance which inhibits the activity of Siglec-15 of inducing differentiation into mature osteoclasts, can be exemplified.

The "test substance" refers to a substance to be used for examining the activity of inhibiting differentiation into osteoclasts by the screening method of the invention. Examples of the test substance include a compound, a microbial metabolite, an extract from a plant or animal tissue, a derivative thereof, and a mixture thereof Further, a nucleic acid designed to decrease the expression level of Siglec-15 or a derivative thereof (such as an antisense oligonucleotide, a ribozyme, dsRNA or siRNA) can also be used as the test substance. The dose or concentration of the test substance may be appropriately set or a plurality of doses may be set by, for example, preparing dilution series thereof. The test substance can be administered in an appropriate state such as a solid or a liquid, and may be dissolved in an appropriate buffer or a stabilizer or the like may be added thereto. In the case of a screening method using cultured cells, the test substance is added to a medium and cells can be cultured therein. In the case where the test substance is added to a medium, the test substance may be added at the initiation of the culturing or in the middle of the culturing, and the number of addition operations is not limited to one. The period of culturing in the presence of a test substance may be appropriately set, however, it is preferably from 30 minutes to 2 weeks, more preferably from 30 minutes to 72 hours. In the case where the test substance is administered to a mammalian individual, the route of administration, including oral administration, intravenous injection, intraperitoneal injection, transdermal administration, subcutaneous injection and the like, is suitably determined depending on the physical properties and the like of the test substance. Incidentally, a suitable time until the test sample is obtained, after the administration of the test substance, can be selected.

The cultured cells to be used in the screening method of the invention may be normal cells, an established cell line, or cells showing abnormal growth such as cancer cells as long as they are mammalian cells expressing Siglec-15. Examples thereof include, but are not limited to, normal human osteoclast precursor cells (Normal Human Natural Osteoclast Precursor Cells, available from Sanko Junyaku Co., Ltd., Cat. No. 2T-110), mouse monocyte-derived cells RAW 264.7 (ATCC Cat. No. TIB-71), RAW 264 cells (ECACC Cat. No. 85062803), and mouse bone marrow-derived primary cultured cells. As an animal species of the cultured cells, human, mouse, or other mammals (guinea pig, rat, rabbit, pig, sheep, cattle, monkey, etc.), chicken and the like are preferred, but the species is not limited thereto. Incidentally, as the cultured cells, it is more preferred to use mammalian cells overexpressing Siglec-15, and for example, RAW 264.7 cells, RAW 264 cells, 293 cells, CHO cells and COST cells modified by introducing the Siglec-15 gene along with the promoter region thereof to overexpress Siglec-15, and the like can be exemplified.

The screening method of the invention also includes a method of detecting the expression of the Siglec-15 gene in cells of an organ or a tissue resected from a mammalian individual after administering a test substance to the mammalian individual without using cultured cells. The organ or tissue to be used for detecting the expression of the gene may be any as long as it expresses Siglec-15, however, a tissue associated with abnormal bone metabolism is preferred, and a bone tissue and bone marrow are more preferred. As a mammalian species, a non-human mammal can be used, and mouse, rat or hamster is preferred, and mouse or rat is more preferred. As an animal model having abnormal bone metabolism, an animal having the ovary removed, an animal having the testicle removed, a cancer-bearing animal having tumor cells implanted under the skin, into the skin, left ventricle, bone marrow, vein, abdominal cavity or the like, an animal having a sciatic nerve removed, an animal model of adjuvant arthritis, an animal model of collagen-induced arthritis, an animal model of glucocorticoid-induced osteoporosis, a senescence-accelerated mouse (SAM P6 mouse, Matsushita et al., Am. J. Pathol. 125, 276-283 (1986)), an animal having the thyroid/parathyroid removed, an animal receiving a continuous infusion of a parathyroid hormone-related peptide (PTHrP), an osteoclastogenesis inhibitory factor (OCIF) knockout mouse (Mizuno et al., Biochem. Biophys. Res. Commun., (1998) 247, 610-615), an animal with the administration of soluble RANKL or the like can be used. Further, an animal model with tooth loss due to periodontal disease or an animal modified to overexpress Siglec-15 can also be used. Further, a test substance selected by screening is administered to any of the above-mentioned animal models, and each parameter which can be obtained by the measurement of the number of mature osteoclasts in a bone tissue, a bone density, a bone strength or a bone morphology, bone metabolism parameters (CTx, NTx, etc.) in blood and urine or parameters that vary due to abnormal bone metabolism such as blood calcium levels are measured, whereby the therapeutic effect and/or preventive effect of the test substance on abnormal bone metabolism can be evaluated.

The cultured cells to be used in the method of the invention may be cultured under any conditions as long as the conditions enable the cultured cells to express Siglec-15 without the addition of a test substance. For example, there are known culture conditions for the cultured cells, and when the cells express Siglec-15 under the conditions, the cells may be cultured under the conditions. Further, in the case where the expression of Siglec-15 in an organ or a tissue resected from a mammalian individual is detected, rearing conditions for the animal may be any as long as the conditions enable the animal to express Siglec-15 without the addition of a test substance.

In order to examine the effect of a test substance on the expression of Siglec-15, there are a method of measuring the expression level of the Siglec-15 gene and a method of measuring the expression level of Siglec-15 which is a translation product of the Siglec-15 gene. A test substance which inhibits the expression of the Siglec-15 gene and/or Siglec-15 is considered to be a substance having a therapeutic effect and/or preventive effect on abnormal bone metabolism, preferably osteoporosis, or bone destruction accompanying rheumatoid arthritis and/or cancer metastasis to bone.

The measurement of the expression level of the Siglec-15 gene or Siglec-15 in cultured cells can be performed by a Northern analysis, a quantitative PCR method, an ELISA method or the like. In the case where mammalian cultured cells are used, an appropriate amount of RANKL, TNF-α, M-CSF, active vitamin $D_3$, or the like is added, as needed, to a medium along with a test substance, and also in a control without the addition of the test substance, an appropriate amount of RANKL, TNF-α, M-CSF, active vitamin $D_3$, or the like is added.

Further, an experimental system for measuring the binding amount of an endogenous ligand to Siglec-15 is constructed, and whether or not the binding of the endogenous ligand to Siglec-15 is inhibited by the addition of a test substance is evaluated, whereby screening of a substance which inhibits differentiation into osteoclasts can be performed.

The respective screening methods will be described in the following (1) to (3).

(1) Method Using Siglec-15 Gene

As the screening method of the invention, for example, there are a method using mammalian cultured cells and a method using mammalian individuals, which will be described below, respectively.

(a) Method using mammalian cultured cells (i) A method including the following steps a) to c):

a) a step of extracting total RNA from mammalian cultured cells cultured in a medium with the addition of a test substance;

b) a step of detecting a difference in the expression level of the Siglec-15 gene between the total RNA obtained in a) and total RNA obtained from mammalian cultured cells cultured without the addition of the test substance; and c) a step of determining the therapeutic and/or preventive effect of the test substance on abnormal bone metabolism by analyzing the difference in the expression level of the gene described in b).

(ii) A method including the following steps a) to d):

a) a step of extracting total RNA from mammalian cultured cells cultured in a medium with the addition of a test substance;

b) a step of extracting total RNA from mammalian cultured cells cultured in a medium without the addition of the test substance;

c) a step of measuring the expression level of the Siglec-15 gene in the total RNA obtained in a) and in the total RNA obtained in b), respectively; and d) a step of determining the therapeutic and/or preventive effect of the test substance on abnormal bone metabolism by analyzing a difference in the expression level of the gene measured in c) between the total RNA obtained in a) and the total RNA obtained in b).

(b) Method using mammalian individuals (i) A method including the following steps (a) to (c):

a) a step of extracting total RNA from a test sample collected from a mammalian individual with the administration of a test substance;

b) a step of detecting a difference in the expression level of the Siglec-15 gene between the total RNA obtained in a) and total RNA obtained from a test sample collected from a mammalian individual without the administration of the test substance; and c) a step of determining the therapeutic and/or preventive effect of the test substance on abnormal bone metabolism by analyzing the difference in the expression level of the gene described in b).

(ii) A method including the following steps a) to d):

a) a step of extracting total RNA from a test sample collected from a mammalian individual with the administration of a test substance;

b) a step of extracting total RNA from a test sample collected from a mammalian individual without the administration of the test substance;

c) a step of measuring the expression level of the Siglec-15 gene in the total RNA obtained in the step a) and in the total RNA obtained in the step b), respectively; and d) a step of determining the therapeutic and/or preventive effect of the test substance on abnormal bone metabolism by analyzing a difference in the expression level of the gene described in c).

(2) Method Using Siglec-15

As the screening method utilizing the measurement of the expression level of Siglec-15, there are a method using mammalian cultured cells and a method using animal individuals each of which includes the following steps.

(a) Method using mammalian cultured cells (i) A method including the following steps a) and b):

a) a step of measuring the expression level of Siglec-15 in mammalian cultured cells cultured in a medium with the addition of a test substance; and b) a step of determining the therapeutic effect and/or preventive effect of the test substance on abnormal bone metabolism by analyzing a difference between the expression level of the protein measured in a) and the expression level of the protein in mammalian cultured cells cultured in a medium without the addition of the test substance.

(ii) A method including the following steps a) to c):

a) a step of measuring the expression level of Siglec-15 in mammalian cultured cells cultured in a medium with the addition of a test substance;

b) a step of measuring the expression level of the protein described in a) in mammalian cultured cells cultured in a medium without the addition of the test substance; and c) a step of determining the therapeutic effect and/or preventive effect of the test substance on abnormal bone metabolism by detecting a difference between the expression level of the protein measured in a) and the expression level of the protein measured in b).

(iii) A method including the following steps a) to c):

a) a step of immobilizing total protein obtained from mammalian cultured cells cultured in a medium with the addition of a test substance;

b) a step of measuring the expression level of Siglec-15 in the immobilized protein; and c) a step of determining the therapeutic effect and/or preventive effect of the test substance on abnormal bone metabolism by analyzing a difference between the expression level of Siglec-15 detected in b) and the expression level of the protein in total protein obtained from mammalian cultured cells cultured in a medium without the addition of the test substance.

(iv) A method including the following steps a) to e):

a) a step of immobilizing total protein obtained from mammalian cultured cells cultured in a medium with the addition of a test substance;

b) a step of immobilizing total protein obtained from mammalian cultured cells cultured in a medium without the addition of the test substance;

c) a step of measuring the expression level of Siglec-15 in the immobilized protein described in the step a) using an antibody or a ligand specifically binding to the protein;

d) a step of measuring the expression level of Siglec-15 in the immobilized protein described in the step b) using an antibody or a ligand specifically binding to the protein; and e) a step of determining the therapeutic effect and/or preventive effect of the test substance on abnormal bone metabolism by analyzing a difference between the expression level of the protein measured in the step c) and the expression level of the protein measured in the step d).

(b) Method using mammalian individuals (i) A method including the following steps a) and b):

a) a step of measuring the expression level of Siglec-15 in a test sample collected from a mammalian individual to whom a test substance has been administered; and b) a step of determining the therapeutic effect and/or preventive effect of the test substance on abnormal bone metabolism by analyzing a difference between the expression level of Siglec-15 measured in the step a) and the expression level of the protein in a test sample collected from a mammalian individual without the administration of the test substance.

(ii) A method including the following steps a) to c):

a) a step of measuring the expression level of Siglec-15 in a test sample collected from a mammalian individual, to whom a test substance has been administered, using an antibody or a ligand specifically binding to the protein;

b) a step of measuring the expression level of the protein in a test sample collected from a mammalian individual without the administration of the test substance; and c) a step of determining the therapeutic effect and/or preventive effect of the test substance on abnormal bone metabolism by analyzing a difference between the expression level of Siglec-15 measured in a) and the expression level of the protein measured in b).

(iii) A method including the following steps a) to c):

a) a step of immobilizing total protein in a test sample collected from a mammalian individual to whom a test substance has been administered;

b) a step of measuring the expression level of Siglec-15 in the immobilized protein; and c) a step of determining the therapeutic and/or preventive effect of the test substance on abnormal bone metabolism by analyzing a difference between the expression level of Siglec-15 detected in b) and the expression level of the protein in a test sample collected from a mammalian individual without the administration of the test substance.

(iv) A method including the following steps a) to e):

a) a step of immobilizing total protein in a test sample collected from a mammalian individual to whom a test substance has been administered;

b) a step of immobilizing total protein in a test sample collected from a mammalian individual without the administration of the test substance;

c) a step of detecting the expression level of Siglec-15 in the immobilized protein described in the step a) using an antibody or a ligand specifically binding to the protein;

d) a step of detecting the expression level of Siglec-15 in the immobilized protein described in b) using an antibody or a ligand specifically binding to the protein; and e) a step of determining the therapeutic effect and/or preventive effect of the test substance on abnormal bone metabolism by analyzing a difference between the expression level of the protein detected in c) and the expression level of the protein detected in d).

(3) Screening Method Using Endogenous Ligand

Screening of a substance which inhibits differentiation into osteoclasts can also be performed by observing whether or not the binding of an endogenous ligand to Siglec-15 is inhibited by the addition of a test substance. Examples of a sialylated glycan serving as an endogenous ligand for Siglec-15 include Neu5Acα2-6GalNAc binding to human and mouse Siglec-15 and Neu5Acα2-3Galβ1-4Glc binding to mouse Siglec-15. However, the endogenous ligand for Siglec-15 is not limited to these glycans as long as it has a binding affinity for Siglec-15. These endogenous ligands can be labeled with an appropriate tag, radioisotope or fluorescent substance for the purpose of examining the binding thereof to Siglec-15. For example, biotinylated polyacrylamide to which a sialylated oligosaccharide such as Neu5Acα2-6GalNAc has been bound can be used in screening as a probe binding to Siglec-15. As Siglec-15 to which an endogenous ligand is bound, Siglec-15-expressing cells or a membrane fraction prepared from the cells can be used. Further, Siglec-15 can be subjected to screening after Siglec-15 is isolated from Siglec-15-expressing cells, followed by purification. As the Siglec-15-expressing cells, any of a cultured cell line expressing Siglec-15, cells caused to transiently or constantly express the Siglec-15 gene by subjecting appropriate cultured cells to genetic engineering, and cells expressing Siglec-15 obtained in vivo can be used. The screening method using such an endogenous ligand can be performed according to the steps as described below.

(i) A method including the following steps a) and b):

a) a step of adding an endogenous ligand for Siglec-15 and a test substance to Siglec-15-expressing cells; and b) a step of determining the therapeutic and/or preventive effect of the test substance on abnormal bone metabolism by comparing the binding amount of the endogenous ligand to the Siglec-15-expressing cells between the case where the test substance was added and the case where the test substance was not added.

(ii) A method including the following steps a) to c):

a) a step of preparing a cell membrane fraction of Siglec-15-expressing cells;

b) a step of adding an endogenous ligand for Siglec-15 and a test substance to the cell membrane fraction; and c) a step of determining the therapeutic and/or preventive effect of the test substance on abnormal bone metabolism by comparing the binding amount of the endogenous ligand to the cell membrane fraction between the case where the test substance was added and the case where the test substance was not added.

(iii) A method including the following steps a) to c):

a) a step of preparing Siglec-15;

b) a step of adding an endogenous ligand for Siglec-15 and a test substance to Siglec-15 in a); and c) a step of determining the therapeutic and/or preventive effect of the test substance on abnormal bone metabolism by comparing the binding amount of the endogenous ligand to Siglec-15 between the case where the test substance was added and the case where the test substance was not added.

In the case where appropriate cells are caused to express Siglec-15 by genetic engineering and the resulting Siglec-15 is purified and subjected to screening, Siglec-15 to be screened can be selected from polypeptides composed of the amino acid sequences shown in the following (a) to (i):

(a) an amino acid sequence represented by SEQ ID NO: 2 in the Sequence Listing;

(b) an amino acid sequence composed of amino acid residues 21 to 328 of the amino acid sequence represented by SEQ ID NO: 2 in the Sequence Listing;

(c) an amino acid sequence composed of amino acid residues 1 to 260 of the amino acid sequence represented by SEQ ID NO: 2 in the Sequence Listing;

(d) an amino acid sequence composed of amino acid residues 21 to 260 of the amino acid sequence represented by SEQ ID NO: 2 in the Sequence Listing;

(e) an amino acid sequence represented by SEQ ID NO: 4 in the Sequence Listing;

(f) an amino acid sequence composed of amino acid residues 21 to 341 of the amino acid sequence represented by SEQ ID NO: 4 in the Sequence Listing;

(g) an amino acid sequence composed of amino acid residues 1 to 258 of the amino acid sequence represented by SEQ ID NO: 4 in the Sequence Listing;

(h) an amino acid sequence composed of amino acid residues 21 to 258 of the amino acid sequence represented by SEQ ID NO: 4 in the Sequence Listing; and (i) an amino acid sequence including substitution, deletion or addition of one or several amino acid residues in the amino acid sequence described in (a) to (h).

Siglec-15 to be screened can also be selected from polypeptides composed of amino acid sequences encoded by the nucleotide sequences shown in the following (j) to (n):

(j) a nucleotide sequence represented by SEQ ID NO: 1;

(k) a nucleotide sequence represented by SEQ ID NO: 3;

(l) a nucleotide sequence represented by SEQ ID NO: 19;

(m) a nucleotide sequence represented by SEQ ID NO: 43; and (n) a nucleotide sequence of a polynucleotide which hybridizes to a polynucleotide composed of a nucleotide sequence complementary to the nucleotide sequence described in (j) to (m) under stringent conditions.

Further, it is also possible to use a polypeptide obtained by attaching an appropriate tag to any of these polypeptides, or a polypeptide fused with a different soluble protein, as a target for screening. Incidentally, the polypeptide composed of the amino acid residues 1 to 20 of the amino acid sequence represented by SEQ ID NO: 2 in the Sequence Listing corresponds to the signal peptide of human Siglec-15, and the polypeptide composed of the amino acid residues 21 to 260 thereof corresponds to the extracellular domain of the mature protein of human Siglec-15. Further, the polypeptide composed of the amino acid residues 1 to 20 of the amino acid sequence represented by SEQ ID NO: 4 in the Sequence Listing corresponds to the signal peptide of mouse Siglec-15, and the polypeptide composed of the amino acid residues 21 to 258 thereof corresponds to the extracellular domain of the mature protein of mouse Siglec-15. Further, the nucleotide sequence represented by SEQ ID NO: 43 encodes the extracellular domain of human Siglec-15 encoded by the nucleotide sequence represented by SEQ ID NO: 1, and the nucleotide sequence represented by SEQ ID NO: 19 encodes the extracellular domain of mouse Siglec-15 encoded by the nucleotide sequence represented by SEQ ID NO: 3.

Candidate substances for a substance which inhibits differentiation into osteoclasts selected by any of the screening methods (1) to (3) can be secondarily evaluated by using the inhibition of tartrate-resistant acid phosphatase (TRAP) activity of osteoclasts as an index as shown in Examples 17, 19 and 20. Further, the secondary evaluation thereof can also be performed by using the inhibition of formation of TRAP-positive multinucleated osteoclasts, i.e., the inhibition of cell fusion of osteoclasts as an index as shown in Examples 19, 21, 22 and 35.

(4) Other Methods

The incidence rate of abnormal bone metabolism over time, the degree of abnormal bone metabolism, and/or the survival rate, etc. are determined for the case where a test substance was administered to a mammalian individual caused to overexpress Siglec-15 and the case where the test substance was not administered thereto. In the case where, in the mammal with the administration of the test substance, the incidence rate of abnormal bone metabolism is significantly decreased, the degree of abnormal bone metabolism is significantly lower, and/or the survival rate is increased by about 10% or more, preferably about 30% or more, more preferably about 50% or more, the test substance can be selected as a compound having a therapeutic and/or preventive effect on abnormal bone metabolism.

4. Production of Anti-Siglec-15 Antibody

The antibody against Siglec-15 of the invention can be obtained by immunizing an animal with Siglec-15 or an arbitrary polypeptide selected from the amino acid sequence of Siglec-15, and collecting and purifying the antibody produced in vivo according to a common procedure. The biological species of Siglec-15 to be used as an antigen is not limited to human, and an animal can be immunized with Siglec-15 derived from an animal other than human such as mouse or rat. In this case, by examining the cross-reactivity between an antibody binding to the obtained heterologous Siglec-15 and human Siglec-15, an antibody applicable to a human disease can be selected.

Further, a monoclonal antibody can be obtained by fusing antibody-producing cells which produce an antibody against Siglec-15 with myeloma cells to establish a hybridoma according to a known method (for example, Kohler and Milstein, Nature, (1975) 256, pp. 495-497; Kennet, R. ed., Monoclonal Antibody, pp. 365-367, Prenum Press, N.Y. (1980)).

Siglec-15 to be used as an antigen can be obtained by genetic engineering to cause a host cell to express the Siglec-15 gene.

Specifically, the genetic engineering can be performed as follows. A vector capable of expressing the Siglec-15 gene is produced, and the resulting vector is transfected into a host cell to express the gene, and then, the expressed Siglec-15 is purified. Hereinafter, a method of obtaining an antibody against Siglec-15 will be specifically described.

(1) Preparation of Antigen

Examples of the antigen to be used for producing the anti-Siglec-15 antibody include Siglec-15, a polypeptide composed of a partial amino acid sequence consisting of at least 6 consecutive amino acid residues of Siglec-15, and a derivative obtained by adding a given amino acid sequence or carrier thereto. Further, in the section "3. Method of screening substance which inhibits differentiation into osteoclasts", Siglec-15 exemplified as a target for screening can also be exemplified as an antigen to be used for producing the anti-Siglec-15 antibody.

Siglec-15 can be used after purifying directly from human tumor tissues or tumor cells. Further, Siglec-15 can be obtained by synthesizing it in vitro or by causing a host cell to produce it by genetic engineering.

In the genetic engineering, specifically, Siglec-15 cDNA is integrated into a vector capable of expressing Siglec-15 cDNA and Siglec-15 is synthesized in a solution containing enzymes, substrates, and energy substances required for transcription and translation, or another prokaryotic or eucaryotic host cell is transformed to express Siglec-15, whereby the antigen can be obtained.

Further, the antigen can also be obtained as a secretory protein by expressing a fusion protein obtained by ligating the extracellular domain of Siglec-15 which is a membrane protein to the constant region of the antibody in an appropriate host-vector system.

Siglec-15 cDNA can be obtained by, for example, a so-called PCR method in which a polymerase chain reaction (hereinafter referred to as "PCR") is performed using a cDNA library expressing Siglec-15 cDNA as a template and primers which specifically amplify Siglec-15 cDNA (see Saiki, R. K., et al., Science, (1988) 239, pp. 487-489).

As the in vitro synthesis system of the polypeptide, for example, the Rapid Translation System (RTS) manufactured by Roche Diagnostics, Inc. can be exemplified, but it is not limited thereto.

Examples of the prokaryotic host include *Escherichia coli* and *Bacillus subtilis*. In order to transform the host cell with a target gene, the host cell is transformed using a plasmid vector containing a replicon, i.e., a replication origin derived from a species compatible with the host, and a regulator sequence. Further, the vector preferably has a sequence capable of imposing phenotypic selectivity on the transformed cell.

Examples of the eucaryotic host cell include vertebrate cells, insect cells, and yeast cells. As the vertebrate cells, for example, dihydrofolate reductase-deficient strains (Urlaub, G. and Chasin, L. A., Proc. Natl. Acad. Sci. USA (1980) 77, pp. 4126-4220) of simian COS cells (Gluzman, Y., Cell, (1981) 23, pp. 175-182, ATCC CRL-1650), murine fibroblasts NIH3T3 (ATCC No. CRL-1658), and Chinese hamster ovarian cells (CHO cells; ATCC: CCL-61); and the like are often used, however, it is not limited thereto.

The thus obtained transformant can be cultured according to a common procedure, and by the culturing of the transformant, a target polypeptide is produced intracellularly or extracellularly.

A suitable medium to be used for the culturing can be selected from various commonly used culture media depending on the employed host cell. If *Escherichia coli* is employed, an LB medium supplemented with an antibiotic such as ampicillin or IPMG; if necessary, can be used.

A recombinant protein produced intracellularly or extracellularly by the transformant through the culturing can be separated and purified by any of various known separation methods utilizing a physical or chemical property of the protein.

Specific examples of the methods include treatment with a common protein precipitant, ultrafiltration, various types of liquid chromatography such as molecular sieve chromatography (gel filtration), adsorption chromatography, ion exchange chromatography and affinity chromatography, dialysis, and a combination thereof.

Further, by attaching six histidine residues to a recombinant protein to be expressed, the protein can be efficiently purified with a nickel affinity column. Alternatively, by attaching the IgG Fc region to a recombinant protein to be expressed, the protein can be efficiently purified with a protein A column.

By combining the above-mentioned methods, a large amount of a target polypeptide can be easily produced in high yield and high purity.

(2) Production of Anti-Siglec-15 Monoclonal Antibody

Examples of the antibody specifically binding to Siglec-15 include a monoclonal antibody specifically binding to Siglec-15, and a method of obtaining the antibody is as described below.

Production of a monoclonal antibody generally requires the following operational steps of:

(a) purifying a biopolymer to be used as an antigen;

(b) preparing antibody-producing cells by immunizing an animal by injection of the antigen, collecting the blood, assaying its antibody titer and determining when the spleen is to be resected;

(c) preparing myeloma cells (hereinafter referred to as "myeloma");

(d) fusing the antibody-producing cells with the myeloma;

(e) screening a group of hybridomas producing a target antibody;

(f) dividing the hybridomas into single cell clones (cloning);

(g) optionally, culturing the hybridoma or rearing an animal implanted with the hybridoma for producing a large amount of a monoclonal antibody;

(h) examining the thus produced monoclonal antibody for biological activity and binding specificity, or assaying the same for properties with a labeled reagent; and the like.

Hereinafter, the method of producing a monoclonal antibody will be described in detail following the above steps, however, the method is not limited thereto, and, for example, antibody-producing cells and myeloma other than spleen cells may be used.

(a) Purification of Antigen

As the antigen, Siglec-15 prepared by the method as described above or a partial peptide thereof can be used.

Further, a membrane fraction prepared from recombinant cells expressing Siglec-15 or the recombinant cells expressing Siglec-15 themselves, and also a partial peptide of the protein of the invention chemically synthesized by a method known to those skilled in the art can also be used as the antigen.

(b) Preparation of Antibody-Producing Cells

The antigen obtained in step (a) is mixed with an adjuvant such as Freund's complete or incomplete adjuvant, or aluminum potassium sulfate and the resulting mixture is used as an immunogen to immunize an experimental animal. As the experimental animal, any animal used in a known hybridoma production method can be used without any trouble. Specifically, for example, mouse, rat, goat, sheep, cattle, horse or the like can be used. However, from the viewpoint of ease of availability of myeloma cells to be fused with the extracted antibody-producing cells, mouse or rat is preferably used as the animal to be immunized.

Further, the strain of mouse or rat to be actually used is not particularly limited, and in the case of mouse, for example, various lines such as A, AKR, BALB/c, BDP, BA, CE, C3H, 57BL, C57BL, C57L, DBA, FL, HTH, HT1, LP, NZB, NZW, RF, R III, SJL, SWR, WB, and 129 can be used, and in the case of rat, for example, Wistar, Low, Lewis, Sprague Dawley, ACI, BN, Fischer and the like can be used.

These mice and rats are commercially available from breeders/distributors of experimental animals, for example, CLEA Japan, Inc. and Charles River Laboratories Japan, Inc.

Among these, in consideration of fusing compatibility with myeloma cells described below, in the case of mice, BALB/c strain, and in the case of rats, Wistar and Low lines are particularly preferred.

Further, in consideration of antigenic homology between humans and mice, it is also preferred to use a mouse having decreased biological function to remove autoantibodies, that is, a mouse with an autoimmune disease.

The age of the mouse or rat at the time of immunization is preferably 5 to 12 weeks of age, more preferably 6 to 8 weeks of age.

In order to immunize an animal with Siglec-15 or a recombinant thereof, for example, a known method is described in detail in, for example, Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Spigfield, Illinois (1964), or the like.

Among these immunization methods, a preferred specific method in the invention is, for example, as follows.

That is, first, a membrane protein fraction serving as the antigen or cells caused to express the antigen is/are intradermally or intraperitoneally administered to an animal.

However, the combination of both routes of administration is preferred for increasing the immunization efficiency, and when intradermal administration is performed in the first half and intraperitoneal administration is performed in the latter half or only at the last dosing, the immunization efficiency can be particularly increased.

The administration schedule of the antigen varies depending on the type of animal to be immunized, individual differences or the like. However, in general, the frequency of administration of the antigen is preferably 3 to 6 times, more preferably 3 to 4 times, and the dosing interval is preferably 2 to 6 weeks, more preferably 2 to 4 weeks.

Further, the dose of the antigen varies depending on the type of animal to be immunized, individual differences or the like. However, the dose is generally set to 0.05 to 5 mg, preferably about 0.1 to 0.5 mg.

A booster immunization is performed 1 to 6 weeks, preferably 2 to 4 weeks, more preferably 2 to 3 weeks after the administration of the antigen as described above.

The dose of the antigen at the time of performing the booster immunization varies depending on the type or size of animal or the like, however, in the case of a mouse, the dose is generally set to 0.05 to 5 mg, preferably 0.1 to 0.5 mg, more preferably about 0.1 to 0.2 mg.

Spleen cells or lymphocytes including antibody-producing cells are aseptically removed from the immunized animal 1 to 10 days, preferably 2 to 5 days, more preferably 2 to 3 days after the booster immunization.

At this time, the antibody titer is measured, and if an animal having a sufficiently increased antibody titer is used as a supply source of the antibody-producing cells, the subsequent procedure can be carried out more efficiently.

The method of measuring the antibody titer to be used here includes, for example, an RIA method and an ELISA method, but is not limited thereto.

For example, if an ELISA method is employed, the measurement of the antibody titer in the invention can be carried out according to the procedures as described below.

First, a purified or partially purified antigen is adsorbed on the surface of a solid phase such as a 96-well plate for ELISA, and the surface of the solid phase having no antigen adsorbed thereon is covered with a protein unrelated to the antigen such as bovine serum albumin (hereinafter referred to as "BSA"). After washing the surface, the surface is brought into contact with a serially-diluted sample (for example, mouse serum) as a primary antibody to allow the antibody contained in the sample to bind to the antigen.

Further, as a secondary antibody, an antibody labeled with an enzyme against a mouse antibody is added and is allowed to bind to the mouse antibody. After washing, a substrate for the enzyme is added and the change in absorbance which occurs due to color development induced by degradation of the substrate or the like is measured to calculate the antibody titer.

The separation of the antibody-producing cells from the spleen cells or lymphocytes can be carried out according to a known method (for example, Kohler et al., Nature (1975), 256, p. 495; Kohler et al., Eur. J. Immunol. (1977), 6, p. 511; Milstein et al., Nature (1977), 266, p. 550; Walsh, Nature (1977), 266, p. 495).

For example, in the case of spleen cells, a general method in which the antibody-producing cells are separated by homogenizing the spleen to obtain cells through filtration with a stainless steel mesh and suspending the cells in Eagle's Minimum Essential Medium (MEM) can be employed.

(c) Preparation of Myeloma Cells (Hereinafter Referred to as "Myeloma")

The myeloma cells to be used for cell fusion are not particularly limited and suitable cells can be selected from known cell lines. However, in consideration of convenience when a hybridoma is selected from fused cells, it is preferred to use an HGPRT (hypoxanthine-guanine phosphoribosyl transferase) defective strain whose selection procedure has been established.

More specifically, examples of the HGPRT defective strain include X63-Ag8(X63), NS1-ANS/1(NS1), P3X63-Ag8.U1 (P3U1), X63-Ag8.653(X63.653), SP2/0-Ag14(SP2/0), MPC11-45.6TG1.7(45.6TG), F0, S149/5XXO and BU.1 derived from mice, 210.RSY3 .Ag.1.2.3 (Y3) derived from rats; and U266AR(SKO-007), GM1500.GTG-A12 (GM1500), UC729-6, LICR-LOW-HMy2(HMy2) and 8226AR/NIP4-1(NP41) derived from humans.

These HGPRT defective strains are available from, for example, the American Type Culture Collection (ATCC) or the like.

These cell strains are subcultured in an appropriate medium such as an 8-azaguanine medium [a medium obtained by adding 8-azaguanine to an RPMI-1640 2 0 medium supplemented with glutamine, 2-mercaptoethanol, gentamicin and fetal calf serum (hereinafter referred to as "FCS")]; Iscove's Modified Dulbecco's Medium (hereinafter referred to as "IMDM"), or Dulbecco's Modified Eagle Medium (hereinafter referred to as "DMEM"). In this case, 3 to 4 days before performing cell fusion, the cells are subcultured in a normal medium [for example, an ASF104 medium (manufactured by Ajinomoto Co., Ltd.) containing 10% FCS] to obtain not less than $2 \times 10^7$ cells on the day of cell fusion.

(d) Cell Fusion

Fusion between the antibody-producing cells and the myeloma cells is appropriately performed according to a known method (Weir, D. M. Handbook of Experimental Immunology Vol. I. II. III., Blackwell Scientific Publications, Oxford (1987), Kabat, E. A. and Mayer, M. M., Experimental Immunochemistry, Charles C Thomas Publisher, Springfield, Ill. (1964), etc.), under conditions such that the survival rate of cells is not excessively reduced.

Examples of the method include a chemical method in which the antibody-producing cells and the myeloma cells are mixed in a high concentration polymer solution of polyethylene glycol or the like, and a physical method using electric stimulation.

Among these methods, a specific example of the chemical method is as described below.

That is, in the case where polyethylene glycol is used for the high concentration polymer solution, the antibody-producing cells and the myeloma cells are mixed in a solution of polyethylene glycol having a molecular weight of 1500 to 6000, more preferably 2000 to 4000 at a temperature of 30 to 40° C., preferably 35 to 38° C. for 1 to 10 minutes, preferably 5 to 8 minutes.

(e) Selection of a Group of Hybridomas

The method of selecting hybridomas obtained by the above-mentioned cell fusion is not particularly limited. Usually, an HAT (hypoxanthine, aminopterin, thymidine) selection method (Kohler et al., Nature (1975), 256, p. 495; Milstein et al., Nature (1977), 266, p. 550) is used.

This method is effective when hybridomas are obtained using the myeloma cells of an HGPRT defective strain incapable of surviving in the presence of aminopterin.

That is, by culturing unfused cells and hybridomas in an HAT medium, only hybridomas resistant to aminopterin are selectively allowed to survive and proliferate.

(f) Division into Single Cell Clone (Cloning)

As a cloning method for hybridomas, a known method such as a methylcellulose method, a soft agarose method, or a limiting dilution method can be used (see, for example, Barbara, B. M. and Stanley, M. S.: Selected Methods in Cellular Immunology, W. H. Freeman and Company, San Francisco (1980)). Among these methods, particularly, a limiting dilution method is preferred.

In this method, a fibroblast cell strain derived from a rat fetus or feeder cells such as normal mouse spleen cells, thymus gland cells, or ascites cells are seeded in a microplate.

Meanwhile, hybridomas are diluted in a medium to give a cell density of 0.2 to 0.5 cells per 0.2 ml. A 0.1 ml aliquot of the diluted hybridoma suspension is placed in each well and culturing is continued for about 2 weeks while replacing about ⅓ of the culture solution with a fresh medium at predetermined time intervals (for example, every 3 days), whereby hybridoma clones can be proliferated.

The hybridomas in wells for which the antibody titer has been confirmed are subjected to, for example, cloning by the limiting dilution method repeatedly 2 to 4 times. A hybridoma which has been confirmed to have a stable antibody titer is selected as an anti-Siglec-15 monoclonal antibody- producing hybridoma strain.

Examples of the hybridoma strain thus cloned include hybridoma #32A1 and hybridoma #41B1. Hybridoma #32A1 and hybridoma #41B1 were deposited at the International Patent Organism Depositary of the National Institute of Advanced Industrial Science and Technology (located at Central 6, 1-1-1 Higashi, Tsukuba-shi, Ibaraki-ken, 305-8566, Japan) on Aug. 28, 2008. The hybridoma #32A1 has been given a deposition number of FERM BP-10999 under the name of anti-Siglec-15 Hybridoma #32A1, and the hybridoma #41B1 has been given a deposition number of FERM BP-11000 under the name of anti-Siglec-15 Hybridoma #41 B 1. In this description, the antibody produced by the hybridoma #32A1 is represented by "#32A1 antibody" or simply "#32A1", and the antibody produced by the hybridoma #41B1 is represented by "#41B1 antibody" or simply "#41B1". Further, antibodies obtained in the Examples of this description other than from hybridoma #32A1 and hybridoma #41B1 are also represented by the antibody names in the same manner.

(g) Preparation of Monoclonal Antibody by Culturing Hybridoma

By culturing the thus selected hybridoma, a monoclonal antibody can be efficiently obtained. However, prior to the culturing, it is preferred to perform screening of a hybridoma which produces a target monoclonal antibody.

In the screening, a known method can be employed.

The measurement of the antibody titer in the invention can be carried out by, for example, an ELISA method explained in item (b) described above.

The hybridoma obtained by the method as described above can be stored in a frozen state in liquid nitrogen or in a freezer at −80° C. or below.

After completion of cloning, the medium is changed from an HT medium to a normal medium, and the hybridoma is cultured.

Large-scale culture is performed by rotation culture using a large culture bottle or by spinner culture.

From the supernatant obtained by the large-scale culture, a monoclonal antibody which specifically binds to the protein of the invention can be obtained by purification using a method known to those skilled in the art such as gel filtration.

Further, the hybridoma is injected into the abdominal cavity of a mouse of the same strain as the hybridoma (for example, the above-mentioned BALB/c) or a Nu/Nu mouse to proliferate the hybridoma, whereby the ascites containing a large amount of the monoclonal antibody of the invention can be obtained.

In the case where the hybridoma is administered in the abdominal cavity, if a mineral oil such as 2,6,10,14-tetramethyl pentadecane (pristine) is administered 3 to 7 days prior thereto, a larger amount of the ascites can be obtained.

For example, an immunosuppressant is previously injected into the abdominal cavity of a mouse of the same strain as the hybridoma to inactivate T cells. 20 days thereafter, $10^6$ to $10^7$ hybridoma clone cells are suspended in a serum-free medium (0.5 ml), and the suspension is injected into the abdominal cavity of the mouse. In general, when the abdomen is expanded and filled with the ascites, the ascites is collected.

By this method, the monoclonal antibody can be obtained at a concentration about 100-fold higher than that of the culture solution.

The monoclonal antibody obtained by the above-mentioned method can be purified by the method described in, for example, Weir, D. M.: Handbook of Experimental Immunology Vol. I, II, III, Blackwell Scientific Publications, Oxford (1978).

That is, examples of the method include an ammonium sulfate precipitation method, gel filtration, ion exchange chromatography, and affinity chromatography.

As a simple purification method, a commercially available monoclonal antibody purification kit (for example, MAbTrap GII kit manufactured by Pharmacia, Inc.) or the like can also be used.

The thus obtained monoclonal antibody has high antigen specificity for Siglec-15.

(h) Assay of Monoclonal Antibody

The isotype and subclass of the thus obtained monoclonal antibody can be determined as follows.

First, examples of the identification method include the Ouchterlony method, an ELISA method and an RIA method.

The Ouchterlony method is simple, but when the concentration of the monoclonal antibody is low, a condensation operation is required.

On the other hand, when an ELISA method or an RIA method is used, by directly reacting the culture supernatant with an antigen-adsorbed solid phase and using antibodies corresponding to various types of immunoglobulin isotypes and subclasses as secondary antibodies, the isotype and subclass of the monoclonal antibody can be identified.

In addition, as a simpler method, a commercially available identification kit (for example, Mouse Typer kit manufactured by Bio-Rad Laboratories, Inc.) or the like can also be used.

Further, quantitative determination of a protein can be performed by the Folin Lowry method and a method of calculation based on the absorbance at 280 nm [1.4 (OD 280)=Immunoglobulin 1 mg/ml].

(3) Other Antibodies

The antibody of the invention includes not only the above-mentioned monoclonal antibody against Siglec-15 but also a recombinant antibody obtained by artificial modification for the purpose of decreasing heterologous antigenicity to humans such as a chimeric antibody, a humanized antibody and a human antibody. These antibodies can be produced using a known method.

As the chimeric antibody, an antibody in which antibody variable and constant regions are derived from different species, for example, a chimeric antibody in which a mouse-derived antibody variable region is connected to a human-derived constant region can be exemplified (see Proc. Natl. Acad. Sci. USA, 81, 6851-6855, (1984)).

As the humanized antibody, an antibody obtained by integrating only a complementarity determining region (CDR) into a human-derived antibody (see Nature (1986) 321, pp. 522-525), and an antibody obtained by grafting a part of the amino acid residues of the framework as well as the CDR sequence into a human antibody by a CDR-grafting method (WO 90/07861) can be exemplified.

Further, the antibody of the invention includes a human antibody. An anti-Siglec-15 human antibody refers to a human antibody having only a gene sequence of an antibody derived from a human chromosome. The anti-Siglec-15 human antibody can be obtained by a method using a human antibody-producing mouse having a human chromosome fragment containing H-chain and L-chain genes of a human antibody (see Tomizuka, K. et al., Nature Genetics (1997) 16, pp. 133-143; Kuroiwa, Y. et al., Nuc. Acids Res. (1998) 26, pp. 3447-3448; Yoshida, H. et al., Animal Cell Technology: Basic and Applied Aspects vol. 10, pp. 69-73 (Kitagawa, Y., Matuda, T. and Iijima, S. eds.), Kluwer Academic Publishers, 1999; Tomizuka, K. et al., Proc. Natl. Acad. Sci. USA (2000) 97, pp. 722-727, etc.).

Such a transgenic animal can be created specifically as follows. A genetically modified animal in which non-human mammalian endogenous immunoglobulin heavy and light chain gene loci have been disrupted, and instead, human immunoglobulin heavy and light chain gene loci have been introduced via a yeast artificial chromosome (YAC) vector or the like is created by producing a knockout animal and a transgenic animal and mating these animals.

Further, according to a genetic engineering technique, by using cDNAs encoding such a heavy chain and a light chain of a human antibody, respectively, preferably a vector containing the cDNAs, eukaryotic cells are transformed, and a transformant which produces a recombinant human monoclonal antibody is cultured, whereby the antibody can also be obtained from the culture supernatant.

Here, as the host, for example, eukaryotic cells, preferably mammalian cells such as CHO cells, lymphocytes or myeloma cells can be used.

Further, a method of obtaining a phage display-derived human antibody screened from a human antibody library (see Wormstone, I. M. et al., Investigative Ophthalmology & Visual Science. (2002) 43 (7), pp. 2301-2308; Carmen, S. et al., Briefings in Functional Genomics and Proteomics (2002), 1 (2), pp. 189-203; Siriwardena, D. et al., Opthalmology (2002) 109 (3), pp. 427-431, etc.) is also known.

For example, a phage display method in which a variable region of a human antibody is expressed on the surface of a phage as a single-chain antibody (scFv), and a phage which binds to an antigen is selected (Nature Biotechnology (2005), 23, (9), pp. 1105-1116) can be used.

By analyzing the gene of the phage selected based on the binding to an antigen, the DNA sequence encoding the variable region of a human antibody which binds to an antigen can be determined.

If the DNA sequence of scFv which binds to an antigen is determined, a human antibody can be obtained by preparing an expression vector having the sequence and introducing the vector into an appropriate host to express it (WO 92/01047, WO 92/20791, WO 93/06213, WO 93/11236, WO 93/19172, WO 95/01438, WO 95/15388, Annu. Rev. Immunol (1994) 12, pp. 433-455, Nature Biotechnology (2005) 23 (9), pp. 1105-1116).

In the case where an antibody is produced by once isolating an antibody gene and then introducing the gene into an appropriate host, a combination of appropriate host and expression vector can be used.

In the case where eukaryotic cells are used as the host, animal cells, plant cells and eukaryotic microorganisms can be used.

As the animal cells, mammalian cells, for example, dihydrofolate reductase-deficient strains (Urlaub, G. and Chasin, L. A., Proc. Natl. Acad. Sci. USA (1980) 77, pp. 4126-4220) of simian COS cells (Gluzman, Y., Cell, (1981) 23, pp. 175-182, ATCC CRL-1650), murine fibroblasts NIH3T3 (ATCC No. CRL-1658), and Chinese hamster ovarian cells (CHO cells; ATCC: CCL-61); can be exemplified.

In cases where prokaryotic cells are used, for example, *Escherichia coli* and *Bacillus subtilis* can be exemplified.

By introducing a gene of a target antibody into these cells through transformation, and culturing the thus transformed cells in vitro, the antibody can be obtained.

There is no limitation on isotype of the antibody of the invention, and examples thereof include IgG (IgG1, IgG2, IgG3, IgG4), IgM, IgA (IgA1, IgA2), IgD and IgE, and preferred examples thereof include IgG and IgM.

Further, the antibody of the invention may be a functional fragment of the antibody having an antigen-binding site of the antibody or a modified fragment thereof. The fragment of the antibody can be obtained by treating the antibody with a protease such as papain or pepsin, or modifying the antibody gene according to a genetic engineering technique and expressing the modified gene in suitable cultured cells. Among these antibody fragments, a fragment having all or part of the functions of the full-length molecule of the antibody can be called a functional fragment of the antibody. As the functions of the antibody, generally an antigen-binding activity, an activity of neutralizing the activity of an antigen, an activity of increasing the activity of an antigen, an antibody-dependent cytotoxic activity, a complement-dependent cytotoxic activity, and a complement-dependent cellular cytotoxic activity can be exemplified. The function of the functional fragment of the antibody according to the invention is preferably an activity of inhibiting the formation of osteoclasts, more preferably an activity of inhibiting the process of cell fusion of osteoclasts.

Examples of the fragment of the antibody include Fab, F(ab')2, Fv, single-chain Fv (scFv) in which Fv molecules of the heavy chain and the light chain are ligated via an appropriate linker, a diabody (diabodies), a linear antibody, and a polyspecific antibody composed of the antibody fragment. Further, Fab' which is a monovalent fragment in a variable region of an antibody obtained by treating F(ab')2 under reducing conditions is also included in the fragment of the antibody.

Further, the antibody of the invention may be a polyspecific antibody with specificity for at least two different antigens.

In general, such a molecule binds to two antigens (that is, bispecific antibody), however, the "polyspecific antibody" as used herein includes an antibody having specificity for two or more (for example, three) antigens.

The antibody of the invention may be a polyspecific antibody composed of a full-length antibody or a fragment of such an antibody (for example, F(ab')2 bispecific antibody).

The bispecific antibody can be produced by ligating the heavy and light chains (HL pairs) of two types of antibodies, or can also be produced by fusing hybridomas which produce different monoclonal antibodies to prepare fused cells which produce the bispecific antibody (Millstein et al., Nature (1983) 305, pp. 537-539).

The antibody of the invention may be a single-chain antibody (also referred to as scFv). The single-chain antibody can be obtained by ligating the V regions of the heavy chain and the light chain of the antibody via a polypeptide linker (Pluckthun, The Pharmacology of Monoclonal Antibodies, 113 (edited by Rosenburg and Moore, Springer Verlag, New York, pp. 269-315 (1994), Nature Biotechnology (2005), 23, pp. 1126-1136). Further, a BiscFv fragment produced by ligating two scFv molecules via a polypeptide linker can also be used as the bispecific antibody.

A method of producing a single-chain antibody is known in this technical field (see, for example, U.S. Pat. Nos. 4,946,778, 5,260,203, 5,091,513, 5,455,030, etc.). In this scFv, the V regions of the heavy chain and the light chain are ligated via a linker which does not form a conjugate, preferably via a polypeptide linker (Huston, J. S. et al., Proc. Natl. Acad. Sci. USA (1988), 85, pp. 5879-5883). In the scFv, the V regions of the heavy chain and the light chain may be derived from the same antibody or different antibodies. As the polypeptide linker to be used for ligating the V regions, for example, a given single-chain peptide composed of 12 to 19 residues is used.

DNA encoding scFv can be obtained by performing amplification using a partial DNA encoding the entire or a desired amino acid sequence of a DNA selected from a DNA encoding the heavy chain or the V region of the heavy chain of the above-mentioned antibody and a DNA encoding the light chain or the V region of the light chain thereof as a template by a PCR method using a primer pair that defines both ends thereof, and further performing amplification combining a DNA encoding a polypeptide linker portion and a primer pair that defines both ends thereof so as to ligate both the ends to the heavy chain and the light chain, respectively.

Further, once DNA encoding scFv is produced, an expression vector containing the same and a host transformed by the expression vector can be obtained according to a common procedure. Further, by using the resulting host, scFv can be obtained according to a common procedure.

An antibody fragment thereof can be produced in a host by obtaining a gene and expressing the gene in the same manner as described above.

The antibody of the invention may be multimerized to increase the affinity for an antigen. The antibody to be multimerized may be one type of antibody or a plurality of antibodies which recognize a plurality of epitopes of the same antigen. As a method of multimerization of the antibody, binding of the IgG CH3 domain to two scFv molecules, binding to streptavidin, introduction of a helix-turn-helix motif and the like can be exemplified.

The antibody of the invention may be a polyclonal antibody which is a mixture of plural types of anti-Siglec-15 antibodies having different amino acid sequences. As one example of the polyclonal antibody, a mixture of plural types of antibodies having different CDR can be exemplified. As such a polyclonal antibody, a mixture of cells which produce different antibodies is cultured, and an antibody purified from the resulting culture can be used (see WO 2004/061104).

As a modified antibody, an antibody bound to any of various types of molecules such as polyethylene glycol (PEG) can also be used.

Further, the antibody of the invention may be in the form of a conjugate formed between any of these antibodies and another medicinal agent (immunoconjugate). Examples of such an antibody include one in which the antibody is conjugated to a radioactive material or a compound having a pharmacological action (Nature Biotechnology (2005) 23, pp. 1137-1146).

The obtained antibody can be purified to homogeneity. The separation and purification of the antibody can be performed employing a conventional protein separation and purification method.

For example, the antibody can be separated and purified by appropriately selecting and combining use of a chromatography column, filter, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of chromatography include affinity chromatography, ion exchange chromatography, hydrophobic chromatography, gel filtration chromatography, reverse phase chromatography, and adsorption chromatography.

Such chromatography can be performed employing liquid chromatography such as HPLC or FPLC.

As a column to be used in affinity chromatography, a Protein A column and a Protein G column can be exemplified.

For example, as a column using a Protein A column, Hyper D, POROS, Sepharose F. F. (Pharmacia) and the like can be exemplified.

Further, by using a carrier having an antigen immobilized thereon, the antibody can also be purified utilizing the binding property of the antibody to the antigen.

5. Medicine Containing Anti-Siglec-15 Antibody

From the anti-Siglec-15 antibodies obtained by the method described in the above item "4. Production of anti-Siglec-15 antibody", an antibody which neutralizes the biological activity of Siglec-15 can be obtained. Such an antibody which neutralizes the biological activity of Siglec-15 inhibits the biological activity of Siglec-15 in vivo, i.e., the differentiation and/or maturation of osteoclasts, and therefore can be used as a therapeutic and/or preventive agent for abnormal bone metabolism caused by abnormal differentiation and/or maturation of osteoclasts as a medicine. The abnormal bone metabolism may be any disorder characterized by net bone loss (osteopenia or osteolysis). In general, the treatment and/or prevention by the anti-Siglec-15 antibody are/is applied to a case where inhibition of bone resorption is required. Examples of the abnormal bone metabolism which can be treated and/or prevented by the anti-Siglec-15 antibody include osteoporosis (postmenopausal osteoporosis, senile osteoporosis, secondary osteoporosis due to the use of a therapeutic agent such as a steroid or an immunosuppressant, or osteoporosis accompanying rheumatoid arthritis), bone destruction accompanying rheumatoid arthritis, cancerous hypercalcemia, bone destruction accompanying multiple myeloma or cancer metastasis to bone, giant cell tumor, tooth loss due to periodontitis, osteolysis around a prosthetic joint, bone destruction in chronic osteomyelitis, Paget's disease of bone, renal osteodystrophy and osteogenesis imperfecta, however, the abnormal bone metabolism is not limited thereto as long as it is a disease accompanied by net bone loss caused by osteoclasts. Examples of the anti-Siglec-15 antibody to be used as the above-mentioned medicine include a chimeric antibody and a humanized antibody produced from the #32A1 antibody or #41B1 antibody by the method described in 4. (3) "Other antibodies". Further, a chimeric antibody, a humanized antibody and a human antibody sharing the same epitope as the #32A1 antibody or #41B1 antibody can also be used as a medicine. Whether a certain anti-Siglec-15 antibody shares the same epitope as the #32A1 antibody or #41B1 antibody can be confirmed by observing whether or not these antibodies bind to the same specific partial peptide of Siglec-15. Further, it can also be determined that if the certain anti-Siglec-15 antibody competes with the #32A1 antibody or #41B1 antibody for binding to Siglec-15, these antibodies share the same epitope.

The in vitro activity of the anti-Siglec-15 antibody of neutralizing the biological activity of Siglec-15 can be determined by, for example, the activity of inhibiting the differentiation of the cells which overexpress Siglec-15 into osteoclasts. For example, the anti-Siglec-15 antibody is added to RAW 264.7 cells or Raw 264 cells which are a mouse monocyte-derived cell line at various concentrations, and the activity of inhibiting the differentiation into osteoclasts by stimulation with RANKL or TNF-α can be determined. Further, the anti-Siglec-15 antibody is added to bone marrow-derived primary cultured cells at various concentrations, and the activity of inhibiting the differentiation into osteoclasts by stimulation with RANKL, TNF-α or active vitamin $D_3$ can be determined. Further, the anti-Siglec-15 antibody is added to normal human osteoclast precursor cells (Normal Human Natural Osteoclast Precursor Cells, available from Sanko Junyaku Co., Ltd., Cat. No. 2T-110) at various concentrations, and the activity of inhibiting the differentiation into osteoclasts by stimulation with RANKL or M-CSF can be determined. Such an inhibitory effect on osteoclast differentiation can be determined by using the inhibition of tartrate-resistant acid phosphatase (TRAP) activity of osteoclasts as an index as shown in Examples 17, 19, 20 and 26. Further, the inhibitory effect on osteoclast differentiation can also be determined by using the inhibition of formation of TRAP-positive multinucleated osteoclasts, i.e., the inhibition of cell fusion of osteoclasts as an index as shown in Examples 19, 21, 22 and 35. The antibodies of the invention exhibited an inhibitory effect on cell fusion at a concentration of 30 μg/ml or less in the above-mentioned test system for osteoclast differentiation, and some antibodies exhibited the inhibitory effect even at a concentration of 3 μg/ml or less or 1 μg/ml or less. Further, in the case where the effect at a further lower concentration was tested, it was found that a plurality of antibodies exhibited an inhibitory effect on osteoclast differentiation even at a concentration range of from 63 ng/ml to 1 μg/ml. Further, in an experiment of a pit assay (Takada et al., Bone and Mineral, (1992) 17, 347-359) using femur- and/or tibia-derived cells, the in vitro activity of inhibiting the bone resorption by osteoclasts can be determined by adding the anti-Siglec-15 antibody to femur- and/or tibia-derived cells at various concentrations, and observing pit formation on a dentine slice. As a system for determining the in vitro activity of inhibiting the bone resorption by osteoclasts, as shown in Example 37, it is also possible to use a plate coated with human collagen conjugated to europium. In the above-mentioned test system for bone resorption by osteoclasts, the antibody of the invention inhibited bone resorption at a concentration of 3 μg/ml or less, that is, at a concentration range of from 0.3 μg/ml to 3 μg/ml. The in vivo therapeutic or preventive effect of the anti-Siglec-15 antibody on abnormal bone metabolism using an experimental animal can be confirmed by administering the anti-Siglec-15 antibody to a model animal of osteoporosis or a transgenic animal which overexpresses siglec-15 and measuring a change in osteoclasts.

The thus obtained antibody which neutralizes the biological activity of Siglec-15 is useful as a medicine, particularly as a pharmaceutical composition for treating or preventing abnormal bone metabolism such as osteoporosis, bone destruction accompanying rheumatoid arthritis or bone destruction accompanying cancer metastasis to bone, or as an antibody for immunological diagnosis of such a disease.

In the treatment of rheumatoid arthritis (RA), a major problem is bone loss accompanying the occurrence of the disease. It has been reported that in this bone loss accompanying RA, osteoclasts play a primary role. The cytokines considered to be most important for osteoclast induction (differentiation and maturation) and activation and the cause of bone destruction in RA are RANKL and TNF-α (Romas E. et al., Bone 30, pp. 340-346, 2002). As shown in Example 19 of this description, OCIF/OPG which is a decoy receptor for RANKL can inhibit osteoclast formation induced by RANKL but does not inhibit osteoclast formation induced by TNF-α. On the other hand, the anti-Siglec-15 antibody according to the invention effectively inhibited osteoclast formation induced by both RANKL and TNF-α. Therefore, it is expected that the anti-Siglec-15 antibody of the invention can inhibit bone loss and bone destruction induced by TNF-α in RA or the like more strongly than an RANKL blocker (OCIF/OPG, an anti-RANKL antibody or the like).

As one example, for the treatment or prevention of abnormal bone metabolism, the anti-Siglec-15 antibody can be administered alone or along with at least one therapeutic agent for a bone-related disease. As another example, the anti-Siglec-15 antibody can be administered along with a therapeutically effective amount of a therapeutic agent for abnormal bone metabolism. Examples of the therapeutic agent which can be administered along with the anti-Siglec-15 antibody include, but are not limited to, bisphosphonates, active vitamin $D_3$, calcitonin and derivatives thereof, hormone preparations such as estradiol, SERMs (selective estrogen receptor modulators), ipriflavone, vitamin $K_2$ (menatetrenone), calcium preparations, PTH (parathyroid hormone) preparations, nonsteroidal anti-inflammatory agents, soluble TNF receptor preparations, anti-TNF-α antibodies or functional fragments of the antibodies, anti-PTHrP (parathyroid hormone-related protein) antibodies or functional fragments of the antibodies, IL-1 receptor antagonists, anti-IL-6 receptor antibodies or functional fragments of the antibodies, anti-RANKL antibodies or functional fragments of the antibodies and OCIF (osteoclastogenesis inhibitory factor). Depending on the state of abnormal bone metabolism or the intended degree of the treatment and/or prevention, two or three, or more types of medicinal agents can be administered, and these medicinal agents can be supplied all together by encapsulating them in the same preparation. These medicinal agents and the anti-Siglec-15 antibody can be supplied all together by encapsulating them in the same preparation. Further, these medicinal agents can be supplied all together by encapsulating them as a kit to be used for treatment and/or prevention. Further, these medicinal agents and the anti-Siglec-15 antibody can be supplied separately. In the case of administration in gene therapy, a gene of a proteinous therapeutic agent for a bone disease and a gene of the anti-Siglec-15 antibody can be inserted downstream of the same promoter region or different promoter regions, and can be introduced into the same vector or different vectors.

By conjugating a therapeutic agent for a bone disease to the anti-Siglec-15 antibody or a fragment thereof, a targeted drug conjugate as described in M. C. Garnet "Targeted drug conjugates: principles and progress", Advanced Drug Delivery Reviews, (2001) 53, 171-216 can be produced. For achieving this purpose, other than the antibody molecule, any antibody fragment can be applied as long as it does not completely lose the ability to recognize osteoclasts, and examples thereof include fragments such as Fab, F(ab')2, and Fv. In the invention, the antibody and the fragment can be used in the same manner. The conjugate formed by the anti-Siglec-15 antibody or a fragment thereof and a therapeutic agent for a bone disease can be any of various forms described in M. C. Garnet "Targeted drug conjugates: principles, and progress", Advanced Drug Delivery Reviews, (2001) 53, 171-216, G. T. Hermanson "Bioconjugate Techniques" Academic Press, California (1996), Putnam and J. Kopecek "Polymer Conjugates with Anticancer Activity" Advances in Polymer Science (1995) 122, 55-123 and the like. That is, a conjugate form in which the anti-Siglec-15 antibody and a therapeutic agent for a bone disease are conjugated to each other chemically and directly or via a spacer such as an oligopeptide and a conjugate form via an appropriate drug carrier can be exemplified. Examples of the drug carrier include a liposome and a water-soluble polymer. More specific examples of the conjugate form via such a drug carrier include a conjugate form in which the antibody and a therapeutic agent for a bone disease are incorporated in a liposome and the liposome and the antibody are conjugated to each other, and a conjugate form in which a therapeutic agent for a bone disease is conjugated to a water-soluble polymer (a compound having a molecular weight of from about 1000 to 100000) chemically and directly or via a spacer such as an oligopeptide and the antibody is conjugated to the water-soluble polymer. The conjugation of the antibody (or a fragment thereof) to a therapeutic agent for a bone disease or a drug carrier such as a liposome or a water-soluble polymer can be effected by a method known to those skilled in the art such as the method described in G. T. Hermanson "Bioconjugate Techniques" Academic Press, California (1996), Putnam and J. Kopecek "Polymer Conjugates with Anticancer Activity" Advances in Polymer Science (1995) 122, 55-123. The incorporation of a therapeutic agent for a bone disease in a liposome can be effected by a method known to those skilled in the art such as the method described in D. D. Lasic "Liposomes: From Physics to Applications" Elsevier Science Publishers B. V., Amsterdam (1993) or the like. The conjugation of a therapeutic agent for a bone disease to a water-soluble polymer can be effected by a method known to those skilled in the art such as the method described in D. Putnam and J. Kopecek "Polymer Conjugates with Anticancer Activity" Advances in Polymer Science (1995) 122, 55-123. A conjugate between the antibody (or a fragment thereof) and a proteinous therapeutic agent for a bone disease (or a fragment thereof) can be produced by a method known to those skilled in the art through genetic engineering other than the above-mentioned method.

The invention also provides a pharmaceutical composition containing a therapeutically and/or preventively effective amount of the anti-Siglec-15 antibody and a pharmaceutically acceptable diluent, carrier, solubilizing agent, emulsifying agent, preservative and/or adjuvant.

The invention also provides a pharmaceutical composition containing a therapeutically and/or preventively effective amount of the anti-Siglec-15 antibody, a therapeutically and/or preventively effective amount of at least one therapeutic agent for a bone disease, and a pharmaceutically acceptable diluent, carrier, solubilizing agent, emulsifying agent, preservative and/or adjuvant. Examples of the therapeutic agent for a bone disease include, but are not limited to, bisphosphonates, active vitamin $D_3$, calcitonin and derivatives thereof, hormone preparations such as estradiol, SERMs (selective estrogen receptor modulators), ipriflavone, vitamin $K_2$ (menatetrenone), calcium preparations, PTH (parathyroid hormone) preparations, nonsteroidal anti-inflammatory agents, soluble TNF receptor preparations, anti-TNF-α antibodies or functional fragments of the antibodies, anti-PTHrP (parathyroid hormone-related protein) antibodies or functional fragments of the antibodies, IL-1 receptor antagonists, anti-IL-6 receptor antibodies or functional fragments of the antibodies, anti-RANKL antibodies or functional fragments of the antibodies and OCIF (osteoclastogenesis inhibitory factor).

A substance to be used in a preparation acceptable in a pharmaceutical composition according to the present invention is preferably non-toxic to a person to which the pharmaceutical composition is to be administered, in terms of the dose and concentration.

The pharmaceutical composition of the invention can contain a substance for pharmaceutical use which is capable of changing or maintaining the pH, osmotic pressure, viscosity, transparency, color, isotonicity, color, aseptic condition, stability, solubility, release rate, absorption rate, and permeability. Examples of the substance for pharmaceutical use include, but are not limited to, amino acids such as glycine, alanine, glutamine, asparagine, arginine and lysine; antimicrobial agents; antioxidants such as ascorbic acid, sodium sulfate and sodium hydrogen sulfite; buffers such as phosphate, citrate, borate buffers, bicarbonate and Tris-HCl solutions; fillers such as mannitol and glycine; chelating agents such as ethylenediamine tetraacetate (EDTA); complexing agents such as caffeine, polyvinylpyrrolidine, β-cyclodextrin and hydroxypropyl-β-cyclodextrin; expanders such as glucose, mannose and dextrin; other carbohydrates such as monosaccharides and disaccharides; coloring agents; flavors; diluents; emulsifying agents; hydrophilic polymers such as polyvinylpyrrolidine; preservatives such as low molecular weight polypeptides, base forming counter ions, benzalkonium chloride, benzoate, salicylic acid, thimerosal, phenethyl alcohol, methylparaben, propylparaben, chlorhexidine, sorbic acid, and hydrogen peroxide; solvents such as glycerin, propylene glycol and polyethylene glycol; sugar alcohols such as mannitol and sorbitol; suspending agents; surfactants such as sorbitan ester, polysorbates including polysorbate 20 and polysorbate 80, Triton, tromethamine, lecithin and cholesterol; stability enhancing agents such as sucrose and sorbitol; elasticity enhancing agents such as sodium chloride, potassium chloride and mannitol and sorbitol; transport agents; diluents; excipients; and/or pharmaceutical adjuvants. The addition amount of these substances for pharmaceutical use is preferably from 0.01 to 100 times, particularly preferably from 0.1 to 10 times the weight of the anti-Siglec-15 antibody. Those skilled in the art can appropriately determine a preferred formulation of the pharmaceutical composition in a preparation depending on the disease to be applied, the route of administration to be applied or the like.

The excipient or carrier in the pharmaceutical composition may be in the form of a liquid or a solid. An appropriate excipient or carrier may be injectable water, physiological saline, an artificial cerebral spinal fluid or other substance commonly used for parenteral administration. Further, neutral physiological saline or physiological saline containing serum albumin can also be used as a carrier. The pharmaceutical composition may contain a Tris buffer of pH 7.0 to 8.5 or an acetate buffer of pH 4.0 to 5.5 which may be supplemented with sorbitol or another compound. Examples of the pharmaceutical composition of the invention include a pharmaceutical composition containing the anti-Siglec-15 antibody and a pharmaceutical composition containing the anti-Siglec-15 antibody and at least one therapeutic agent for a bone disease.

The pharmaceutical composition of the invention is prepared in the form of a lyophilized product or a liquid as a medicinal agent having a selected composition and a required purity. The pharmaceutical composition containing the anti-Siglec-15 antibody and the pharmaceutical composition containing the anti-Siglec-15 antibody and at least one therapeutic agent for abnormal bone metabolism can also be formed into a lyophilized product using an appropriate excipient such as sucrose.

The pharmaceutical composition of the invention can be prepared for parenteral administration or for gastrointestinal absorption through oral administration. The composition and concentration of a preparation can be determined depending on the administration method. As the affinity of the anti-Siglec-15 antibody contained in the pharmaceutical composition of the invention for Siglec-15 is higher, that is, as the dissociation constant (Kd value) for Siglec-15 is lower, the anti-Siglec-15 antibody can exhibit its drug efficacy at a lower dose for humans, and therefore, the dose of the pharmaceutical composition of the invention for humans can also be determined based on this result. As for the dose, in the case where a human anti-Siglec-15 antibody is administered to humans, the antibody may be administered at a dose of from about 0.1 to 100 mg/kg once per one to 180 days.

Examples of the dosage form of the pharmaceutical composition of the invention include injections including infusions, suppositories, transnasal agents, sublingual agents and percutaneous absorbents.

6. Search for Directly Interacting Substance

Another embodiment of the invention includes a drug design method based on the conformation of Siglec-15 for obtaining a substance which inhibits the activity of Siglec-15. Such a method is known as a rational drug design method and is used for searching for a compound which efficiently inhibits or activates the enzymatic activity or binding to a ligand, a cofactor or a DNA. As an example of such a compound, a protease inhibitor serving as an anti-HIV agent which has already been placed on the market is well known. Also in a three-dimensional structural analysis of Siglec-15 of the invention, a generally well known method such as an X-ray crystallographic analysis or a nuclear magnetic resonance method can be used. Further, in searching for a substance which inhibits the function of Siglec-15, drug design utilizing computer-aided drug design (CADD) can also be effected. As an example of this case, a low molecular weight compound (WO 99/58515) which inhibits the action of AP-1 and is expected to be a novel genomic drug for treating rheumatoid arthritis and the like are known. By virtue of such a method, it is possible to obtain a substance which inhibits the function of Siglec-15 by directly binding to Siglec-15 or by inhibiting the interaction between Siglec-15 and other factors.

Further, another embodiment relates to a polypeptide with which the Siglec-15 of the invention associates, in other words, a partner protein of the Siglec-15. That is, the invention relates to a method of screening a partner protein which regulates the activity of Siglec-15.

One embodiment of this screening method includes a step of bringing a test protein sample into contact with Siglec-15 and selecting a protein which binds to Siglec-15. As such a method, for example, a method in which purified Siglec-15 is used and affinity purification of a protein binding thereto is performed can be exemplified. One specific example of the method will be described below. A sequence composed of six histidines as an affinity tag is fused with Siglec-15 to prepare a fusion protein, and the resulting protein is incubated at 4° C. for 12 hours along with a cell extract solution (a fraction passed through a nickel-agarose column after charging the column with a cell solution). Then, another nickel-agarose carrier is added to the mixture and the mixture is incubated at 4° C. for 1 hour. After the nickel-agarose carrier is sufficiently washed with a washing buffer, 100 mM imidazole is added to the mixture to elute and purify a protein which specifically binds to Siglec-15 in the cell extract solution. Then, the purified protein is analyzed to determine its structure. In this manner, a protein which directly binds to Siglec-15 and a protein which does not have an activity of binding to Siglec-15 but indirectly binds to Siglec-15 by forming a complex with a protein as a subunit which directly binds to Siglec-15 can be purified. As an alternative method, it is also possible to perform cloning by a far-Western blotting assay or a two-hybrid system assay using yeast or mammalian cells, however, it is not limited to these methods.

If a cDNA of a partner protein which directly or indirectly interacts with Siglec-15 is obtained in this manner, the cDNA can be used in functional screening of a substance which inhibits the interaction between Siglec-15 and the partner protein. Specifically, a fusion protein between Siglec-15 and glutathione-S-transferase is prepared and bound to a microplate covered with an anti-glutathione-S-transferase antibody. Then, a biotinylated partner protein is brought into contact with the fusion protein, and the binding of the partner protein with the fusion protein is detected using streptavidin-conjugated alkaline phosphatase. When the biotinylated partner protein is added, a test substance is also added to select a substance which promotes or inhibits the binding of the fusion protein to the partner protein. By this method, a substance which directly acts on the fusion protein or a substance which directly acts on the partner protein can be obtained.

In the case where the fusion protein binds indirectly to the partner protein via another factor, the assay is performed in the presence of for example, a cell extract solution containing this factor. In this case, there is a possibility that a substance which may act on the factor may also be selected.

Further, in the case where the obtained partner protein has the activity of promoting the function of Siglec-15, it is possible to screen a candidate substance useful as a therapeutic and/or preventive agent for abnolinal bone metabolism, for example, a therapeutic and/or preventive agent for osteoporosis according to a test method employing an expression vector of the Siglec-15 gene as described above. Further, in the case where the obtained partner protein has an activity of inhibiting the function of Siglec-15, it is possible to use a polynucleotide encoding such an inhibitor in gene therapy for abnormal bone metabolism.

Such a polynucleotide can be obtained by, for example, analyzing the amino acid sequence of the identified inhibitor, synthesizing an oligonucleotide probe encoding the amino acid sequence, and performing screening of a cDNA library or a genome library. Further, in the case where a polypeptide having the activity of inhibiting the function of Siglec-15 is derived from a randomly synthesized artificial peptide library, a DNA composed of a nucleotide sequence encoding the amino acid sequence of the peptide is chemically synthesized.

In the gene therapy, the thus obtained gene encoding the inhibitor is integrated into, for example, a viral vector and a patient is infected with a virus (attenuated) having the resultant recombinant viral vector. In the body of the patient, an anti-bone destruction factor is produced and functions to inhibit osteoclast differentiation, and therefore, treatment and/or prevention of abnormal bone metabolism can be realized.

As a method of introducing a gene therapeutic agent into a cell, either a gene transfer method using a viral vector or a non-viral gene transfer method can be used. Examples of the gene transfer method using a viral vector include a method of integrating a DNA encoding a Siglec-15 inhibitor or a mutant thereof into a DNA virus or an RNA virus such as a retrovirus, an adenovirus, an adeno-associated virus, a herpes virus, a vaccinia virus, a pox virus, a polio virus, or a sindbis virus to effect gene transfer. Among them, a method using a retrovirus, an adenovirus, an adeno-associated virus, or a vaccinia virus is particularly preferred. Examples of the non-viral gene transfer method include a method of administering an expression plasmid directly into the muscle (a DNA vaccination method), a liposome method, a lipofection method, a microinjection method, a calcium phosphate method, and an electroporation method. In particular, a DNA vaccination method and a liposome method are preferred.

Further, in order to actually use the gene therapeutic agent as a medicinal agent, there are an in vivo method in which a DNA is directly introduced in the body and an ex vivo method in which a certain type of cell is taken from a human and a DNA is introduced into the cell ex vivo, and the cell is returned in the body.

For example, in the case where the gene therapeutic agent is administered by the in vivo method, it is administered through an appropriate administration route such as through a vein or artery, under the skin, into the skin, or into the muscle according to the disease, symptoms or the like. Further, in the case where it is administered by the in vivo method, the gene therapeutic agent is generally formulated as an injection, however, a commonly used carrier may be added as needed. Further, in the case where it is formed into a liposome or a membrane fusion liposome (such as Sendai virus liposome), it can be formulated into a liposome preparation such as a suspension, a lyophilized agent, or a centrifugally concentrated and lyophilized agent.

A nucleotide sequence complementary to a full-length or partial sequence of the nucleotide sequence represented by SEQ ID NO: 1 or 3 in the Sequence Listing can be used for so-called antisense therapy. An antisense molecule can be used as a DNA which is composed generally of from 15 to 30 nucloetides and is complementary to a part of a nucleotide sequence selected from the nucleotide sequences represented by SEQ ID NOS: 1 and 3 in the Sequence Listing or a stable DNA derivative thereof such as a phosphorothioate, methylphosphonate, or morpholino derivative thereof, or a stable RNA derivative such as 2'-O-alkyl RNA. Such an antisense molecule can be introduced into a cell by a method known in the technical field of the invention, for example, by injecting an extremely small amount of the antisense molecule, by forming the molecule into a liposome capsule, or by expressing the molecule with the use of a vector having an antisense sequence. Such antisense therapy is useful for treating a disease caused by excessively increasing the activity of a protein encoded by the nucleotide sequence represented by Sequence ID NO: 1 or 3 in the Sequence Listing.

Further, a method using a double-stranded short RNA (siRNA) can also be exemplified (Genes and Developments, January 15, 2001, vol. 15, No. 2, pp. 188-200). For example, siRNA against Siglec-15 gene is prepared and introduced into a cell according to the method described in the document, whereby a therapeutic agent for a bone metabolic disease accompanied by overexpression of Siglec-15 can be prepared.

EXAMPLES

Hereinafter, the invention will be more specifically described with reference to Examples, however, the invention is not limited thereto. Note that the respective operations regarding gene manipulation in the following Examples were performed according to the methods described in "Molecular Cloning" (written by Sambrook, J., Fritsch, E. F. and Maniatis, T., published by Cold Spring Harbor Laboratory Press in 1989), or in the case of using commercially available reagents or kits, performed according to the protocols attached thereto.

Example 1

Expression of Human Siglec-15 Gene in Giant Cell Tumor Tissue

A giant cell tumor (GCT) is histologically a bone tumor with a large number of osteoclast-like multinucleated giant cells arising and is characterized by clinical findings of osteolytic bone destruction (Bullough et al., Atlas of Orthopedic Pathology 2nd edition, 17.6-17.8, Lippincott Williams & Wilkins Publishers (1992)). An expression profile analysis was performed for an EST probe (Affymetrix GeneChip HG-U133 probe 215856_at: manufactured by Affymetrix, Inc.) having a nucleotide sequence partially overlapping with that of human Siglec-15 gene in GCT tissues using the database (Genesis 2006 Release 3.0) made by Gene Logic, Inc. Further, an expression profile analysis was also performed for the EST probes for RANK (Affymetrix GeneChip HG-U133 probe 207037_at, manufactured by Affymetrix, Inc.) and RANKL (Affymetrix GeneChip HG-U133 probe 210643_at, manufactured by Affymetrix, Inc.) which play a key role in differentiation into osteoclasts, and for cathepsin K (Affymetrix GeneChip HG-U133 probe 202450_s_at, manufactured by Affymetrix, Inc.) and TRAP (Affymetrix GeneChip HG-U133 probe 204638_at, manufactured by Affymetrix, Inc.) which are markers for differentiation into osteoclasts in GCT tissues in the same manner.

Figure 2:
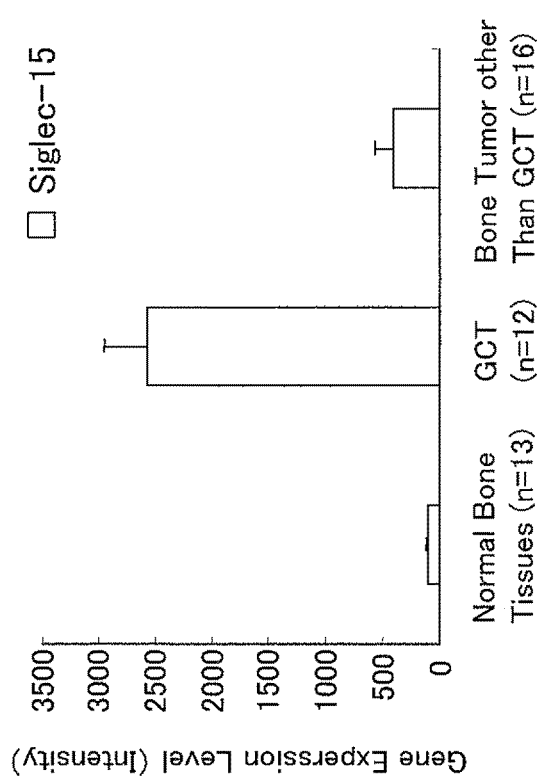
FIG. 2 shows a graph depicting an expression profile analysis for the Siglec-15 gene in human giant cell tumor tissues.

When the expression levels were compared among 13 cases of normal bone tissues, 12 cases of GCT tissues and 16 cases of bone tumor tissues other than GCT, it was revealed that transcription of RANK and RANKL is specifically increased in the GCT tissues compared with in the normal tissues (FIG. 1-A). On the other hand, in the bone tumor tissues other than GCT in which an increase in bone resorption is believed not to be always caused, transcription of RANK and RANKL was lower than in GCT, and therefore, it was suggested that GCT provides an environment in which osteoclast formation and activation are promoted. Further, when the expression levels of genes of cathepsin K and TRAP were compared, the genes were transcribed at a high level in GCT (FIG. 1-B), and it was suggested that a large number of osteoclasts having a bone resorption activity arise. Similarly, when the transcription levels of Siglec-15 gene were compared, it was revealed that the gene was transcribed at a high level specifically in GCT in the same manner as the respective RANK, RANKL, cathepsin K and TRAP genes (FIG. 2). From these results, it was suggested that Siglec-15 is associated with human pathology in which bone resorption is increased as GCT.

Example 2

Extraction of Total RNA from Mouse-Derived Mature Osteoclasts a) Mouse monocyte-derived cells RAW 264.7 (ATCC Cat. No. TIB-71) were prepared at $4.5 \times 10^4$ cells/ml in α-MEM medium containing 10% fetal bovine serum. The resulting cell preparation was put in a 75 cm² flask at 10 ml/flask, and human RANKL (manufactured by PeproTech Inc.) was added thereto to give a final concentration of 40 ng/ml, and the cells were cultured for 3 days in a $CO_2$ incubator. Further, the culturing without the addition of human RANKL was performed in the same manner.

After completion of the culturing, the total RNA was extracted from RAW 264.7 cultured under the respective conditions using a total RNA extraction reagent (ISOGEN, manufactured by Nippon Gene Co., Ltd.) according to the protocol attached to the reagent. The collected total RNA was stored at −80° C.

b) When mouse bone marrow-derived primary cultured cells are cultured in the presence of active vitamin $D_3$, a large number of TRAP-positive multinucleated osteoclasts arise (Takahashi et al., Endocrinology, (1988) 122, 1373-1382).

A male ddY mouse at the age of 8 weeks was euthanized by cervical dislocation under ether anesthesia and the femur and tibia were resected. After soft tissues were removed, both ends of the femur or tibia were cut off. Then, α-MEM medium containing 10% fetal bovine serum was injected into the bone marrow using a syringe barrel with a 25-gauge injection needle, and bone marrow cells were collected. After the number of cells was counted, the cells were prepared at $5 \times 10^6$ cells/ml in α-MEM medium containing 10% fetal bovine serum. The resulting cell preparation was plated in 60 wells of a 96-well plate at 100 μl/well, and active vitamin $D_3$ (manufactured by Sigma Co., Ltd.) was added thereto to give a final concentration of $2 \times 10^{-8}$ M, and the cells were cultured for 8 days in a $CO_2$ incubator. Further, the culturing without the addition of active vitamin $D_3$ was performed in the same manner. Incidentally, the medium replacement and addition of active vitamin $D_3$ were performed on days 3 and 6.

Thereafter, the total RNA was extracted from the cells cultured under the respective conditions using a total RNA extraction reagent (ISOGEN, manufactured by Nippon Gene Co., Ltd.) according to the protocol attached to the reagent. The collected total RNA was stored at −80° C. until use.

Example 3

Acquisition of Sequence of Open Reading Frame (ORF) for Mouse Siglec-15 a) Synthesis of First Strand cDNA

To 1 μg of the total RNA produced in a) of Example 2, 1 μl of 1 U/μl DNase I and 1 μl of 10×DNase I buffer (manufactured by Invitrogen, Inc.) were added, and then, the final volume was brought to 10 μl with $H_2O$. After a reaction was allowed to proceed at room temperature for 15 minutes, 1 μl of 25 mM EDTA was added thereto and the resulting mixture was heated at 65° C. for 10 minutes. From this solution, an 8 μl aliquot was taken, and 1 μl of 50 μM oligo(dT)$_{20}$ primer and 1 μl of 10 mM dNTPs were added thereto, and resulting mixture was heated at 65° C. for 5 minutes and then incubated in ice. To this solution, 2 μl of 10×RT buffer (manufactured by Invitrogen, Inc.), 4 μl of 25 mM $MgCl_2$, 2 μl of 0.1 M dithiothreitol, 1 μl of RNase inhibitor (RNaseOUT, 40 U/μl, manufactured by Invitrogen, Inc.), and 1 μl of Superscript III reverse transcriptase (200 U/μl, manufactured by Invitrogen, Inc.) were added and the total volume was brought to 20 μl. After a reaction was allowed to proceed at 50° C. for 50 minutes, the mixture was heated at 85° C. for 5 minutes and then incubated in ice for 1 minute. Thereafter, the mixture was stored at −20° C.

b) PCR Reaction

Oligonucleotides having the sequences of: 5'-agaattccac cATGGAGGGG TCCCTCCAAC TC-3' (mSiglec-15-EcoRI kozak-F: SEQ ID NO: 5 in the Sequence Listing); and 5'-cgccgctcga gTTATTTCTCATGGTGAATGAC-3' (mSiglec-15-XhoI-R: SEQ ID NO: 6 in the Sequence Listing) as primers for amplifying the ORF cDNA for mouse Siglec-15 by PCR were synthesized according to a common procedure. The PCR was performed using this combination of primers and the cDNA produced in a) and high fidelity polymerase (manufactured by Invitrogen, Inc.) according to a common procedure. The conditions for a thermal cycler were set as follows: after heating at 94° C. for 2 minutes, a temperature cycle of "94° C. for 0.5 minutes, 55° C. for 0.5 minutes and 68° C. for 1.5 minutes" was repeated 35 times, followed by heating at 68° C. for 5 minutes and incubating at 4° C.

c) Cloning into pcDNA3.1(+) Vector

The PCR reaction solution obtained in b) and pcDNA3.1 (+) vector (manufactured by Invitrogen, Inc.) were treated with restriction enzymes (EcoRI, XhoI), followed by column purification, and then, a ligase reaction was performed according to a common procedure. *Escherichia coli* DH5α-T1 was transformed with the resulting vector and plated on a plate containing ampicillin. From the thus obtained *Escherichia coli* colonies, transformed *Escherichia coli* containing the mouse Siglec-15/pcDNA3.1(+) plasmid was isolated.

The entire nucleotide sequence of the ORF cDNA inserted into the obtained plasmid was analyzed using a DNA sequencer, and as a result, it was found to be the sequence represented by SEQ ID NO: 3 in the Sequence Listing. This nucleotide sequence was the same as an ORF coding region of a predicted sequence registered in NCBI GenBank database as "mouse CD33L3" (accession number: XM 884636), and further, the amino acid sequence (SEQ ID NO: 4 in the Sequence Listing) encoded by the nucleotide sequence was 100% identical to the predicted amino acid sequence of the mouse CD33L3.

Example 4

Expression of mRNA for Siglec-15 Accompanying Mouse Osteoclast Differentiation (Real-Time PCR Analysis)

a) To 1 μg of the total RNA produced in a) or b) of Example 2, 1 μl of 1 U/μl DNase I and 1 μl of 10×DNase I buffer (manufactured by Invitrogen, Inc.) were added, and then, the final volume was brought to 10 μl with $H_2O$. After a reaction was allowed to proceed at room temperature for 15 minutes, 1 μl of 25 mM EDTA was added thereto and the resulting mixture was heated at 65° C. for 10 minutes. From this solution, an 8 μl aliquot was taken, and 1 μl of 50 μM oligo(dT)$_{20}$ primer and 1 μl of 10 mM dNTPs were added thereto, and the resulting mixture was heated at 65° C. for 5 minutes and then incubated in ice. To this solution, 2 μl of 10×RT buffer (manufactured by Invitrogen, Inc.), 4 μl of 25 mM $MgCl_2$, 2 μl of 0.1 M dithiothreitol, 1 μl of RNase inhibitor (RNaseOUT, 40 U/μl, manufactured by Invitrogen, Inc.), and 1 μl of Superscript III reverse transcriptase (200 U/μl, manufactured by Invitrogen, Inc.) were added and the total volume was brought to 20 μl. After a reaction was allowed to proceed at 50° C. for 50 minutes, the mixture was heated at 85° C. for 5 minutes and then incubated in ice.

By using the thus produced single-stranded cDNA, real-time PCR was performed on a combination of the following primers and fluorescently labeled probes (TaqMan probe, manufactured by Applied Biosystems, Inc.).

```
Conditions for real-time PCR:
Primers for amplifying mouse Siglec-15:
5'-tcaggctcag gagtccaatt at-3'
(TqM-mSiglec-15-F: SEQ ID NO: 7 in the Sequence
Listing)
and 5'-ggtctagcct ggtactgtcc ttt-3'
(TqM-mSiglec-15-R: SEQ ID NO: 8 in the Sequence
Listing)

TaqMan probe for detecting mouse Siglec-15:
5'-Fam-atttgagcca gatgagtcct ccaggcca-TAMRA-3'
(TqM-mSiglec-15-probe: SEQ ID NO: 9 in the
Sequence Listing)

Primers for amplifying mouse L32 ribosomal
protein:
5'-aagaagttca tcaggcacca gt-3'
(TqM-mL32-F: SEQ ID NO: 10 in the Sequence
Listing)
and 5'-cttgacattg tggaccagga ac-3'
(TqM-mL32-R: SEQ ID NO: 11 in the Sequence
Listing)

TaqMan probe for detecting mouse L32 ribosomal
protein:
5'-Fam-aaacccagag gcattgacaa cagggtgc-TAMRA-3'
(TqM-mL32-probe: SEQ ID NO: 12 in the Sequence
Listing)
```

A real-time PCR analysis was performed using a real-time PCR system (ABI Prism 7700 Sequence Detector, manufactured by Perkin Elmer Japan Applied Biosystems Division) under the following conditions. In the reaction, TaqMan Universal PCR Master Mix (manufactured by Applied Biosystems, Inc.) was used. First, distilled water was added to 25 pmol of each primer, 8 ng of single-stranded cDNA and 10 pmol of TaqMan probe to bring the final volume to 25 μl, and then, 25 μl of TaqMan Universal PCR Master Mix was added thereto, whereby 50 μl of a reaction solution was prepared. This reaction solution was heated at 50° C. for 2 minutes and then heated at 95° C. for 10 minutes, and thereafter subjected to 40 temperature cycles of "95° C. for 0.25 minutes and 60° C. for 1 minute", whereby a real-time PCR analysis was performed. Incidentally, the expression level of mRNA for mouse Siglec-15 was corrected by the expression level of mRNA for L32 ribosomal protein.

Figure 3:
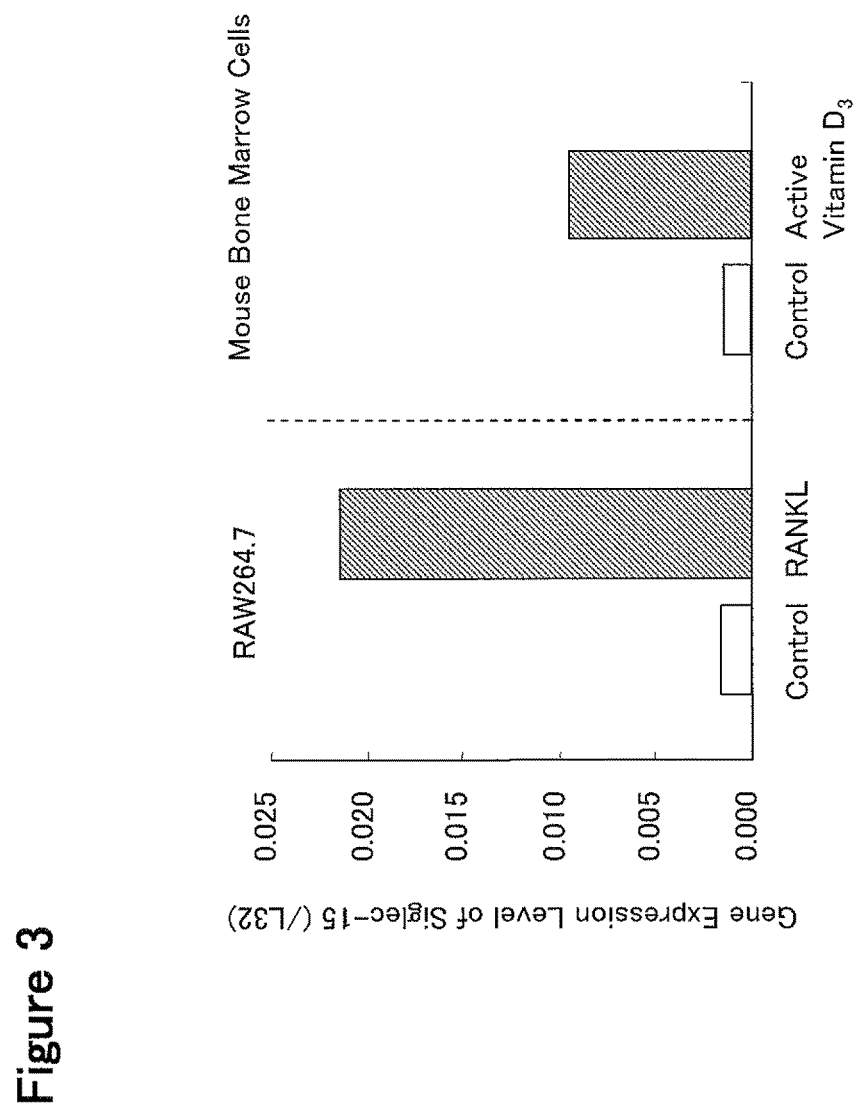
FIG. 3 shows a graph depicting a change in the expression level of the Siglec-15 gene when osteoclast differentiation was induced from RAW 264.7 or mouse bone marrow cells.

As a result, the expression level of the Siglec-15 gene significantly increased in both cases where osteoclasts were induced by adding RANKL to RAW 264.7 and where osteoclasts were induced by adding active vitamin $D_3$ to mouse bone marrow-derived primary cultured cells (FIG. 3).

b) RAW 264.7 was prepared at $4.5 \times 10^4$ cells/ml in α-MEM medium containing 10% fetal bovine serum, and the resulting cell preparation was put in a 75 $cm^2$ flask at 10 ml/flask, and then, human RANKL (manufactured by PeproTech Inc.) was added thereto to give a final concentration of 40 ng/ml. The cells were cultured for 0, 1, 2, and 3 days in a $CO_2$ incubator. Further, the culturing without the addition of human RANKL was performed in the same manner.

After completion of the culturing, the total RNA was extracted from RAW 264.7 cultured under the respective conditions using a total RNA extraction reagent (ISOGEN, manufactured by Nippon Gene Co., Ltd.) according to the protocol attached to the reagent. The collected total RNA was stored at −80° C.

To 1 μg of the thus collected total RNA, 1 μl of 1 U/μl DNase I and 1 μl of 10×DNase I buffer (manufactured by Invitrogen, Inc.) were added, and then, the final volume was brought to 10 μl with $H_2O$. After a reaction was allowed to proceed at room temperature for 15 minutes, 1 μl of 25 mM EDTA was added thereto and the resulting mixture was heated at 65° C. for 10 minutes. From this solution, an 8 μl aliquot was taken, and 1 μl of 50 μM oligo(dT)$_{20}$ primer and 1 μl of 10 mM dNTPs were added thereto, and the resulting mixture was heated at 65° C. for 5 minutes and then incubated in ice. To this solution, 2 μl of 10×RT buffer (manufactured by Invitrogen, Inc.), 4 μl of 25 mM MgCl$_2$, 2 μl of 0.1 M dithiothreitol, 1 μl of RNase inhibitor (RNaseOUT, 40 U/μl, manufactured by Invitrogen, Inc.), and 1 μl of Superscript III reverse transcriptase (200 U/μl manufactured by Invitrogen, Inc.) were added and the total volume was brought to 20 μl. After a reaction was allowed to proceed at 50° C. for 50 minutes, the mixture was heated at 85° C. for 5 minutes and then incubated in ice.

By using the thus produced single-stranded cDNA, real-time PCR was performed on a combination of the following primers and fluorescently labeled probes (TaqMan probe, manufactured by Applied Biosystems, Inc.).

```
Conditions for real-time PCR:
Primers for amplifying mouse cathepsin K:
5'-ggcatctttc cagtttaca gc-3'
(TqM-mcatK-F: SEQ ID NO: 13 in the Sequence
Listing)
and 5'-gttgttctta ttccgagcca ag-3'
(TqM-mcatK-R: SEQ ID NO: 14 in the Sequence
Listing)

TaqMan probe for detecting mouse cathepsin K:
5'-Fam-atgtgaacca tgcagtgttg gtggtggg-TAMRA-3'
(TqM-mcatK-probe: SEQ ID NO: 15 in the Sequence
Listing)

Primers for amplifying mouse TRAP:
5'-gaacttcccc agcccttact ac-3'
(TqM-mTRAP-F: SEQ ID NO: 16 in the Sequence
Listing)
and 5'-aactgctttt tgagccagga c-3'
(TqM-mTRAP-R: SEQ ID NO: 17 in the Sequence
Listing)

TaqMan probe for detecting mouse TRAP:
5'-Fam-ttgccagtca gcagcccaaa atgcct-TAMRA-3'
(TqM-mTRAP-probe: SEQ ID NO: 18 in the Sequence
Listing)

Primers for amplifying mouse Siglec-15:
5'-tcaggctcag gagtccaatt at-3'
(TqM-mSiglec-15-F: SEQ ID NO: 7 in the Sequence
Listing)
and 5'-ggtctagcct ggtactgtcc ttt-3'
(TqM-mSiglec-15-R: SEQ ID NO: 8 in the Sequence
Listing)

TaqMan probe for detecting mouse Siglec-15:
5'-Fam-atttgagcca gatgagtcct ccaggcca-TAMRA-3'
(TqM-mSiglec-15-probe: SEQ ID NO: 9 in the
Sequence Listing)

Primers for amplifying mouse L32 ribosomal
protein:
5'-aagaagttca tcaggcacca gt-3'
(TqM-mL32-F: SEQ ID NO: 10 in the Sequence
Listing)
and 5'-cttgacattg tggaccagga ac-3'
(TqM-mL32-R: SEQ ID NO: 11 in the Sequence
Listing)
```

```
-continued
TaqMan probe for detecting mouse L32 ribosomal
protein:
5'-Fam-aaacccagag gcattgacaa cagggtgc-TAMRA-3'
(TqM-mL32-probe: SEQ ID NO: 12 in the Sequence
Listing)
```

A real-time PCR analysis was performed using a real-time PCR system (ABI Prism 7700 Sequence Detector, manufactured by Perkin Elmer Japan Applied Biosystems Division) under the following conditions. In the reaction, TaqMan Universal PCR Master Mix (manufactured by Applied Biosystems, Inc.) was used. First, distilled water was added to 25 pmol of each primer, 8 ng of single-stranded cDNA and 10 pmol of TaqMan probe to bring the final volume to 25 μl, and then, 25 μl of TaqMan Universal PCR Master Mix was added thereto, whereby 50 μl of a reaction solution was prepared. This reaction solution was heated at 50° C. for 2 minutes and then heated at 95° C. for 10 minutes, and thereafter subjected to 40 temperature cycles of "95° C. for 0.25 minutes and 60° C. for 1 minute", whereby a real-time PCR analysis was performed. Incidentally, the expression level of mRNA for each gene was corrected by the expression level of mRNA for L32 ribosomal protein.

Figure 4:
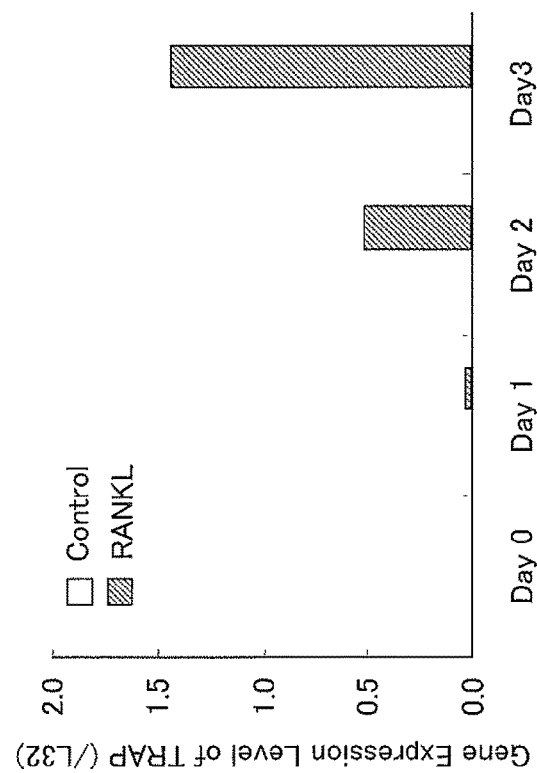
FIG. 4 shows graphs depicting the expression of cathepsin K and TRAP genes accompanying osteoclast differentiation of RAW 264.7 cells.
Figure 4:
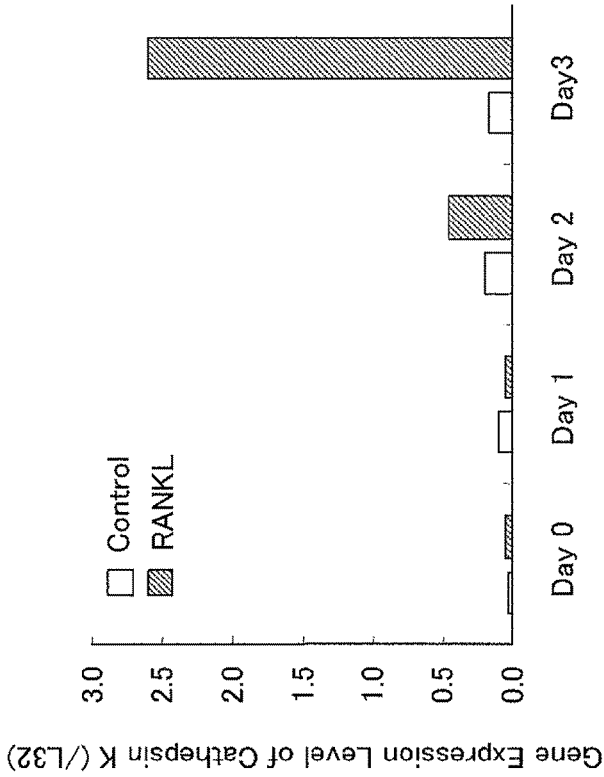
Figure 5:
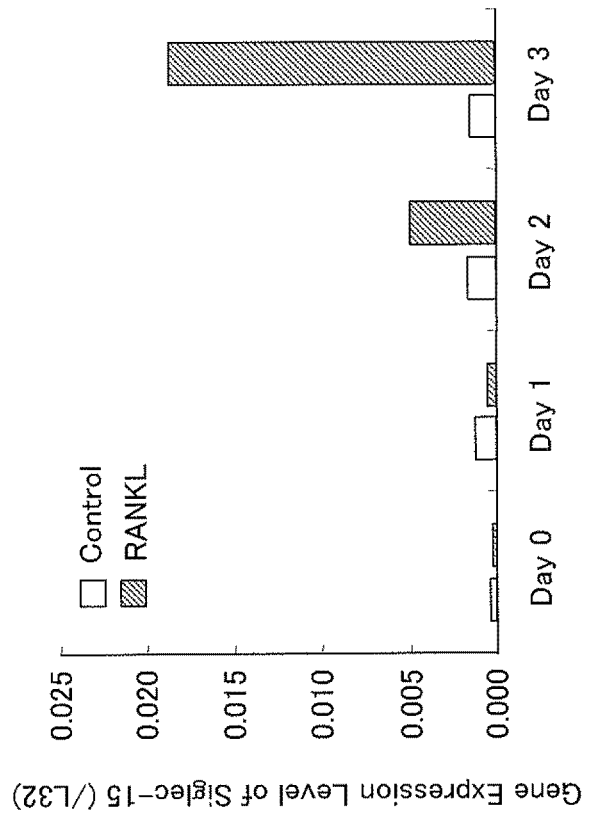
FIG. 5 shows a graph depicting the expression of the Siglec-15 gene accompanying osteoclast differentiation of RAW 264.7 cells.

As a result, the expression levels of cathepsin K and TRAP genes which are known as marker molecules for osteoclasts significantly increased from day 2 to day 3 after the addition of RANKL (FIGS. 4-A, B). Similarly, the expression level of the Siglec-15 gene also significantly increased from day 2 to day 3 after the addition of RANKL (FIG. 5). From these results, it was revealed that the expression of the Siglec-15 gene increases accompanying osteoclast differentiation, and particularly, the Siglec-15 gene is expressed strongly at a late differentiation stage.

Example 5

Production of Soluble Mouse Siglec-15 Protein Expression Construct

A partial nucleic acid sequence encoding the extracellular domain of mouse Siglec-15 protein is represented by SEQ ID NO: 19 in the Sequence Listing and the amino acid sequence thereof is represented by SEQ ID NO: 20 in the Sequence Listing. By utilizing such a partial sequence, soluble mouse Siglec-15 protein can be produced in a culture supernatant of an animal cell or the like.

a) Amplification of Soluble Mouse Siglec-15 Gene by PCR

Oligonucleotides having the sequences of: 5'-ggggacaagt ttgtacaaaa aagcaggctt caccATGGAG GGGTCCCTCC AACTC-3' (mSiglec-15-ECD-F: SEQ ID NO: 21 in the Sequence Listing); and 5'-ggggaccact ttgtacaaga aagctgggtc TCCGGGGGCG CCGTGGAAGC GGAAC-3' (mSiglec-15-ECD-R: SEQ ID NO: 22 in the Sequence Listing) as primers for amplifying the mouse Siglec-15 extracellular domain cDNA by PCR were synthesized according to a common procedure. Incidentally, these primers were designed, as amplification primers for producing a gateway entry clone, such that an attB1 sequence is added to mSiglec-15-ECD-F and an attB2 sequence is added to mSiglec-15-ECD-R. The PCR was performed using this combination of primers and the mouse Siglec-15/pcDNA3.1(+) plasmid produced in Example 3 as a template according to a common procedure. The conditions for a thermal cycler were set as follows: after heating at 94° C. for 2 minutes, a temperature cycle of "94° C. for 0.5 minutes, 55° C. for 0.5 minutes and 68° C. for 1.5 minutes" was repeated 15 times, followed by heating at 68° C. for 5 minutes and incubating at 4° C.

b) Production of Entry Clone by Gateway BP Reaction

An entry clone into which the mouse Siglec-15 extracellular domain cDNA was integrated by the Gateway technology (Invitrogen, Inc.) employing a lambda phage site-specific recombination system was produced by the following method. First, a BP reaction using BP Clonase was performed between the PCR product having an attB sequence at both ends produced in a) and pDNOR221 (manufactured by Invitrogen, Inc.) which is a donor vector having an attP sequence. By using this reaction solution, *Escherichia coli* DH10B was transformed, and colony PCR was performed for drug-resistant clones, and the size of inserts was confirmed. Then, for a clone confirmed to have an insert with a correct size, a sequence analysis of the total DNA sequence of the insert was performed. As a result, an entry clone which is completely identical to the target nucleic acid sequence (SEQ ID NO: 19 in the Sequence Listing) encoding the extracellular domain of mouse Siglec-15 protein was obtained.

c) Production of Expression Clone by Gateway LR Reaction

An expression clone into which the mouse Siglec-15 extracellular domain cDNA was integrated by the Gateway technology (Invitrogen, Inc.) employing a lambda phage site-specific recombination system was produced by the following method. The entry clone produced in b) contains an insert having an attL sequence at both ends. An LR reaction using LR Clonase was performed between this entry clone and two types of destination vectors having an attR sequence. Incidentally, as the destination vectors, two types of destination vectors: pDONM designed such that a V5 epitope tag and a 6×His tag are added to the C terminus of the insert; and phIgFc designed such that a human Fc tag is added to the C terminus of the insert were used. By using the reaction solution obtained by the LR reaction, *Escherichia coli* DH10B was transformed, and colony PCR was performed for the obtained drug-resistant clones, and the size of inserts was confirmed. Then, for a clone confirmed to have an insert with a correct size, a sequence analysis of both ends from the insert side to the vector side was performed.

```
Primer sequences for sequence analysis
5'-tgcgtgaaggtgcagggcag-3'
(mSiglec-15-ECD-seq-upstm: SEQ ID NO: 23 in the
Sequence Listing)
and 5'-cctcgcctgg tcgggtc-3'
(mSiglec-15-ECD-seq-dnstm: SEQ ID NO: 24 in the
Sequence Listing)
```

As a result of the sequence analysis, expression clones (soluble mouse Siglec-15/pDONM and soluble mouse Siglec-15/phIgFc) in which correct recombination occurred were obtained for both pDONM and phIgFc, respectively. By transfecting the soluble mouse Siglec-15/pDONM into an animal cell or the like, mRNA having the base sequence represented by SEQ ID NO: 25 in the Sequence Listing is transcribed and translated into a protein (mouse Siglec-15-His) having the amino acid sequence represented by SEQ ID NO: 26 in the Sequence Listing. Further, by transfecting the soluble mouse Siglec-15/phIgFc into an animal cell or the like, mRNA having the base sequence represented by SEQ ID NO: 27 in the Sequence Listing is transcribed and translated into a protein (mouse Siglec-15-Fc) having the amino acid sequence represented by SEQ ID NO: 28 in the Sequence Listing.

Example 6

Figure 6:
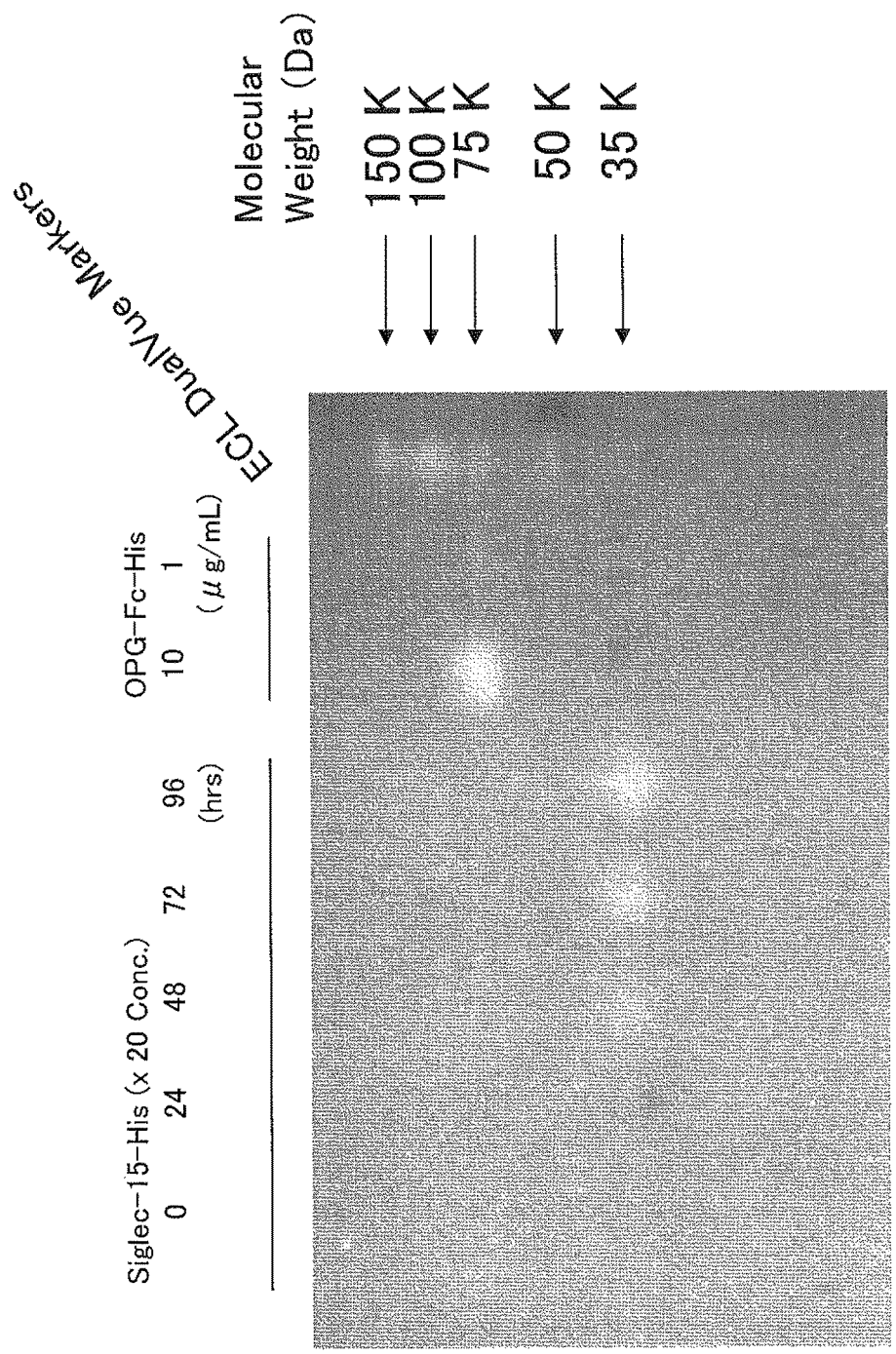
FIG. 6 shows the results of detecting a change in the expression of mouse Siglec-15-His in 293F cells with culture time by SDS-polyacrylamide electrophoresis and Western blotting using an anti-6-His-HRP antibody.
Figure 7:
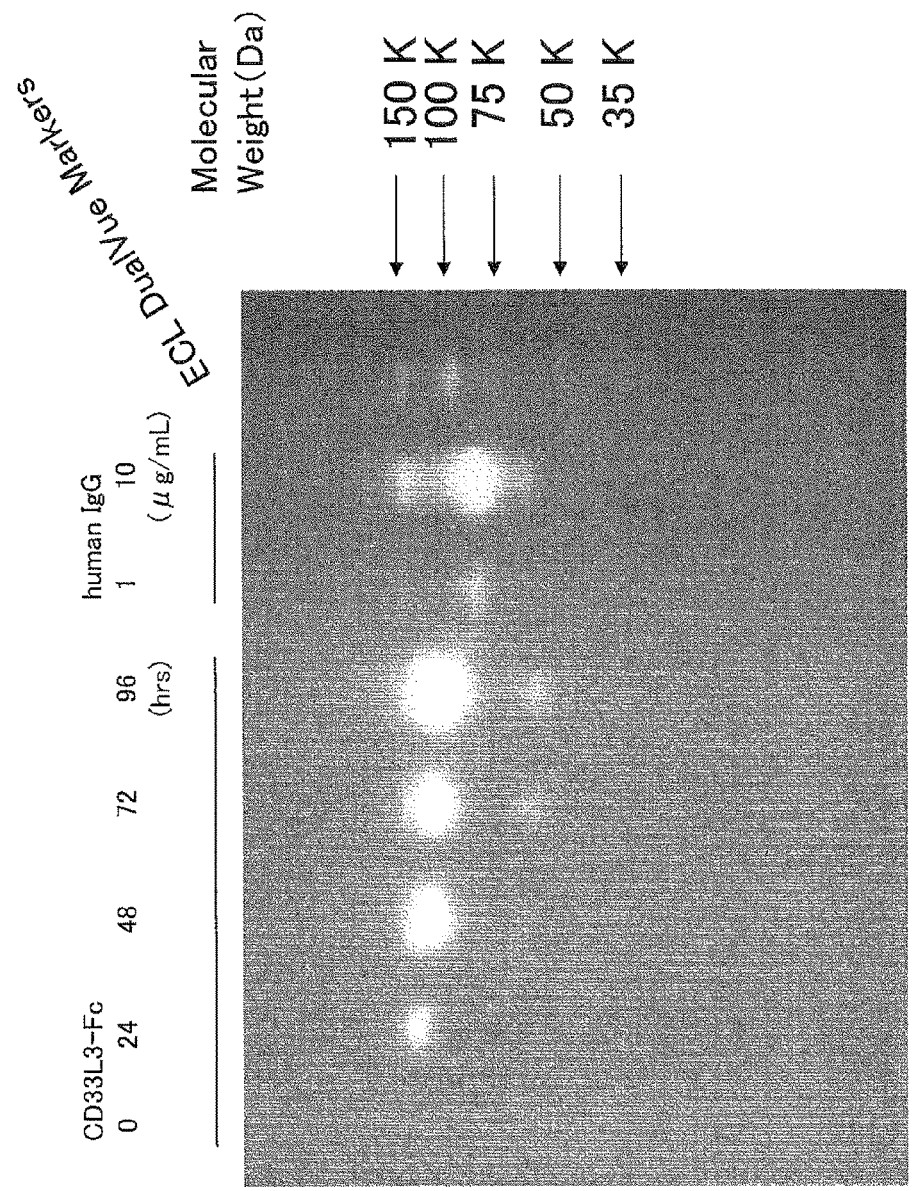
FIG. 7 shows the results of detecting a change in the expression of mouse Siglec-15-Fc in 293F cells with culture time by SDS-polyacrylamide electrophoresis and Western blotting using an anti-human IgG-Fc-HRP antibody.

Examination of Optimal Culture Time for Producing Soluble Mouse Siglec-15 Protein a) Expression of Protein Using 293-F Cells The two types of expression plasmids (soluble mouse Siglec-15/pDONM and soluble mouse Siglec-15/phIgFc) obtained in Example 5 were prepared in an amount of about 100 µg, respectively. 50 µg of each of the prepared plasmids was mixed with Opti-MEM (manufactured by Invitrogen, Inc.), followed by filter sterilization. Then, 64 µl of a transfection reagent 293fectin (manufactured by Invitrogen, Inc.) was added thereto, and the resulting mixture was incubated at room temperature for 25 minutes. Each of the thus obtained mixtures was added to FreeStyle 293-F cells (manufactured by Invitrogen, Inc.) cultured in a shake flask such that the cell density reached $1.0 \times 10^6$ cells/ml×50 ml in FreeStyle 293 Expression Medium (manufactured by Invitrogen, Inc.), and the cells were subjected to rotary culture (125 rotations/min) at a $CO_2$ concentration of 8.0% for 96 hours (4 days) at 37° C. A small portion of the culture solution was collected at 24-hour intervals (culture time: 0, 24, 48, 72, 96 hours), and centrifuged to prepare a culture supernatant. It is considered that in the thus prepared culture supernatants, a protein in which a V5 epitope tag and a 6×His tag have been added to the C-terminal side of the mouse Siglec-15 extracellular domain (mouse Siglec-15-His) and a protein in which a human Fc tag has been added to the C-terminal side of the mouse Siglec-15 extracellular domain (mouse Siglec-15-Fc) are expressed, respectively.

b) Change in Expression Level with Culture Time of Mouse Siglec-15-His-Expressing 293F Cells By using the culture solution (culture time: 0, 24, 48, 72, 96 hours) samples of mouse Siglec-15-His-expressing 293F cells prepared in a) and a commercially available His tag-containing protein, recombinant human osteoprotegerin/his (OPG-Fc-His) (manufactured by R&D systems, Inc.), the expression levels were analyzed by SDS-polyacrylamide electrophoresis under reducing conditions and Western blotting. That is, to 5 µl of a sample obtained by concentrating each culture solution by 20-fold using Microcon YM-10 (manufactured by Millipore Co., Ltd.) or 5 µl of an OPG-Fc-His solution, an equivalent amount of an SDS-treatment solution (10 mM Tris-HCl buffer (pH 8.0) containing 1 mM EDTA, 2.5% SDS, 0.1% bromophenol blue, and 5% 2-mercaptoethanol) was added, and the resulting mixture was heated at 95° C. for 10 minutes. 0.8 µl of each of the thermally treated samples was used for SDS-polyacrylamide electrophoresis. As a gel for electrophoresis, an 8-25% polyacrylamide gradient gel (manufactured by Amersham Biosciences, Inc.) was used, and the electrophoresis was performed using PhastSystem (manufactured by Amersham Biosciences, Inc.). Further, as molecular weight markers, ECL DualVue Western Blotting Markers (manufactured by Amersham Biosciences, Inc.) were used. After completion of the electrophoresis, the protein in the gel was transferred (blotted) to a PVDF membrane (Hybond-P, manufactured by Amersham Biosciences, Inc.) using PhastTransfer Semi-dry Transfer Kit (manufactured by Amersham Biosciences, Inc.) and PhastSystem. This PVDF membrane was transferred in 10 ml of a blocking agent (BlockAce, manufactured by Snow Brand Milk Products, Co., Ltd.) containing 0.1% Tween 20 and gently shaken at room temperature for 1 hour. To this blocking solution, 5 µl of an S-protein HRP solution (ECL DualVue Western Blotting Markers, manufactured by Amersham Biosciences, Inc.) and 2 µl of an anti-6-His-HRP antibody (PentaHis HRP Conjugate kit, manufactured by Qiagen, Inc.) were added and the membrane in the solution was gently shaken at room temperature for an additional 1 hour. This PVDF membrane was washed 4 times by gently shaking it in 50 mL of phosphate-buffered saline (PBS) containing 0.01% Tween 20 for 5 minutes. After washing, the PVDF membrane was treated according to the protocol attached to an ECL detection kit (ECL Western blotting detection reagents and analysis system, manufactured by Amersham Biosciences, Inc.) to develop the color of the band of the His tag-containing protein, and the developed color was detected using an ECL Mini-Camera (manufactured by Amersham Biosciences, Inc.) and Polaroid film (Polapan 3200B, manufactured by Polaroid, Inc.). The results are shown in FIG. 6. From these results, a 96-hour culture time was selected as the culture time for 293F cells which produced the highest concentration of a protein (mouse Siglec-15-His) which has a molecular weight of about 35 kDa and reacts with an anti-6-His-HRP antibody.

c) Change in Expression Level with Culture Time of Mouse Siglec-15-Fc-Expressing 293F Cells By using the culture solution (culture time: 0, 24, 48, 72, 96 hours) samples of mouse Siglec-15-Fc-expressing 293F cells prepared in a) and human IgG (manufactured by Sigma Co., Ltd), the expression levels were analyzed by SDS-polyacrylamide electrophoresis under non-reducing conditions and Western blotting. That is, to 5 µl of each culture solution sample or 5 µl of a human IgG solution, an equivalent amount of an SDS-treatment solution was added, and the resulting mixture was heated at 95° C. for 10 minutes. In the same manner as the method described in the above b) using 0.8 µl of each of the thermally treated samples, SDS-polyacrylamide electrophoresis, transfer (blotting) to a PVDF membrane, and blocking of the PVDF membrane were performed. To the PVDF membrane after blocking, 5 µl of an S-protein HRP solution (ECL DualVue Western Blotting Markers, manufactured by Amersham Biosciences, Inc.) and 2 µl of an anti-human IgG-Fc-HRP antibody (Anti-Humam IgG (Fc specific) Peroxidase Conjugate, manufactured by Sigma Co., Ltd) were added and the membrane in the solution was gently shaken at room temperature for an additional 1 hour. After washing was performed in the same manner as the method described in the above b), the developed color of the band of the Fc-containing protein was detected. The results are shown in FIG. 7. From these results, a 96-hour culture time was selected as the culture time for 293F cells which produced the highest concentration of a protein (mouse Siglec-15-Fc) which has a molecular weight of about 110 kDa and reacts with an anti-human Fc antibody.

Example 7

Large-Scale Preparation of Culture Solution Containing Soluble Mouse Siglec-15 Protein Using 293-F Cells The two types of expression plasmids (soluble mouse Siglec-15/pDONM and soluble mouse Siglec-15/phIgFc) obtained in Example 5 were prepared in an amount of about 5 mg, respectively. Incidentally, in the purification of plasmids from *Escherichia coli* cultured on a large scale, Invitrogen PureLink HiPure Plasmid Gigaprep Kit (manufactured by Invitrogen, Inc.) was used. The thus prepared plasmids were mixed with Opti-MEM (manufactured by Invitrogen, Inc.), followed by filter sterilization. Then, 10 ml of a transfection reagent 293fectin (manufactured by Invitrogen, Inc.) was added thereto, and the resulting mixture was incubated at room temperature for 20 minutes. Each of the thus obtained mixtures was added to FreeStyle 293-F cells (manufactured by Invitrogen, Inc.) cultured in Erlenmeyer flasks such that the cell density reached $1.1 \times 10^6$ cells/ml×5 L (1 L/flask×5 flasks) in FreeStyle 293 Expression Medium (manufactured by Invitrogen, Inc.). After the cells were subjected to rotary culture (125 rotations/min) at a $CO_2$ concentration of 8.0% for 96 hours (4 days) at 37° C., the culture solution was collected and centrifuged to prepare a culture supernatant. It is considered that in the thus prepared culture supernatants, a protein in which a V5 epitope tag and a 6×His tag have been added to the C-terminal side of the mouse Siglec-15 extracellular domain (mouse Siglec-15-His) and a protein in which a human Fc tag has been added to the C-terminal side of the mouse Siglec-15 extracellular domain (mouse Siglec-15-Fc) are expressed, respectively.

Example 8

Purification of Mouse Siglec-15-His a) HisTrap HP Column Chromatography

To 2 L of the culture solution of mouse Siglec-15-His-expressing 293F cells prepared in Example 7, 225 mL of 10×buffer (500 mM Tris, 1.5 M NaCl, 200 mM imidazole, pH 8.0) was added, and the resulting mixture was stirred well and filtered through a Sterivex-GV filter (manufactured by Millipore Co., Ltd.). This culture solution was applied to a column which comprised three HisTrap HP 5 ml columns (manufactured by Amersham Biosciences, Inc.) connected in series and was previously treated with a pyrogen removing agent PyroCLEAN (manufactured by ALerCHEK, Inc.) and washed with distilled water for injection at a flow rate of 2 ml/min. After the column was washed with 60 ml of 50 mM Tris-HCl buffer (pH 8.0) containing 300 mM NaCl at a flow rate of 1 ml/min, a protein adsorbed onto the column was eluted with 50 ml of 50 mM Tris-HCl buffer (pH 8.0) containing 300 mM NaCl and 500 mM imidazole at a flow rate of 1 ml/min. The eluate was fractionated at 1 ml per fraction into mini-sorp tubes (manufactured by Nunc, Inc.) to which 10 µl of 10% Tween 20 had previously been added. After about 20 ml of a solution obtained by combining the fractions (fractions 14 to 20) containing the eluted protein was concentrated to 2.5 ml with a centrifugal membrane concentrator Amicon Ultra-15 (manufactured by Millipore Co., Ltd.), the concentrate was applied to a PD-10 desalting column (manufactured by Amersham Biosciences, Inc.) which was previously equilibrated with phosphate-buffered saline containing 0.01% Tween 20 (T-PBS), followed by elution with T-PBS, whereby 3.5 ml of a sample whose solvent was replaced with T-PBS was obtained.

b) Resource Q Column Chromatography

To 3.5 ml of the sample which was purified by HisTrap HP column chromatography and whose solvent was replaced with TBS-P, 22.5 ml of 50 mM Tris-HCl buffer (pH 7.5) containing 0.1% CHAPS was added and the resulting mixture was stirred. Then, the mixture was centrifuged at 4° C. for 30 minutes at 3,000 rpm and the precipitate was removed. After the resulting supernatant was filtered through a Millex-GV filter (manufactured by Millipore Co., Ltd.), the filtrate was applied to a Resource Q 6 ml column (manufactured by Amersham Biosciences, Inc.) which was previously equilibrated with 50 mM Tris-HCl buffer (pH 7.5) containing 0.1% CHAPS at a flow rate of 1 ml/min. Thereafter, the column was washed with this buffer at a flow rate of 1 ml/min and a protein fraction which was not adsorbed onto the column was collected. A protein adsorbed onto the column was eluted with 50 mM Tris-HCl buffer (pH 7.5) containing 0.1% CHAPS and 1 M NaCl at a flow rate of 1 ml/min. After 26.5 ml of the fraction which was not adsorbed onto the column was concentrated to 2.0 ml with a centrifugal membrane concentrator Amicon Ultra-15 (manufactured by Millipore Co., Ltd.), the concentrate was centrifuged at 4° C. for 10 minutes at 3,000 rpm and the precipitate was removed. The supernatant after centrifugation was cryopreserved at −80° C. until use. The above-mentioned purification procedure (HisTrap HP column chromatography and Resource Q column chromatography) was performed twice by repeating it.

c) Detection and Purity Assay of Purified Mouse Siglec-15-His

Figure 8:
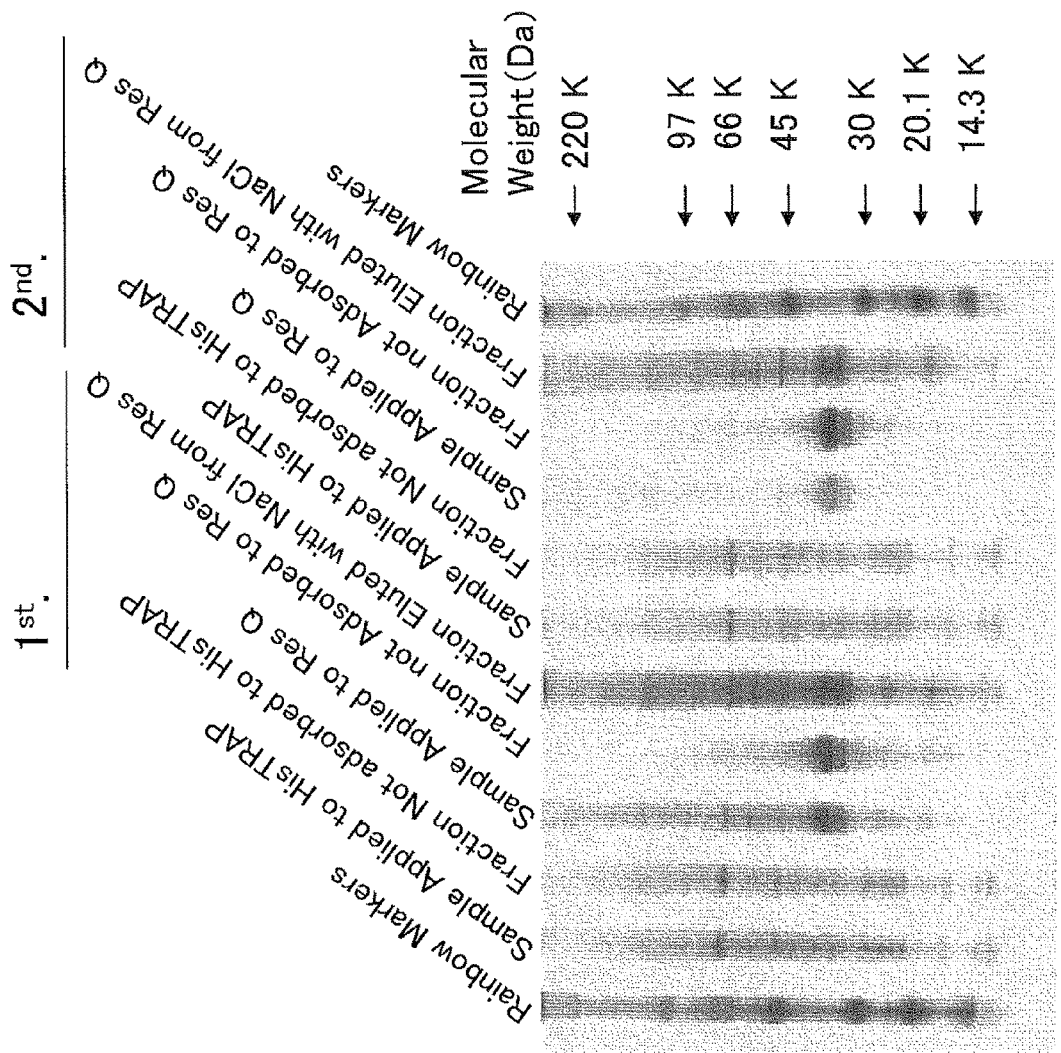
FIG. 8 shows the results of evaluating the purity of mouse Siglec-15-His purified by HisTrap HP column chromatography and Resource Q column chromatography through
SDS-polyacrylamide electrophoresis and silver staining.

By using a sample prepared by the above-mentioned purification procedure (HisTrap HP column chromatography and Resource Q column chromatography), SDS-polyacrylamide electrophoresis under reducing conditions and silver staining were performed. That is, to 5 μl of each of the samples purified by the respective purification steps, an equivalent amount of an SDS-treatment solution was added, and the resulting mixture was thermally treated at 95° C. for 10 minutes. 0.3 μl of each of the thermally treated samples was used for SDS-polyacrylamide electrophoresis. The electrophoresis procedure was performed in the same manner as in the above-mentioned b) of Example 6 except that Rainbow Molecular Weight Markers (manufactured by Amersham Biosciences, Inc.) were used as the molecular weight markers. After completion of the electrophoresis, silver staining was performed using PhastGel Silver Kit (manufactured by Amersham Biosciences, Inc.) and PhastSystem. The results are shown in FIG. 8. It was shown that a protein having a molecular weight of about 35 kDa (mouse Siglec-15-His) was efficiently purified and concentrated in the protein fraction which was not adsorbed onto the Resource Q column.

Figure 9:
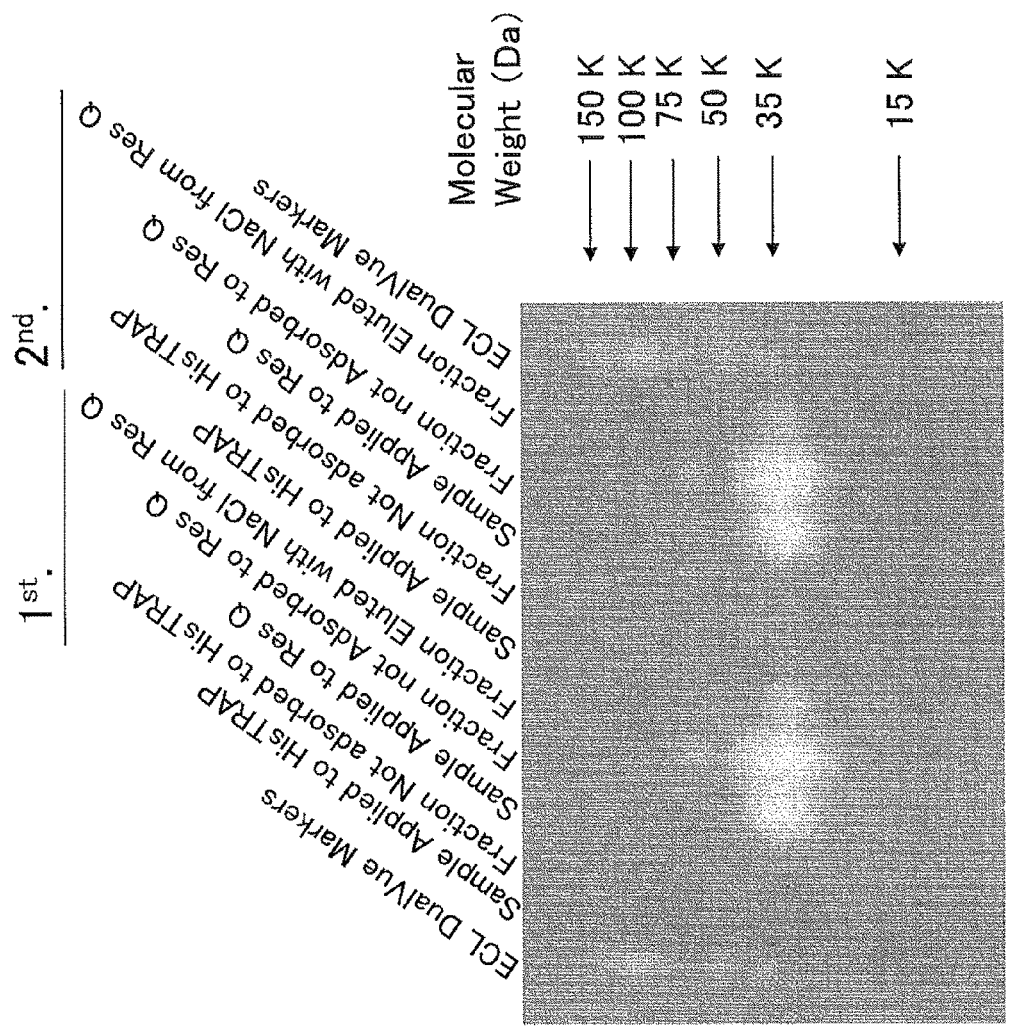
FIG. 9 shows the results of detecting the behavior of mouse Siglec-15-His purified by HisTrap HP column chromatography and Resource Q column chromatography through SDS-polyacrylamide electrophoresis and Western blotting using an anti-V5-HRP antibody.

Electrophoresis was performed under the same conditions except that ECL DualVue Western Blotting Markers (manufactured by Amersham Biosciences, Inc.) were used as the molecular weight markers, and the protein in the gel was transferred (blotted) to a PVDF membrane (Hybond-P, manufactured by Amersham Biosciences, Inc.) using PhastTransfer Semi-dry Transfer Kit (manufactured by Amersham Biosciences, Inc.) and PhastSystem. This PVDF membrane was gently shaken in 10 ml of a blocking agent (BlockAce, manufactured by Snow Brand Milk Products, Co., Ltd.) containing 0.1% Tween 20 at room temperature for 1 hour. To this blocking solution, 10 μl of S-protein HRP (manufactured by Amersham Biosciences, Inc.) and 10 μl of an anti-V5-HRP antibody (Monoclonal Antibody to Pk-TAG-HRP, manufactured by Acris Antibodies GmbH) were added and the membrane in the solution was gently shaken at room temperature for an additional 1 hour. The PVDF membrane was washed 4 times by gently shaking it in 50 mL of phosphate-buffered saline (PBS) containing 0.01% Tween 20 for 5 minutes. After washing, the PVDF membrane was treated according to the protocol attached to an ECL detection kit (manufactured by Amersham Biosciences, Inc.) to develop the color of the band of the protein, and the developed color was detected using an ECL Mini-Camera (manufactured by Amersham Biosciences, Inc.) and Polaroid film (Polapan 3200B, manufactured by Polaroid, Inc.). The results are shown in FIG. 9. Also from these results, it could be confirmed that a protein which has a molecular weight of about 35 kDa (mouse Siglec-15-His) and reacts with an anti-V5-HRP antibody was efficiently purified and concentrated in the protein fraction which was not adsorbed onto the Resource Q column.

d) Measurement of Protein Concentration of Purified Mouse Siglec-15-His

For the purified mouse Siglec-15-His (the protein fraction which was not adsorbed onto the Resource Q column), the protein concentration was measured with a DC-Protein Assay kit (manufactured by Bio-Rad Laboratories, Inc.) using bovine serum albumin as a standard sample. As shown in Table 1, a total of 1.66 mg of purified mouse Siglec-15-His protein was obtained by performing the purification procedure twice.

TABLE 1

|  | Protein Conc. (mg/ml) | Sample Vol. (ml) | Total protein (mg) |
| --- | --- | --- | --- |
| 1st | 0.475 | 2.0 | 0.95 |
| 2nd | 0.354 | 2.0 | 0.71 |
| Total |  |  | 1.66 |

Example 9

Purification of Mouse Siglec-15-Fc a) HiTrap Protein A Column Chromatography 1.8 L of the culture solution of mouse Siglec-15-Fc-expressing 293F cells prepared in Example 7 was filtered through a Sterivex-GV filter (manufactured by Millipore Co., Ltd.), and then, the filtrate was applied to a HiTrap Protein A 5 ml column (manufactured by Amersham Biosciences, Inc.) which had previously been equilibrated with Dulbecco's PBS (D-PBS, manufactured by Invitrogen, Inc.) at a flow rate of 5 ml/min. After the column was washed with D-PBS at a flow rate of 5 ml/min, a protein adsorbed onto the column was eluted with 50 ml of 0.1 M sodium citrate buffer (pH 3.0) at a flow rate of 5 ml/min. The eluate was fractionated at 5 ml per fraction into mini-sorp tubes (manufactured by Nunc, Inc.), and immediately thereafter, 1.3 ml of 1 M Tris was added thereto to neutralize the eluate. After a solution obtained by combining the fractions (fractions 1 and 2) in which the eluted protein was detected was concentrated to 2.5 ml with a centrifugal membrane concentrator Amicon Ultra-15 (manufactured by Millipore Co., Ltd.), the concentrate was applied to a PD-10 desalting column (manufactured by Amersham Biosciences, Inc.) which was previously equilibrated with Otsuka Physiological Saline for Injection (TO-SS, manufactured by Otsuka Pharmaceutical Co., Ltd.) containing 0.01% Tween 20, followed by elution with TO-SS, whereby 3.5 ml of a sample whose solvent was replaced with TO-SS was obtained. This sample was cryopreserved at −80° C. until use. By using 2.9 L of a culture solution of 293F cells, the same purification procedure was performed once again by repeating it.

b) Detection and Purity Assay of Purified Mouse Siglec-15-Fc

Figure 10:
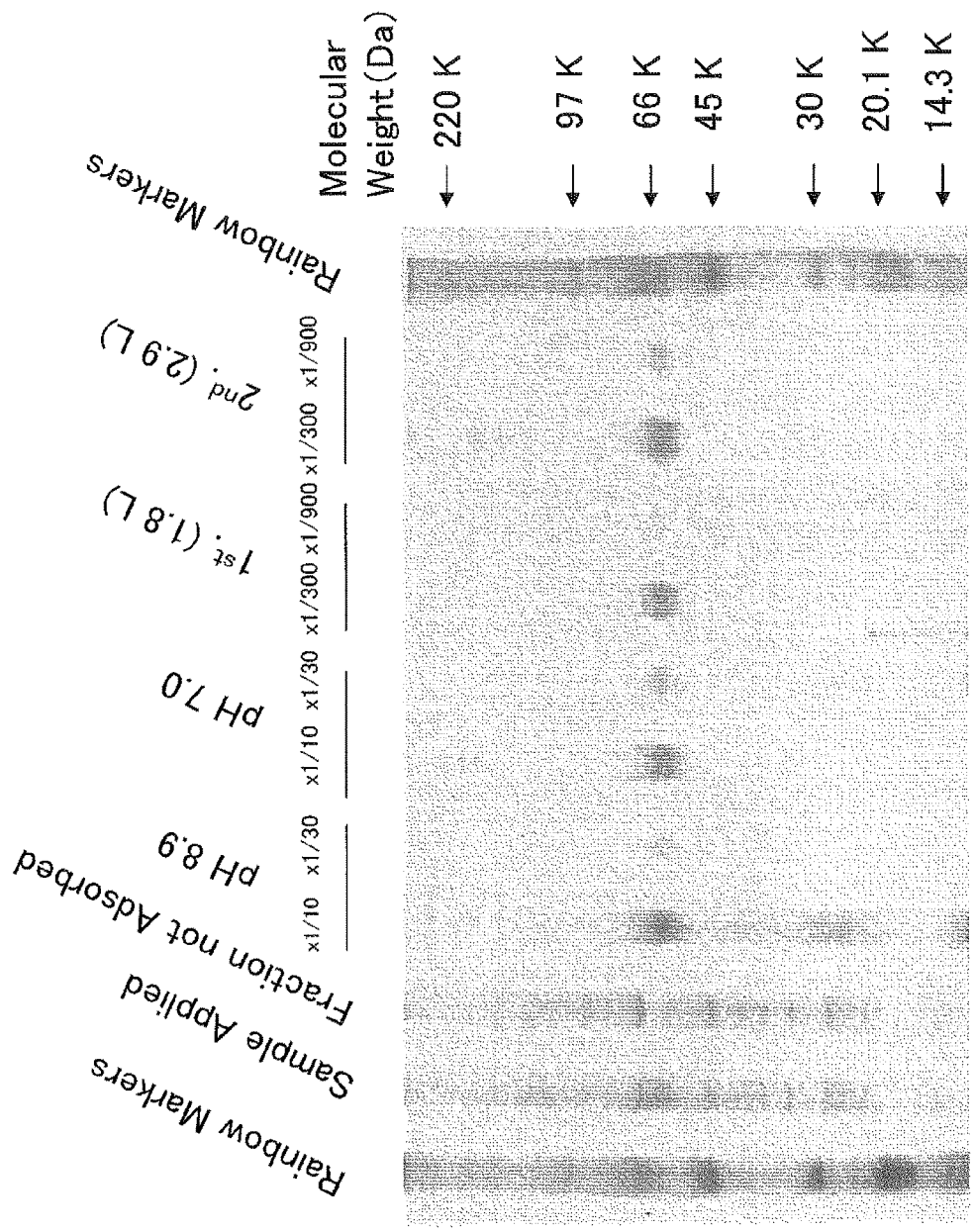
FIG. 10 shows the results of evaluating the purity of mouse Siglec-15-Fc purified by HiTrap Protein A column chromatography through SDS-polyacrylamide electrophoresis and silver staining.

By using a sample prepared by the above-mentioned purification procedure, SDS-polyacrylamide electrophoresis under reducing conditions and silver staining were performed. That is, to 5 μl of each of the samples purified by the respective purification steps, an equivalent amount of an SDS-treatment solution was added, and the resulting mixture was heated at 95° C. for 10 minutes. 0.3 μl of a sample obtained by diluting each of the thermally treated samples to 1/300 or 1/900 with a half concentration of the SDS-treatment solution was used for SDS-polyacrylamide electrophoresis. The electrophoresis and silver staining were performed in the same manner as the purity assay of mouse Siglec-15-His described in c) of Example 8. The results are shown in FIG. 10 along with the results of examining preliminary purification conditions on a small scale (the pH of the applied culture solution was 8.9 or 7.0). It was shown that a protein having a molecular weight of about 55 kDa (mouse Siglec-15-Fc) was efficiently purified and concentrated in the protein fraction which was eluted from the HiTrap Protein A column.

c) Measurement of Protein Concentration of Purified Mouse Siglec-15-Fc

For the purified mouse Siglec-15-Fc (the protein fraction eluted from the PD-10 desalting column), the protein concentration was measured with a DC-Protein Assay kit (manufactured by Bio-Rad Laboratories, Inc.) using bovine serum albumin as a standard sample. As shown in Table 2, a total of 92 mg of purified mouse Siglec-15-Fc protein was obtained by performing the purification procedure twice.

TABLE 2

|  | Protein Conc. (mg/ml) | Sample Vol. (ml) | Total protein (mg) |
| --- | --- | --- | --- |
| 1st | 8.0 | 3.5 | 28 |
| 2nd | 18.5 | 3.5 | 64 |
| Total |  |  | 92 |

Example 10

Production of Rabbit Anti-Mouse Siglec-15 Polyclonal Antibody (Immunization of Rabbit)

a) Preparation of Antigen

The mouse Siglec-15-Fc protein produced in Example 9 was prepared at 100 μg/0.5 ml, and an equivalent amount of an adjuvant was added thereto and an emulsion was produced using a glass syringe. As the adjuvant, Freund's complete adjuvant (FCA, Manufactured by Difco Laboratories, Inc.) was used only for the first immunization, and Freund's incomplete adjuvant (FICA, Manufactured by Difco Laboratories, Inc.) was used for the second and subsequent immunizations.

b) Immunization of Rabbit

Three rabbits (Japanese white female rabbits with a body weight of 3 kg) were used as immunized animals. Incidentally, the blood was collected before immunization, and 1 ml of pre-immune serum was obtained per rabbit. The emulsion obtained in a) was injected subcutaneously and intradermally using a 27 G injection needle at 1 ml/rabbit. Immunization was performed a total of 8 times every 14 days after the first immunization. The whole blood was collected after 7 days from the date of 8th immunization, and 76 to 79 ml of antiserum was obtained per rabbit. The antibody titers in the pre-immune serum and the antiserum were confirmed by an ELISA method using an immobilized antigen. As a result, an increase in antibody titer in the antiserum was confirmed in all the three rabbits. The antiserum was stored at −20° C. until use.

Example 11

Purification of Anti-Mouse Siglec-15 Polyclonal Antibody a) HiTrap Protein A Column Chromatography To 20 ml of each of the three rabbit antiserum lots prepared in Example 10, 20 ml of Dulbecco's PBS (D-PBS, manufactured by Invitrogen, Inc.) was added and mixed, and the resulting mixture was filtered through a Sterivex-GV filter (manufactured by Millipore Co., Ltd.). Then, the filtrate was applied to a HisTrap Protein A 5 ml column (manufactured by Amersham Biosciences, Inc.) which had previously been equilibrated with D-PBS at a flow rate of 2 ml/min. After the column was washed with 37.5 ml of D-PBS at a flow rate of 2.5 ml/min, a protein adsorbed onto the column was eluted with 50 ml of 0.1 M sodium citrate buffer (pH 3.0) at a flow rate of 2.5 ml/min. The eluate was fractionated at 2.5 ml per fraction into mini-sorp tubes (manufactured by Nunc, Inc.), and immediately thereafter, 0.65 ml of 1 M Tris was added thereto to neutralize the eluate. After about 10 ml of a solution obtained by combining the fractions (fractions 2 to 5) containing the eluted protein was concentrated to 2.5 ml with a centrifugal membrane concentrator Amicon Ultra-15 (manufactured by Millipore Co., Ltd.), the concentrate was applied to a PD-10 desalting column (manufactured by Amersham Biosciences, Inc.) which had previously been equilibrated with Otsuka Physiological Saline for Injection (TO-SS) containing 0.01% Tween 20, followed by elution with TO-SS, whereby 3.5 ml of a sample whose solvent was replaced with TO-SS was obtained. The thus prepared sample was cryopreserved at −80° C. until use.

b) Detection and Purity Assay of Anti-Mouse Siglec-15 Polyclonal Antibody

By using the samples (three lots, Nos. 1, 2, and 3) prepared by the purification procedure described in the above a), SDS-polyacrylamide electrophoresis under reducing conditions and silver staining were performed. That is, to 5 μl of each of the samples purified by the respective purification steps, an equivalent amount of an SDS-treatment solution (10 mM Tris-HCl buffer (pH 8.0) containing 1 mM EDTA, 2.5% SDS, 0.1% bromophenol blue, and 5% 2-mercaptoethanol) was added, and the resulting mixture was heated at 95° C. for 10 minutes. 0.3 μl of a sample obtained by diluting each of the thermally treated samples to 1/100, 1/300 or 1/900 with a half concentration of the SDS-treatment solution was used for SDS-polyacrylamide electrophoresis. The electrophoresis and silver staining were performed in the same manner as the purity assay of mouse Siglec-15-His described in c) of Example 8. It was shown that an IgG protein composed of a heavy chain having a molecular weight of about 45 kDa and a light chain having a molecular weight of about 21 kDa was efficiently purified and concentrated in the protein fraction which was eluted from the PD-10 desalting column.

c) Measurement of Protein Concentration of Purified Anti-Mouse Siglec-15 Polyclonal Antibody For the purified anti-mouse Siglec-15 polyclonal antibody (the protein fraction eluted from the PD-10 desalting column), the protein concentration was measured with a DC-Protein Assay kit (manufactured by Bio-Rad Laboratories, Inc.) using bovine IgG as a standard sample. As shown in Table 3, 100 to 170 mg of the anti-mouse Siglec-15 polyclonal antibody could be purified in each of the lots, Nos. 1 to 3.

TABLE 3

Figure 11:
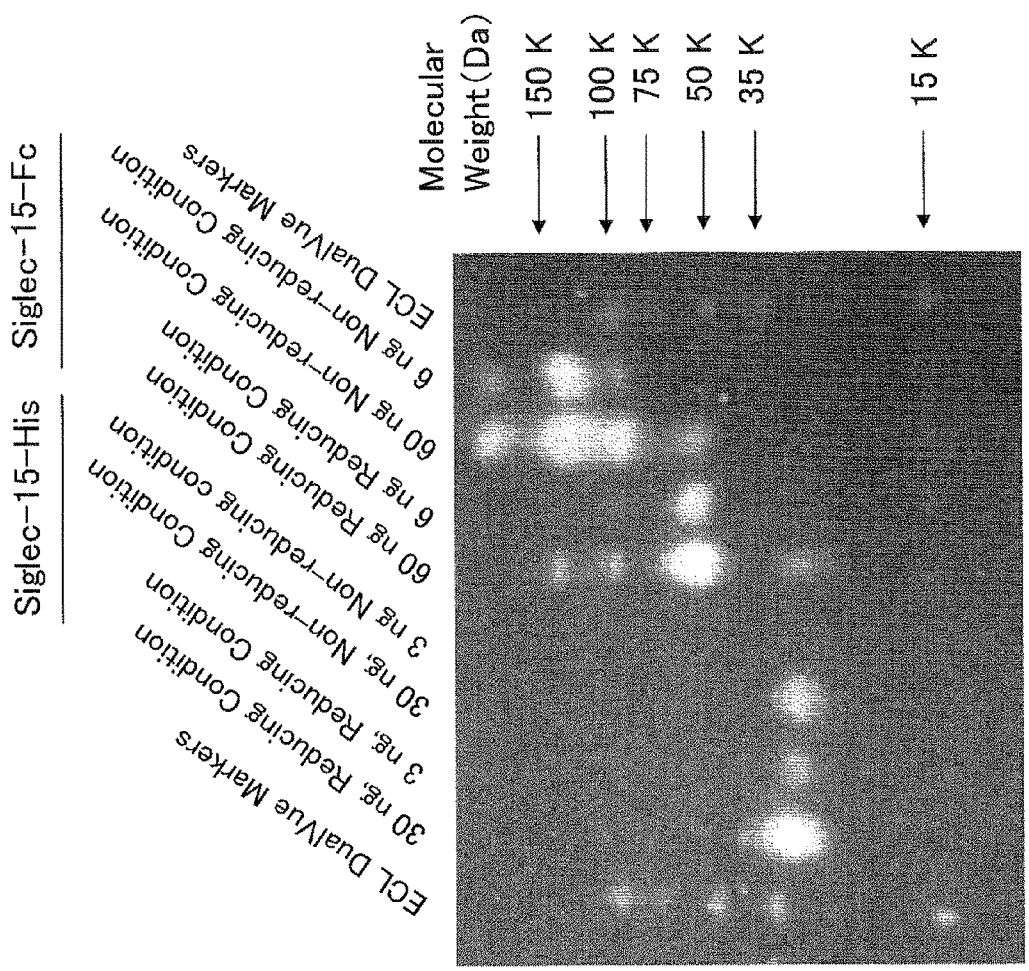
FIG. 11 shows the results of confirming that a purified anti-mouse Siglec-15 polyclonal antibody binds not only to Siglec-15-Fc but also to Siglec-15-His by SDS-polyacrylamide electrophoresis and Western blotting using an anti-mouse Siglec-15 polyclonal antibody and an anti-rabbit IgG-HRP antibody.

|  | Protein Conc. (mg/ml) | Sample Vol. (ml) | Total protein (mg) |
| --- | --- | --- | --- |
| No. 1 | 39.9 | 3.5 | 140 |
| No. 2 | 28.8 | 3.5 | 100 |
| No. 3 | 48.7 | 3.5 | 170 | d) Examination of Reactivity of Purified Anti-Mouse Siglec-15 Polyclonal Antibody to Siglec-15 Extracellular Domain A test for confirming that the anti-mouse Siglec-15 polyclonal antibody prepared in the above item a) binds not only to an Fc tag but also to the extracellular domain of Siglec-15 protein was performed. To 5 μl of the purified mouse Siglec- 15-His sample (Example 8) or 5 µl of the purified mouse Siglec-15-Fc sample, an equivalent amount of an SDS-treatment solution (with or without the addition of 5% 2-mercaptoethanol) was added, and the resulting mixture was heated at 95° C. for 10 minutes. 0.3 µl of each of the thermally treated samples was used for SDS-polyacrylamide electrophoresis, and electrophoresis and transfer (blotting) to a PVDF membrane were performed in the same manner as the method described in the above b) of Example 6. This PVDF membrane was gently shaken in 8 ml of a blocking agent (Block-Ace, manufactured by Snow Brand Milk Products, Co., Ltd.) containing 0.1% Tween 20 at room temperature for 1 hour. To this blocking solution, 1.6 µl of the anti-mouse Siglec-15 polyclonal antibody No. 1 (Table 3) was added, and the PVDF membrane in the solution was gently shaken at room temperature for an additional 1 hour. This PVDF membrane was washed 4 times by gently shaking it in 50 mL of PBS containing 0.01% Tween 20 for 5 minutes. The washed PVDF membrane was immersed in 8 ml of Antibody Diluent ECL Advance Blocking Agent (ECL Advance Western Blotting Detection Kit, manufactured by Amersham Biosciences, Inc.), and anti-rabbit IgG-HRP (manufactured by Amersham Biosciences, Inc.) was added thereto to give a final concentration of 1/200,000. Then, 0.8 µl of an S-protein HRP solution (ECL DualVue Western Blotting Markers, manufactured by Amersham Biosciences, Inc.) was added thereto, and the membrane in the solution was gently shaken at room temperature for an additional 1 hour. This PVDF membrane was washed 4 times by gently shaking it in 50 mL of PBS containing 0.01% Tween 20 for 5 minutes. After washing, the PVDF membrane was treated according to the protocol attached to ECL Advance Western Blotting Detection Kit (manufactured by Amersham Biosciences, Inc.), and the developed color of the band of the protein was detected using an ECL Mini-Camera (manufactured by Amersham Biosciences, Inc.) and Polaroid film (Polapan 3200B, manufactured by Polaroid, Inc.). The results are shown in FIG. 11. From these results, it was shown that the purified anti-mouse Siglec-15 polyclonal antibody also binds to mouse Siglec-15-His, and it could be confirmed that the anti-mouse Siglec-15 polyclonal antibody binds not only to an Fc tag but also to the extracellular domain of the Siglec-15 protein. The same test was performed by repeating it, and it was confirmed that the anti-mouse Siglec-15 polyclonal antibodies No. 2 and No. 3 also bind to mouse Siglec-15-His.

Example 12

Purification of Pre-Immune Tabbit IgG

Blood had previously been collected from each of the three rabbits used in Example 10, before initiation of immunization with mouse Siglec-15-Fc, and pre-immune serum was prepared therefrom. After a 0.8 ml aliquot of each of these serum samples was mixed with one another, 2.4 ml of Dulbecco's PBS (D-PBS, manufactured by Invitrogen, Inc.) was added thereto, and the resulting mixture was filtered through a Millex-GV filter (manufactured by Millipore Co., Ltd.). Then, the resulting serum sample was applied to a HiTrap Protein A 5 ml column (manufactured by Amersham Biosciences, Inc.) which had previously been equilibrated with D-PBS at a flow rate of 1 ml/min. After the column was washed with 50 ml of D-PBS at a flow rate of 2.5 ml/min, a protein adsorbed onto the column was eluted with 50 ml of 0.1 M sodium citrate buffer (pH 3.0) at a flow rate of 2.5 ml/min. The eluate was fractionated at 2.5 ml per fraction into minisorp tubes (manufactured by Nunc, Inc.), and immediately thereafter, 0.65 ml of 1 M Tris was added thereto to neutralize the eluate. After a solution obtained by combining the fractions (fractions 2 to 4) containing the eluted protein was concentrated to 2.5 ml with a centrifugal membrane concentrator Amicon Ultra-15 (manufactured by Millipore Co., Ltd.), the concentrate was applied to a PD-10 desalting column (manufactured by Amersham Biosciences, Inc.) which was previously equilibrated with Otsuka Physiological Saline for Injection (TO-SS) containing 0.01% Tween 20, followed by elution with TO-SS, whereby 3.5 ml of a sample whose solvent was replaced with TO-SS was obtained. The thus purified pre-immune rabbit IgG sample was subjected to polyacrylamide electrophoresis and silver staining by the method described in the above c) of Example 8 to confirm that the IgG protein was sufficiently purified, and then the protein concentration was measured. The thus purified sample was cryopreserved at −80° C. until use.

Example 13

Preparation of Affinity Column Having Mouse Siglec-15-Fc Immobilized Thereon

After 0.54 ml of the solvent of the 18.5 mg/ml purified mouse Siglec-15-Fc solution described in Example 9 (a total of 10 mg of protein) was replaced with a coupling buffer (0.2 M $NaHCO_3$, 0.5 M NaCl, pH 8.3) using a PD-10 desalting column, the resulting solution was concentrated to 1 ml using a centrifugal membrane concentrator Amicon Ultra-4 (manufactured by Millipore Co., Ltd.). After isopropanol in an NHS-activated HiTrap column (1 ml, manufactured by Amersham Biosciences, Inc.) was replaced with 1 mM hydrochloric acid, 1 ml of a coupling buffer containing 10 mg/ml mouse Siglec-15-Fc was injected into the column using a syringe. After a reaction was allowed to proceed at room temperature for 30 minutes, in order to inactivate excess active groups, 6 ml of a blocking buffer (an ethanolamine buffer containing 0.5 M NaCl, pH 8.3), 6 ml of a washing buffer (a sodium acetate buffer containing 0.5 M NaCl, pH 4.0), and 6 ml of the blocking buffer were injected in sequence according to the protocol of Amersham Biosciences, Inc., and then, the column was left at room temperature for 30 minutes. Thereafter, 6 ml of the washing buffer, 6 ml of the blocking buffer, and 6 ml of the washing buffer were injected into the column in sequence again, and finally, the buffer in the column was replaced with 50 mM Tris-HCl buffer (pH 7.0) containing 1 M NaCl and 0.01% Tween 20. This column was stored at 4° C. until use.

Example 14

Figure 12:
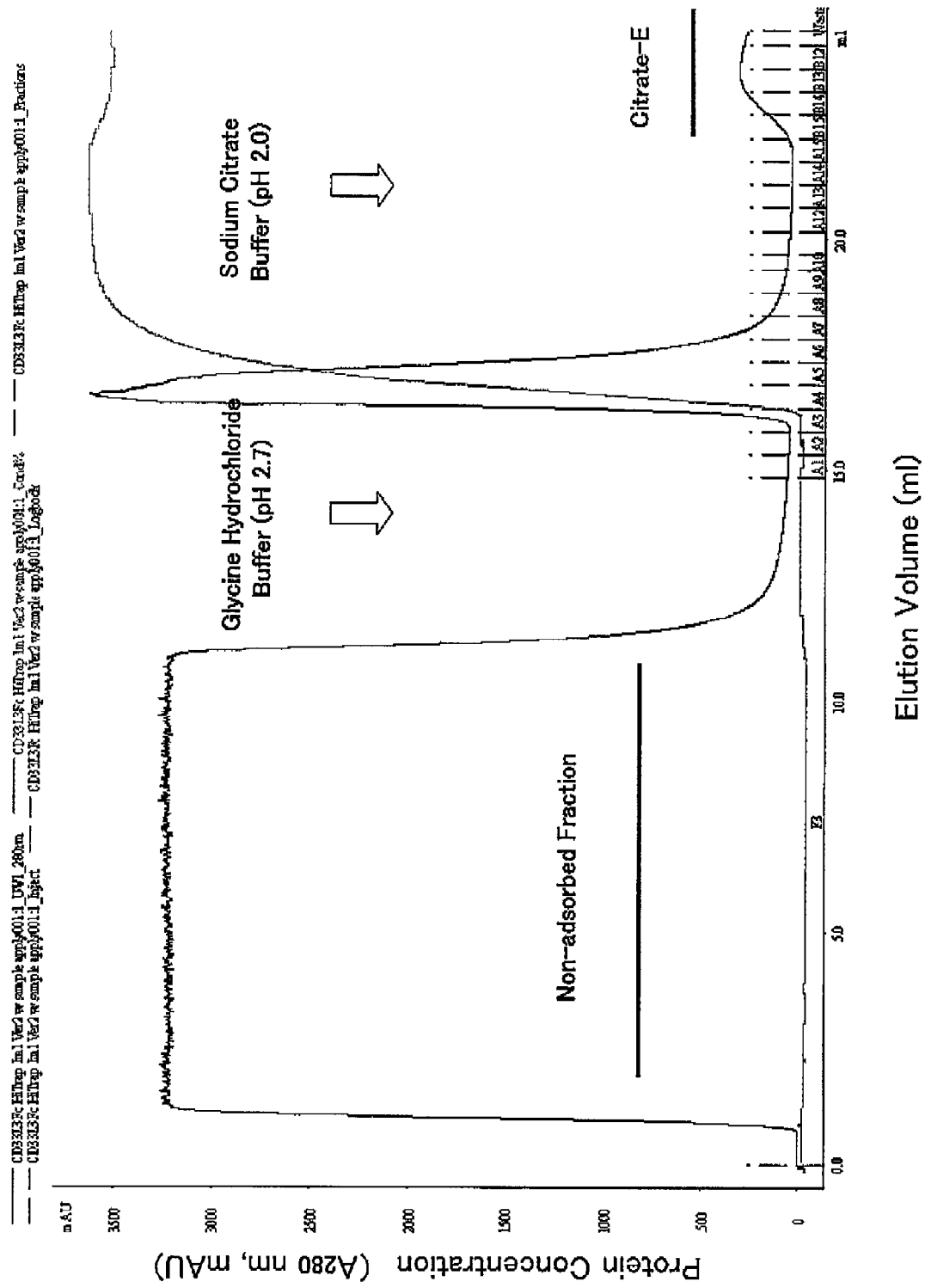
FIG. 12 shows a chromatogram of an anti-mouse Siglec-15 polyclonal antibody purified with an affinity column having mouse Siglec-15-Fc immobilized thereon.
Figure 13:
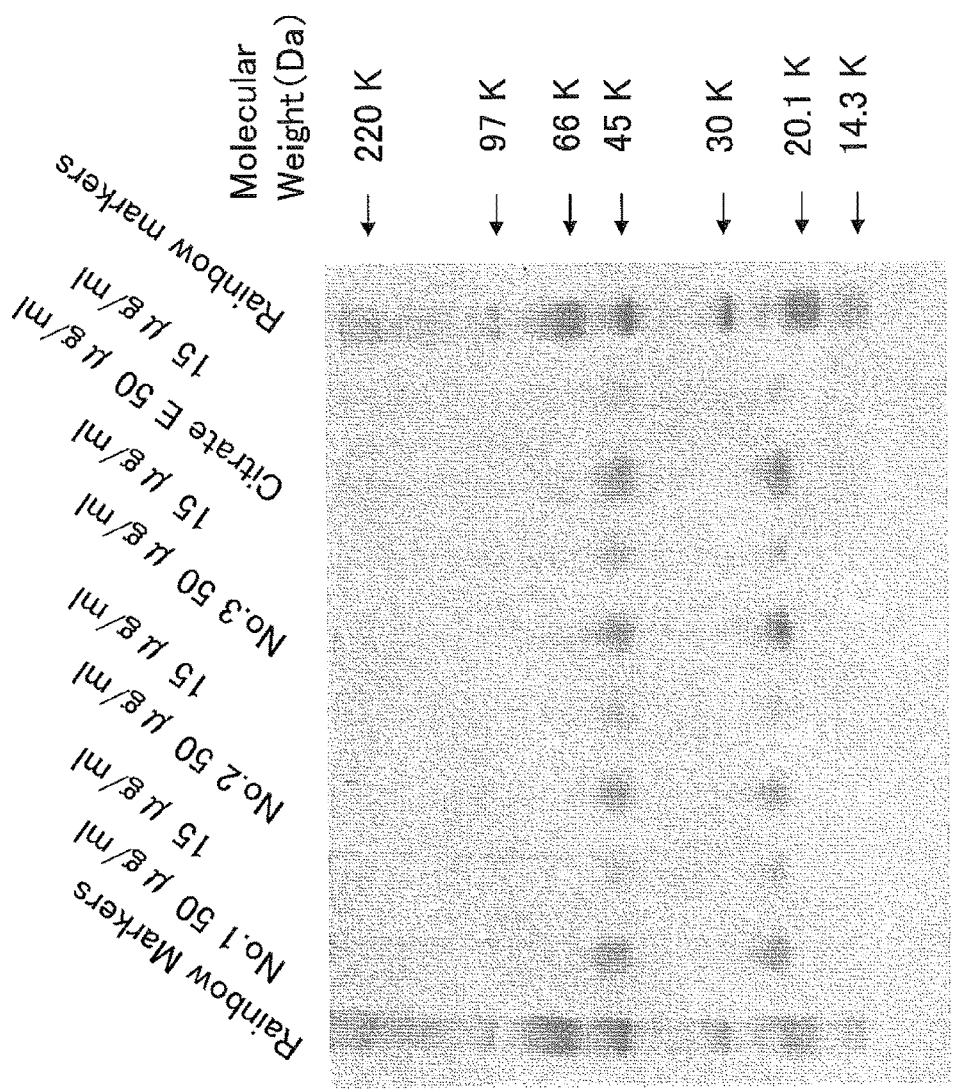
FIG. 13 shows the results of evaluating the purity of mouse Siglec-15-Fc purified by chromatography using an affinity column having mouse Siglec-15-Fc immobilized thereon.

Purification of Anti-Mouse Siglec-15 Polyclonal Antibody with Affinity Column a) Affinity Column Chromatography To 2 ml of each of the purified anti-mouse Siglec-15 polyclonal antibodies Nos. 1, 2 and 3 prepared in Example 11, 8 ml of an Apply Buffer (10 mM Tris-HCl buffer containing 0.15 M NaCl, pH 7.2) was added, and the resulting mixture was applied to the affinity column (Example 13) which had previously been equilibrated with the Apply Buffer at a flow rate of 0.25 ml/min. After the column was washed with 5 ml of the Apply Buffer at a flow rate of 0.25 ml/min, first, a protein adsorbed onto the column was eluted with 5 ml of 0.1 M glycine hydrochloride buffer (pH 2.7) containing 0.5 M NaCl at a flow rate of 0.25 ml/min, and subsequently, a protein adsorbed onto the column was eluted with 5 ml of 0.1 M sodium citrate buffer (pH 2.0) containing 0.5 M NaCl at a flow rate of 0.25 ml/min. The chromatogram of the anti-mouse Siglec-15 polyclonal antibody No. 3 purified with the affinity column is shown in FIG. 12. The eluate was fractionated at 0.5 ml per fraction into mini-sorp tubes (manufactured by Nunc, Inc.), and immediately thereafter, 16 µl of 1 M Tris was added to 0.5 ml of each fraction eluted with the glycine hydrochloride buffer, and 150 µl of 1 M Tris was added to 0.5 ml of each fraction eluted with the sodium citrate buffer to neutralize the eluate. Most of the anti-mouse Siglec-15 polyclonal antibody was eluted with the 0.1 M glycine hydrochloride buffer (pH 2.7) containing 0.5 M NaCl. About 2.5 ml of a solution, obtained by combining the fractions (fractions 3 to 7) in which the IgG protein eluted with the glycine hydrochloride buffer was detected for each lot, was applied to a PD-10 desalting column (manufactured by Amersham Biosciences, Inc.) which had previously been equilibrated with Otsuka Physiological Saline for Injection (TO-SS) containing 0.01% Tween 20, followed by elution with TO-SS, whereby 3.5 ml of a sample whose solvent was replaced with TO-SS was obtained. With respect to the IgG protein fractions (fractions 16 to 19) eluted with the sodium citrate buffer in an amount of about 2.5 ml, the fractions for all the three lots were combined and the resulting solution was concentrated to 2.5 ml with a centrifugal membrane concentrator Amicon Ultra-4 (manufactured by Millipore Co., Ltd.). Then, the concentrate was applied to a PD-10 desalting column (manufactured by Amersham Biosciences, Inc.) which was previously equilibrated with TO-SS, followed by elution with TO-SS, whereby 3.5 ml of a sample (Citrate-E) whose solvent was replaced with TO-SS was obtained. The thus prepared samples were cryopreserved at −80° C. until use.

b) Measurement of Protein Concentration of Affinity-Purified Anti-Mouse Siglec-15 Polyclonal Antibody For the purified anti-mouse Siglec-15 polyclonal antibody samples (the protein fractions eluted from the PD-10 desalting column), the protein concentration was measured with a DC-Protein Assay kit (manufactured by Bio-Rad Laboratories, Inc.) using bovine IgG as a standard sample. The samples in which the protein concentration was measured were prepared such that the antibody concentration was 15 or 50 µg/ml, and subjected to electrophoresis and silver staining in the same manner as in b) of Example 11. The results are shown in FIG. 13. It was shown that an IgG protein composed of a heavy chain having a molecular weight of about 45 kDa and a light chain having a molecular weight of about 21 kDa was efficiently purified and concentrated in the protein fractions eluted from the PD-10 column. As shown in Table 4, about 2.3 to 7.4 mg of an affinity-purified anti-mouse Siglec-15 polyclonal antibody could be prepared in each of lot Nos. 1 to 3 or as Citrate-E fraction.

TABLE 4

|  | Protein Conc. (mg/ml) | Sample Vol. (ml) | Total protein (mg) |
| --- | --- | --- | --- |
| No. 1 | 0.661 | 3.5 | 2.31 |
| No. 2 | 1.715 | 3.5 | 6.00 |
| No. 3 | 2.112 | 3.5 | 7.39 |
| Citrate-E | 1.155 | 3.5 | 4.04 |

Example 15

Figure 14:
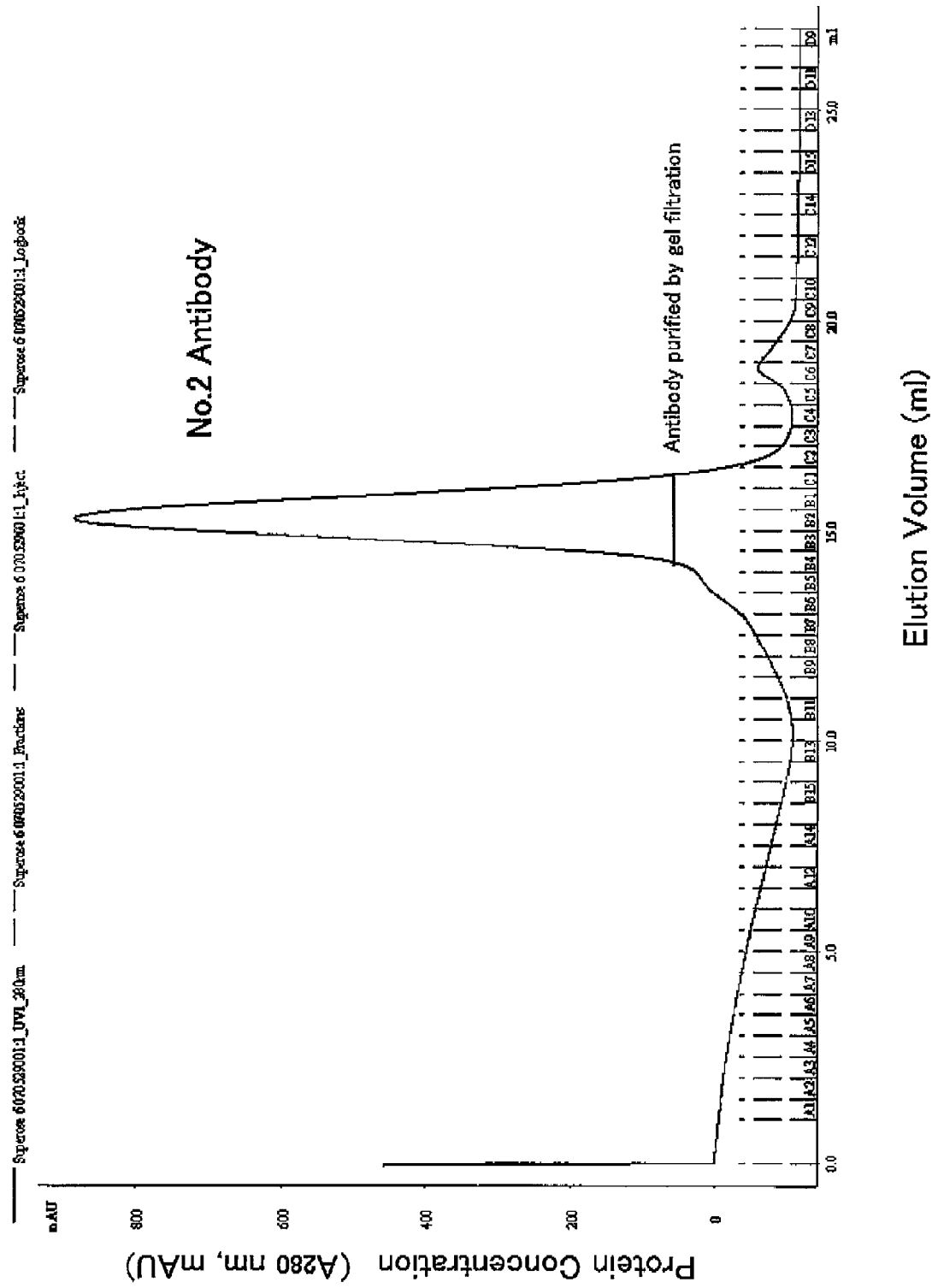
FIG. 14a and FIG. 14b show chromatograms of anti-mouse Siglec-15 polyclonal antibodies purified with a Superose 6 gel filtration column.
Figure 14B:
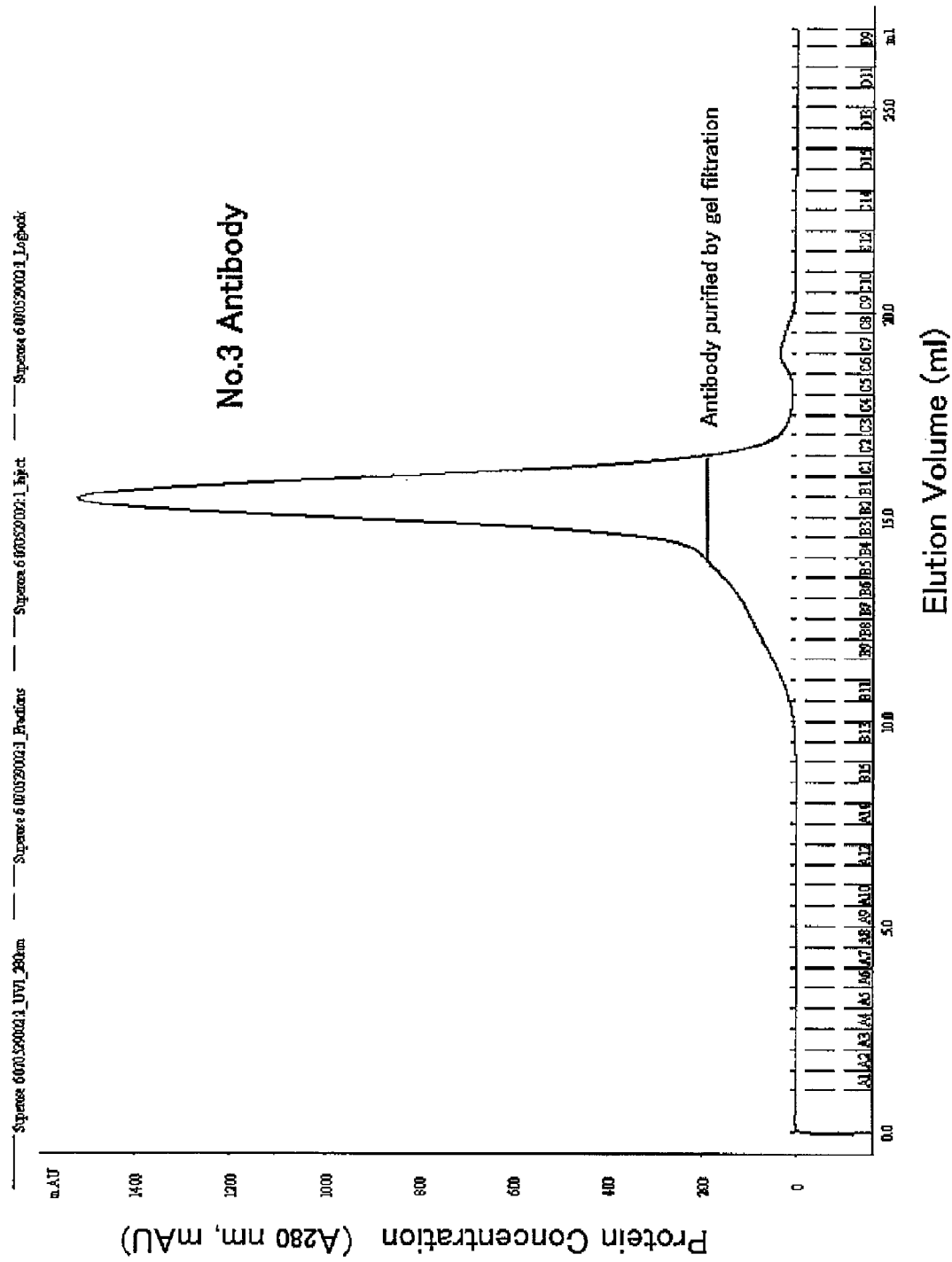

Purification of Affinity-Purified Anti-Mouse Siglec-15 Polyclonal Antibody with Gel Filtration Column a) Superose 6 Column Chromatography In order to completely remove endotoxin and low molecular weight impurities from the affinity-purified anti-mouse Siglec-15 polyclonal antibody prepared in Example 14, purification was further performed with a gel filtration column. 1 ml of each of the affinity-purified anti-mouse Siglec-15 polyclonal antibodies Nos. 2 and 3 was applied to a Superose 6 HR 10/30 column (manufactured by Amersham Biosciences, Inc.) which was previously treated with a pyrogen removing agent PyroCLEAN (manufactured by ALerCHEK, Inc.) and equilibrated with Dulbecco's PBS (D-PBS, manufactured by Invitrogen, Inc.) containing 0.01% Tween 20, followed by elution with D-PBS containing 0.01% Tween 20 at a flow rate of 0.4 ml/min. The chromatograms thereof are shown in FIGS. 14a and 14b. The eluate was fractionated at 0.5 ml per fraction into mini-sorp tubes (manufactured by Nunc, Inc.), and 2.0 ml of a gel filtration-purified anti-mouse Siglec-15 polyclonal antibody sample (fractions 28 to 31) was obtained. The thus prepared sample was cryopreserved at −80° C. until use.

b) Measurement of Protein Concentration of Rabbit IgG Purified with Gel Filtration Column Also for the gel filtration-purified anti-mouse Siglec-15 polyclonal antibody sample (the protein fractions eluted from the Superose 6 column), the protein concentration was measured. As shown in Table 5, the gel filtration-purified anti-mouse Siglec-15 polyclonal antibody in an amount of 2.25 mg and 3.34 mg could be prepared in lot Nos. 2 and 3, respectively.

TABLE 5

|  | Protein Conc. (mg/ml) | Sample Vol. (ml) | Total protein (mg) |
| --- | --- | --- | --- |
| No. 2 | 0.643 | 3.5 | 2.25 |
| No. 3 | 0.955 | 3.5 | 3.34 |

Example 16

Preparation of Mouse Bone Marrow Nonadherent Cells

The femur and tibia were resected from a male ddY mouse at the age of 5 to 8 weeks and soft tissues were removed. Both ends of the femur or tibia were cut off, and D-PBS was injected using a syringe with a 25-gauge injection needle to push out bone marrow cells, which were collected in a centrifugal tube. Centrifugation was performed at room temperature for 5 minutes at 100 g, and the supernatant was removed. To the cell pellet, 1 ml of a hemolytic buffer (Red Blood Cell Lysing Buffer, manufactured by Sigma Co., Ltd.) was added to suspend it, and the resulting suspension was left at room temperature for 5 minutes. 20 ml of D-PBS was added thereto, and the suspension was centrifuged at room temperature for 5 minutes at 100 g, and the supernatant was removed. To the cell pellet, 10 ml of MEM-α medium (manufactured by Invitrogen, Inc.) containing 5 ng/ml of M-CSF (manufactured by R&D systems, Inc.) and 10% fetal bovine serum (FBS) was added to suspend it. Then, the resulting suspension was passed through a cell strainer (40 µm Nylon, manufactured by BD Falcon) to remove aggregates. The resulting cells were transferred to a 75 $cm^2$-T flask (for the use of adherent cells) and cultured overnight in a $CO_2$ incubator. After the overnight culture, the cells which did not adhere to the T-flask were recovered and used as mouse bone marrow nonadherent cells.

Example 17

Effect of Addition of Anti-Mouse Siglec-15 Polyclonal Antibody on Osteoclast Differentiation of Mouse Bone Marrow Nonadherent Cells (Stimulation with RANKL)

Figure 15:
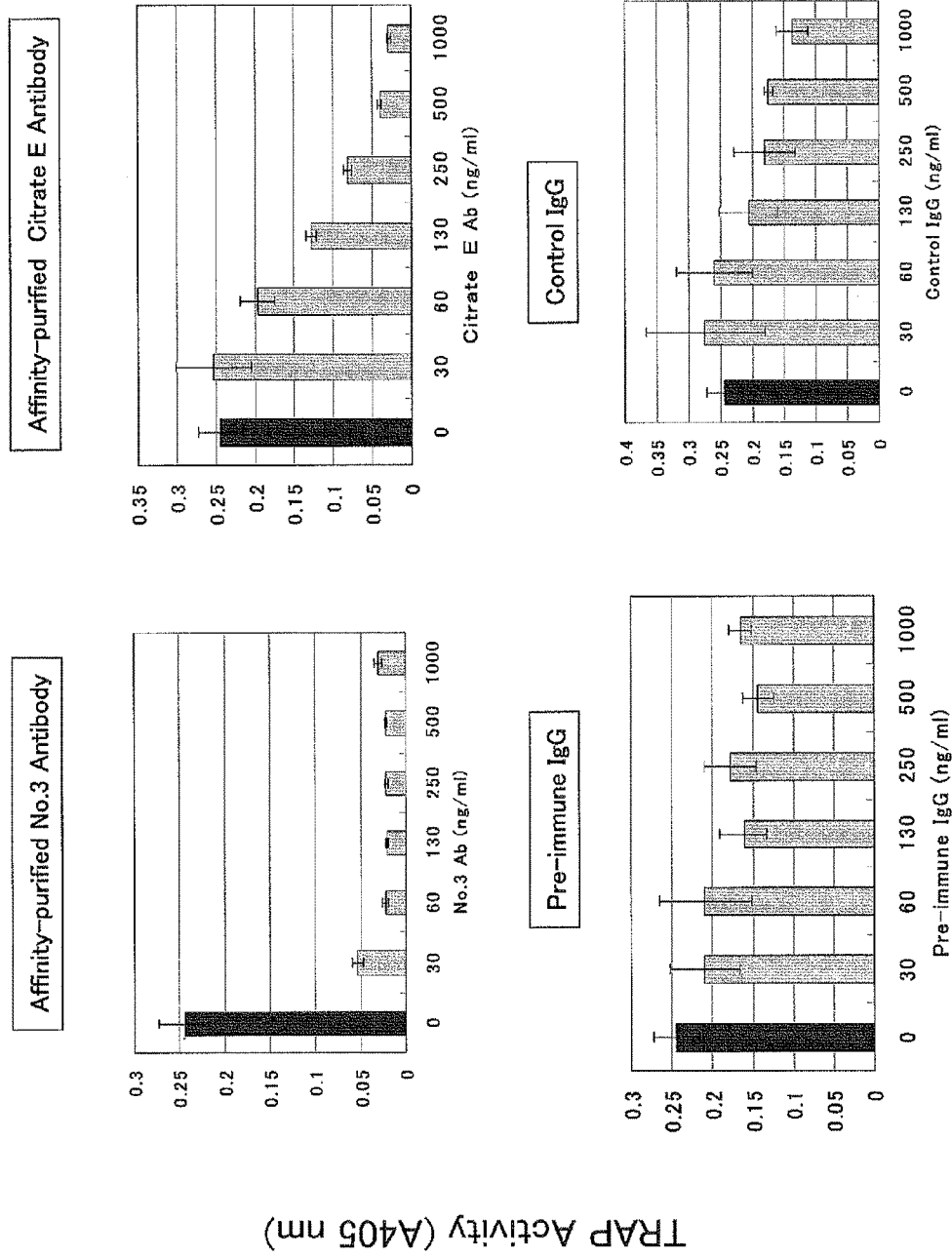
FIG. 15 shows the results of testing the effect of the addition of an affinity-purified anti-mouse Siglec-15 polyclonal antibody on osteoclast differentiation (stimulation with RANKL) of mouse bone marrow nonadherent cells (N=3).
Figure 16:
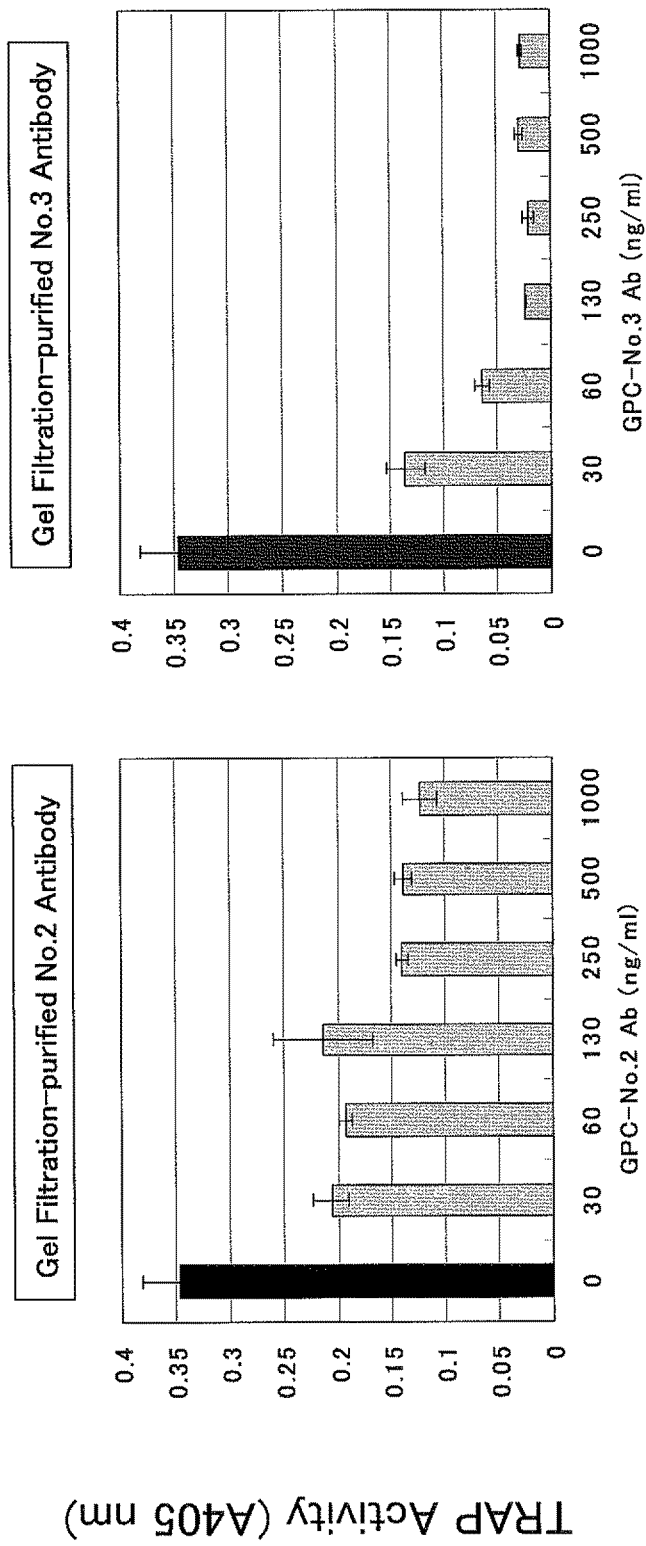
FIG. 16 shows the results of testing the effect of the addition of a gel filtration-purified anti-mouse Siglec-15 polyclonal antibody on osteoclast differentiation (stimulation with RANKL) of mouse bone marrow nonadherent cells based on the enzymatic activity of TRAP (N=3).

By using the anti-mouse Siglec-15 polyclonal antibodies produced in Examples 14 and 15, an effect on osteoclast differentiation of mouse bone marrow nonadherent cells was studied. Mouse bone marrow nonadherent cells prepared by the above-mentioned method in Example 16 were prepared at $1.5\times10^5$ cells/ml in α-MEM medium containing 10% FBS and 10 ng/ml of M-CSF (manufactured by R&D systems, Inc.), and the resulting cell preparation was seeded in each well of a 96-well plate in an amount of 200 μl and the cells were cultured for 2 days in a $CO_2$ incubator. The old culture solution in the 96-well plate was removed, and 100 μl of MEM-α medium containing 10% FBS to which human RANKL (RANKL, manufactured by Peprotech, Inc.) and M-CSF were added to give final concentrations of 20 ng/ml and 10 ng/ml, respectively, was added to each well. To the cell culture solution, the affinity-purified No. 3 antibody, Citrate-E antibody, gel filtration-purified No. 2 antibody, gel filtration-purified No. 3 antibody, pre-immune rabbit IgG (produced in Examples 12, 14, and 15), or commercially available rabbit control IgG (Non-immune Rabbit IgG CLRB00, manufactured by Cedarlane Laboratories Ltd.) was added at a concentration of from 30 to 1,000 ng/ml, and the cells were cultured for an additional 3 days in a $CO_2$ incubator. After completion of the culturing, the activity of tartrate-resistant acid phosphatase (TRAP) of the formed osteoclasts was measured by the following procedure. The culture solution in each well of the 96-well plate was removed by suction, and 50 μl of 50 mM sodium citrate buffer (pH 6.1) containing 1% Triton X-100 was added to each well. Then, the plate was shaken for 5 minutes on a plate shaker to lyse the cells. To each well, 50 μl of a substrate solution (50 mM sodium citrate buffer (pH 6.1) containing 5 mg/ml p-nitrophenyl phosphate and 0.46% sodium tartrate) was added, and the plate was incubated at room temperature for 5 minutes. After the incubation, 50 μl of a 1 N sodium hydroxide solution was added to each well of the 96-well plate to stop the enzymatic reaction. After stopping the enzymatic reaction, an absorbance of each well at 405 nm was measured, and the measurement was used as an index of TRAP activity. The results are shown in FIGS. 15 and 16. A significant inhibition of TRAP activity was not observed in the cases of the pre-immune rabbit IgG and the commercially available rabbit control IgG. On the other hand, a significant inhibition of TRAP activity was observed in the cases of the affinity-purified No. 3 antibody at 30 ng/ml or higher and the Citrate-E antibody at about 130 ng/ml or higher (FIG. 15). Also in the case of the gel filtration-purified No. 3 antibody, a significant inhibition of TRAP activity was observed at 30 ng/ml or higher. Moreover, a more potent inhibitory activity was observed in the case of the gel filtration-purified No. 3 antibody than in the case of the gel filtration-purified No. 2 antibody (FIG. 16). Since the activity of inhibiting osteoclast formation was observed also in the gel filtration-purified antibody, it was shown that the activity of inhibiting osteoclast formation observed in the anti-mouse Siglec-15 polyclonal antibody is not attributed to endotoxin or low molecular weight impurities contained in the antibody sample, but is attributed to the activity of the antibody molecule itself. From the above results, it was shown that the anti-mouse Siglec-15 polyclonal antibody has a potent inhibitory effect on osteoclast formation (osteoclast differentiation and maturation).

Example 18

Neutralization by Antigen of Inhibition of Osteoclast Differentiation of Mouse Bone Marrow Nonadherent Cells by Addition of Anti-Mouse Siglec-15 Polyclonal Antibody (Stimulation with RANKL)

Figure 17:
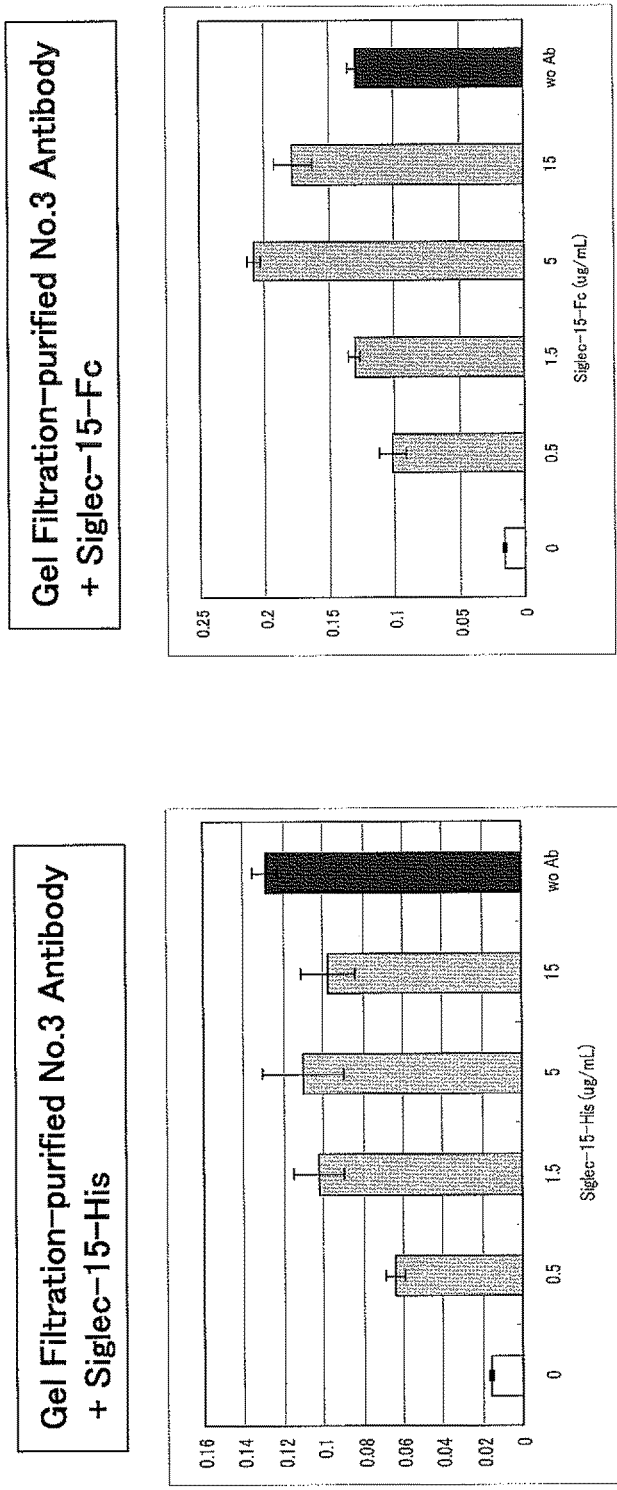
FIG. 17 shows the results of testing neutralization by an antigen of inhibition of osteoclast differentiation (stimulation with RANKL) of mouse bone marrow nonadherent cells by the addition of an anti-mouse Siglec-15 polyclonal antibody based on the enzymatic activity of TRAP (N=3).

It was confirmed that the effect of the anti-mouse Siglec-15 polyclonal antibody depends on the binding thereof to an antigen by previously adding the antigen to the anti-mouse Siglec-15 polyclonal antibody to form an immune precipitate. To 10 μg/ml of the affinity-purified No. 3 antibody produced in Example 14, the mouse Siglec-15-His or Siglec-15-Fc prepared in Example 8 or 9 was added at a concentration of 10, 30, 100 or 300 μg/ml, and the resulting mixture was incubated at 37° C. for 2 hours. After the incubation, the mixture was centrifuged for 5 minutes by Chibitan, and the resulting supernatant was sterilized by filtration through a Millex-GV filter (manufactured by Millipore Co., Ltd.). Mouse bone marrow nonadherent cells prepared by the method in Example 16 were seeded in a 96-well plate at 200 μl/well, and the cells were cultured for 2 days in a $CO_2$ incubator. The old culture solution in the 96-well plate was removed, and 100 μl of MEM-α medium containing 10% FBS to which human RANKL (RANKL, manufactured by Peprotech, Inc.) and M-CSF were added to give final concentrations of 20 ng/ml and 10 ng/ml, respectively, was added to each well. To the cell culture solution, each of the test samples prepared in the above was added at 1/200 (v/v), and the cells were cultured for an additional 3 days in a $CO_2$ incubator. After completion of the culturing, the activity of tartrate-resistant acid phosphatase (TRAP) of the formed osteoclasts was measured by the method described in Example 17. The results are shown in FIG. 17. In both cases where the antibody was neutralized by Siglec-15-His and where the antibody was neutralized by Siglec-15-Fc, the effect of the antibody was neutralized and lost. These results demonstrated that the inhibitory effect of the anti-mouse Siglec-15 polyclonal antibody on osteoclast formation is due to binding thereof to Siglec-15 protein and blocking of its function.

Example 19

Effect of Addition of Anti-Mouse Siglec-15 Polyclonal Antibody on Osteoclast Differentiation of Mouse Bone Marrow Nonadherent Cells (Stimulation with TNF)

Figure 18:
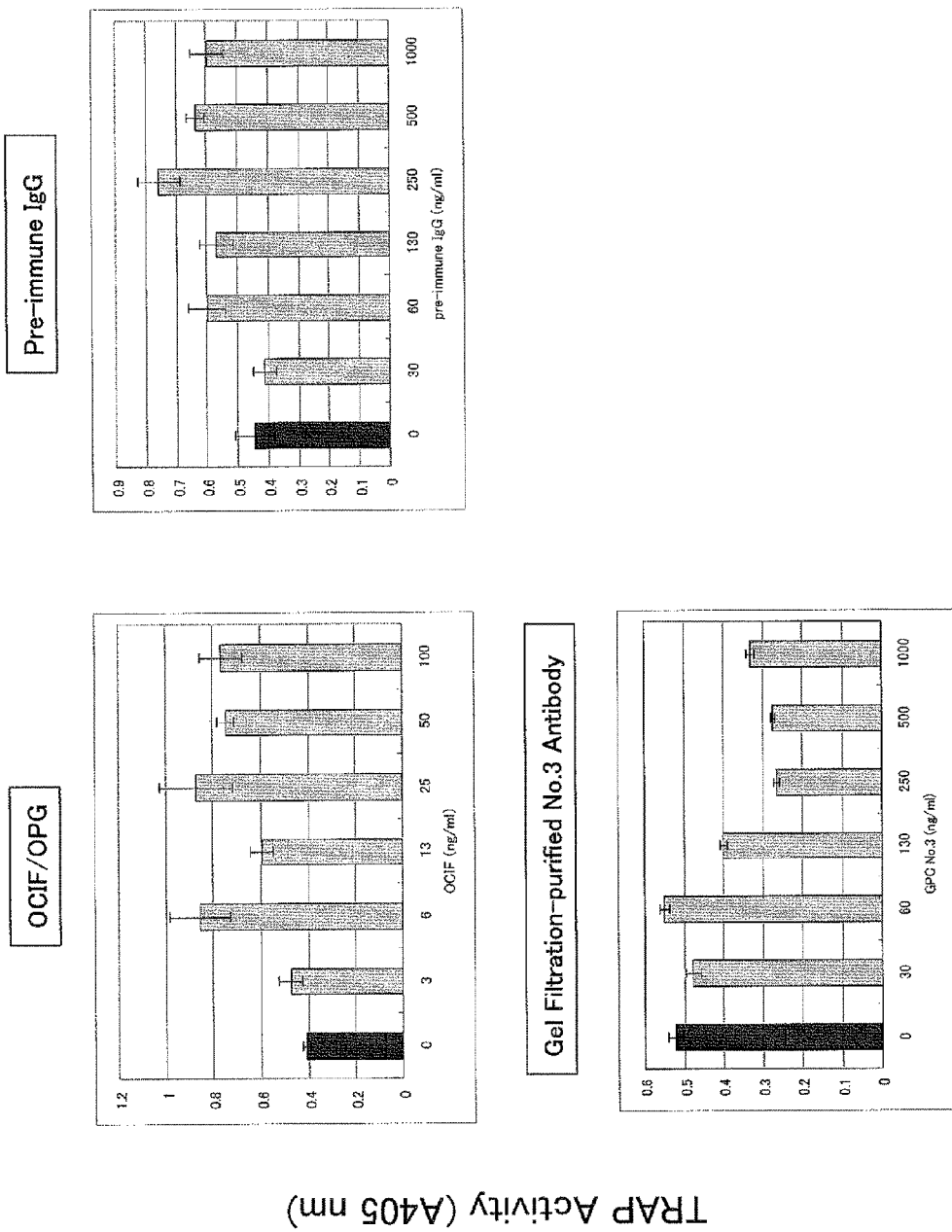
FIG. 18 shows the results of testing the effect of the addition of an anti-mouse Siglec-15 polyclonal antibody on osteoclast differentiation (stimulation with TNF-α) of mouse bone marrow nonadherent cells based on the enzymatic activity of TRAP (N=3).

By using the anti-mouse Siglec-15 polyclonal antibody, an effect on osteoclast differentiation of mouse bone marrow nonadherent cells by stimulation with TNF was studied. Mouse bone marrow nonadherent cells prepared by the method in Example 16 were prepared at $1.5\times10^5$ cells/ml in α-MEM medium containing 10% fetal bovine serum (FBS), 10 ng/ml of M-CSF and 2 ng/ml of TGF-β (manufactured by R&D systems, Inc.), and the resulting cell preparation was seeded in each well of a 96-well plate in an amount of 200 μl and the cells were cultured for 2 days in a $CO_2$ incubator. The old culture solution in the 96-well plate was removed, and 100 μl of MEM-α medium containing 10% FBS to which human recombinant TNF-α (manufactured by R&D systems, Inc.) and M-CSF were added to give final concentrations of 30 ng/ml and 10 ng/ml, respectively, was added to each well. To the cell culture solution, the pre-immune IgG produced in Example 12 or the gel filtration-purified anti-mouse Siglec-15 No. 3 antibody produced in Example 15 was added at a concentration of from 30 to 1,000 ng/ml, and the cells were cultured for an additional 3 days in a $CO_2$ incubator. At the same time, a well in which the cells were cultured by adding human recombinant OCIF/OPG prepared by the method described in the description of Patent No. WO 96/26217 at a concentration of from 3 to 100 ng/ml was also prepared. After completion of the culturing, the activity of tartrate-resistant acid phosphatase (TRAP) of the formed osteoclasts was measured by the method described in Example 17. The results are shown in FIG. 18. In the cases of the pre-immune IgG and OCIF/OPG, a significant inhibition of TRAP activity was not observed. On the other hand, in the case of the gel filtration-purified anti-mouse Siglec-15 No. 3 antibody, about 50% inhibition of TRAP activity was observed at a concentration of 250 ng/ml or higher. From these results, it was shown that the anti-mouse Siglec-15 polyclonal antibody can inhibit also TNF-induced osteoclast formation (osteoclast differentiation and maturation) which cannot be inhibited by OCIF/OPG.

Figure 19:
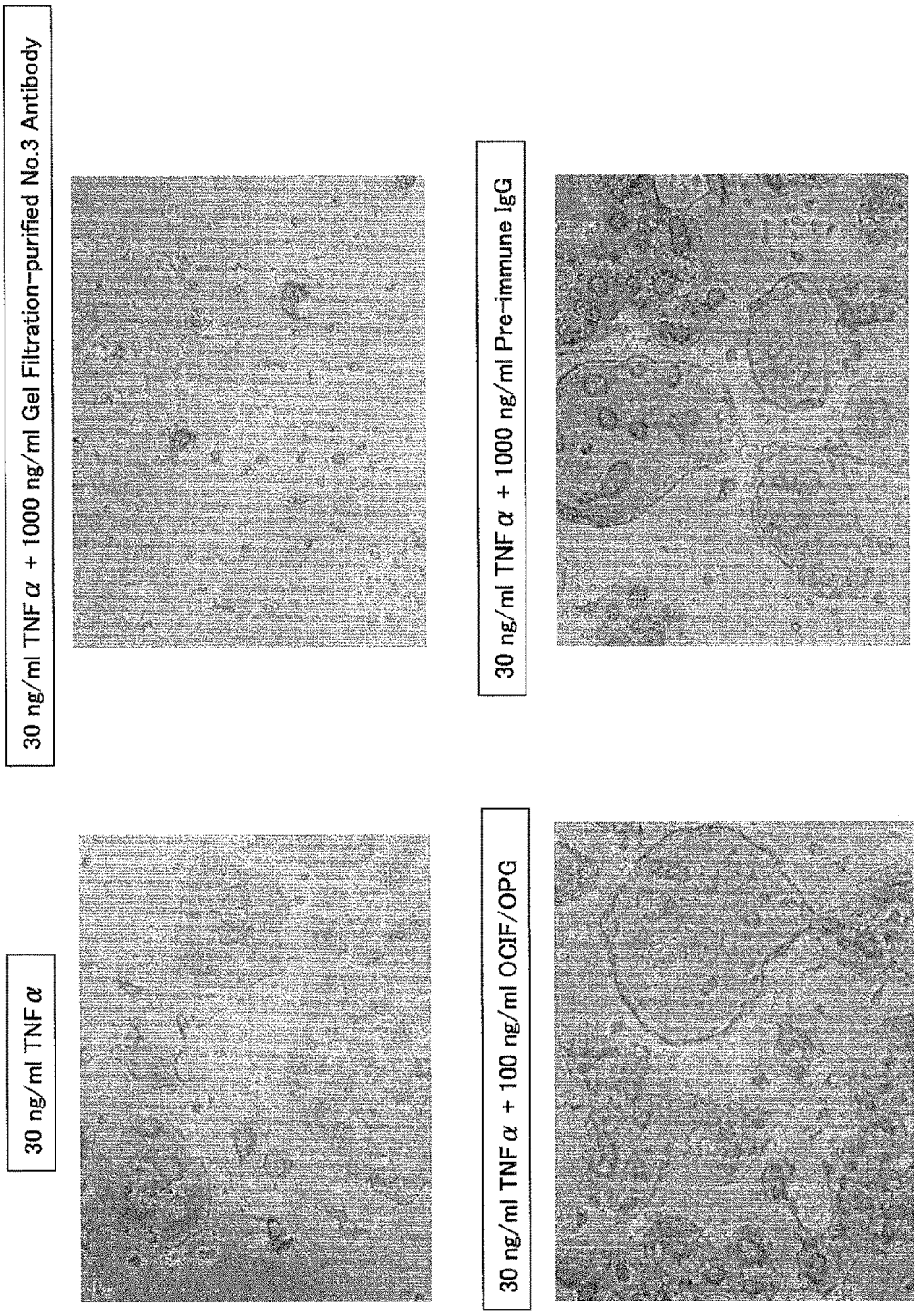
FIG. 19 shows photomicrographs used for evaluating the effect of the addition of an anti-mouse Siglec-15 polyclonal antibody on osteoclast differentiation (stimulation with TNF-α) of mouse bone marrow nonadherent cells by TRAP staining.

For each well of a 96-well plate prepared by performing culturing in the same manner as described above, TRAP staining was performed using a Leukocyte Acid Phosphatase kit (manufactured by Sigma Co., Ltd.) according to the protocol attached to the kit, and the formation of TRAP-positive multinucleated osteoclasts was observed. As a result, the formation of TRAP-positive giant multinucleated osteoclasts was inhibited by the addition of the anti-mouse Siglec-15 polyclonal antibody (FIG. 19). Since mononuclear osteoclasts were formed even in the case where the anti-mouse Siglec-15 polyclonal antibody was added, it was shown that the anti-mouse Siglec-15 polyclonal antibody strongly inhibits the process of cell fusion in osteoclast differentiation and maturation induced by TNF.

Example 20

Effect of Addition of Anti-Mouse Siglec-15 Polyclonal Antibody on Osteoclast Differentiation of Mouse Bone Marrow-Derived Primary Cultured Cells (TRAP Activity)

Figure 20:
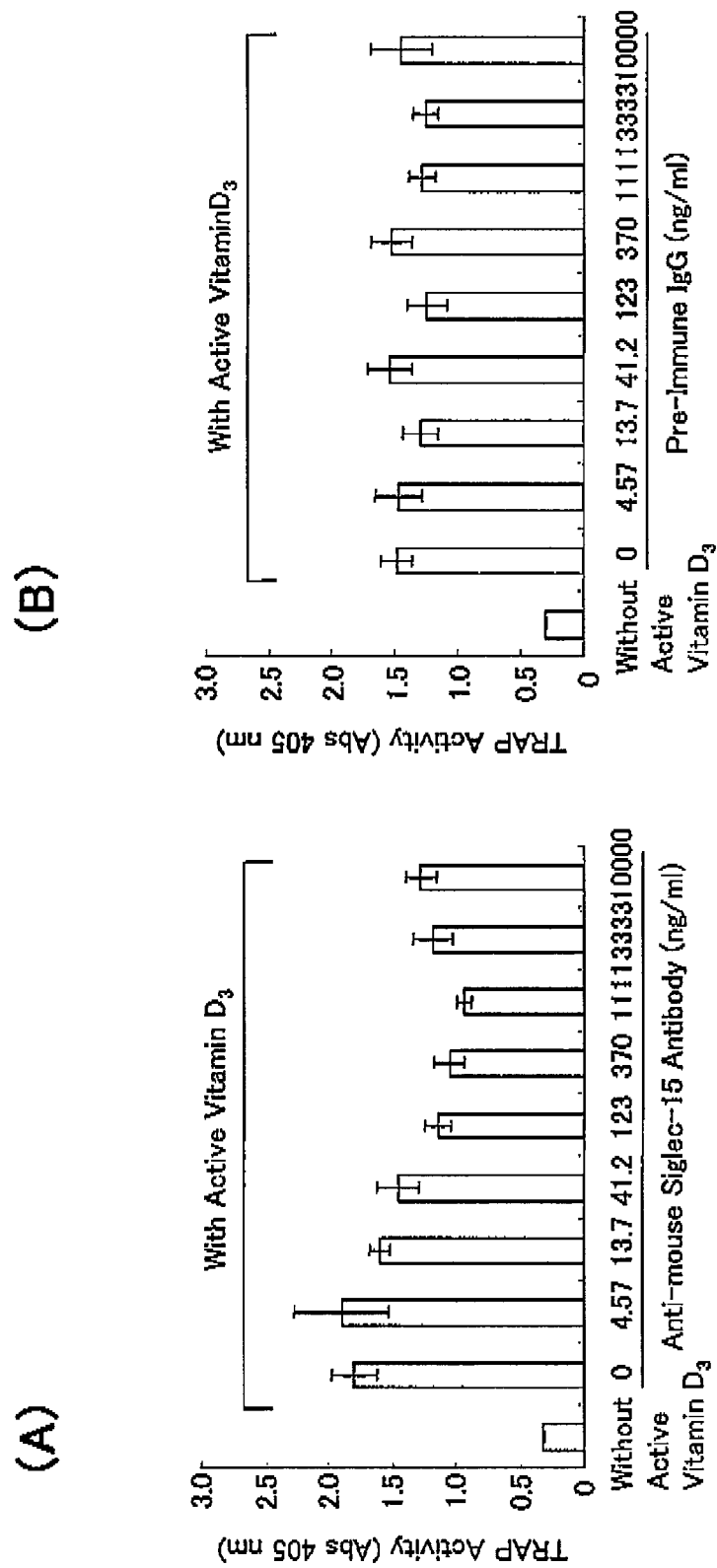
FIG. 20 shows graphs depicting, by the enzymatic activity of TRAP, the inhibition of osteoclast differentiation (stimulation with active vitamin $D_3$) from mouse bone marrow cells by the addition of an anti-mouse Siglec-15 polyclonal antibody (N=6).

A male ddY mouse at the age of 7 weeks was euthanized by cervical dislocation under ether anesthesia and the femur and tibia were resected. After soft tissues were removed, both ends of the femur or tibia were cut off Then, α-MEM medium containing 10% fetal bovine serum was injected into the bone marrow using a syringe barrel with a 25-gauge injection needle, and bone marrow cells were collected. After the number of cells was counted, the cells were prepared at $5 \times 10^6$ cells/ml in α-MEM medium containing 10% fetal bovine serum. The resulting cell preparation was plated in a 96-well plate at 100 µl/well, and active vitamin $D_3$ (manufactured by Sigma Co., Ltd.) was added thereto to give a final concentration of $2 \times 10^{-8}$ M. To this cell culture supernatant, the affinity-purified anti-mouse Siglec-15 No. 3 antibody produced in Example 14 or the pre-immune rabbit IgG produced in Example 12 was added to give a final concentration of 4.57, 13.7, 41.2, 123, 370, 1,111, 3,333, or 10,000 ng/ml, and the cells were cultured for 8 days in a $CO_2$ incubator. Incidentally, the medium replacement and addition of a test substance were performed on days 3 and 6. The culture supernatant was removed on day 8 of culture, and 10% neutral formalin was added to fix the cells. After fixing the cells, the cells were washed twice with distilled water, and a TRAP substrate solution (15 mM p-nitrophenyl phosphate, 50 mM sodium tartrate, 0.1 M sodium acetate buffer (pH 5.0)) was added thereto at 100 µl/well, and a reaction was allowed to proceed at room temperature for 30 minutes. Then, 1 N NaOH was added thereto at 50 µl/well to stop the reaction, and an absorbance at 405 nm was measured using a microplate reader, whereby the TRAP activity in the cells was evaluated. As a result, the TRAP activity was inhibited depending on the dose of the added anti-mouse Siglec-15 polyclonal antibody (FIG. 20-A). On the other hand, in the case where the pre-immune IgG was added, a decrease in the TRAP activity was not observed (FIG. 20-B). In this manner, it was revealed that the formation of TRAP-positive osteoclasts from mouse bone marrow cells induced by active vitamin $D_3$ is inhibited by the antibody specifically binding to Siglec-15.

Example 21

Effect of Addition of Anti-Mouse Siglec-15 Polyclonal Antibody on Cell Fusion of Osteoclasts from Mouse Bone Marrow-Derived Primary Cultured Cells (TRAP Staining)

Figure 21:
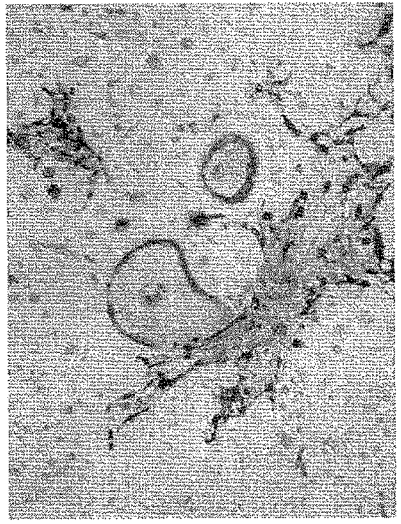
FIG. 21 shows photomicrographs depicting, by TRAP staining, the inhibition of giant osteoclast formation (stimulation with active vitamin $D_3$) from mouse bone marrow cells by the addition of an anti-mouse Siglec-15 polyclonal antibody.
Figure 21:
Figure 21:
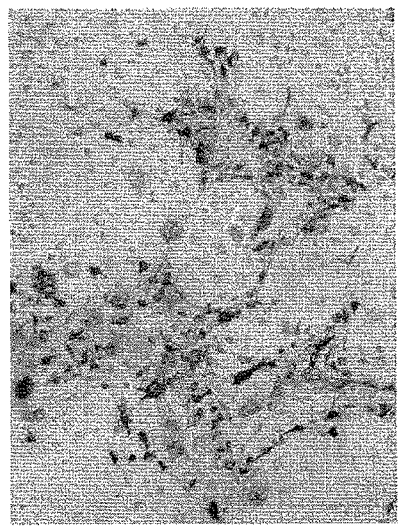
Figure 21:
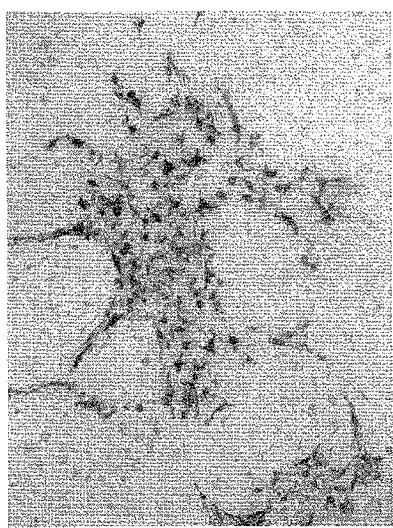
Figure 22:
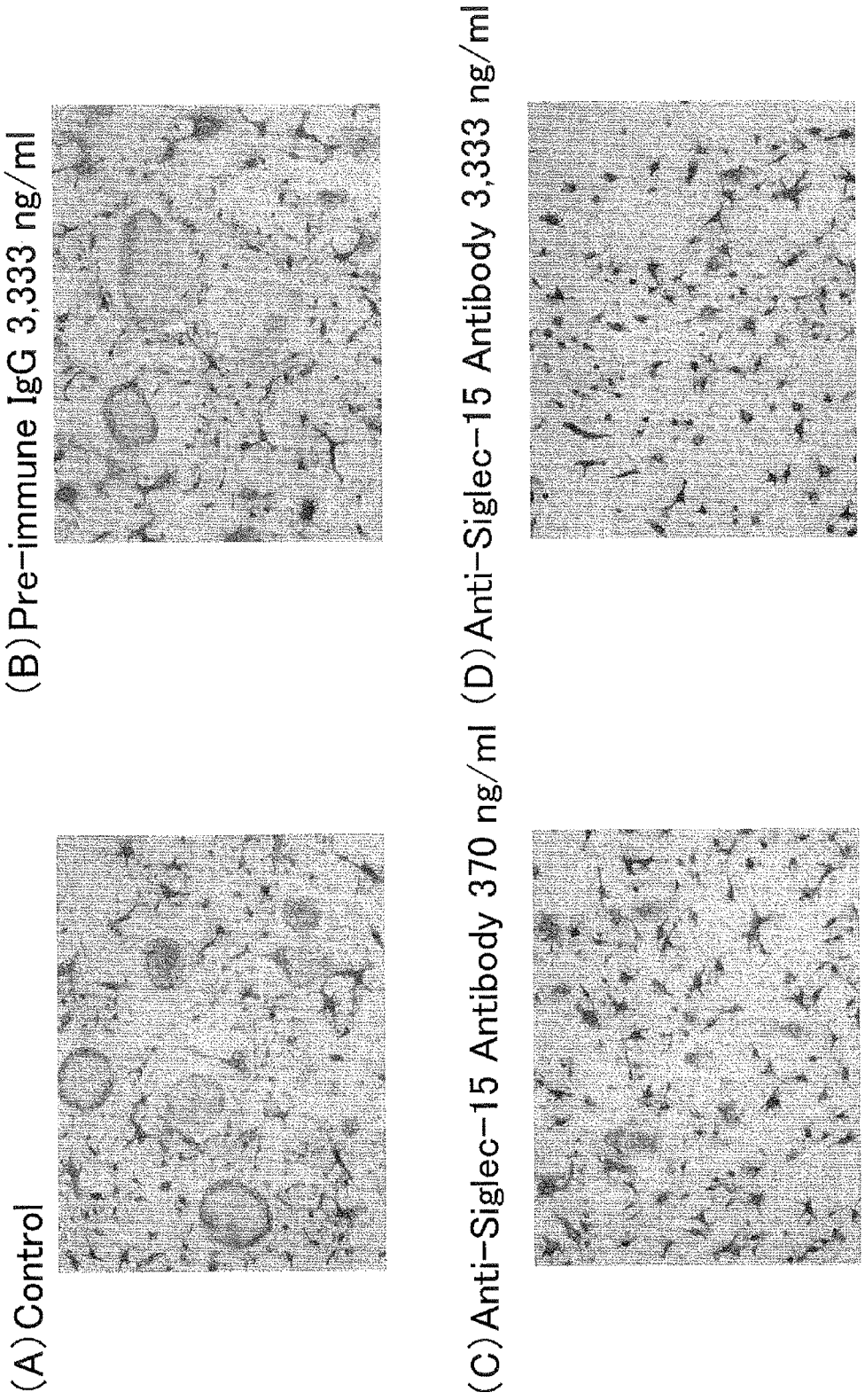
FIG. 22 shows photomicrographs depicting, by TRAP staining, the inhibition of giant osteoclast formation (stimulation with human RANKL) from mouse bone marrow cells by the addition of an anti-mouse Siglec-15 polyclonal antibody.

A male ddY mouse at the age of 7 weeks was euthanized by cervical dislocation under ether anesthesia and the femur and tibia were resected. After soft tissues were removed, both ends of the femur or tibia were cut off. Then, α-MEM medium containing 10% fetal bovine serum was injected into the bone marrow using a syringe barrel with a 25-gauge injection needle, and bone marrow cells were collected. After the number of cells was counted, the cells were prepared at $5 \times 10^6$ cells/ml in α-MEM medium containing 10% fetal bovine serum. The resulting cell preparation was plated in a 96-well plate at 100 µl/well. By adding active vitamin $D_3$ (manufactured by Sigma Co., Ltd.) at a final concentration of $2 \times 10^{-8}$ M or human RANKL (manufactured by PeproTech Inc.) at a final concentration of 80 ng/ml to this culture supernatant as an osteoclast differentiation-inducing factor, cell culture supernatants were prepared. To each of these cell culture supernatants, the affinity-purified anti-mouse Siglec-15 No. 3 antibody produced in Example 14 was added to give a final concentration of 370 or 3,333 ng/ml, or the pre-immune rabbit IgG produced in Example 12 was added to give a final concentration of 3,333 ng/ml. In the culture system of inducing osteoclast differentiation by active vitamin $D_3$, the cells were cultured for 8 days in a $CO_2$ incubator, and in the system of inducing the differentiation by human RANKL, the cells were cultured for 6 days in a $CO_2$ incubator. Incidentally, the medium replacement and addition of a test substance were performed on days 3 and 6. After the culturing, the supernatant was removed, and 10% neutral formalin was added to fix the cells. After fixing the cells, the cells were washed twice with distilled water, and a TRAP staining solution (0.27 mM naphthol AS-MX phosphate (manufactured by Sigma Co., Ltd.), 1.6 mM fast red violet LB salt (manufactured by Sigma Co., Ltd.), 1% dimethylformamide, 50 mM sodium tartrate, 0.1 M sodium acetate buffer (pH 5.0)) was added at 100 µl/well, and a reaction was allowed to proceed at room temperature for 5 minutes. Then, the cells were washed twice with distilled water, and then, observed by microscopy. As a result, in the case where osteoclast differentiation was induced by either active vitamin $D_3$ (FIG. 21) or human RANKL (FIG. 22), cell fusion of osteoclasts was inhibited by the addition of the anti-mouse Siglec-15 polyclonal antibody, and the formation of giant osteoclasts was not observed. On the other hand, in the case where the pre-immune IgG was added, such inhibition of cell fusion of osteoclasts was not observed. In this manner, it was revealed that multinucleation and cell fusion of TRAP-positive osteoclasts from mouse bone marrow cells induced by active vitamin $D_3$ or human RANKL are inhibited by the antibody specifically binding to Siglec-15.

Example 22

Effect of Addition of Anti-Mouse Siglec-15 Polyclonal Antibody on Cell Fusion of Osteoclasts from RAW 264.7 Cells (TRAP Staining)

a) Production of Antigenic Protein-Absorbed Anti-Mouse Siglec-15 Polyclonal Antibody Five mixed solutions (A to E) were prepared using D-PBS (manufactured by Invitrogen, Inc.) containing 0.01% Tween 20, such that the respective concentrations of the affinity-purified anti-mouse Siglec-15 No. 3 antibody produced in Example 14, the mouse Siglec-15-His protein and the mouse Siglec-15-Fc protein produced in Examples 8 and 9 were as shown in Table 6. These mixed solutions were incubated at 37° C. for 2 hours and centrifuged at 20,000×g for 10 minutes. The resulting supernatants were used as 20-fold concentration test samples.

TABLE 6

|  | A | B | C | D | E |
|---|---|---|---|---|---|
| anti-Siglec-15 antibody | 20 | 20 | 20 | 20 | 20 |
| Siglec-15-Fc | 0 | 20 | 200 | 0 | 0 |
| Siglec-15-His | 0 | 0 | 0 | 20 | 200 |

(Unit: μg/ml)

b) Evaluation Using RAW 264.7 by TRAP Staining

Figure 23:
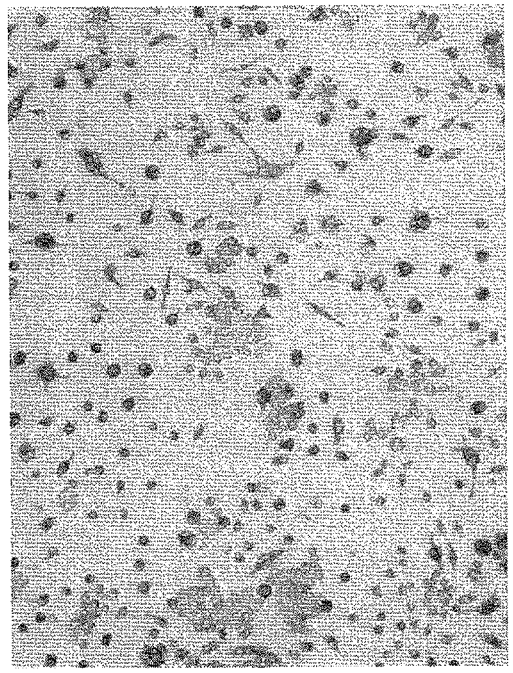
FIG. 23 shows photomicrographs depicting, by TRAP staining, the inhibition of giant osteoclast formation (stimulation with human RANKL) from RAW 264.7 cells by the addition of an anti-mouse Siglec-15 polyclonal antibody and cancellation of the inhibitory effect by soluble Siglec-15.
Figure 23:
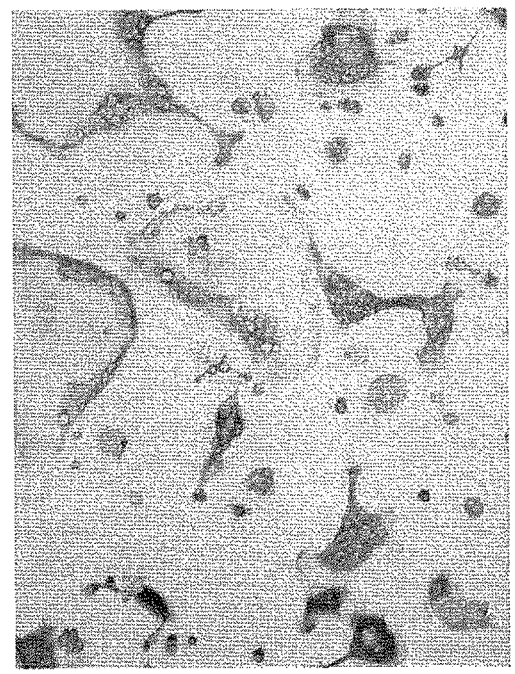
Figure 23:
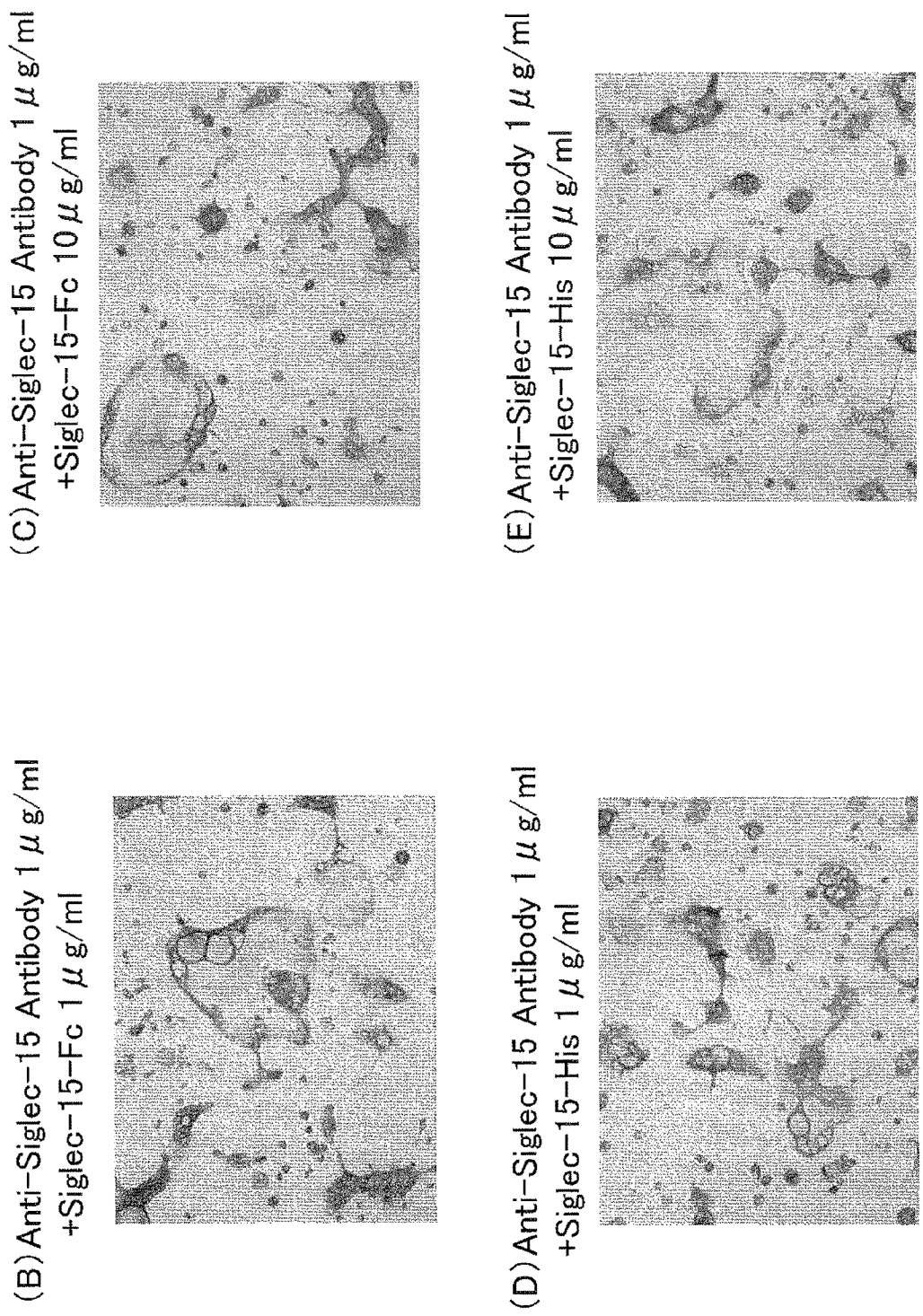

RAW 264.7 was prepared at $2.25 \times 10^4$ cells/ml in α-MEM medium containing 10% fetal bovine serum, and the resulting cell preparation was plated in a 96-well plate at 200 μl/well, and human RANKL (manufactured by PeproTech Inc.) was added thereto to give a final concentration of 40 ng/ml. To this cell culture supernatant, each of the test samples A to E produced in a) was added at a final concentration of 1/20, and the cells were cultured for 3 days in a $CO_2$ incubator. After the culturing, the supernatant was removed, and 10% neutral formalin was added to fix the cells. After fixing the cells, the cells were washed twice with distilled water, and a TRAP staining solution (0.27 mM naphthol AS-MX phosphate (manufactured by Sigma Co., Ltd.), 1.6 mM fast red violet LB salt (manufactured by Sigma Co., Ltd.), 1% dimethylformamide, 50 mM sodium tartrate, 0.1 M sodium acetate buffer (pH 5.0)) was added at 100 μl/well, and a reaction was allowed to proceed at room temperature for 5 minutes. Then, the cells were washed twice with distilled water, and then, observed by microscopy. As a result, by adding the anti-mouse Siglec-15 polyclonal antibody, cell fusion of osteoclasts was significantly inhibited (FIG. 23-A) as compared with the case of the control (FIG. 23-0) without the addition of the test sample. However, by absorbing the anti-mouse Siglec-15 polyclonal antibody in the mouse Siglec-15-Fc protein used as the immunizing antigen, the inhibitory effect of the anti-mouse Siglec-15 polyclonal antibody on cell fusion of osteoclasts was cancelled (FIGS. 23-B, C). Further, also by absorbing the anti-mouse Siglec-15 polyclonal antibody in the mouse Siglec-15-His protein, the inhibitory effect of the anti-mouse Siglec-15 polyclonal antibody on cell fusion of osteoclasts was cancelled in the same manner (FIGS. 23-D, E). From these results, it was revealed that multinucleation and cell fusion of TRAP-positive osteoclasts from RAW 264.7 cells induced by human RANKL are inhibited by the antibody specifically binding to Siglec-15. Incidentally, the results represented by the symbols A to E in FIG. 23 correspond to the test samples A to E in Table 6, respectively.

Example 23

Establishment of Rat Anti-Mouse Siglec-15 Monoclonal Antibody-Producing Hybridoma a) Preparation of Antigen The mouse Siglec-15-His protein produced in Example 8 was prepared at 100 μg/0.5 ml, and an equivalent amount of an adjuvant was added thereto and an emulsion was produced using a glass syringe. As the adjuvant, Freund's complete adjuvant (FCA, Manufactured by Difco Laboratories, Inc.) was used only for the first immunization, and Freund's incomplete adjuvant (FICA, Manufactured by Difco Laboratories, Inc.) was used for the second and subsequent immunizations.

b) Immunization of Rat

Four rats (Wistar, female, 6 weeks of age, purchased from CLEA Japan, Inc.) were used as immunized animals. The emulsion obtained in a) was injected subcutaneously and intradermally using a 27 G injection needle such that the amount of the antigen was 50 μg per rat. Immunization was performed a total of 4 times every 7 days after the first immunization. A small amount (200 μl) of the blood was collected from the tail vein after 7 days from the date of the 4th immunization, and an antiserum was prepared. In order to confirm the antibody titer of the antiserum, ELISA using immobilized mouse Siglec-15-His protein used as the antigen, the mouse Siglec-15-Fc protein produced in Example 9, or bovine serum albumin (BSA) was performed. As a result, the reactivity with the mouse Siglec-15-His protein and mouse Siglec-15-Fc protein was observed in all four rats (rat Nos. 1 to 4). On the other hand, the reactivity with BSA was not observed. From these results, it was confirmed that the antibody titer in the serum of each of the immunized rats increased, and therefore, the No. 2 rat which showed the highest antibody titer was subjected to a cell fusion procedure.

c) Cell Fusion

Cell fusion was performed according to a common method of fusing mouse (rat) spleen cells with myeloma cells. The whole blood was collected from the heart of the rat under ether anesthesia and the rat was euthanized, and then, the spleen was resected. The collected spleen cells and P3X63Ag8.653 cells (ATCC CRL 1580) which are mouse myeloma cells were subjected to cell fusion using polyethylene glycol (PEG). The resulting cells were seeded in a 96-well plate, and a medium containing hypoxanthine (H), aminopterin (A) and thymidine (T) (HAT selection medium) was added thereto, and then, the cells were cultured for 7 to 10 days. The culture supernatant was collected from 61 wells in which the survival of hybridomas obtained by cell fusion was confirmed. Then, the antibody titer was evaluated by ELISA using immobilized mouse Siglec-15-His protein, mouse Siglec-15-Fc protein produced in Example 9, or BSA as the antigen, and anti-mouse Siglec-15 monoclonal antibody-producing hybridomas were screened. From the results of the screening, 12 wells showing a high antibody titer were selected and the hybridomas contained in the wells were subjected to a cloning procedure.

d) Cloning of Hybridoma

For the thus selected hybridomas, first cloning was performed by a limiting dilution method. After limiting dilution, the hybridomas were cultured for 2 weeks, and the antibody titer in the culture supernatant was confirmed by ELISA using immobilized mouse Siglec-15-Fc protein produced in Example 9 or BSA. For 11 clones which were confirmed to be positive clones, second cloning was performed (in the same manner as the first cloning), whereby 10 clones of the anti-mouse Siglec-15 monoclonal antibody-producing hybridomas (#1A1, #3A1, #8A1, #24A1, #32A1, #34A1, #39A1, #40A1, #41B1, #61A1) were established in the end. Incidentally, the hybridomas #32A1 and #41B1 were deposited at the International Patent Organism Depositary of the National Institute of Advanced Industrial Science and Technology (located at Central 6, 1-1-1 Higashi, Tsukuba-shi, Ibaraki-ken, 305-8566, Japan) on Aug. 28, 2008. The hybridoma #32A1 has been given a deposit number of FERM BP-10999 under the name of anti-Siglec-15 Hybridoma #32A1, and the hybridoma #41B1 has been given a deposit number of FERM BP-11000 under the name of anti-Siglec-15 Hybridoma #41 B1.

Example 24

Preparation of Rat Anti-Mouse Siglec-15 Monoclonal Antibody a) Preparation of Nude Mouse Ascites The hybridomas established in Example 23 were cultured using TIL Media I (manufactured by Immuno-biological Laboratories Co., Ltd.) medium containing 10% FCS. Subculturing of the cells was carried out by performing a procedure in which the culture solution was diluted to about one-fourth every two to three days by using the time point when the cells were grown to about $5 \times 10^5$ cells/ml as a guide. Each thus cultured hybridoma was intraperitoneally implanted in a nude mouse to which pristane had previously been intraperitoneally administered (0.2 ml/mouse) at $1 \times 10^7$ cells per mouse. In the implantation, three nude mice were used for each of the 10 clones of hybridomas. After the implantation, the ascites was collected at the time when sufficient accumulation of ascites was observed, which was combined with those collected from the other two mice implanted with the same hybridoma and the amount of the ascites thus combined was measured, and the ascites was cryopreserved until purification of the antibody. The amounts of the collected ascites for the respective hybridomas were summarized in Table 7.

TABLE 7

| Hybridoma | Amount of collected ascites (ml) |
|---|---|
| #1A1 | 12.5 |
| #3A1 | 8.0 |
| #8A1 | 6.0 |
| #24A1 | 7.8 |
| #32A1 | 5.5 |
| #34A1 | 8.2 |
| #39A1 | 14.5 |
| #40A1 | 20.3 |
| #41B1 | 10.5 |
| #61A1 | 12.3 | b) Purification of Antibody

The total amount of the collected ascites was subjected to IgG purification using a 20 ml Protein G column (manufactured by GE Healthcare, Co., Ltd.). The purified IgG was assayed for purity by a gel filtration analysis (Superdex 200 column chromatography), and some of the antibodies were subjected to centrifugal membrane concentration. That is, 9 types of antibodies except for the #24A1 antibody were concentrated to about one-sixth to one-eighth of the original volume by centrifuging the antibodies at 3,000 rpm for 30 to 60 minutes at 4° C. using a centrifugal membrane concentrator Amicon Ultra-15 (manufactured by Millipore Co., Ltd.). Subsequently, for the #24A1 antibody and the other concentrated 9 types of antibodies, the protein concentration was measured with a DC-Protein Assay kit (manufactured by Bio-Rad Laboratories, Inc.) using bovine serum albumin (BSA) as a standard sample. By the above-mentioned procedure, the anti-mouse Siglec-15 monoclonal antibody was prepared.

Example 25

Figure 24:
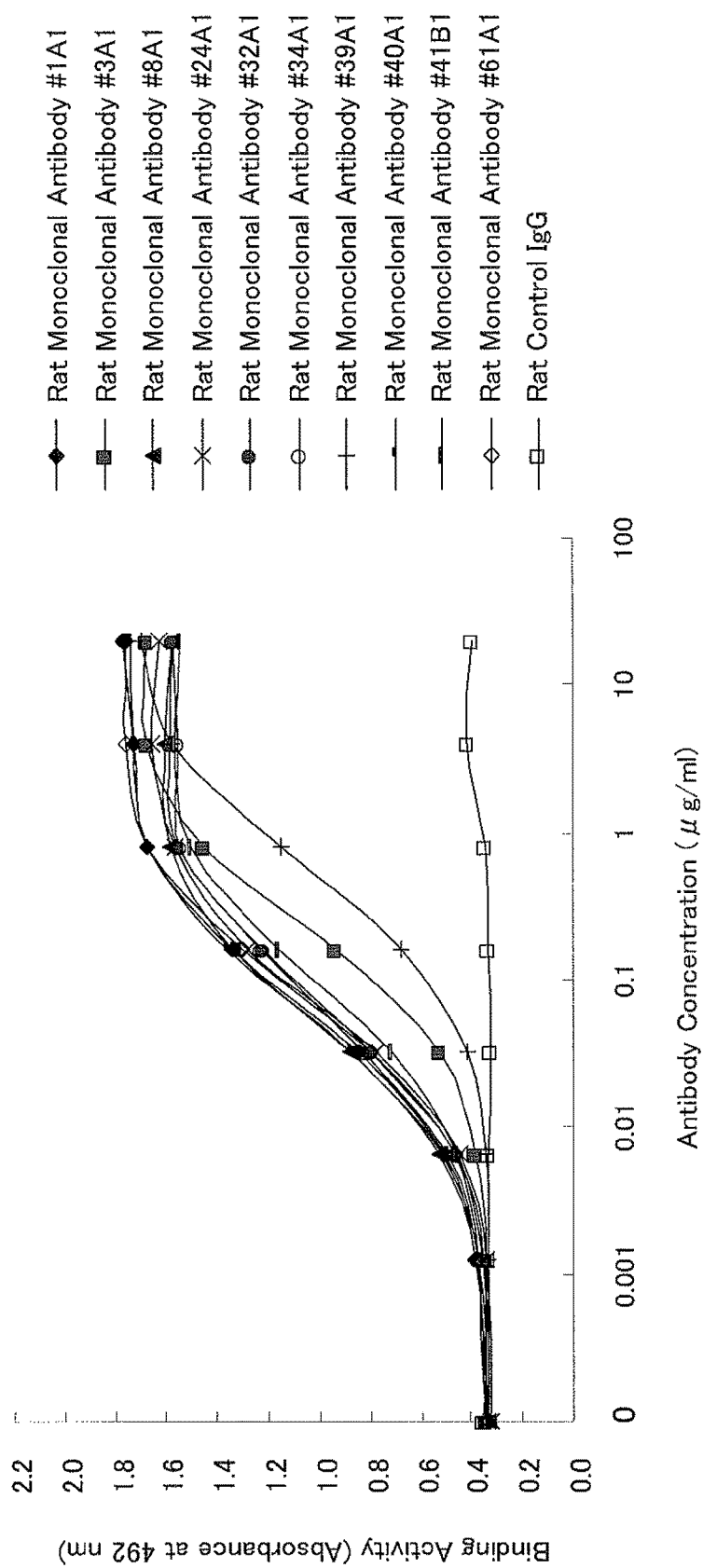
FIG. 24 shows the results of testing the binding of a rat anti-mouse Siglec-15 monoclonal antibody to a plate having mouse Siglec-15-Fc immobilized thereon by an ELISA method. The symbol (◆) denotes #1A1 antibody, the symbol (■) denotes #3A1 antibody, the symbol (▲) denotes #8A1 antibody, the symbol (×) denotes #24A1 antibody, the symbol (●) denotes #32A1 antibody, the symbol (○) denotes #34A1 antibody, the symbol (+) denotes #39A1 antibody, the symbol (–) denotes #40A1 antibody, the symbol (—) denotes #41B1 antibody, the symbol (◇) denotes #61A1 antibody, and the symbol (□) denotes control IgG.

Evaluation of Binding Property of Rat Anti-Mouse Siglec-15 Monoclonal Antibody to Mouse Siglec-15 Protein The binding property of the rat anti-mouse Siglec-15 monoclonal antibody to mouse Siglec-15 protein was evaluated by an ELISA method. The mouse Siglec-15-Fc protein produced in Example 9 was diluted to 5 µg/ml with 0.1 M sodium carbonate buffer (pH 9.5), and the resulting solution was added to a 96-well plate (manufactured by Nalge Nunc International, Inc., Cat. No. 430341) at 100 µl/well. After the plate was left at room temperature for 1 hour, the solution was removed and a washing buffer (phosphate-buffered saline containing 0.05% Tween 20) was added at 300 µl/well and removed. After this washing procedure was performed one more time, phosphate-buffered saline containing 25% Block-Ace (manufactured by Dainippon Sumitomo Pharma Co., Ltd.) was added at 200 µl/well, and the plate was left at room temperature for 1 hour, whereby blocking was effected. The liquid was removed, and the plate was washed twice with 300 µl/well of washing buffer. Then, each of the rat anti-mouse Siglec-15 monoclonal antibodies prepared in Example 24 or rat control IgG (manufactured by R&D systems, Inc.) was diluted to a final concentration of from 1.28 to 20,000 ng/ml (5-fold dilution series) with an ELISA buffer (phosphate-buffered saline containing 12.5% BlockAce and 0.05% Tween 20), and the resulting diluted antibody solution was added to the plate at 100 µl/well. After the plate was left at room temperature for 1 hour, the liquid was removed, and the plate was washed three times with 300 µl/well of washing buffer. Subsequently, HRP (horseradish peroxidase)-labeled goat anti-rat IgG antibody (manufactured by Beckman Coulter, Inc.) diluted to 1,000-fold with the ELISA buffer was added at 100 µl/well, and the plate was left at room temperature for 1 hour. The liquid was removed and the plate was washed three times with 300 µl/well of washing buffer, and then, by using a color developing kit for peroxidase (manufactured by Sumitomo Bakelite Co., Ltd.), the color was developed according to the protocol attached to the kit. After developing the color, the absorbance at 492 nm was measured using a microplate reader (manufactured by Molecular Devices Corporation, Japan). As a result, it was confirmed that all the 10 test substances of the rat anti-mouse Siglec-15 monoclonal antibodies examined bind to the mouse Siglec-15 protein in an antibody concentration-dependent manner (FIG. 24). On the other hand, in the case of the rat control IgG, binding to the mouse Siglec-15 protein was not observed.

Example 26

Figure 25:
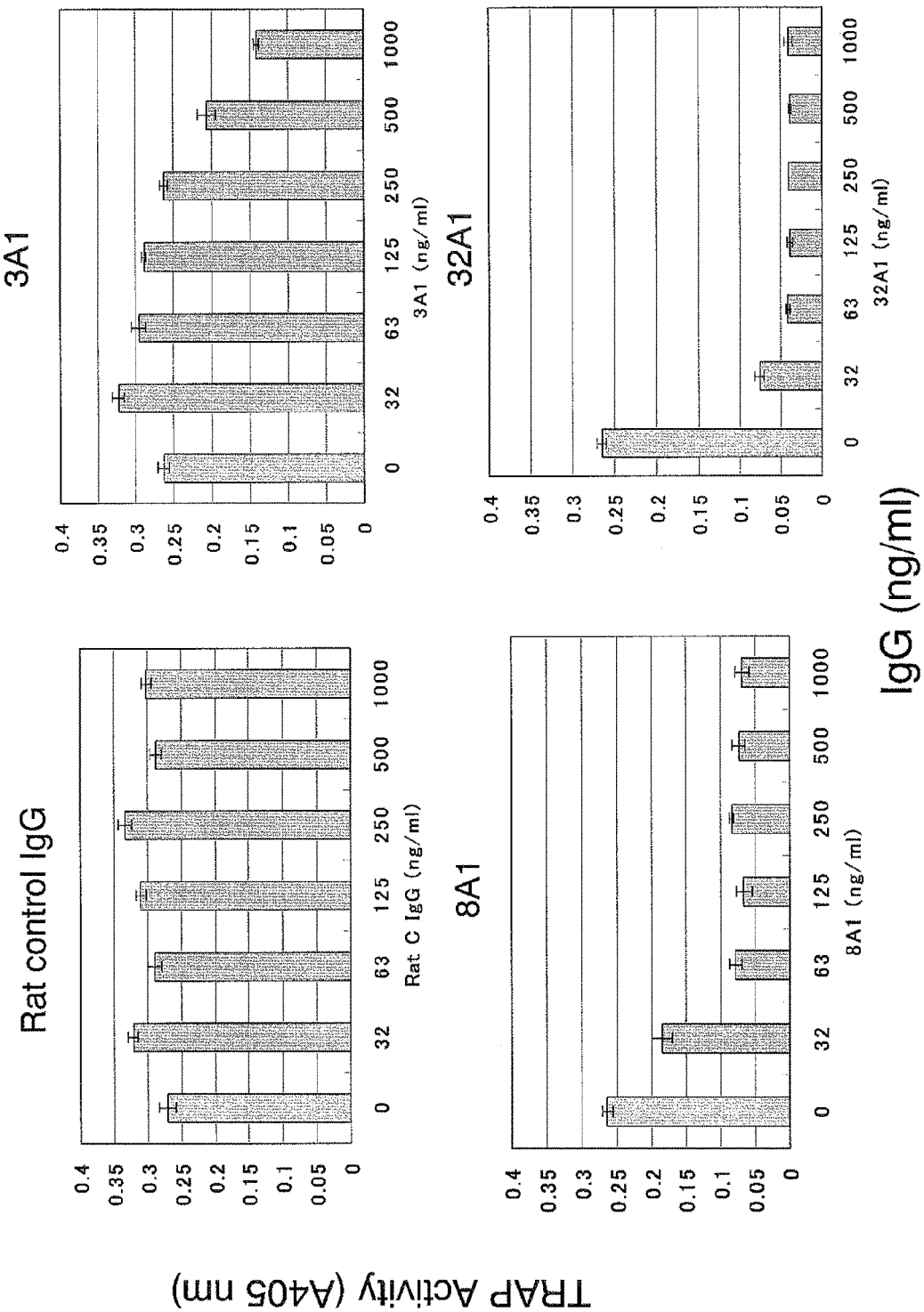
FIG. 25 shows the results of testing the effect of the addition of an anti-mouse Siglec-15 monoclonal antibody (#3A1, #8A1, or #32A1) on osteoclast differentiation (stimulation with RANKL) of mouse bone marrow nonadherent cells. The rat control IgG in the figure is a negative control common to FIGS. 25 and 26.
Figure 26:
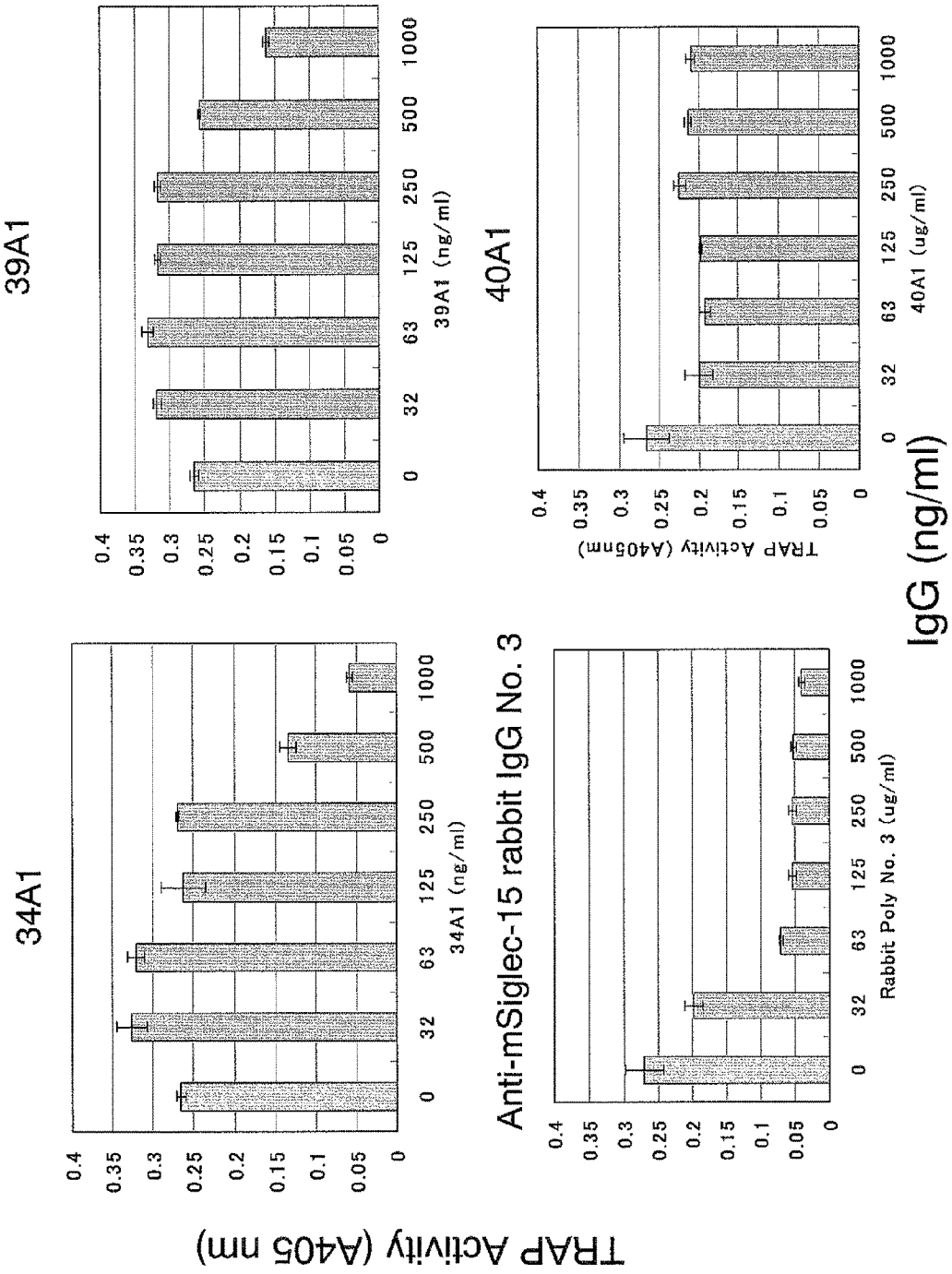
FIG. 26 shows the results of testing the effect of the addition of an anti-mouse Siglec-15 monoclonal antibody (#34A1, #39A1, or #40A1) on osteoclast differentiation (stimulation with RANKL) of mouse bone marrow nonadherent cells. The rabbit anti-mouse Siglec-15 polyclonal antibody No. 3 in the figure is a positive control common to FIGS. 25 and 26.

Evaluation of Biological Activity of Rat Anti-Mouse Siglec-15 Monoclonal Antibody Based on Test for Mouse Osteoclast Formation By using all the 10 test substances of the anti-mouse Siglec-15 monoclonal antibodies produced in Example 24, an effect on osteoclast differentiation of mouse bone marrow nonadherent cells was examined. Mouse bone marrow nonadherent cells prepared by the method in Example 16 were prepared at $1.5 \times 10^5$ cells/ml in α-MEM medium containing 10% FBS and 10 ng/ml of M-CSF (manufactured by R&D systems, Inc.), and the resulting cell preparation was seeded in each well of a 96-well plate in an amount of 200 µl and the cells were cultured for 2 days in a $CO_2$ incubator. The old culture solution in the 96-well plate was removed, and 100 µl of MEM-α medium containing 10% FBS to which human RANKL (RANKL, manufactured by Peprotech, Inc.) and M-CSF were added to give final concentrations of 20 ng/ml and 10 ng/ml, respectively, was added to each well. To the cell culture solution, each of the rat anti-mouse Siglec-15 monoclonal antibodies produced in Example 24, a sample obtained by removing sodium azide from commercially available rat control IgG (purified rat IgG, manufactured by R&D systems, Inc.) or the rabbit anti-mouse Siglec-15 polyclonal antibody (No. 3) produced in Example 14 was added at a concentration of from 32 to 1,000 ng/ml, and the cells were cultured for an additional 3 days in a $CO_2$ incubator. After completion of the culturing, the activity of tartrate-resistant acid phosphatase (TRAP) of the formed osteoclasts was measured by the method described in Example 17. After stopping the enzymatic reaction, the absorbance of each well at 405 nm was measured, and the measurement was used as an index of TRAP activity. The results are shown in FIGS. 25 and 26. A significant inhibition of TRAP activity was not observed in the case of the commercially available rat control IgG. On the other hand, a significant inhibition of TRAP activity was observed in the cases of the #32A1 antibody in the range of from 32 ng/ml to 1000 ng/ml, the #8A1 antibody and the affinity-purified rabbit polyclonal No. 3 antibody in the range of from 63 ng/ml to 1000 ng/ml. Also in the cases of the #3A1 antibody, #34A1 antibody, and #39A1 antibody, a dose-dependent inhibition of TRAP activity was observed at a relatively higher concentration of 500 ng/ml or higher. The inhibition of mouse osteoclast formation by the other antibodies was not observed. From the above results, antibodies which strongly inhibit mouse osteoclast formation (osteoclast differentiation and maturation) were found among the prepared rat anti-mouse Siglec-15 monoclonal antibodies. Further, as a property common to the #3A1 antibody, #8A1 antibody, #32A1 antibody, #34A1 antibody, and #39A1 antibody, an activity of inhibiting osteoclast formation at a concentration of 1000 ng/ml, i.e., 1 μg/ml or less can be exemplified.

Example 27

Extraction of Total RNA from Human-Derived Mature Osteoclasts

When normal human osteoclast precursor cells (Normal Human Natural Osteoclast Precursor Cells, purchased from Sanko Junyaku Co., Ltd., Cat. No. 2T-110) are cultured in a minimal essential medium for osteoclast precursor cells (OPBM, purchased from Sanko Junyaku Co., Ltd., Cat. No. PT-8201) supplemented with an OPGM supplement set (Osteoclast SingleQuot™ Kit, purchased from Sanko Junyaku Co., Ltd., Cat. No. PT-9501) containing fetal bovine serum (final concentration: 10%), human RANKL, human M-CSF and the like, a large number of TRAP-positive multinucleated osteoclasts arise after 3 to 7 days. By using this cell culturing system according to the protocol attached to the kit, human-derived mature osteoclasts were produced.

a) The normal human osteoclast precursor cells were seeded in 60 wells of a 96-well plate at $1 \times 10^4$ cells/well, and human RANKL was added thereto to give a final concentration of 66 ng/ml, and the cells were cultured for 4 days in a $CO_2$ incubator. Then, the total RNA was extracted from the multinucleated osteoclasts using a total RNA extraction reagent (ISOGEN, manufactured by Nippon Gene Co., Ltd.) according to the protocol attached to the reagent. The collected total RNA was stored at −80° C. until use.

b) The normal human osteoclast precursor cells were seeded in 84 wells of each of two 96-well plates at $1 \times 10^4$ cells/well, and human RANKL was added to each well of one of the plates to give a final concentration of 53.2 ng/ml, and human RANKL was not added to the other plate, and the cells were cultured for 3 days in a $CO_2$ incubator. Then, the total RNA was extracted from the cells using a total RNA extraction reagent (ISOGEN, manufactured by Nippon Gene Co., Ltd.) according to the protocol attached to the reagent. The collected total RNA was stored at −80° C. until use.

Example 28

Acquisition of Sequence of Open Reading Frame (ORF) for Human Siglec-15 a) Synthesis of First Strand cDNA

By using the total RNA produced in a) of Example 27 as a template, synthesis of cDNA was performed using oligo(dT) primer (manufactured by Invitrogen, Inc.) and Superscript III reverse transcriptase (manufactured by Invitrogen, Inc.). The procedure was performed according to the protocol attached to the enzyme.

b) PCR Reaction

Oligonucleotides having the sequences of: 5'-attaagcttc accATGGAAA AGTCCATCTG GCTGC-3' (hSiglec-15-HindIII kozak-F: SEQ ID NO: 29 in the Sequence Listing); and 5'-agtggatecT CACGGTGAGC ACATGGTGGC-3' (hSiglec-15-BamHI-R: SEQ ID NO: 30 in the Sequence Listing) as primers for amplifying the ORF cDNA for human Siglec-15 by PCR were synthesized according to a common procedure. The PCR was performed using this combination of primers and the cDNA produced in a) according to a common procedure. The resulting PCR reaction solution was purified using PureLink PCR Purification Kit (manufactured by Invitrogen, Inc.).

c) Cloning into pcDNA3.1(+) Vector

The purified PCR reaction solution obtained in b) and pcDNA3.1(+) vector (manufactured by Invitrogen, Inc.) were treated with restriction enzymes (BamHI, HindIII), followed by gel cutting and purification, and then, a ligase reaction was performed according to a common procedure. *Escherichia coli* TOP 10 was transformed, and colony PCR was performed for the resulting drug-resistant clones. The entire nucleotide sequence of the ORF cDNA inserted into a plasmid was analyzed using a DNA sequencer for a clone in which an amplified product with a predicted size was obtained, and as a result, it was found to be the sequence represented by SEQ ID NO: 1 in the Sequence Listing. This nucleotide sequence was the same as the ORF coding region of the sequence registered in NCBI GeneBank database as "human Siglec-15" (accession number: NM_213602), and further, the amino acid sequence (SEQ ID NO: 2 in the Sequence Listing) encoded by the nucleotide sequence was 100% identical to the amino acid sequence of human Siglec-15.

Example 29

Expression of mRNA for Human Siglec-15 Accompanying Human Osteoclast Differentiation (Real-Time PCR Analysis)

To 1 μg of the total RNA produced in b) of Example 27, 1 μl of 1 U/μl DNase I and 1 μl of 10×DNase I buffer (manufactured by Invitrogen, Inc.) were added, and then, the final volume was brought to 10 μl with $H_2O$. After a reaction was allowed to proceed at room temperature for 15 minutes, 1 μl of 25 mM EDTA was added thereto and the resulting mixture was heated at 65° C. for 10 minutes. From this solution, an 8 μl aliquot was taken, and 1 μl of 50 μM oligo(dT)$_{20}$ primer and 1 μl of 10 mM dNTPs were added thereto, and the resulting mixture was heated at 65° C. for 5 minutes and then incubated in ice. To this solution, 2 µl of 10×RT buffer (manufactured by Invitrogen, Inc.), 4 µl of 25 mM MgCl$_2$, 2 µl of 0.1 M dithiothreitol, 1 µl of RNase inhibitor (RNaseOUT, 40 U/µl, manufactured by Invitrogen, Inc.), and 1 µl of Superscript III reverse transcriptase (200 U/µl, manufactured by Invitrogen, Inc.) were added and the total volume was brought to 20 µl. After a reaction was allowed to proceed at 50° C. for 50 minutes, the mixture was heated at 85° C. for 5 minutes and then incubated in ice.

By using the thus produced single-stranded cDNA, real-time PCR was performed using a combination of the following primers and fluorescently labeled probes (TaqMan probe, manufactured by Applied Biosystems, Inc.).

```
Conditions for real-time PCR:
Primers for amplifying human cathepsin K:
5'-ccgcagtaat gacacccttt-3'
(TqM-hcatK-F: SEQ ID NO: 31 in the Sequence
Listing)
and 5'-aaggcattgg tcatgtagcc-3'
(TqM-hcatK-R: SEQ ID NO: 32 in the Sequence
Listing)

TaqMan probe for detecting human cathepsin K:
5'-Fam-tcagggtcag tgtggttcct gttgggct-TAMRA-3'
(TqM-hcatK-probe: SEQ ID NO: 33 in the Sequence
Listing)

Primers for amplifying human TRAP:
5'-ctgtcctggc tcaagaaaca-3'
(TqM-hTRAP-F: SEQ ID NO: 34 in the Sequence
Listing)
and 5'-ccatagtgga agcgcagata-3'
(TqM-hTRAP-R: SEQ ID NO: 35 in the Sequence
Listing)

TaqMan probe for detecting human TRAP:
5'-Fam-tgagaatggc gtgggctacg tgctgagt-TAMRA-3'
(TqM-hTRAP-probe: SEQ ID NO: 36 in the Sequence
Listing)

Primers for amplifying human Siglec-15:
5'-cagccaccaa catccatttc-3'
(TqM-hSiglec-15-F: SEQ ID NO: 37 in the Sequence
Listing)
and 5'-cgctcaagct aatgcgtgta-3'
(TqM-hSiglec-15-R: SEQ ID NO: 38 in the Sequence
Listing)

TaqMan probe for detecting human Siglec-15
5'-Fam-aagaacaaag gccagtgcga ggcttggc-TAMRA-3'
(TqM-hSiglec-15-probe: SEQ ID NO: 39 in the
Sequence Listing)

Primers for amplifying human L32 ribosomal
protein:
5'-gagatcgctc acaatgtttc ct-3'
(TqM-hL32-F: SEQ ID NO: 40 in the Sequence
Listing)
and 5'-gatgccagat ggcagttttt ac-3'
(TqM-hL32-R: SEQ ID NO: 41 in the Sequence
Listing)

TaqMan probe for detecting human L32 ribosomal
protein:

5'-Fam-accgcaaagc catcgtggaa agagctg-TAMRA-3'
(TqM-hL32-probe: SEQ ID NO: 42 in the Sequence
Listing)
```

A real-time PCR analysis was performed using a real-time PCR system (ABI Prism 7700 Sequence Detector, manufactured by Perkin Elmer Japan Applied Biosystems Division) under the following conditions. In the reaction, TaqMan Universal PCR Master Mix (manufactured by Applied Biosystems, Inc.) was used. First, distilled water was added to 25 pmol of each primer, 8 ng of single-stranded cDNA and 10 pmol of TaqMan probe to bring the final volume to 25 µl, and then, 25 µl of TaqMan Universal PCR Master Mix was added thereto, whereby 50 µl of a reaction solution was prepared. This reaction solution was heated at 50° C. for 2 minutes and then heated at 95° C. for 10 minutes, and thereafter subjected to 40 temperature cycles of "95° C. for 0.25 minutes and 60° C. for 1 minute", whereby a real-time PCR analysis was performed. Incidentally, the expression level of mRNA for each gene was corrected by the expression level of mRNA for L32 ribosomal protein.

Figure 27:
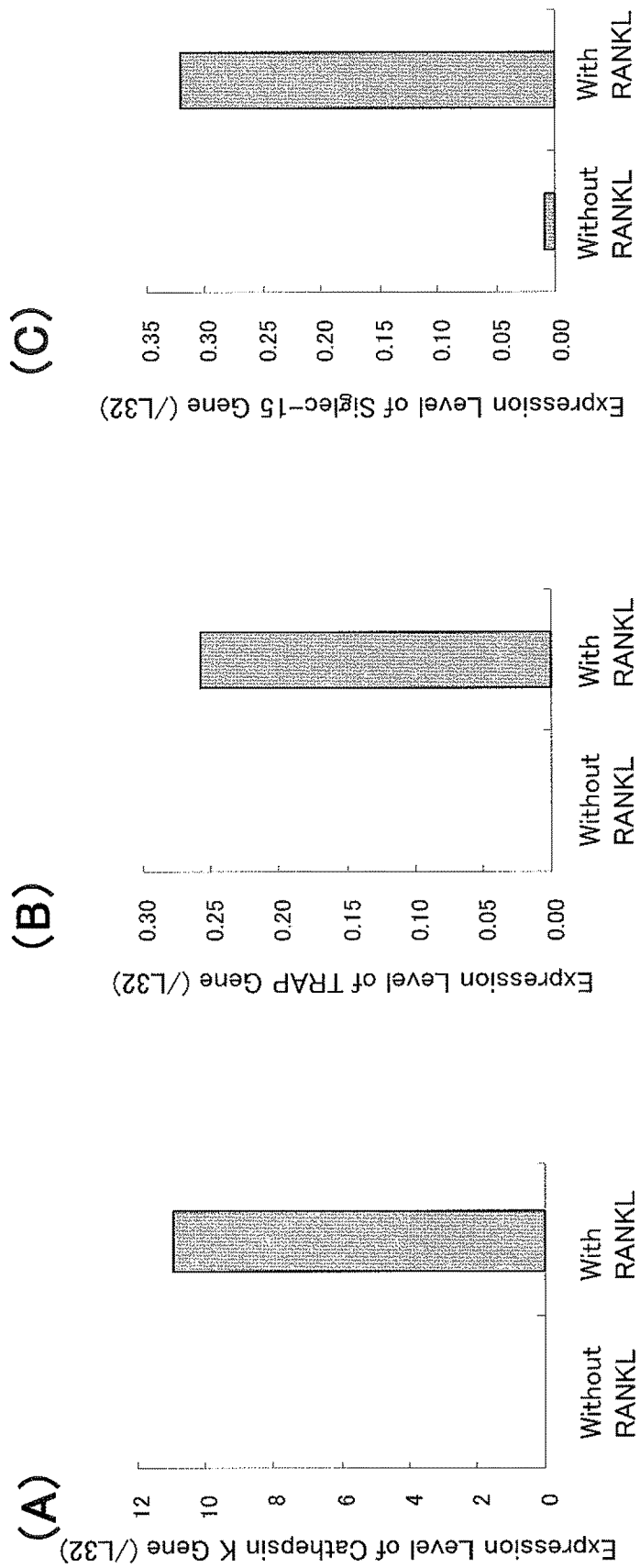
FIG. 27 shows graphs depicting a change in the expression of cathepsin K, TRAP or the Siglec-15 gene when osteoclast differentiation was induced from normal human osteoclast precursor cells.

As a result, it was revealed that the expression level of the Siglec-15 gene significantly increased in the case where human osteoclast differentiation was induced by adding RANKL in the same manner as cathepsin K and TRAP genes which are known as marker molecules for osteoclasts (FIG. 27).

Example 30

Production of Soluble Human Siglec-15 Protein Expression Construct

A partial nucleic acid sequence encoding the extracellular domain of human Siglec-15 protein is represented by SEQ ID NO: 43 in the Sequence Listing and the amino acid sequence thereof is represented by SEQ ID NO: 44 in the Sequence Listing. By utilizing such a partial sequence, soluble human Siglec-15 protein can be produced in a culture supernatant of an animal cell or the like.

a) Amplification of Soluble Human Siglec-15 Gene by PCR

Oligonucleotides having the sequences of: 5'-ggggacaagt ttgtacaaaa aagcaggctt caccATGGAA AAGTCCATCT GGCTGC-3' (hSiglec-15-ECD-F: SEQ ID NO: 45 in the Sequence Listing); and 5'-ggggaccact ttgtacaaga aagctgggtc CCCGCTGGCG CCATGGAAGC GG-3' (hSiglec-15-ECD-R: SEQ ID NO: 46 in the Sequence Listing) as primers for amplifying the human Siglec-15 extracellular domain cDNA by PCR were synthesized according to a common procedure. Incidentally, these primers were designed, as amplification primers for producing a gateway entry clone, such that an attB1 sequence is added to hSiglec-15-ECD-F and an attB2 sequence is added to hSiglec-15-ECD-R. The PCR was performed using this combination of primers and the human Siglec-15/pcDNA3.1(+) plasmid produced in Example 28 as a template according to a common procedure. The resulting PCR reaction solution was purified using PureLink PCR Purification Kit (manufactured by Invitrogen, Inc.).

b) Production of Entry Clone by Gateway BP Reaction

An entry clone into which the human Siglec-15 extracellular domain cDNA was integrated by the Gateway technology (Invitrogen, Inc.) employing a lambda phage site-specific recombination system was produced in the following method. First, a BP reaction using BP Clonase was performed between the PCR product having an attB sequence at both ends produced in a) and pDNOR221 (manufactured by Invitrogen, Inc.) which is a donor vector having an attP sequence. By using this reaction solution, *Escherichia coli* TOP10 was transformed, colony PCR was performed for drug-resistant clones, and the size of inserts was confirmed. Then, for a clone confirmed to have an insert with a correct size, a sequence analysis of the total DNA sequence of the insert was performed. As a result, an entry clone which is completely identical to the target nucleic acid sequence (SEQ ID NO: 43 in the Sequence Listing) encoding the extracellular domain of human Siglec-15 protein was obtained.

c) Production of Expression Clone by Gateway LR Reaction

An expression clone into which the human Siglec-15 extracellular domain cDNA was integrated by the Gateway technology (Invitrogen, Inc.) employing a lambda phage site-specific recombination system was produced by the following method. The entry clone produced in b) contains an insert having an attL sequence at both ends. An LR reaction using LR Clonase was performed between this entry clone and two types of destination vectors having an attR sequence. Incidentally, as the destination vectors, two types of destination vectors: pDONM designed such that a V5 epitope tag and a 6×His tag are added to the C terminus of the insert; and phIgFc designed such that a human Fc tag is added to the C terminus of the insert were used. By using the reaction solution obtained by the LR reaction, *Escherichia coli* TOP 10 was transformed, and a sequence analysis was performed for the resulting drug-resistant clones to confirm whether correct recombination occurred.

As a result of the sequence analysis, expression clones (soluble human Siglec-15/pDONM and soluble human Siglec-15/phIgFc) in which correct recombination occurred were obtained for both pDONM and phIgFc, respectively. By transfecting the soluble human Siglec-15/pDONM into an animal cell or the like, mRNA having the base sequence represented by SEQ ID NO: 47 in the Sequence Listing is transcribed and translated into a protein (human Siglec-15-His) having the amino acid sequence represented by SEQ ID NO: 48 in the Sequence Listing. Further, by transfecting the soluble human Siglec-15/phIgFc into an animal cell or the like, mRNA having the base sequence represented by SEQ ID NO: 49 in the Sequence Listing is transcribed and translated into a protein (human Siglec-15-Fc) having the amino acid sequence represented by SEQ ID NO: 50 in the Sequence Listing.

Example 31

Large-Scale Preparation of Culture Solution Containing Soluble Human Siglec-15 Protein Using 293-F Cells a) Preparation of Culture Solution Containing Human Siglec-15-His The soluble human Siglec-15/pDONM obtained in Example 30 was prepared in an amount of about 25 mg. Incidentally, in the purification of a plasmid from *Escherichia coli* cultured on a large scale, Invitrogen PureLink HiPure Plasmid Gigaprep Kit (manufactured by Invitrogen, Inc.) was used. The thus prepared plasmid was mixed with Opti-MEM (manufactured by Invitrogen, Inc.), and 50 ml of a transfection reagent 293fectin (manufactured by Invitrogen, Inc.) was added thereto, and the resulting mixture was incubated at room temperature for 20 minutes. This mixture was added to FreeStyle 293-F cells (manufactured by Invitrogen, Inc.) cultured in FreeStyle 293 Expression Medium (manufactured by Invitrogen, Inc.) containing 1% penicillin-streptomycin such that the cell density reached 1.0 to 3.4×10$^6$ cells/ml using a 25 L bioprocess culture apparatus (WAVE Bioreactor). After the cells were subjected to spinner culture (30 rotations/min) at a $CO_2$ concentration of from 6 to 12% for 96 hours (4 days) at 37° C., the culture solution was collected and centrifuged to prepare a culture supernatant. It is considered that in the thus prepared culture supernatant, a protein in which a V5 epitope tag and a 6×His tag have been added to the C-terminal side of the human Siglec-15 extracellular domain (human Siglec-15-His) is expressed.

b) Preparation of Culture Solution Containing Human Siglec-15-Fc

The soluble human Siglec-15/phIgFc obtained in Example 30 was prepared in an amount of about 5 mg. Incidentally, in the purification of plasmid from *Escherichia coli* cultured on a large scale, Invitrogen PureLink HiPure Plasmid Gigaprep Kit (manufactured by Invitrogen, Inc.) was used. The thus prepared plasmid was mixed with Opti-MEM (manufactured by Invitrogen, Inc.), followed by filter sterilization. Then, 10 ml of a transfection reagent 293fectin (manufactured by Invitrogen, Inc.) was added thereto, and the resulting mixture was incubated at room temperature for 20 minutes. This mixture was added to FreeStyle 293-F cells (manufactured by Invitrogen, Inc.) cultured in Erlenmeyer flasks such that the cell density reached 1.0 to 3.0×10$^6$ cells/ml×5 L (1 L/flask×5 flasks) in FreeStyle 293 Expression Medium (manufactured by Invitrogen, Inc.). After the cells were subjected to rotary culture (125 rotations/min) at a $CO_2$ concentration of 8.0% for 96 hours (4 days) at 37° C., the culture solution was collected and centrifuged to prepare a culture supernatant. It is considered that in the thus prepared culture supernatant, a protein in which a human Fc tag has been added to the C-terminal side of the human Siglec-15 extracellular domain (human Siglec-15-Fc) is expressed.

Example 32

Purification of Soluble Human Siglec-15 Protein a) Purification of Soluble Human Siglec-15-His
a-i) HisTrap HP Column Chromatography To 12 L of the culture solution of 293F cells expressing human Siglec-15-His prepared in a) of Example 31, 1350 mL of 10×buffer (500 mM Tris, 1.5 M NaCl, 200 mM imidazole, pH 8.0) was added, and the resulting mixture was stirred well and filtered through a MilliPak-60 filter (manufactured by Millipore Co., Ltd.). This culture solution was applied to a Ni-Sepharose HP (manufactured by Amersham Biosciences, Inc.) 100 ml column which had previously been washed with pure water (Milli-Q water) at a flow rate of 10 ml/min. After the column was washed with 400 ml of 50 mM Tris-HCl buffer (pH 8.0) containing 300 mM NaCl at a flow rate of 8 mL/min, a protein adsorbed onto the column was eluted with 200 ml of 50 mM Tris-HCl buffer (pH 8.0) containing 300 mM NaCl and 500 mM imidazole at a flow rate of 2.5 ml/min, and the eluate was fractionated into mini-sorp tubes (manufactured by Nunc, Inc.). In order to prevent precipitation of the protein, 8 ml of a 5 M NaCl solution was added to about 40 ml of a fraction containing the eluted protein, followed by stirring, and then, the resulting mixture was concentrated to about 20 ml with a centrifugal membrane concentrator Amicon Ultra-15 (manufactured by Millipore Co., Ltd.). Insoluble matter generated during the concentration was removed by centrifugation at 3000 rpm for 30 minutes at 4° C., and 2.5 ml of the resulting supernatant was applied to a PD-10 desalting column (manufactured by Amersham Biosciences, Inc.) which was previously equilibrated with phosphate-buffered saline containing 1 M NaCl (N-PBS), followed by elution with N-PBS, whereby 3.5 ml of a sample whose solvent was replaced with N-PBS was obtained. This procedure was performed 7 more times by repeating it, and about 28 ml of a solution of partially purified human Siglec-15-His was obtained.

a-ii) Resource Q Column Chromatography 12 ml of the sample which was purified by Ni-Sepharose HP column chromatography and whose solvent was replaced with N-PBS was dialyzed overnight at 4° C. against 50 mM Tris-HCl buffer (pH 7.5) containing 0.1% CHAPS (1 L, three times) and the resulting dialysate was centrifuged at 3,000 rpm for 30 minutes at 4° C., and the precipitate was removed. After the resulting supernatant was filtered through a Millex-GV filter (manufactured by Millipore Co., Ltd.), the filtrate was applied to a Resource Q 6 ml column (manufactured by Amersham Biosciences, Inc.) which was previously equilibrated with 50 mM Tris-HCl buffer (pH 7.5) containing 0.1% CHAPS at a flow rate of 1 ml/min. Thereafter, the column was washed with this buffer at a flow rate of 1 ml/min and a protein fraction which was not adsorbed onto the column was collected. A protein adsorbed onto the column was eluted with 50 mM Tris-HCl buffer (pH 7.5) containing 0.1% CHAPS and 1 M NaCl at a flow rate of 1 ml/min. After 26.5 ml of the fraction which was not adsorbed onto the column was concentrated to 3.0 ml with a centrifugal membrane concentrator Amicon Ultra-15 (manufactured by Millipore Co., Ltd.), the concentrate was centrifuged at 3,000 rpm for 10 minutes at 4° C. and the precipitate was removed. 2.5 ml of the resulting supernatant was applied to a PD-10 desalting column (manufactured by Amersham Biosciences, Inc.) which had previously been equilibrated with phosphate-buffered saline containing 50 mM arginine hydrochloride (pH 7.0, A-PBS), followed by elution with A-PBS, whereby 3.5 ml of a sample whose solvent was replaced with A-PBS was obtained. The arginine hydrochloride in the solvent of the prepared sample was added for preventing soluble human Siglec-15-His from precipitating. The supernatant after centrifugation was cryopreserved at −80° C. until use. The above-mentioned purification procedure (Resource Q column chromatography) was performed twice by repeating it.

a-iii) Detection and Purity Assay of Purified Human Siglec-15-His

Figure 28:
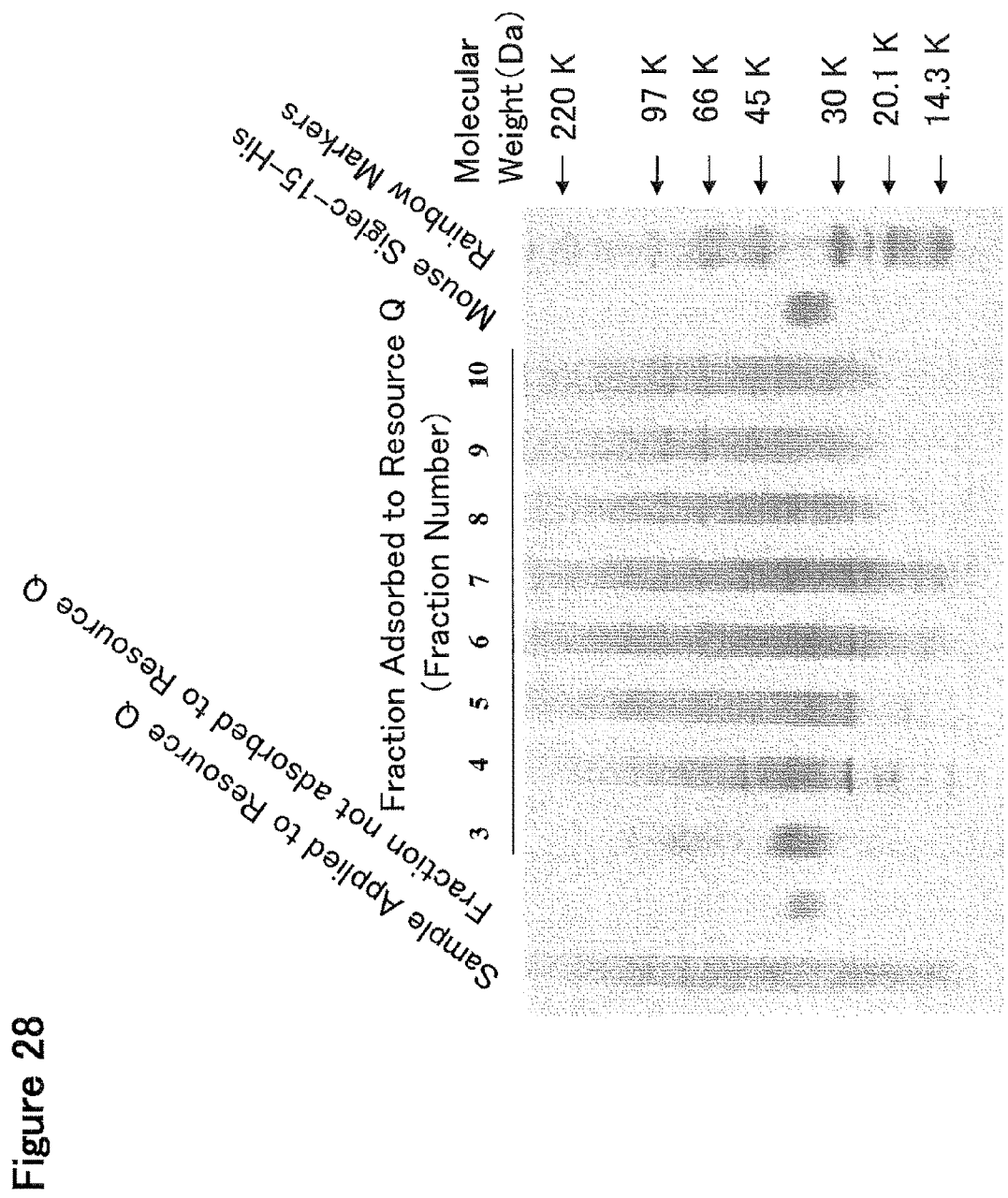
FIG. 28 shows the results of examining the purity of human Siglec-15-His purified by HisTrap HP column chromatography and Resource Q column chromatography through SDS-polyacrylamide electrophoresis.

By using a sample prepared by the above-mentioned purification procedure (Ni-Sepharose HP column chromatography and Resource Q column chromatography), SDS-polyacrylamide electrophoresis under reducing conditions and silver staining were performed. That is, to 5 µl of each of the samples purified by the respective purification steps, an equivalent amount of an SDS-treatment solution was added, and the resulting mixture was thermally treated at 95° C. for 10 minutes. 0.3 µl of each of the thermally treated samples was used for SDS-polyacrylamide electrophoresis. The electrophoresis procedure was performed in the same manner as the method described in Example 8 except that Rainbow Molecular Weight Markers (manufactured by Amersham Biosciences, Inc.) were used as the molecular weight markers. After completion of the electrophoresis, silver staining was performed using PhastGel Silver Kit (manufactured by Amersham Biosciences, Inc.) and PhastSystem. The results are shown in FIG. 28. It was shown that a protein having a molecular weight of about 35 kDa (human Siglec-15-His) was efficiently purified and concentrated in the protein fraction which was not adsorbed onto the Resource Q column.

a-iv) Measurement of Protein Concentration of Purified Human Siglec-15-His

For the purified human Siglec-15-His (the protein fraction which was not adsorbed onto the Resource Q column), the protein concentration was measured with a DC-Protein Assay kit (manufactured by Bio-Rad Laboratories, Inc.) using bovine serum albumin as a standard sample. By performing the purification procedure twice, a total of 1.66 mg of purified human Siglec-15-His was obtained.

b) Purification of Soluble Human Siglec-15-Fc b-i) HiTrap Protein A Column Chromatography 1.5 L of the culture solution of 293F cells expressing human Siglec-15-Fc prepared in b) of Example 31 was filtered through a Sterivex-GV filter (manufactured by Millipore Co., Ltd.), and then, the filtrate was applied to a HiTrap Protein A 5 ml column (manufactured by Amersham Biosciences, Inc.) which was previously equilibrated with Dulbecco's PBS (D-PBS, manufactured by Invitrogen, Inc.) at a flow rate of 5 ml/min. After the column was washed with 70 ml of D-PBS at a flow rate of 5 ml/min, a protein adsorbed onto the column was eluted with 24 ml of 0.1 M sodium citrate buffer (pH 3.0) at a flow rate of 1.2 ml/min. The eluate was fractionated at 1.2 ml per fraction into mini-sorp tubes (manufactured by Nunc, Inc.), and immediately thereafter, 0.31 ml of 1 M Tris was added thereto to neutralize the eluate. A 2.5 ml aliquot of a solution (about 7.5 ml) obtained by combining the eluted protein fractions (fractions 5 to 9) was applied to a PD-10 desalting column (manufactured by Amersham Biosciences, Inc.) which had previously been equilibrated with phosphate-buffered saline containing 50 mM arginine hydrochloride (pH 7.0, A-PBS), followed by elution with A-PBS, whereby 3.5 ml of a sample whose solvent was replaced with A-PBS was obtained. This procedure was performed twice by repeating it. The arginine hydrochloride in the solvent was added to prevent soluble human Siglec-15-Fc from precipitating. 2.5 ml of the remaining solution of the eluted protein fractions (fractions 5 to 9) was applied to a PD-10 desalting column (manufactured by Amersham Biosciences, Inc.) which had previously been equilibrated with phosphate-buffered saline containing 1 M NaCl (pH 6.7, N-PBS), followed by elution with N-PBS, whereby 3.5 ml of a sample whose solvent was replaced with N-PBS was obtained. NaCl in the solvent in the prepared sample was added to prevent soluble human Siglec-15-Fc from precipitating without adding an amino group-containing compound such as arginine. The human Siglec-15-Fc sample whose solvent was replaced with N-PBS was used only when an immobilized column was prepared in the following c) of Example 34, and in all the other Examples, human Siglec-15-Fc whose solvent was replaced with A-PBS was used. The samples prepared by the above-mentioned procedure were cryopreserved at −80° C. until use.

b-ii) Detection and Purity Assay of Purified Human Siglec-15-Fc

Figure 29:
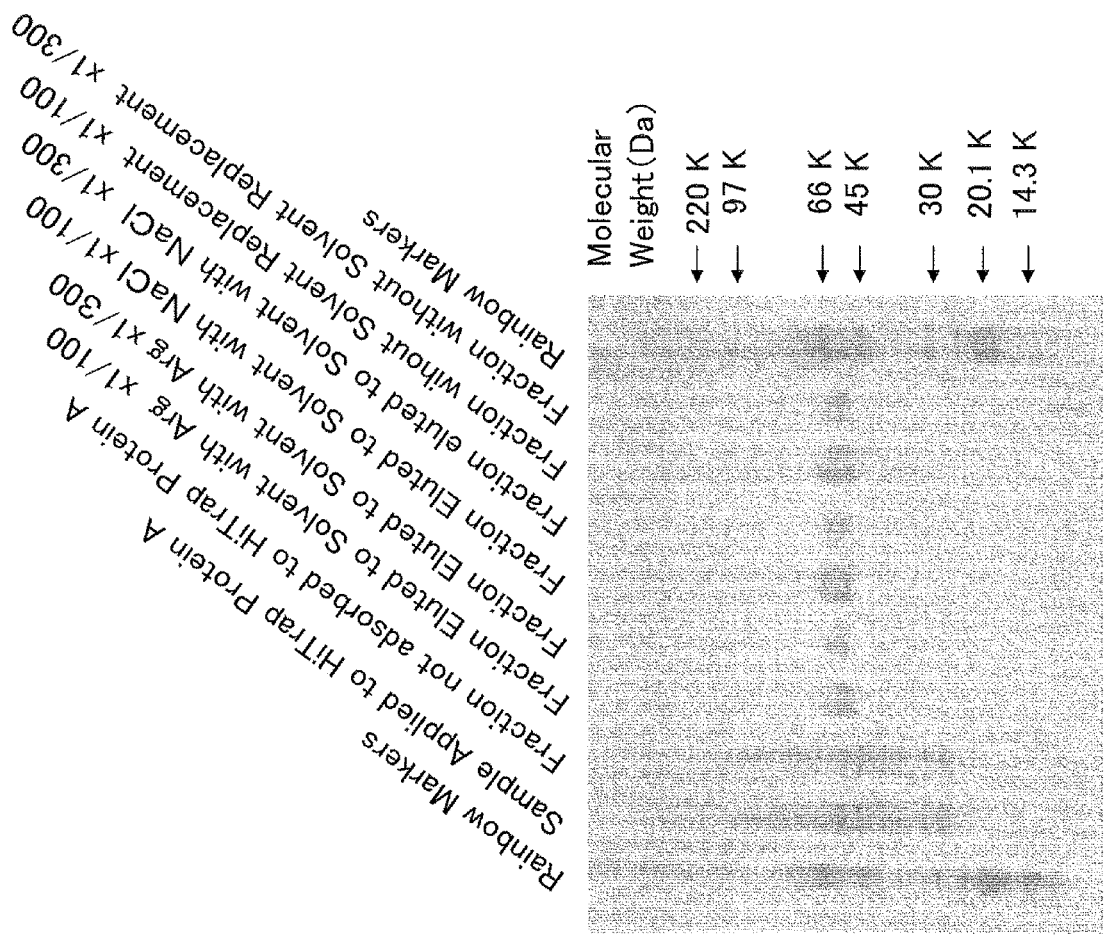
FIG. 29 shows the results of examining the purity of human Siglec-15-Fc purified by Protein A column chromatography through SDS-polyacrylamide electrophoresis.

By using the samples prepared by the above-mentioned purification procedure, SDS-polyacrylamide electrophoresis under reducing conditions and silver staining were performed. That is, to 5 µl of each of the samples purified by the respective purification steps, an equivalent amount of an SDS-treatment solution was added, and the resulting mixture was heated at 95° C. for 10 minutes. 0.3 µl of a sample obtained by diluting each of the thermally treated samples to 1/100 or 1/300 with a half concentration of the SDS-treatment solution was used for SDS-polyacrylamide electrophoresis. The electrophoresis and silver staining were performed in the same manner as the purity assay of human Siglec-15-His described in a-iii). The results are shown in FIG. 29. It was shown that a protein having a molecular weight of about 55 kDa (human Siglec-15-Fc) was efficiently purified and concentrated in the protein fraction which was eluted from the HiTrap Protein A column.

b-iii) Measurement of Protein Concentration of Purified Human Siglec-15-Fc

For the purified human Siglec-15-Fc (the protein fraction eluted from the PD-10 desalting column), the protein concentration was measured with a DC-Protein Assay kit (manufactured by Bio-Rad Laboratories, Inc.) using bovine serum albumin as a standard sample. As shown in Table 8, a total of 25.2 mg of purified human Siglec-15-Fc was obtained by performing the purification procedure twice.

TABLE 8

|  | Protein Conc. (mg/ml) | Sample Vol. (ml) | Total protein (mg) |
|---|---|---|---|
| Arg-containing solvent | 2.3 | 7.0 | 16.1 |
| NaCl-containing solvent | 2.6 | 3.5 | 9.1 |
| Total |  |  | 25.2 |

Example 33

Production of Rabbit Anti-Human Siglec-15 Polyclonal Antibody (Immunization of Rabbit)

a) Preparation of Antigen

The human Siglec-15-Fc protein produced in b) of Example 32 was prepared at 100 μg/0.5 ml, and an equivalent amount of an adjuvant was added thereto and an emulsion was produced using a glass syringe. As the adjuvant, Freund's complete adjuvant (FCA, Manufactured by Difco Laboratories, Inc.) was used only for the first immunization, and Freund's incomplete adjuvant (FICA, Manufactured by Difco Laboratories, Inc.) was used for the second and subsequent immunizations.

b) Immunization of Rabbit

Three rabbits (Japanese white female rabbits with a body weight of 3 kg) were used as immunized animals. Incidentally, blood was collected before immunization, and 10 ml of pre-immune serum was obtained per rabbit. The emulsion obtained in a) was injected subcutaneously and intradermally using a 27 G injection needle such that the amount of the antigen was 50 μg per rabbit. Immunization was performed a total of 8 times every 14 days after the first immunization. The whole blood was collected after 7 days from the date of 8th immunization, and 74.4 to 74.9 ml of antiserum was obtained per rabbit. The antibody titers in the pre-immune serum and the antiserum were confirmed by an ELISA method using an immobilized antigen. As a result, an increase in antibody titer in the antiserum was confirmed in all the three rabbits. The antiserum was stored at −20° C. until use.

Example 34

Purification of Rabbit Anti-Human Siglec-15 Polyclonal Antibody a) HiTrap Protein A Column Chromatography To 40 ml of each of the three rabbit antiserum lots prepared in b) of Example 33, 40 ml of Dulbecco's PBS (D-PBS, manufactured by Invitrogen, Inc.) was added and mixed, and the resulting mixture was filtered through a Sterivex-GV filter (manufactured by Millipore Co., Ltd.). Then, the filtrate was applied to a column which comprised two HiTrap Protein A 5 ml columns (the two columns were connected in series, manufactured by Amersham Biosciences, Inc.) and had previously been equilibrated with D-PBS at a flow rate of 2 ml/min. After the column was washed with 35 ml of D-PBS at a flow rate of 1 ml/min, a protein adsorbed onto the column was eluted with 50 ml of 0.1 M sodium citrate buffer (pH 3.0) at a flow rate of 1 ml/min. The eluate was fractionated at 2.5 ml per fraction into mini-sorp tubes (manufactured by Nunc, Inc.), and immediately thereafter, 0.6 ml of 1 M Tris was added thereto to neutralize the eluate. After about 15.5 ml of a solution obtained by combining the fractions (fractions 3 to 7) containing the eluted protein was concentrated to 5 ml with a centrifugal membrane concentrator Amicon Ultra-15 (manufactured by Millipore Co., Ltd.), a 2.5 ml aliquot of the concentrate was applied to a PD-10 desalting column (manufactured by Amersham Biosciences, Inc.) which had previously been equilibrated with Otsuka Physiological Saline for Injection (TO-SS) containing 0.01% Tween 20, followed by elution with TO-SS, whereby 3.5 ml of a sample whose solvent was replaced with TO-SS was obtained. This procedure was performed twice by repeating it. The thus prepared samples were cryopreserved at −80° C. until use.

b) Purification of Pre-Immune Rabbit IgG

Figure 30:
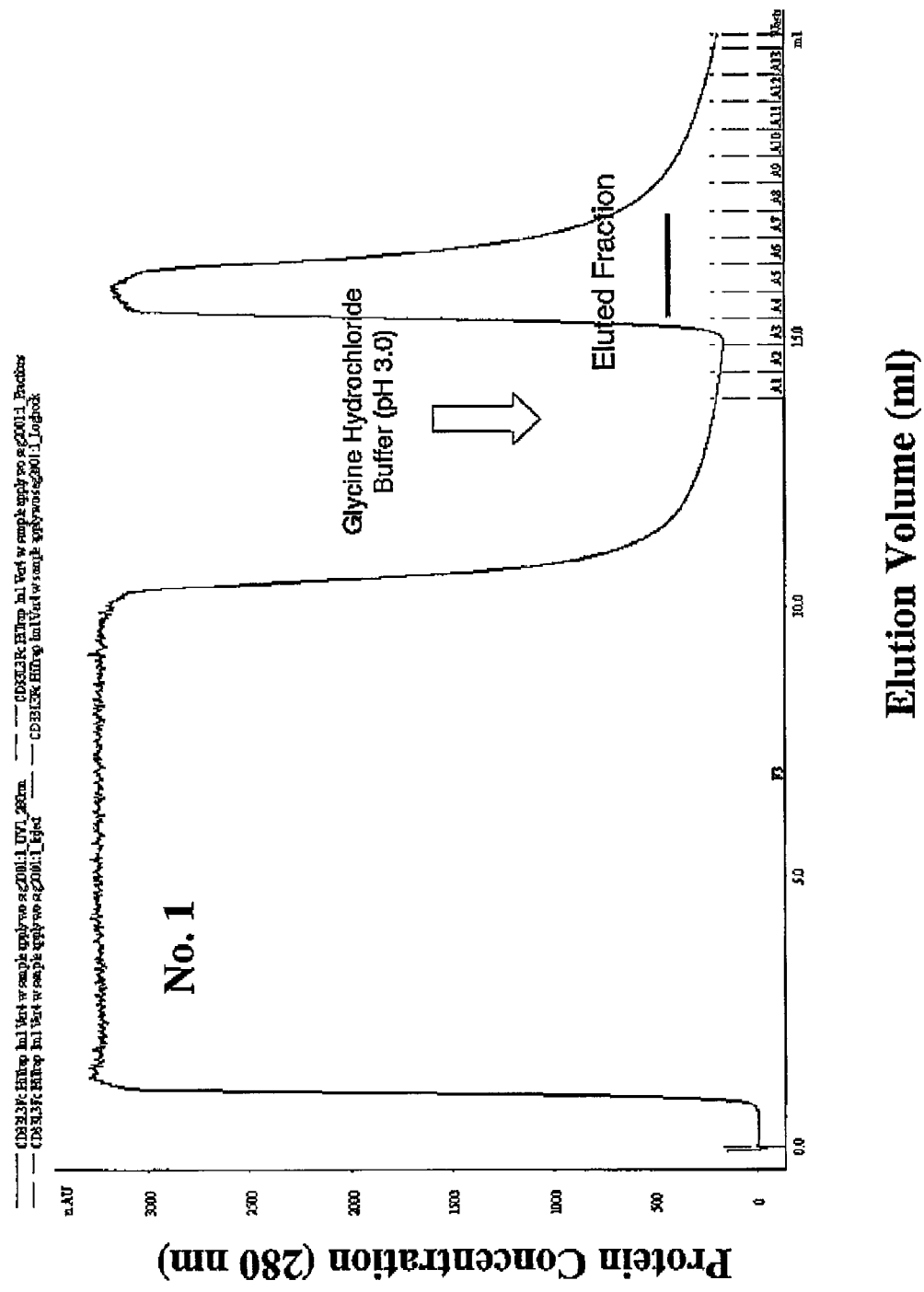
FIG. 30a, FIG. 30b, and FIG. 30c show chromatograms of anti-human Siglec-15polyclonal antibodies purified using an affinity column having human Siglec-15-Fc immobilized thereon.
Figure 30:
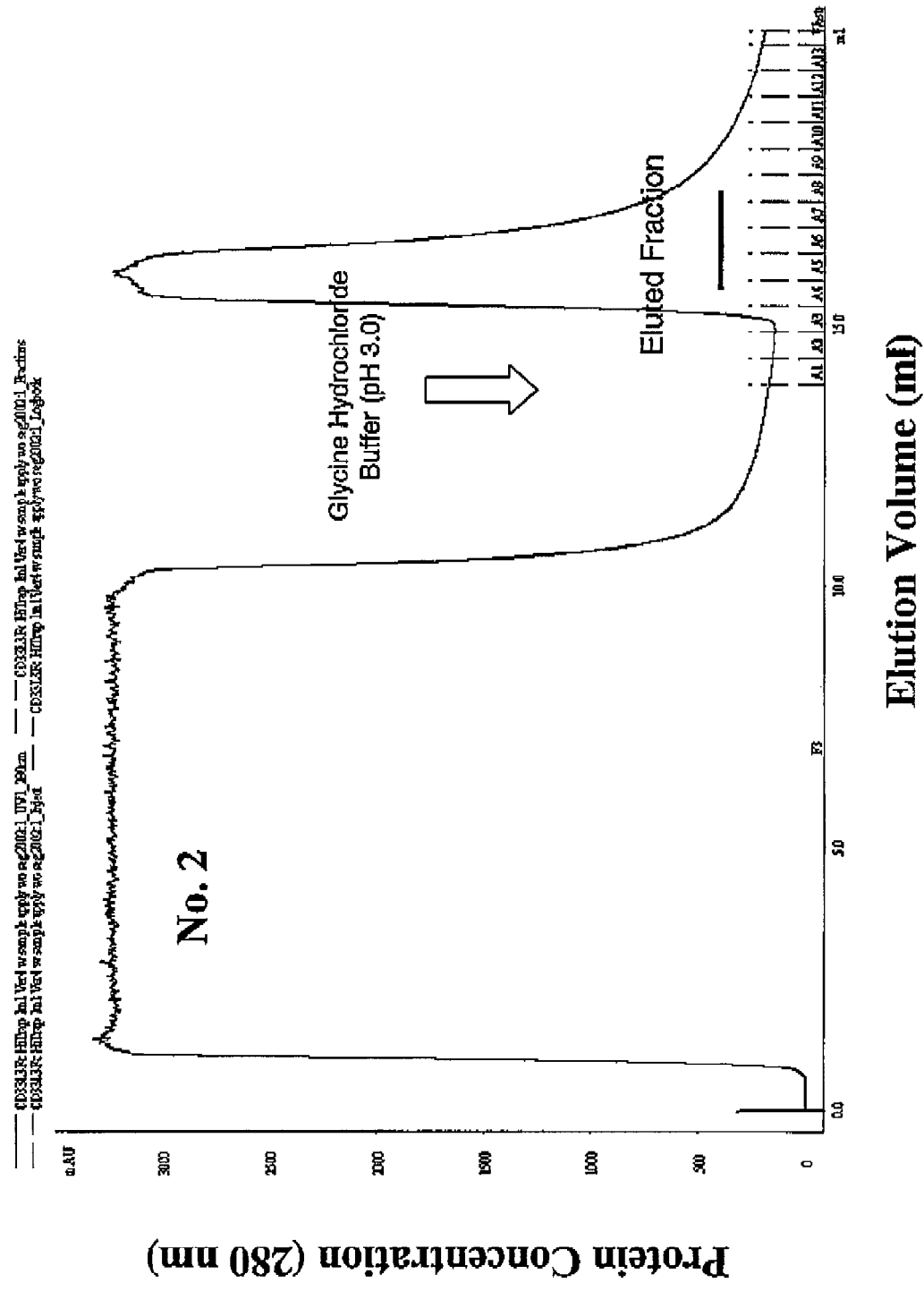
Figure 30:
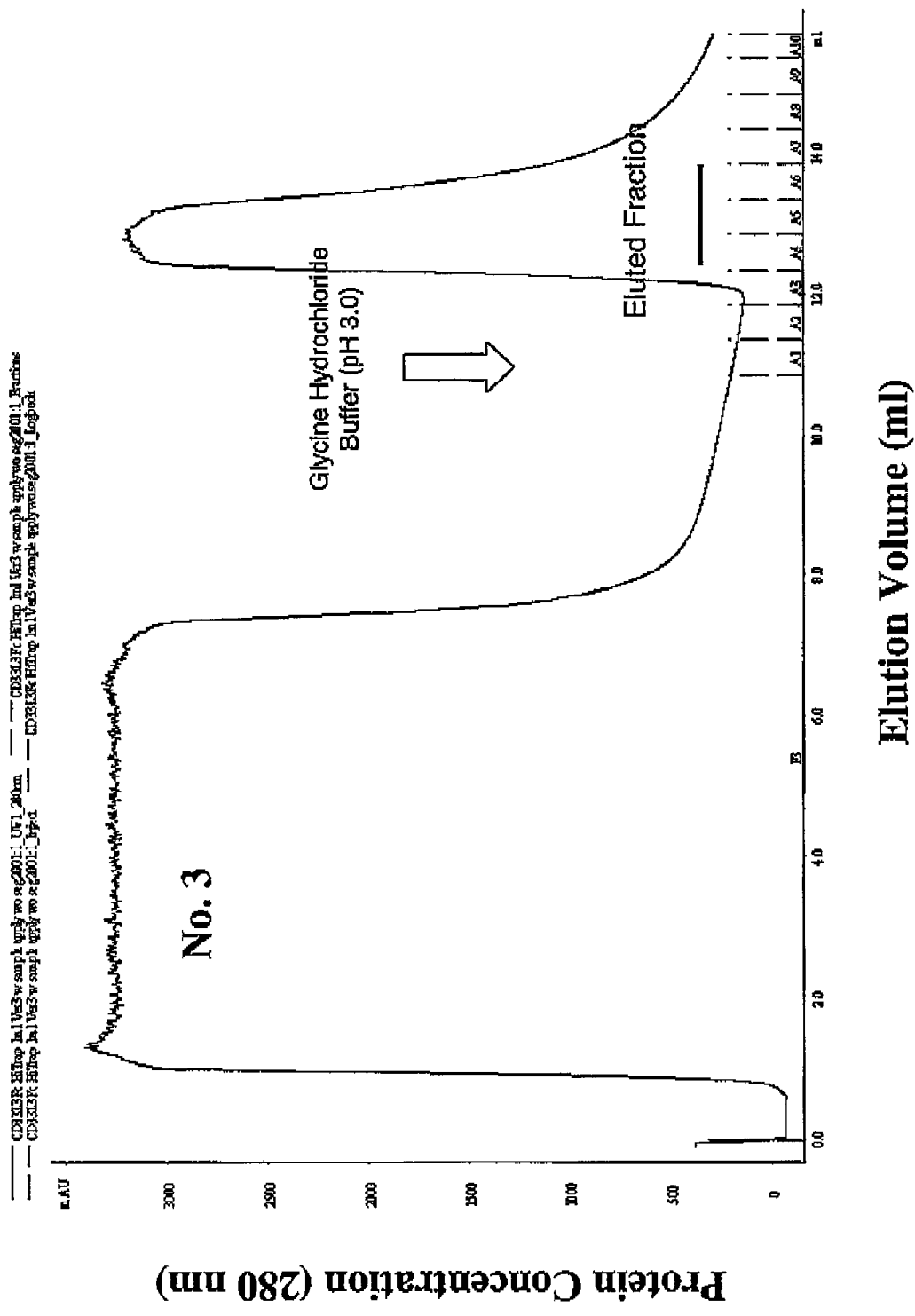
Figure 31:
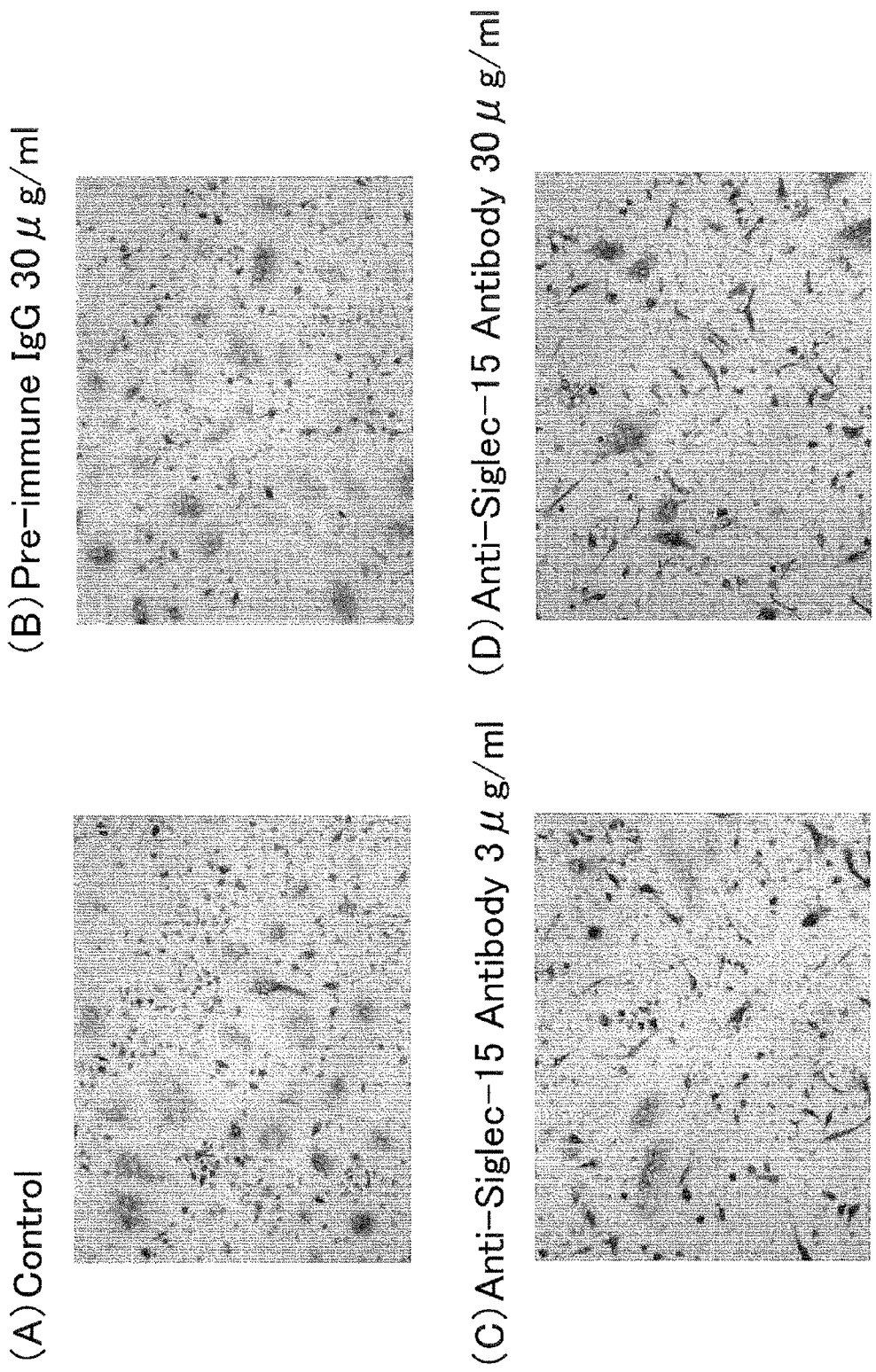
FIG. 31 shows photomicrographs depicting, by TRAP staining, the inhibition of giant osteoclast formation from normal human osteoclast precursor cells by the addition of an anti-human Siglec-15 polyclonal antibody.
Figure 32:
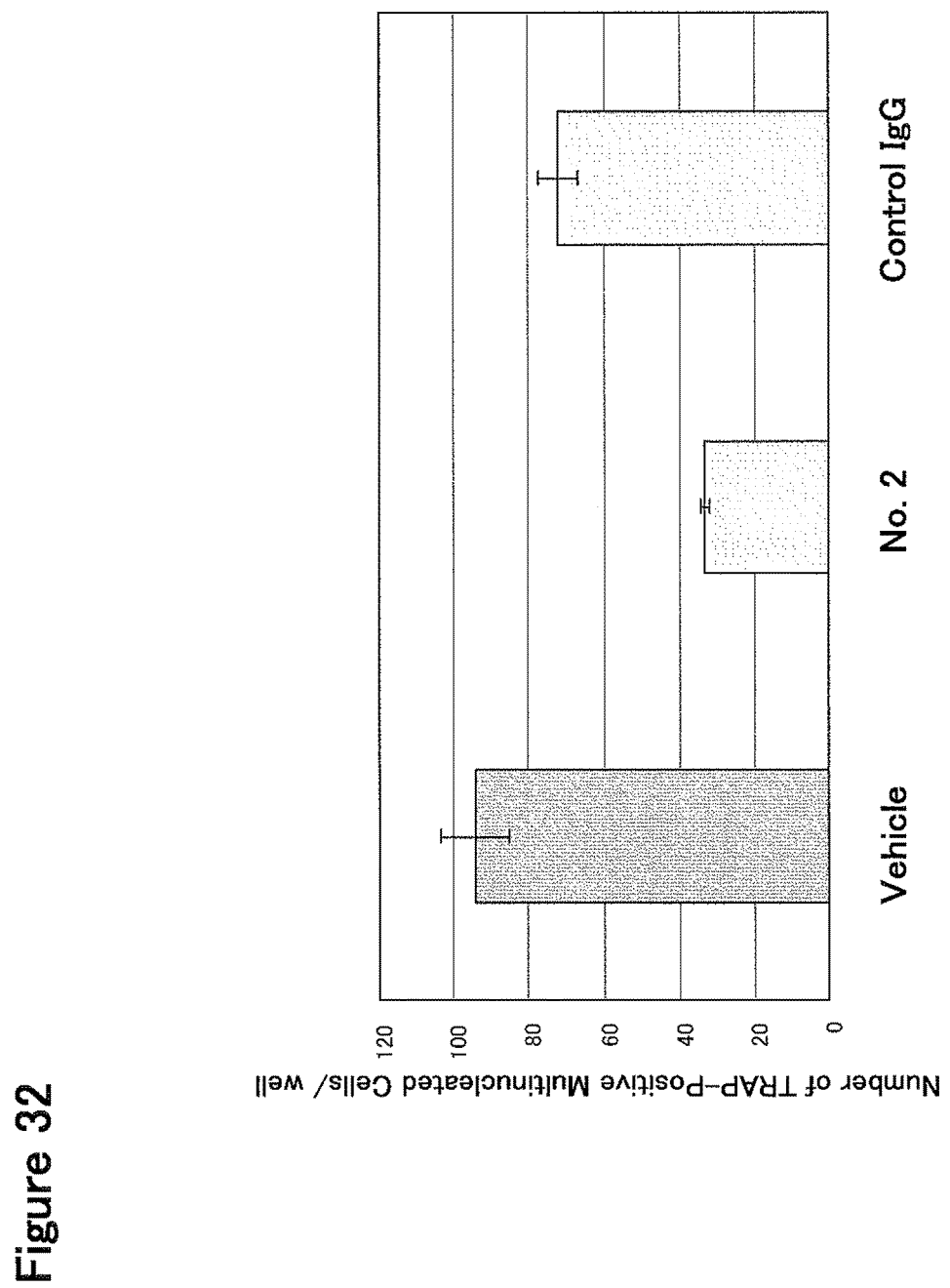
FIG. 32 shows the results of evaluating the effect of the addition of an anti-human Siglec-15 polyclonal antibody on multinucleated osteoclast formation from normal human osteoclast precursor cells by counting the number of TRAP-positive cells having 5 or more nuclei with an inverted microscope.

Blood had previously been collected from the three rabbits used in Example 33, before initiation of immunization with human Siglec-15-Fc, and pre-immune serum was prepared. After 5 ml aliquots of each of these serum samples were mixed with one another, 15 ml of D-PBS was added thereto, and the resulting mixture was filtered through a Millex-GV filter (manufactured by Millipore Co., Ltd.). Then, the resulting serum sample was applied to a column which comprised two HiTrap Protein A 5 ml columns (manufactured by Amersham Biosciences, Inc.) and had previously been equilibrated with D-PBS at a flow rate of 1 ml/min. After the column was washed with 35 ml of D-PBS at a flow rate of 1 ml/min, a protein adsorbed onto the column was eluted with 50 ml of 0.1 M sodium citrate buffer (pH 3.0) at a flow rate of 1 ml/min. The eluate was fractionated at 2.5 ml per fraction into mini-sorp tubes (manufactured by Nunc, Inc.), and immediately thereafter, 0.6 ml of 1 M Tris was added thereto to neutralize the eluate. After a solution obtained by combining the fractions (fractions 4 to 6) containing the eluted protein was concentrated to 2.5 ml with a centrifugal membrane concentrator Amicon Ultra-15 (manufactured by Millipore Co., Ltd.), the concentrate was applied to a PD-10 desalting column (manufactured by Amersham Biosciences, Inc.) which had previously been equilibrated with Otsuka Physiological Saline for Injection (TO-SS) containing 0.01% Tween 20, followed by elution with TO-SS, whereby 3.5 ml of a sample whose solvent was replaced with TO-SS was obtained. The thus purified pre-immune rabbit IgG sample was subjected to polyacrylamide electrophoresis and silver staining by the method described in Example 8 to confirm that the IgG protein was sufficiently purified, and then, the protein concentration was measured. The thus purified pre-immune rabbit IgG sample was cryopreserved at −80° C. until use.

c) Preparation of Affinity Column Having Human Siglec-15-Fc Immobilized Thereon 3 ml of the purified human Siglec-15-Fc whose solvent was replaced with N-PBS produced in b) of Example 32 (a total of 7.8 mg of protein) was concentrated to 2 ml using a centrifugal membrane concentrator Amicon Ultra-4 (manufactured by Millipore Co., Ltd.). To the concentrate, a coupling buffer (0.2 M $NaHCO_3$, 0.5 M NaCl, pH 8.3) was added to bring the final volume to 2.5 ml, and the solvent was replaced with 3.5 ml of the coupling buffer using a PD-10 desalting column. After isopropanol in an NHS-activated HiTrap column (1 ml, manufactured by Amersham Biosciences, Inc.) was replaced with 1 mM hydrochloric acid, 3 ml of the prepared human Siglec-15-Fc was injected into the column using a syringe, and the liquid was alternately injected thereinto using another syringe connected to the outlet of the column to effect a coupling reaction. After the reaction was allowed to proceed at room temperature for 30 minutes, in order to inactivate excess active groups, 6 ml of a blocking buffer (an ethanolamine buffer containing 0.5 M NaCl, pH 8.3), 6 ml of a washing buffer (a sodium acetate buffer containing 0.5 M NaCl, pH 4.0), and 6 ml of the blocking buffer were injected in sequence according to the protocol of Amersham Biosciences, Inc., and then, the column was left at room temperature for 30 minutes. Thereafter, 6 ml of the washing buffer, 6 ml of the blocking buffer, and 6 ml of the washing buffer were injected into the column in sequence again, and finally, the buffer in the column was replaced with 10 mM Tris-HCl buffer (pH 7.2) containing 0.15 M NaCl. This column was stored at 4° C. until use.

d) Purification of Rabbit Anti-Human Siglec-15 Polyclonal Antibody with Affinity Column d-i) Affinity Column Chromatography After 7 ml of each of the purified anti-human Siglec-15 polyclonal antibodies (Nos. 1, 2 and 3) prepared in a) was filtered through a Millex-GV filter (manufactured by Millipore Co., Ltd.), the resulting filtrate was applied to the column produced in c) which had the human Siglec-15-Fc immobilized thereon and had previously been equilibrated with the Apply Buffer at a flow rate of 0.25 ml/min. After the column was washed with 5 ml of the Apply Buffer at a flow rate of 0.25 ml/min, a protein adsorbed onto the column was eluted with 5 ml of 0.1 M glycine hydrochloride buffer (pH 2.7) containing 0.5 M NaCl at a flow rate of 0.25 ml/min. The chromatograms of the anti-human Siglec-15 polyclonal antibodies (Nos. 1, 2 and 3) purified with the affinity column are shown in FIGS. 30a-30c. The eluate was fractionated at 0.5 ml per fraction into mini-sorp tubes (manufactured by Nunc, Inc.), and immediately thereafter, 16 µl of 1 M Tris was added thereto to neutralize the eluate. About 2.5 ml of a solution obtained by combining the IgG protein fractions (fractions 3 to 7) eluted with the glycine hydrochloride buffer for each antibody was applied to a PD-10 desalting column (manufactured by Amersham Biosciences, Inc.) which had previously been equilibrated with Dulbecco's phosphate-buffered balanced salt solution containing 0.01% Tween 20 (T-PBS), followed by elution with T-PBS, whereby 3.5 ml of a sample whose solvent was replaced with T-PBS was obtained. The thus prepared samples were cryopreserved at -80° C. until use.

d-ii) Measurement of Protein Concentration of Affinity-Purified Rabbit Anti-Human Siglec-15 Polyclonal Antibody For the purified rabbit anti-human Siglec-15 polyclonal antibody samples (the protein fractions eluted from the PD-10 desalting column), the protein concentration was measured with a DC-Protein Assay kit (manufactured by Bio-Rad Laboratories, Inc.) using bovine IgG as a standard sample. As shown in Table 9, about 9.1 to 11.9 mg of the affinity-purified anti-human Siglec-15 polyclonal antibody could be prepared in each of lot Nos. 1 to 3.

TABLE 9

|  | Protein Conc. (mg/ml) | Sample Vol. (ml) | Total protein (mg) |
| --- | --- | --- | --- |
| No. 1 | 3.0 | 3.5 | 10.5 |
| No. 2 | 2.6 | 3.5 | 9.1 |
| No. 3 | 3.4 | 3.5 | 11.9 |

Example 35

Effect of Addition of Rabbit Anti-Human Siglec-15 Polyclonal Antibody on Cell Fusion of Normal Human Osteoclast Precursor Cells (TRAP Staining)

Figure 36:
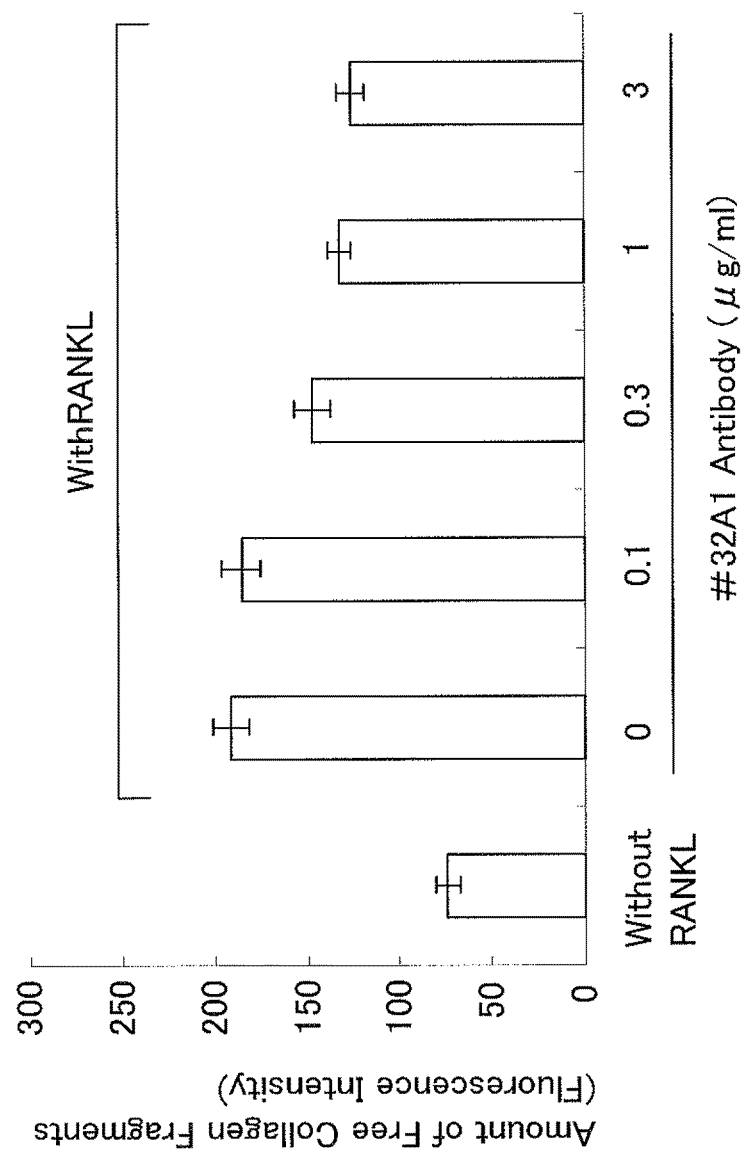
FIG. 36 shows a graph depicting the inhibition of the bone resorption activity of normal human osteoclasts by the addition of a rat anti-mouse Siglec-15 monoclonal antibody (#32A1 antibody) (N=6).

Normal human osteoclast precursor cells (Normal Human Natural Osteoclast Precursor Cells, purchased from Sanko Junyaku Co., Ltd., Cat. No. 2T-110) were seeded in a 96-well OsteoLyse cell culture plate at $1 \times 10^4$ cells/well according to the protocol attached to the cells. As the medium, a minimal essential medium for osteoclast precursor cells (OPBM, purchased from Sanko Junyaku Co., Ltd., Cat. No. PT-8201) supplemented with an OPGM supplement set (Osteoclast SingleQuot™ Kit, purchased from Sanko Junyaku Co., Ltd., Cat. No. PT-9501) containing fetal bovine serum (final concentration: 10%), human RANKL (final concentration: 68.4 ng/ml), human M-CSF (final concentration: 33 ng/ml) and the like was used. To the resulting culture supernatant, the rat anti-mouse Siglec-15monoclonal antibody (#32A1 antibody) prepared in Example 24 was added to give a final concentration of 0.1, 0.3, 1, or 3 µg/ml, and the cells were cultured for 3 days in a $CO_2$ incubator. A 10 µl aliquot of the culture supernatant was collected, and 200 µl of Fluorophore Releasing Reagent included in the OsteoLyse Assay Kit was added thereto, and a fluorescence intensity was measured (Excitation: 340 nm, Emission: 615 nm) using a fluorescence plate reader ARVO MX, manufactured by Perkin Elmer Inc.), whereby the amount of free fluorescent collagen fragments released in the culture supernatant was determined (FIG. 36). As a result, the amount of fluorescent collagen fragments increased by the addition of RANKL was reduced by the #32A1 antibody in a concentration-dependent manner within the range of from 0.3 µg/ml to 3 µg/ml. From this result, it was revealed that the bone resorption activity of human osteoclasts is inhibited by the monoclonal antibody specifically binding to the Siglec-15 protein.

Example 36

Figure 33:
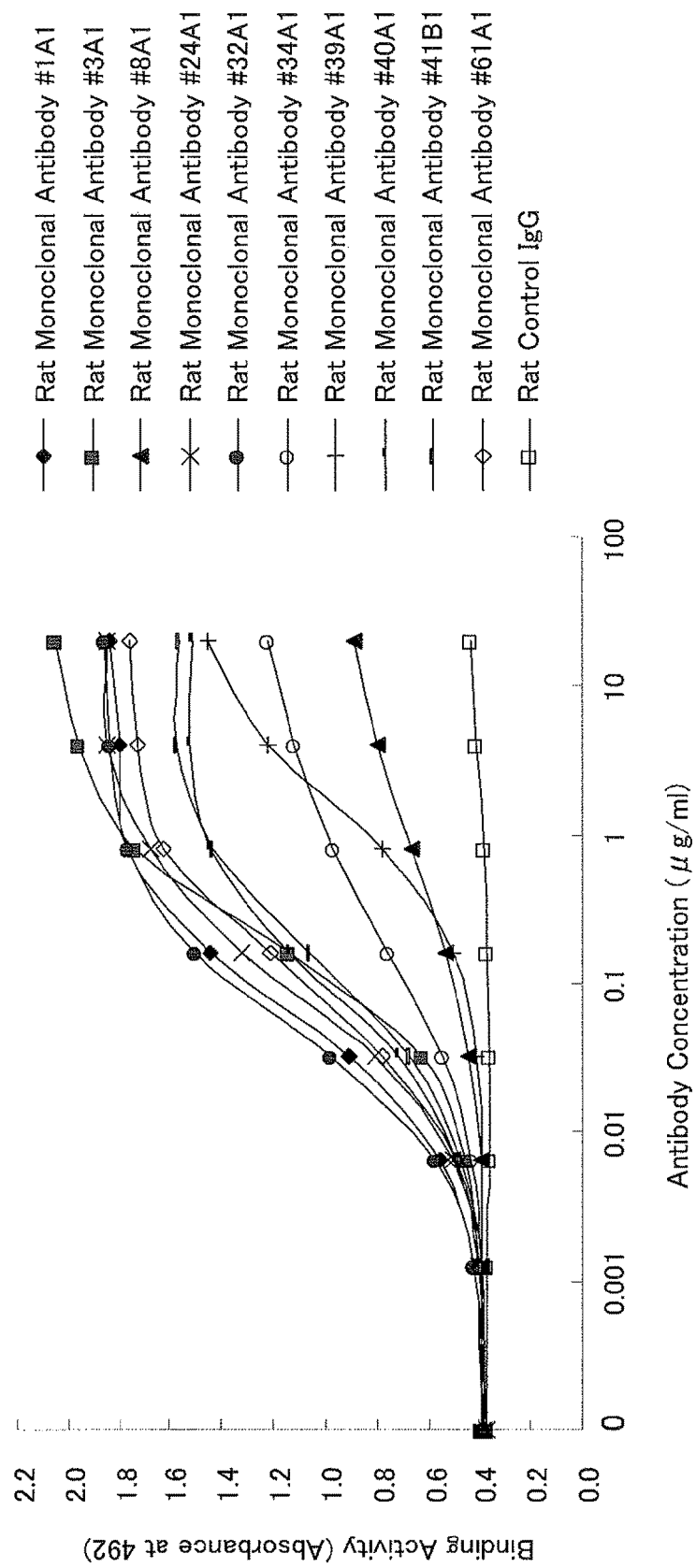
FIG. 33 shows the results of testing the binding of a rat anti-mouse Siglec-15 monoclonal antibody to a plate having human Siglec-15-Fc immobilized thereon by an ELISA method. The symbol (♦) denotes #1A1 antibody, the symbol (■) denotes #3A1 antibody, the symbol (▲) denotes #8A1 antibody, the symbol (×) denotes #24A1 antibody, the symbol (●) denotes #32A1 antibody, the symbol (○) denotes #34A1 antibody, the symbol (+) denotes #39A1 antibody, the symbol (-) denotes #40A1 antibody, the symbol (—) denotes #41B1 antibody, the symbol (◇) denotes #61A1 antibody, and the symbol (□) denotes control IgG.

Evaluation of Binding Property of Rat Anti-Mouse Siglec-15 Monoclonal Antibody to Human Siglec-15 Protein The binding property of the rat anti-mouse Siglec-15 monoclonal antibody to human Siglec-15 protein was evaluated by an ELISA method. The human Siglec-15-Fc protein produced in b) of Example 32 was diluted to 5 µg/ml with 0.1 M sodium carbonate buffer (pH 9.5), and the resulting solution was added to a 96-well plate (manufactured by Nalge Nunc International, Inc., Cat. No. 430341) at 100 µl/well. After the plate was left at room temperature for 1 hour, the solution was removed and a washing buffer (phosphate-buffered saline containing 0.05% Tween 20) was added at 300 µl/well and removed. After this washing procedure was performed one more time, phosphate-buffered saline containing 25% BlockAce (manufactured by Dainippon Sumitomo Pharma Co., Ltd.) was added at 200 µl/well, and the plate was left at room temperature for 1 hour, whereby blocking was effected. The liquid was removed, and the plate was washed twice with 300 µl/well of washing buffer. Then, each of the rat anti-mouse Siglec-15 monoclonal antibodies prepared in Example 24 or rat control IgG (manufactured by R&D systems, Inc.) was diluted to a final concentration of from 1.28 to 20,000 ng/ml (5-fold dilution series) with an ELISA buffer (phosphate-buffered saline containing 12.5% BlockAce and 0.05% Tween 20), and the resulting diluted antibody solution was added to the plate at 100 μl/well. After the plate was left at room temperature for 1 hour, the liquid was removed, and the plate was washed three times with 300 μl/well of washing buffer. Subsequently, HRP (horseradish peroxidase)-labeled goat anti-rat IgG antibody (manufactured by Beckman Coulter, Inc.) diluted to 1,000-fold with the ELISA buffer was added at 100 μl/well, and the plate was left at room temperature for 1 hour. The liquid was removed and the plate was washed three times with 300 μl/well of washing buffer, and then, by using a color developing kit for peroxidase (manufactured by Sumitomo Bakelite Co., Ltd.), the color was developed according to the protocol attached to the kit. After developing the color, the absorbance at 492 nm was measured using a microplate reader (manufactured by Nihon Molecular Devices Corporation). As a result, it was confirmed that all the 10 test substances of the rat anti-mouse Siglec-15 monoclonal antibodies examined bind to the human Siglec-15 protein in an antibody concentration-dependent manner (FIG. 33). In particular, the binding activity of 5 test substances: #1A 1, #3A1, #24A1, #32A1, and #61A1, was high and the binding activity of 3 test substances: #8A1, #34A1, and #39A1, was low. On the other hand, in the case of the rat control IgG, binding to the human Siglec-15 protein was not observed. From the above results, it was shown that the rat anti-mouse Siglec-15 monoclonal antibodies prepared in Example 24 bind not only to mouse Siglec-15, but also to human Siglec-15, and moreover, it was found that some antibodies strongly bind to human Siglec-15.

Example 37

Effect of Addition of Rat Anti-Mouse Siglec-15 Monoclonal Antibody on Cell Fusion and Bone Resorption Activity of Normal Human Osteoclast Precursor Cells (Evaluation of In Vitro Biological Activity)

Since it was confirmed that the rat anti-mouse Siglec-15 monoclonal antibodies bind also to human Siglec-15 in Example 36, the effects of these antibodies on human osteoclast formation and bone resorption activity were examined.
a) Effect of Addition of Rat Anti-Mouse Siglec-15 Monoclonal Antibody on Cell Fusion of Osteoclasts from Normal Human Osteoclast Precursor Cells (TRAP Staining)

Figure 34:
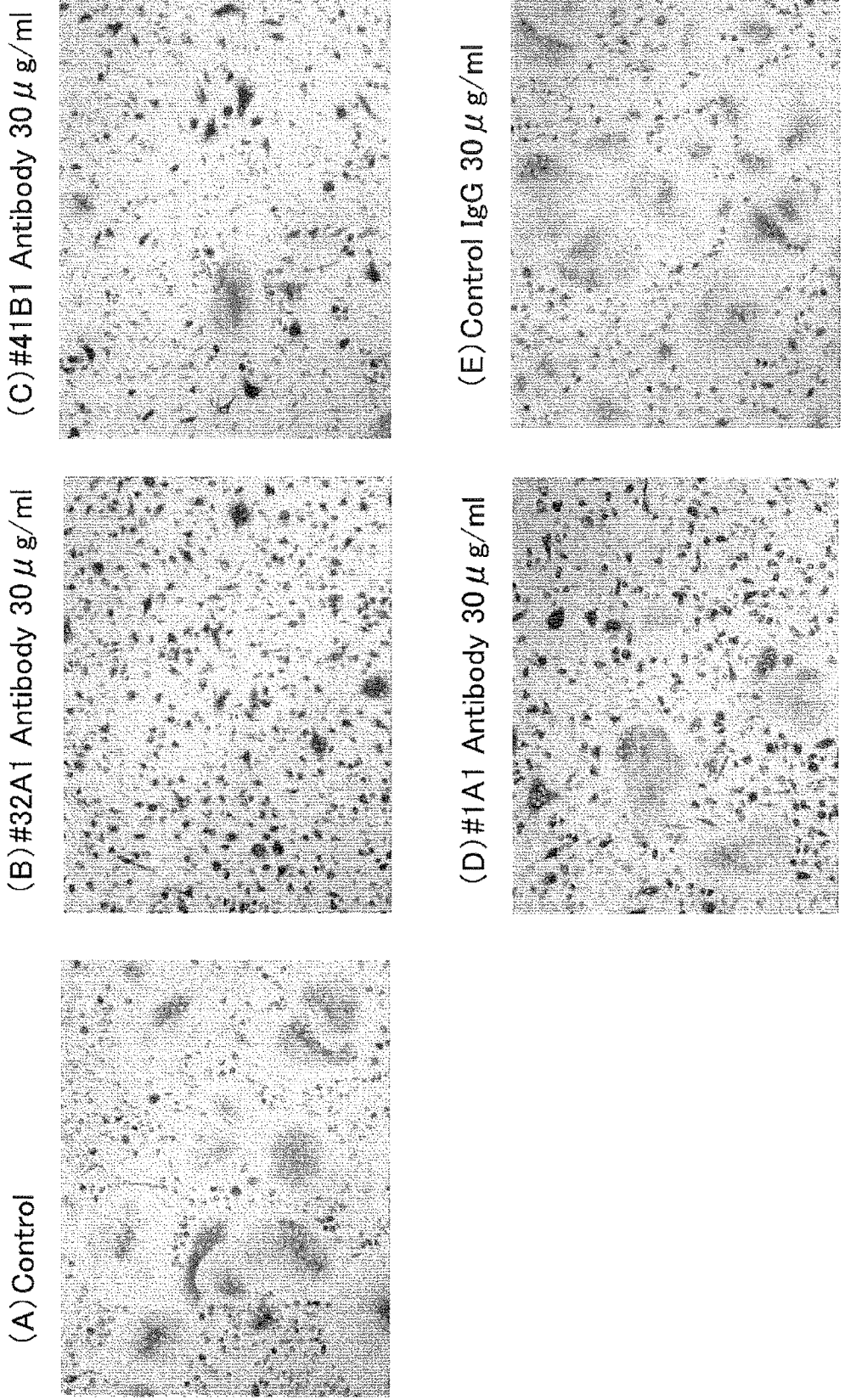
FIG. 34 shows photomicrographs depicting, by TRAP staining, the inhibition of giant osteoclast formation from normal human osteoclast precursor cells by the addition of a rat anti-mouse Siglec-15 monoclonal antibody.

Normal human osteoclast precursor cells (Normal Human Natural Osteoclast Precursor Cells, purchased from Sanko Junyaku Co., Ltd., Cat. No. 2T-110) were seeded in a 96-well plate at 1×10$^4$ cells/well according to the protocol attached to the cells. As the medium, a minimal essential medium for osteoclast precursor cells (OPBM, purchased from Sanko Junyaku Co., Ltd., Cat. No. PT-8201) supplemented with an OPGM supplement set (Osteoclast SingleQuot™ Kit, purchased from Sanko Junyaku Co., Ltd., Cat. No. PT-9501) containing fetal bovine serum (final concentration: 10%), human RANKL (final concentration: 66 ng/ml), human M-CSF (final concentration: 33 ng/ml) and the like was used. To the resulting culture supernatant, each of the rat anti-mouse Siglec-15 monoclonal antibodies prepared in Example 24 or rat control IgG (manufactured by R&D systems) was added to give a final concentration of 30 μg/ml, and the cells were cultured for 4 days in a CO$_2$ incubator. After the culturing, the supernatant was removed, and 10% neutral formalin was added to fix the cells. After fixing the cells, the cells were washed twice with distilled water, and a TRAP staining solution (0.27 mM naphthol AS-MX phosphate (manufactured by Sigma Co., Ltd.), 1.6 mM fast red violet LB salt (manufactured by Sigma Co., Ltd.), 1% dimethylformamide, 50 mM sodium tartrate, 0.1 M sodium acetate buffer (pH 5.0)) was added at 100 μl/well, and a reaction was allowed to proceed at room temperature for 5 minutes. Then, the cells were washed twice with distilled water, and then, observed by microscopy (FIG. 34). As a result, the formation of giant osteoclasts resulting from a high degree of cell fusion was almost completely inhibited by the addition of the #32A1 antibody. Further, also in the case of the #41B1 antibody, the formation of giant osteoclasts resulting from a high degree of cell fusion was significantly inhibited. On the other hand, in the case of the other rat anti-mouse Siglec-15 monoclonal antibodies (such as the #1A1 antibody) and the rat control IgG, such a significant inhibition of osteoclast cell fusion was not observed. In this manner, it was revealed that multinucleation and cell fusion of TRAP-positive osteoclasts from normal human osteoclast precursor cells are inhibited by the monoclonal antibody specifically binding to the Siglec-15 protein.
b) Effect of Addition of Rat Anti-Mouse Siglec-15 Monoclonal Antibody (#32A1) on Cell Fusion of Osteoclasts from Normal Human Osteoclast Precursor Cells (TRAP Staining)

Figure 35:
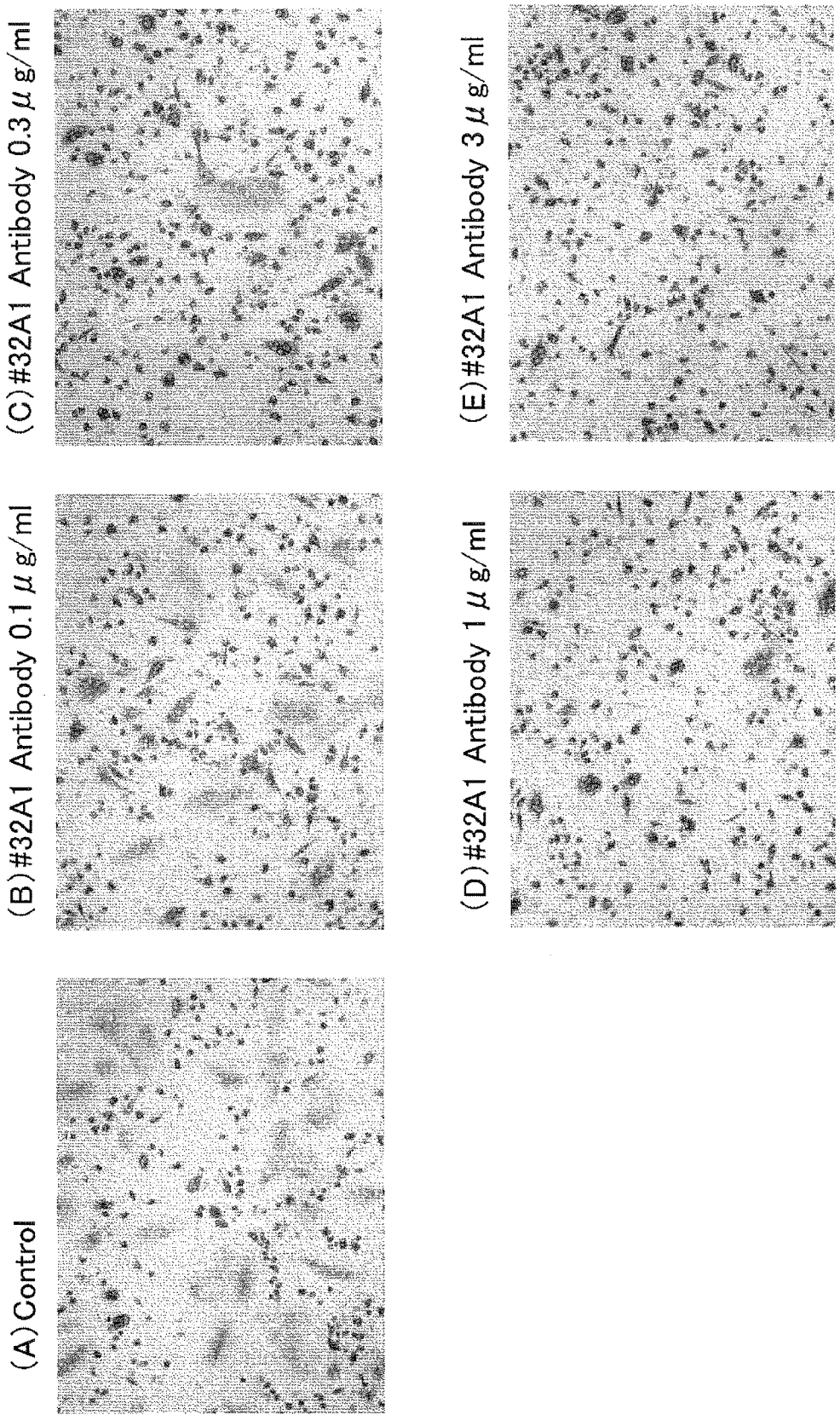
FIG. 35 shows photomicrographs depicting, by TRAP staining, the inhibition of giant osteoclast formation from normal human osteoclast precursor cells by the addition of a rat anti-mouse Siglec-15 monoclonal antibody (#32A1 antibody).

Normal human osteoclast precursor cells (Normal Human Natural Osteoclast Precursor Cells, purchased from Sanko Junyaku Co., Ltd., Cat. No. 2T-110) were seeded in a 96-well plate at 1×10$^4$ cells/well according to the protocol attached to the cells. As the medium, a minimal essential medium for osteoclast precursor cells (OPBM, purchased from Sanko Junyaku Co., Ltd., Cat. No. PT-8201) supplemented with an OPGM supplement set (Osteoclast SingleQuot™ Kit, purchased from Sanko Junyaku Co., Ltd., Cat. No. PT-9501) containing fetal bovine serum (final concentration: 10%), human RANKL (final concentration: 68.4 ng/ml), human M-CSF (final concentration: 33 ng/ml) and the like was used. To the resulting culture supernatant, the rat anti-mouse Siglec-15 monoclonal antibody (#32A1) prepared in Example 24 was added to give a final concentration of 0.1, 0.3, 1, or 3 μg/ml, and the cells were cultured for 3 days in a CO$_2$ incubator. After the culturing, the supernatant was removed, and 10% neutral formalin was added to fix the cells. After fixing the cells, the cells were washed twice with distilled water, and a TRAP staining solution (0.27 mM naphthol AS-MX phosphate (manufactured by Sigma Co., Ltd.), 1.6 mM fast red violet LB salt (manufactured by Sigma Co., Ltd.), 1% dimethylformamide, 50 mM sodium tartrate, 0.1 M sodium acetate buffer (pH 5.0)) was added at 100 μl/well, and a reaction was allowed to proceed at room temperature for 5 minutes. Then, the cells were washed twice with distilled water, and then, observed by microscopy (FIG. 35). As a result, the formation of TRAP-positive multinucleated osteoclasts was inhibited in a #32A1 antibody concentration-dependent manner within the range of from 0.3 μg/ml to 3 μg/ml.
c) Effect of Addition of Rat Anti-Mouse Siglec-15 Monoclonal Antibody (#32A1) on Bone Resorption Activity of Normal Human Osteoclast Precursor Cells (Evaluation using Collagen-Coated Plate)

It is known that osteoclasts release a protease such as cathepsin K and degrade type I collagen which is a constitutional component of bone tissue. OsteoLyse Assay Kit (manufactured by Lonza, Inc., Cat. No. PA-1500) provides a 96-well plate coated with europium-conjugated human collagen (96-well OsteoLyse cell culture plate), and it is possible to evaluate the bone resorption activity of osteoclasts in vitro by measuring the amount of fluorescent collagen fragments released in the supernatant when osteoclasts are cultured in the plate.

Normal human osteoclast precursor cells (Normal Human Natural Osteoclast Precursor Cells, purchased from Sanko Junyaku Co., Ltd., Cat. No. 2T-110) were seeded in a 96-well OsteoLyse cell culture plate at $1\times10^4$ cells/well according to the protocol attached to the cells. As the medium, a minimal essential medium for osteoclast precursor cells (OPBM, purchased from Sanko Junyaku Co., Ltd., Cat. No. PT-8201) supplemented with an OPGM supplement set (Osteoclast SingleQuot™ Kit, purchased from Sanko Junyaku Co., Ltd., Cat. No. PT-9501) containing fetal bovine serum (final concentration: 10%), human RANKL (final concentration: 68.4 ng/ml), human M-CSF (final concentration: 33 ng/ml) and the like was used. To the resulting culture supernatant, the rat anti-mouse Siglec-15 monoclonal antibody (#32A1 antibody) prepared in Example 24 was added to give a final concentration of 0.1, 0.3, 1, or 3 µg/ml, and the cells were cultured for 3 days in a $CO_2$ incubator. A 10 µl aliquot of the culture supernatant was collected, and 200 µl of Fluorophore Releasing Reagent included in the OsteoLyse Assay Kit was added thereto, and a fluorescence intensity was measured (Excitation: 340 nm, Emission: 615 nm) using a fluorescence plate reader (ALVO MX, manufactured by Perkin Elmer Inc.), whereby the amount of free fluorescent collagen fragments released in the culture supernatant was determined (FIG. 36). As a result, the amount of fluorescent collagen fragments increased by the addition of RANKL was reduced by the #32A1 antibody in a concentration-dependent manner within the range of from 0.3 µg/ml to 3 µg/ml. From this result, it was revealed that the bone resorption activity of human osteoclasts is inhibited by the monoclonal antibody specifically binding to the Siglec-15 protein.

Example 38

Production of Mouse Anti-Human Siglec-15 Monoclonal Antibody

It is possible to produce an anti-human Siglec-15 antibody by the steps described below.
(1) Immunization
The soluble human Siglec-15 protein obtained in Examples 30 to 32 is intraperitoneally administered to a female BALB/c mouse at the age of 4 to 10 weeks. After 2 weeks, the same membrane fraction solution is intraperitoneally administered to the mouse for booster immunization.
(2) Cell Fusion
The spleen is resected from the mouse on three days after the booster immunization, placed in a serum-free medium and crushed on a mesh with a spatula. The cell suspension passed through the mesh is centrifuged to precipitate the spleen cells.
On the other hand, myeloma cells NS1 (American Type Culture Collection TIB-18) are washed with a serum-free medium and suspended in the same manner.
By using the thus obtained Siglec-15-expressing cells and myeloma cells, cell fusion is performed according to a common procedure.

(3) Screening
Anti-human Siglec-15 antibody-producing fused cells can be screened by a method using cell-ELISA and a method using a flow cytometer.
(4) Cloning
For a group of cells screened in the above (3), a series of steps comprising the method using cell-ELISA and the method using a flow cytometer described in (3) is repeated 5 times, whereby several clones of hybrdomas capable of producing a single antibody which binds to human Siglec-15-expressing cells, but does not bind to the cells before transfection can be obtained.
(5) Purification of Antibody
A mouse-mouse hybridoma produced through steps (1) to (4) is cultured, and the resulting supernatant is collected. After the obtained supernatant is collected and dialyzed, partial purification of the antibody is performed using a high performance liquid chromatography apparatus. The anti-human Siglec-15 antibody titer in each fraction of chromatography is assayed by an ELISA method using the human Siglec-15 protein. Fractions having a high antibody titer are collected and applied to an antibody affinity purification column. After the inside of the column is washed with a column equilibration buffer, the antibody is eluted with a column elution buffer. Immediately after completion of the elution, each eluate is applied to the top of a centrifugal ultrafilter and centrifuged. After the filtrate collected in the bottom of the filter is removed, washing is performed 5 times by adding PBS to the top. The liquid remaining on the top of the filter is used as an anti-human Siglec-15 antibody sample.

Example 39

Production of Rat Anti-Human Siglec-15 Monoclonal Antibody

A rat anti-human Siglec-15 monoclonal antibody can be produced using the soluble human Siglec-15 protein obtained in Examples 30 to 32 by the method described in Examples 23 and 24.

Example 40

Effect of Anti-Human Siglec-15 Monoclonal Antibody on Osteoclast Differentiation By using the anti-human Siglec-15 monoclonal antibody obtained in Example 38 or 39, the inhibitory effect of the antibody on osteoclast formation can be tested. For testing the effect on mouse osteoclast formation, the method of Example 17, 19, 20, 21, 22 or 26 can be used. For testing the inhibitory effect on human osteoclast formation, the method of Example 35 or 37 can be used.

INDUSTRIAL APPLICABILITY

The anti-Siglec-15 antibody of the invention has the ability to inhibit osteoclast differentiation or bone resorption activity, and a pharmaceutical composition containing the anti-Siglec-15 antibody can be a therapeutic or preventive agent for a disease of abnormal bone metabolism.

The invention claimed is:

1. An isolated hybridoma cell line #32A1 deposited at International Patent Organism Depository, National Institute of Advanced Industrial Science and Technology, having deposit accession number FERM BP-10999.

2. An isolated hybridoma cell line #41B1 deposited at International Patent Organism Depository, National Institute of Advanced Industrial Science and Technology, having deposit accession number FERM BP-11000.

3. An antibody produced by hybridoma cell line #32A1 deposited at International Patent Organism Depository, National Institute of Advanced Industrial Science and Technology, having deposit accession number FERM BP-10999, or a humanized antibody thereof.

4. An antibody produced by hybridoma cell line #41B1 deposited at International Patent Organism Depository, National Institute of Advanced Industrial Science and Technology, having deposit accession number FERM BP-11000, or a humanized antibody thereof.

5. A humanized antibody of claim 3.

6. A humanized antibody of claim 4.

* * * * *

SEQUENCE LISTING

<160> NUMBER OF SEQ ID NOS: 50

<210> SEQ ID NO 1
<211> LENGTH: 987
<212> TYPE: DNA
<213> ORGANISM: Homo sapiens

```
<220> FEATURE:
<221> NAME/KEY: CDS
<222> LOCATION: (1)..(987)

<400> SEQUENCE: 1 atg gaa aag tcc atc tgg ctg ctg gcc tgc ttg gcg tgg gtt ctc ccg      48
Met Glu Lys Ser Ile Trp Leu Leu Ala Cys Leu Ala Trp Val Leu Pro
1               5                   10                  15 aca ggc tca ttt gtg aga act aaa ata gat act acg gag aac ttg ctc      96
Thr Gly Ser Phe Val Arg Thr Lys Ile Asp Thr Thr Glu Asn Leu Leu
            20                  25                  30 aac aca gag gtg cac agc tcg cca gcg cag cgc tgg tcc atg cag gtg     144
Asn Thr Glu Val His Ser Ser Pro Ala Gln Arg Trp Ser Met Gln Val
        35                  40                  45 cca ccc gag gtg agc gcg gag gca ggc gac gcg gca gtg ctg ccc tgc     192
Pro Pro Glu Val Ser Ala Glu Ala Gly Asp Ala Ala Val Leu Pro Cys
    50                  55                  60 acc ttc acg cac ccg cac cgc cac tac gac ggg ccg ctg acg gcc atc     240
Thr Phe Thr His Pro His Arg His Tyr Asp Gly Pro Leu Thr Ala Ile
65                  70                  75                  80 tgg cgc gcg ggc gag ccc tat gcg ggc ccg cag gtg ttc cgc tgc gct     288
Trp Arg Ala Gly Glu Pro Tyr Ala Gly Pro Gln Val Phe Arg Cys Ala
                85                  90                  95 gcg gcg cgg ggc agc gag ctc tgc cag acg gcg ctg agc ctg cac ggc     336
Ala Ala Arg Gly Ser Glu Leu Cys Gln Thr Ala Leu Ser Leu His Gly
            100                 105                 110 cgc ttc cgg ctg ctg ggc aac ccg cgc cgc aac gac ctc tcg ctg cgc     384
Arg Phe Arg Leu Leu Gly Asn Pro Arg Arg Asn Asp Leu Ser Leu Arg
        115                 120                 125 gtc gag cgc ctc gcc ctg gct gac gac cgc cgc tac ttc tgc cgc gtc     432
Val Glu Arg Leu Ala Leu Ala Asp Asp Arg Arg Tyr Phe Cys Arg Val
    130                 135                 140 gag ttc gcc ggc gac gtc cat gac cgc tac gag agc cgc cac ggc gtc     480
Glu Phe Ala Gly Asp Val His Asp Arg Tyr Glu Ser Arg His Gly Val
145                 150                 155                 160 cgg ctg cac gtg aca gcc gcg ccg cgg atc gtc aac atc tcg gtg ctg     528
Arg Leu His Val Thr Ala Ala Pro Arg Ile Val Asn Ile Ser Val Leu
                165                 170                 175 ccc agt ccg gct cac gcc ttc cgc gcg ctc tgc act gcc gaa ggg gag     576
Pro Ser Pro Ala His Ala Phe Arg Ala Leu Cys Thr Ala Glu Gly Glu
            180                 185                 190 ccg ccg ccc gcc ctc gcc tgg tcc ggc ccg gcc ctg ggc aac agc ttg     624
Pro Pro Pro Ala Leu Ala Trp Ser Gly Pro Ala Leu Gly Asn Ser Leu
        195                 200                 205 gca gcc gtg cgg agc ccg cgt gag ggt cac ggc cac cta gtg acc gcc     672
Ala Ala Val Arg Ser Pro Arg Glu Gly His Gly His Leu Val Thr Ala
    210                 215                 220 gaa ctg ccc gca ctg acc cat gac ggc cgc tac acg tgt acg gcc gcc     720
Glu Leu Pro Ala Leu Thr His Asp Gly Arg Tyr Thr Cys Thr Ala Ala
225                 230                 235                 240 aac agc ctg ggc cgc tcc gag gcc agc gtc tac ctg ttc cgc ttc cat     768
Asn Ser Leu Gly Arg Ser Glu Ala Ser Val Tyr Leu Phe Arg Phe His
                245                 250                 255 ggc gcc agc ggg gcc tcg acg gtc gcc ctc ctg ctc ggc gct ctc ggc     816
Gly Ala Ser Gly Ala Ser Thr Val Ala Leu Leu Leu Gly Ala Leu Gly
            260                 265                 270 ttc aag gcg ctg ctg ctg ctc ggg gtc ctg gcc gcc cgc gct gcc cgc     864
Phe Lys Ala Leu Leu Leu Leu Gly Val Leu Ala Ala Arg Ala Ala Arg
        275                 280                 285
```

```
cgc cgc cca gag cat ctg gac acc ccg gac acc cca cgg tcc cag      912
Arg Arg Pro Glu His Leu Asp Thr Pro Asp Thr Pro Arg Ser Gln
    290             295                 300 gcc cag gag tcc aat tat gaa aat ttg agc cag atg aac ccc cgg agc  960
Ala Gln Glu Ser Asn Tyr Glu Asn Leu Ser Gln Met Asn Pro Arg Ser
305             310                 315                 320 cca cca gcc acc atg tgc tca ccg tga                              987
Pro Pro Ala Thr Met Cys Ser Pro
                325
```

```
<210> SEQ ID NO 2
<211> LENGTH: 328
<212> TYPE: PRT
<213> ORGANISM: Homo sapiens

<400> SEQUENCE: 2

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Ala Ser Thr Val Ala Leu Leu Leu Gly Ala Leu Gly
            260                 265                 270

Phe Lys Ala Leu Leu Leu Leu Gly Val Leu Ala Ala Arg Ala Ala Arg
        275                 280                 285

Arg Arg Pro Glu His Leu Asp Thr Pro Asp Thr Pro Arg Ser Gln
    290                 295                 300
```

```
Ala Gln Glu Ser Asn Tyr Glu Asn Leu Ser Gln Met Asn Pro Arg Ser
305                 310                 315                 320

Pro Pro Ala Thr Met Cys Ser Pro
                325

<210> SEQ ID NO 3
<211> LENGTH: 1026
<212> TYPE: DNA
<213> ORGANISM: Mus musculus
<220> FEATURE:
<221> NAME/KEY: CDS
<222> LOCATION: (1)..(1026)

<400> SEQUENCE: 3 atg gag ggg tcc ctc caa ctc ctg gcc tgc ttg gcc tgt gtg ctc cag    48
Met Glu Gly Ser Leu Gln Leu Leu Ala Cys Leu Ala Cys Val Leu Gln
1               5                   10                  15 atg gga tcc ctt gtg aaa act aga aga gac gct tcg ggg gat ctg ctc    96
Met Gly Ser Leu Val Lys Thr Arg Arg Asp Ala Ser Gly Asp Leu Leu
            20                  25                  30 aac aca gag gcg cac agt gcc ccg gcg cag cgc tgg tcc atg cag gtg   144
Asn Thr Glu Ala His Ser Ala Pro Ala Gln Arg Trp Ser Met Gln Val
        35                  40                  45 ccc gcg gag gtg aac gcg gag gct ggc gac gcg gcg gtg ctg ccc tgc   192
Pro Ala Glu Val Asn Ala Glu Ala Gly Asp Ala Ala Val Leu Pro Cys
    50                  55                  60 acc ttc acg cac ccg cac cgc cac tac gac ggg ccg ctg acg gcc atc   240
Thr Phe Thr His Pro His Arg His Tyr Asp Gly Pro Leu Thr Ala Ile
65                  70                  75                  80 tgg cgc tcg ggc gag ccg tac gcg ggc ccg cag gtg ttc cgc tgc acc   288
Trp Arg Ser Gly Glu Pro Tyr Ala Gly Pro Gln Val Phe Arg Cys Thr
                85                  90                  95 gcg gcg ccg ggc agc gag ctg tgc cag acg gcg ctg agc ctg cac ggc   336
Ala Ala Pro Gly Ser Glu Leu Cys Gln Thr Ala Leu Ser Leu His Gly
            100                 105                 110 cgc ttc cgc ctg ctg ggc aac ccg cgc cgc aac gac ctg tcc ctg cgc   384
Arg Phe Arg Leu Leu Gly Asn Pro Arg Arg Asn Asp Leu Ser Leu Arg
        115                 120                 125 gtc gag cgc ctc gcc ctg gcg gac agc ggc cgc tac ttc tgc cgc gtg   432
Val Glu Arg Leu Ala Leu Ala Asp Ser Gly Arg Tyr Phe Cys Arg Val
    130                 135                 140 gag ttc acc ggc gac gcc cac gat cgc tat gag agt cgc cat ggg gtc   480
Glu Phe Thr Gly Asp Ala His Asp Arg Tyr Glu Ser Arg His Gly Val
145                 150                 155                 160 cgt ctg cgc gtg act gct gcg ccg cgg atc gtc aac atc tcg gtg ctg   528
Arg Leu Arg Val Thr Ala Ala Pro Arg Ile Val Asn Ile Ser Val Leu
                165                 170                 175 ccg ggc ccc gcg cac gcc ttc cgc gcg ctc tgc acc gcc gag ggg gag   576
Pro Gly Pro Ala His Ala Phe Arg Ala Leu Cys Thr Ala Glu Gly Glu
            180                 185                 190 ccc ccg ccc gcc ctc gcc tgg tcg ggt ccc gcc cca ggc aac agc tcc   624
Pro Pro Pro Ala Leu Ala Trp Ser Gly Pro Ala Pro Gly Asn Ser Ser
        195                 200                 205 gct gcc ctg cag ggc cag ggt cac ggc tac cag gtg acc gcc gag ttg   672
Ala Ala Leu Gln Gly Gln Gly His Gly Tyr Gln Val Thr Ala Glu Leu
    210                 215                 220 ccc gcg ctg acc cgc gac ggc cgc tac acg tgc acg gcg gcc aat agc   720
Pro Ala Leu Thr Arg Asp Gly Arg Tyr Thr Cys Thr Ala Ala Asn Ser
225                 230                 235                 240 ctg ggc cgc gcc gag gcc agc gtc tac ctg ttc cgc ttc cac ggc gcc   768
Leu Gly Arg Ala Glu Ala Ser Val Tyr Leu Phe Arg Phe His Gly Ala
                245                 250                 255
```

```
ccc gga acc tcg acc cta gcg ctc ctg ctg ggc gcg ctg ggc ctc aag    816
Pro Gly Thr Ser Thr Leu Ala Leu Leu Leu Gly Ala Leu Gly Leu Lys
            260                 265                 270 gcc ttg ctg ctg ctt ggc att ctg gga gcg cgt gcc acc cga cgc cga    864
Ala Leu Leu Leu Leu Gly Ile Leu Gly Ala Arg Ala Thr Arg Arg Arg
        275                 280                 285 cta gat cac ctg gtc ccc cag gac acc cct cca cgg tct cag gct cag    912
Leu Asp His Leu Val Pro Gln Asp Thr Pro Pro Arg Ser Gln Ala Gln
    290                 295                 300 gag tcc aat tat gaa aat ttg agc cag atg agt cct cca ggc cac cag    960
Glu Ser Asn Tyr Glu Asn Leu Ser Gln Met Ser Pro Pro Gly His Gln
305                 310                 315                 320 ctg cca cgt gtt tgc tgt gag gaa ctc ctc agc cat cac cat cta gtc   1008
Leu Pro Arg Val Cys Cys Glu Glu Leu Leu Ser His His His Leu Val
                325                 330                 335 att cac cat gag aaa taa                                           1026
Ile His His Glu Lys
            340
```

<210> SEQ ID NO 4
<211> LENGTH: 341
<212> TYPE: PRT
<213> ORGANISM: Mus musculus

<400> SEQUENCE: 4

```
Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
            20                  25                  30

Asn Thr Glu Ala His Ser Ala Pro Ala Gln Arg Trp Ser Met Gln Val
        35                  40                  45

Pro Ala Glu Val Asn Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Ser Gly Arg Tyr Phe Cys Arg Val
    130                 135                 140

Glu Phe Thr Gly Asp Ala His Asp Arg Tyr Glu Ser Arg His Gly Val
145                 150                 155                 160

Arg Leu Arg Val Thr Ala Ala Pro Arg Ile Val Asn Ile Ser Val Leu
                165                 170                 175

Pro Gly Pro Ala His Ala Phe Arg Ala Leu Cys Thr Ala Glu Gly Glu
            180                 185                 190

Pro Pro Pro Ala Leu Ala Trp Ser Gly Pro Ala Pro Gly Asn Ser Ser
        195                 200                 205

Ala Ala Leu Gln Gly Gln Gly His Gly Tyr Gln Val Thr Ala Glu Leu
    210                 215                 220

Pro Ala Leu Thr Arg Asp Gly Arg Tyr Thr Cys Thr Ala Ala Asn Ser
225                 230                 235                 240

Leu Gly Arg Ala Glu Ala Ser Val Tyr Leu Phe Arg Phe His Gly Ala
                245                 250                 255
```

```
Pro Gly Thr Ser Thr Leu Ala Leu Leu Leu Gly Ala Leu Gly Leu Lys
            260                 265                 270

Ala Leu Leu Leu Gly Ile Leu Gly Ala Arg Ala Thr Arg Arg Arg
275                 280                 285

Leu Asp His Leu Val Pro Gln Asp Thr Pro Pro Arg Ser Gln Ala Gln
        290                 295                 300

Glu Ser Asn Tyr Glu Asn Leu Ser Gln Met Ser Pro Gly His Gln
305                 310                 315                 320

Leu Pro Arg Val Cys Cys Glu Glu Leu Leu Ser His His Leu Val
                325                 330                 335

Ile His His Glu Lys
            340

<210> SEQ ID NO 5
<211> LENGTH: 32
<212> TYPE: DNA
<213> ORGANISM: Artificial Sequence
<220> FEATURE:
<223> OTHER INFORMATION: PCR primer of mouse Siglec-15 cDNA

<400> SEQUENCE: 5
agaattccac catggagggg tccctccaac tc                               32

<210> SEQ ID NO 6
<211> LENGTH: 32
<212> TYPE: DNA
<213> ORGANISM: Artificial Sequence
<220> FEATURE:
<223> OTHER INFORMATION: PCR primer of mouse Siglec-15 cDNA

<400> SEQUENCE: 6
cgccgctcga gttatttctc atggtgaatg ac                               32

<210> SEQ ID NO 7
<211> LENGTH: 22
<212> TYPE: DNA
<213> ORGANISM: Artificial Sequence
<220> FEATURE:
<223> OTHER INFORMATION: PCR primer of mouse Siglec-15 cDNA

<400> SEQUENCE: 7
tcaggctcag gagtccaatt at                                          22

<210> SEQ ID NO 8
<211> LENGTH: 23
<212> TYPE: DNA
<213> ORGANISM: Artificial Sequence
<220> FEATURE:
<223> OTHER INFORMATION: PCR primer of mouse Siglec-15 cDNA

<400> SEQUENCE: 8
ggtctagcct ggtactgtcc ttt                                         23

<210> SEQ ID NO 9
<211> LENGTH: 28
<212> TYPE: DNA
<213> ORGANISM: Artificial Sequence
<220> FEATURE:
<223> OTHER INFORMATION: Detection probe of mouse Siglec-15 cDNA

<400> SEQUENCE: 9
atttgagcca gatgagtcct ccaggcca                                    28
```

```
<210> SEQ ID NO 10
<211> LENGTH: 22
<212> TYPE: DNA
<213> ORGANISM: Artificial Sequence
<220> FEATURE:
<223> OTHER INFORMATION: PCR primer of mouse L32 ribosomal protien cDNA

<400> SEQUENCE: 10
aagaagttca tcaggcacca gt                                            22

<210> SEQ ID NO 11
<211> LENGTH: 22
<212> TYPE: DNA
<213> ORGANISM: Artificial Sequence
<220> FEATURE:
<223> OTHER INFORMATION: PCR primer of mouse L32 ribosomal protein cDNA

<400> SEQUENCE: 11
cttgacattg tggaccagga ac                                            22

<210> SEQ ID NO 12
<211> LENGTH: 28
<212> TYPE: DNA
<213> ORGANISM: Artificial Sequence
<220> FEATURE:
<223> OTHER INFORMATION: Detection probe of mouse L32 ribosomal protein
      cDNA

<400> SEQUENCE: 12
aaacccagag gcattgacaa cagggtgc                                      28

<210> SEQ ID NO 13
<211> LENGTH: 22
<212> TYPE: DNA
<213> ORGANISM: Artificial Sequence
<220> FEATURE:
<223> OTHER INFORMATION: PCR primer of mouse cathepsin K cDNA

<400> SEQUENCE: 13
ggcatctttc cagttttaca gc                                            22

<210> SEQ ID NO 14
<211> LENGTH: 22
<212> TYPE: DNA
<213> ORGANISM: Artificial Sequence
<220> FEATURE:
<223> OTHER INFORMATION: PCR primer of mouse cathepsin K cDNA

<400> SEQUENCE: 14
gttgttctta ttccgagcca ag                                            22

<210> SEQ ID NO 15
<211> LENGTH: 28
<212> TYPE: DNA
<213> ORGANISM: Artificial Sequence
<220> FEATURE:
<223> OTHER INFORMATION: Detection probe of mouse cathepsin K cDNA

<400> SEQUENCE: 15
atgtgaacca tgcagtgttg gtggtggg                                      28

<210> SEQ ID NO 16
<211> LENGTH: 22
<212> TYPE: DNA
<213> ORGANISM: Artificial Sequence
<220> FEATURE:
<223> OTHER INFORMATION: PCR primer of mouse TRAP cDNA
```

```
<400> SEQUENCE: 16
gaacttcccc agcccttact ac                                              22

<210> SEQ ID NO 17
<211> LENGTH: 21
<212> TYPE: DNA
<213> ORGANISM: Artificial Sequence
<220> FEATURE:
<223> OTHER INFORMATION: PCR primer of mouse TRAP cDNA

<400> SEQUENCE: 17
aactgctttt tgagccagga c                                               21

<210> SEQ ID NO 18
<211> LENGTH: 26
<212> TYPE: DNA
<213> ORGANISM: Artificial Sequence
<220> FEATURE:
<223> OTHER INFORMATION: Detection probe of mouse TRAP cDNA

<400> SEQUENCE: 18
ttgccagtca gcagcccaaa atgcct                                          26

<210> SEQ ID NO 19
<211> LENGTH: 774
<212> TYPE: DNA
<213> ORGANISM: Mus musculus
<220> FEATURE:
<221> NAME/KEY: CDS
<222> LOCATION: (1)..(774)

<400> SEQUENCE: 19 atg gag ggg tcc ctc caa ctc ctg gcc tgc ttg gcc tgt gtg ctc cag      48
Met Glu Gly Ser Leu Gln Leu Leu Ala Cys Leu Ala Cys Val Leu Gln
1               5                   10                  15 atg gga tcc ctt gtg aaa act aga aga gac gct tcg ggg gat ctg ctc      96
Met Gly Ser Leu Val Lys Thr Arg Arg Asp Ala Ser Gly Asp Leu Leu
            20                  25                  30 aac aca gag gcg cac agt gcc ccg gcg cag cgc tgg tcc atg cag gtg     144
Asn Thr Glu Ala His Ser Ala Pro Ala Gln Arg Trp Ser Met Gln Val
        35                  40                  45 ccc gcg gag gtg aac gcg gag gct ggc gac gcg gcg gtg ctg ccc tgc     192
Pro Ala Glu Val Asn Ala Glu Ala Gly Asp Ala Ala Val Leu Pro Cys
    50                  55                  60 acc ttc acg cac ccg cac cgc cac tac gac ggg ccg ctg acg gcc atc     240
Thr Phe Thr His Pro His Arg His Tyr Asp Gly Pro Leu Thr Ala Ile
65                  70                  75                  80 tgg cgc tcg ggc gag ccg tac gcg ggc ccg cag gtg ttc cgc tgc acc     288
Trp Arg Ser Gly Glu Pro Tyr Ala Gly Pro Gln Val Phe Arg Cys Thr
                85                  90                  95 gcg gcg ccg ggc agc gag ctg tgc cag acg gcg ctg agc ctg cac ggc     336
Ala Ala Pro Gly Ser Glu Leu Cys Gln Thr Ala Leu Ser Leu His Gly
            100                 105                 110 cgc ttc cgc ctg ctg ggc aac ccg cgc cgc aac gac ctg tcc ctg cgc     384
Arg Phe Arg Leu Leu Gly Asn Pro Arg Arg Asn Asp Leu Ser Leu Arg
        115                 120                 125 gtc gag cgc ctc gcc ctg gcg gac agc ggc cgc tac ttc tgc cgc gtg     432
Val Glu Arg Leu Ala Leu Ala Asp Ser Gly Arg Tyr Phe Cys Arg Val
    130                 135                 140 gag ttc acc ggc gac gcc cac gat cgc tat gag agt cgc cat ggg gtc     480
Glu Phe Thr Gly Asp Ala His Asp Arg Tyr Glu Ser Arg His Gly Val
145                 150                 155                 160
```

```
cgt ctg cgc gtg act gct gcg ccg cgg atc gtc aac atc tcg gtg ctg    528
Arg Leu Arg Val Thr Ala Ala Pro Arg Ile Val Asn Ile Ser Val Leu
            165                 170                 175 ccg ggc ccc gcg cac gcc ttc cgc gcg ctc tgc acc gcc gag ggg gag    576
Pro Gly Pro Ala His Ala Phe Arg Ala Leu Cys Thr Ala Glu Gly Glu
        180                 185                 190 ccc ccg ccc gcc ctc gcc tgg tcg ggt ccc gcc cca ggc aac agc tcc    624
Pro Pro Pro Ala Leu Ala Trp Ser Gly Pro Ala Pro Gly Asn Ser Ser
    195                 200                 205 gct gcc ctg cag ggc cag ggt cac ggc tac cag gtg acc gcc gag ttg    672
Ala Ala Leu Gln Gly Gln Gly His Gly Tyr Gln Val Thr Ala Glu Leu
210                 215                 220 ccc gcg ctg acc cgc gac ggc cgc tac acg tgc acg gcg gcc aat agc    720
Pro Ala Leu Thr Arg Asp Gly Arg Tyr Thr Cys Thr Ala Ala Asn Ser
225                 230                 235                 240 ctg ggc cgc gcc gag gcc agc gtc tac ctg ttc cgc ttc cac ggc gcc    768
Leu Gly Arg Ala Glu Ala Ser Val Tyr Leu Phe Arg Phe His Gly Ala
                245                 250                 255 ccc gga                                                             774
Pro Gly

<210> SEQ ID NO 20
<211> LENGTH: 258
<212> TYPE: PRT
<213> ORGANISM: Mus musculus

<400> SEQUENCE: 20

Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
            20                  25                  30

Asn Thr Glu Ala His Ser Ala Pro Ala Gln Arg Trp Ser Met Gln Val
        35                  40                  45

Pro Ala Glu Val Asn Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Ser Gly Arg Tyr Phe Cys Arg Val
    130                 135                 140

Glu Phe Thr Gly Asp Ala His Asp Arg Tyr Glu Ser Arg His Gly Val
145                 150                 155                 160

Arg Leu Arg Val Thr Ala Ala Pro Arg Ile Val Asn Ile Ser Val Leu
                165                 170                 175

Pro Gly Pro Ala His Ala Phe Arg Ala Leu Cys Thr Ala Glu Gly Glu
            180                 185                 190

Pro Pro Pro Ala Leu Ala Trp Ser Gly Pro Ala Pro Gly Asn Ser Ser
        195                 200                 205

Ala Ala Leu Gln Gly Gln Gly His Gly Tyr Gln Val Thr Ala Glu Leu
    210                 215                 220

Pro Ala Leu Thr Arg Asp Gly Arg Tyr Thr Cys Thr Ala Ala Asn Ser
225                 230                 235                 240
```

```
Leu Gly Arg Ala Glu Ala Ser Val Tyr Leu Phe Arg Phe His Gly Ala
            245                 250                 255

Pro Gly

<210> SEQ ID NO 21
<211> LENGTH: 55
<212> TYPE: DNA
<213> ORGANISM: Artificial Sequence
<220> FEATURE:
<223> OTHER INFORMATION: PCR primer of soluble mouse Siglec-15 cDNA

<400> SEQUENCE: 21
ggggacaagt ttgtacaaaa aagcaggctt caccatggag gggtccctcc aactc          55

<210> SEQ ID NO 22
<211> LENGTH: 55
<212> TYPE: DNA
<213> ORGANISM: Artificial Sequence
<220> FEATURE:
<223> OTHER INFORMATION: PCR primer of soluble mouse Siglec-15 cDNA

<400> SEQUENCE: 22
ggggaccact ttgtacaaga aagctgggtc tccgggggcg ccgtggaagc ggaac          55

<210> SEQ ID NO 23
<211> LENGTH: 20
<212> TYPE: DNA
<213> ORGANISM: Artificial Sequence
<220> FEATURE:
<223> OTHER INFORMATION: Sequencing primer of soluble mouse Siglec-15
      cDNA

<400> SEQUENCE: 23
tgcgtgaagg tgcagggcag                                                 20

<210> SEQ ID NO 24
<211> LENGTH: 17
<212> TYPE: DNA
<213> ORGANISM: Artificial Sequence
<220> FEATURE:
<223> OTHER INFORMATION: Sequencing primer of soluble mouse Siglec-15
      cDNA

<400> SEQUENCE: 24
cctcgcctgg tcgggtc                                                    17

<210> SEQ ID NO 25
<211> LENGTH: 891
<212> TYPE: DNA
<213> ORGANISM: Artificial Sequence
<220> FEATURE:
<223> OTHER INFORMATION: His-tagged mouse Siglec-15 cDNA
<220> FEATURE:
<221> NAME/KEY: CDS
<222> LOCATION: (1)..(891)

<400> SEQUENCE: 25 atg gag ggg tcc ctc caa ctc ctg gcc tgc ttg gcc tgt gtg ctc cag       48
Met Glu Gly Ser Leu Gln Leu Leu Ala Cys Leu Ala Cys Val Leu Gln
1               5                   10                  15 atg gga tcc ctt gtg aaa act aga aga gac gct tcg ggg gat ctg ctc       96
Met Gly Ser Leu Val Lys Thr Arg Arg Asp Ala Ser Gly Asp Leu Leu
            20                  25                  30 aac aca gag gcg cac agt gcc ccg gcg cag cgc tgg tcc atg cag gtg      144
Asn Thr Glu Ala His Ser Ala Pro Ala Gln Arg Trp Ser Met Gln Val
        35                  40                  45
```

```
ccc gcg gag gtg aac gcg gag gct ggc gac gcg gcg gtg ctg ccc tgc     192
Pro Ala Glu Val Asn Ala Glu Ala Gly Asp Ala Ala Val Leu Pro Cys
    50                  55                  60 acc ttc acg cac ccg cac cgc cac tac gac ggg ccg ctg acg gcc atc     240
Thr Phe Thr His Pro His Arg His Tyr Asp Gly Pro Leu Thr Ala Ile
65                  70                  75                  80 tgg cgc tcg ggc gag ccg tac gcg ggc ccg cag gtg ttc cgc tgc acc     288
Trp Arg Ser Gly Glu Pro Tyr Ala Gly Pro Gln Val Phe Arg Cys Thr
                85                  90                  95 gcg gcg ccg ggc agc gag ctg tgc cag acg gcg ctg agc ctg cac ggc     336
Ala Ala Pro Gly Ser Glu Leu Cys Gln Thr Ala Leu Ser Leu His Gly
            100                 105                 110 cgc ttc cgc ctg ctg ggc aac ccg cgc cgc aac gac ctg tcc ctg cgc     384
Arg Phe Arg Leu Leu Gly Asn Pro Arg Arg Asn Asp Leu Ser Leu Arg
        115                 120                 125 gtc gag cgc ctc gcc ctg gcg gac agc ggc cgc tac ttc tgc cgc gtg     432
Val Glu Arg Leu Ala Leu Ala Asp Ser Gly Arg Tyr Phe Cys Arg Val
    130                 135                 140 gag ttc acc ggc gac gcc cac gat cgc tat gag agt cgc cat ggg gtc     480
Glu Phe Thr Gly Asp Ala His Asp Arg Tyr Glu Ser Arg His Gly Val
145                 150                 155                 160 cgt ctg cgc gtg act gct gcg ccg cgg atc gtc aac atc tcg gtg ctg     528
Arg Leu Arg Val Thr Ala Ala Pro Arg Ile Val Asn Ile Ser Val Leu
                165                 170                 175 ccg ggc ccc gcg cac gcc ttc cgc gcg ctc tgc acc gcc gag ggg gag     576
Pro Gly Pro Ala His Ala Phe Arg Ala Leu Cys Thr Ala Glu Gly Glu
            180                 185                 190 ccc ccg ccc gcc ctc gcc tgg tcg ggt ccc gcc cca ggc aac agc tcc     624
Pro Pro Pro Ala Leu Ala Trp Ser Gly Pro Ala Pro Gly Asn Ser Ser
        195                 200                 205 gct gcc ctg cag ggc cag ggt cac ggc tac cag gtg acc gcc gag ttg     672
Ala Ala Leu Gln Gly Gln Gly His Gly Tyr Gln Val Thr Ala Glu Leu
    210                 215                 220 ccc gcg ctg acc cgc gac ggc cgc tac acg tgc acg gcg gcc aat agc     720
Pro Ala Leu Thr Arg Asp Gly Arg Tyr Thr Cys Thr Ala Ala Asn Ser
225                 230                 235                 240 ctg ggc cgc gcc gag gcc agc gtc tac ctg ttc cgc ttc cac ggc gcc     768
Leu Gly Arg Ala Glu Ala Ser Val Tyr Leu Phe Arg Phe His Gly Ala
                245                 250                 255 ccc gga gac cca gct ttc ttg tac aaa gtg gtt gat atc gaa ggt cgt     816
Pro Gly Asp Pro Ala Phe Leu Tyr Lys Val Val Asp Ile Glu Gly Arg
            260                 265                 270 ggg ggt aag cct atc cct aac cct ctc ctc ggt ctc gat tct acg cgt     864
Gly Gly Lys Pro Ile Pro Asn Pro Leu Leu Gly Leu Asp Ser Thr Arg
        275                 280                 285 acc ggt cat cat cac cat cac cat tga                                 891
Thr Gly His His His His His His
    290                 295
```

<210> SEQ ID NO 26
<211> LENGTH: 296
<212> TYPE: PRT
<213> ORGANISM: Artificial Sequence
<220> FEATURE:
<223> OTHER INFORMATION: His-tagged mouse Siglec-15 peptide

<400> SEQUENCE: 26

```
Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
            20                  25                  30
```

```
Asn Thr Glu Ala His Ser Ala Pro Ala Gln Arg Trp Ser Met Gln Val
         35                  40                  45

Pro Ala Glu Val Asn Ala Glu Ala Gly Asp Ala Ala Val Leu Pro Cys
 50                  55                  60

Thr Phe Thr His Pro His Arg His Tyr Asp Gly Pro Leu Thr Ala Ile
 65                  70                  75                  80

Trp Arg Ser Gly Glu Pro Tyr Ala Gly Pro Gln Val Phe Arg Cys Thr
                 85                  90                  95

Ala Ala Pro Gly Ser Glu Leu Cys Gln Thr Ala Leu Ser Leu His Gly
                100                 105                 110

Arg Phe Arg Leu Leu Gly Asn Pro Arg Arg Asn Asp Leu Ser Leu Arg
            115                 120                 125

Val Glu Arg Leu Ala Leu Ala Asp Ser Gly Arg Tyr Phe Cys Arg Val
130                 135                 140

Glu Phe Thr Gly Asp Ala His Asp Arg Tyr Glu Ser Arg His Gly Val
145                 150                 155                 160

Arg Leu Arg Val Thr Ala Ala Pro Arg Ile Val Asn Ile Ser Val Leu
                165                 170                 175

Pro Gly Pro Ala His Ala Phe Arg Ala Leu Cys Thr Ala Glu Gly Glu
            180                 185                 190

Pro Pro Pro Ala Leu Ala Trp Ser Gly Pro Ala Pro Gly Asn Ser Ser
        195                 200                 205

Ala Ala Leu Gln Gly Gln Gly His Gly Tyr Gln Val Thr Ala Glu Leu
    210                 215                 220

Pro Ala Leu Thr Arg Asp Gly Arg Tyr Thr Cys Thr Ala Ala Asn Ser
225                 230                 235                 240

Leu Gly Arg Ala Glu Ala Ser Val Tyr Leu Phe Arg Phe His Gly Ala
                245                 250                 255

Pro Gly Asp Pro Ala Phe Leu Tyr Lys Val Val Asp Ile Glu Gly Arg
            260                 265                 270

Gly Gly Lys Pro Ile Pro Asn Pro Leu Leu Gly Leu Asp Ser Thr Arg
        275                 280                 285

Thr Gly His His His His His His
    290                 295
```

```
<210> SEQ ID NO 27
<211> LENGTH: 1512
<212> TYPE: DNA
<213> ORGANISM: Artificial Sequence
<220> FEATURE:
<223> OTHER INFORMATION: Fc-fused mouse Siglec-15 cDNA
<220> FEATURE:
<221> NAME/KEY: CDS
<222> LOCATION: (1)..(1512)

<400> SEQUENCE: 27
```

```
atg gag ggg tcc ctc caa ctc ctg gcc tgc ttg gcc tgt gtg ctc cag    48
Met Glu Gly Ser Leu Gln Leu Leu Ala Cys Leu Ala Cys Val Leu Gln
 1               5                  10                  15 atg gga tcc ctt gtg aaa act aga aga gac gct tcg ggg gat ctg ctc    96
Met Gly Ser Leu Val Lys Thr Arg Arg Asp Ala Ser Gly Asp Leu Leu
             20                  25                  30 aac aca gag gcg cac agt gcc ccg gcg cag cgc tgg tcc atg cag gtg   144
Asn Thr Glu Ala His Ser Ala Pro Ala Gln Arg Trp Ser Met Gln Val
         35                  40                  45 ccc gcg gag gtg aac gcg gag gct ggc gac gcg gcg gtg ctg ccc tgc   192
Pro Ala Glu Val Asn Ala Glu Ala Gly Asp Ala Ala Val Leu Pro Cys
 50                  55                  60
```

```
acc ttc acg cac ccg cac cgc cac tac gac ggg ccg ctg acg gcc atc     240
Thr Phe Thr His Pro His Arg His Tyr Asp Gly Pro Leu Thr Ala Ile
 65          70                  75                  80 tgg cgc tcg ggc gag ccg tac gcg ggc ccg cag gtg ttc cgc tgc acc     288
Trp Arg Ser Gly Glu Pro Tyr Ala Gly Pro Gln Val Phe Arg Cys Thr
             85                  90                  95 gcg gcg ccg ggc agc gag ctg tgc cag acg gcg ctg agc ctg cac ggc     336
Ala Ala Pro Gly Ser Glu Leu Cys Gln Thr Ala Leu Ser Leu His Gly
            100                 105                 110 cgc ttc cgc ctg ctg ggc aac ccg cgc cgc aac gac ctg tcc ctg cgc     384
Arg Phe Arg Leu Leu Gly Asn Pro Arg Arg Asn Asp Leu Ser Leu Arg
        115                 120                 125 gtc gag cgc ctc gcc ctg gcg gac agc ggc cgc tac ttc tgc cgc gtg     432
Val Glu Arg Leu Ala Leu Ala Asp Ser Gly Arg Tyr Phe Cys Arg Val
    130                 135                 140 gag ttc acc ggc gac gcc cac gat cgc tat gag agt cgc cat ggg gtc     480
Glu Phe Thr Gly Asp Ala His Asp Arg Tyr Glu Ser Arg His Gly Val
145                 150                 155                 160 cgt ctg cgc gtg act gct gcg ccg cgg atc gtc aac atc tcg gtg ctg     528
Arg Leu Arg Val Thr Ala Ala Pro Arg Ile Val Asn Ile Ser Val Leu
                165                 170                 175 ccg ggc ccc gcg cac gcc ttc cgc gcg ctc tgc acc gcc gag ggg gag     576
Pro Gly Pro Ala His Ala Phe Arg Ala Leu Cys Thr Ala Glu Gly Glu
            180                 185                 190 ccc ccg ccc gcc ctc gcc tgg tcg ggt ccc gcc cca ggc aac agc tcc     624
Pro Pro Pro Ala Leu Ala Trp Ser Gly Pro Ala Pro Gly Asn Ser Ser
        195                 200                 205 gct gcc ctg cag ggc cag ggt cac ggc tac cag gtg acc gcc gag ttg     672
Ala Ala Leu Gln Gly Gln Gly His Gly Tyr Gln Val Thr Ala Glu Leu
210                 215                 220 ccc gcg ctg acc cgc gac ggc cgc tac acg tgc acg gcg gcc aat agc     720
Pro Ala Leu Thr Arg Asp Gly Arg Tyr Thr Cys Thr Ala Ala Asn Ser
225                 230                 235                 240 ctg ggc cgc gcc gag gcc agc gtc tac ctg ttc cgc ttc cac ggc gcc     768
Leu Gly Arg Ala Glu Ala Ser Val Tyr Leu Phe Arg Phe His Gly Ala
                245                 250                 255 ccc gga gac cca gct ttc ttg tac aaa gtg gtt gat atc cag gca gag     816
Pro Gly Asp Pro Ala Phe Leu Tyr Lys Val Val Asp Ile Gln Ala Glu
            260                 265                 270 ccc aaa tct tgt gac aaa act cac aca tgc cca ccg tgc cca gca cct     864
Pro Lys Ser Cys Asp Lys Thr His Thr Cys Pro Pro Cys Pro Ala Pro
        275                 280                 285 gaa ctc ctg ggg gga ccg tca gtc ttc ctc ttc ccc cca aaa ccc aag     912
Glu Leu Leu Gly Gly Pro Ser Val Phe Leu Phe Pro Pro Lys Pro Lys
            290                 295                 300 gac acc ctc atg atc tcc cgg acc cct gag gtc aca tgc gtg gtg gtg     960
Asp Thr Leu Met Ile Ser Arg Thr Pro Glu Val Thr Cys Val Val Val
305                 310                 315                 320 gac gtg agc cac gaa gac cct gag gtc aag ttc aac tgg tac gtg gac    1008
Asp Val Ser His Glu Asp Pro Glu Val Lys Phe Asn Trp Tyr Val Asp
                325                 330                 335 ggc gtg gag gtg cat aat gcc aag aca aag ccg cgg gag gag cag tac    1056
Gly Val Glu Val His Asn Ala Lys Thr Lys Pro Arg Glu Glu Gln Tyr
            340                 345                 350 aac agc acg tac cgt gtg gtc agc gtc ctc acc gtc ctg cac cag gac    1104
Asn Ser Thr Tyr Arg Val Val Ser Val Leu Thr Val Leu His Gln Asp
        355                 360                 365 tgg ctg aat ggc aag gag tac aag tgc aag gtc tcc aac aaa gcc ctc    1152
Trp Leu Asn Gly Lys Glu Tyr Lys Cys Lys Val Ser Asn Lys Ala Leu
            370                 375                 380
```

```
cca gcc ccc atc gag aaa acc atc tcc aaa gcc aaa ggg cag ccc cga    1200
Pro Ala Pro Ile Glu Lys Thr Ile Ser Lys Ala Lys Gly Gln Pro Arg
385                 390                 395                 400 gaa cca cag gtg tac acc ctg ccc cca tcc cgg gag gag atg acc aag    1248
Glu Pro Gln Val Tyr Thr Leu Pro Pro Ser Arg Glu Glu Met Thr Lys
                405                 410                 415 aac cag gtc agc ctg acc tgc ctg gtc aaa ggc ttc tat ccc agc gac    1296
Asn Gln Val Ser Leu Thr Cys Leu Val Lys Gly Phe Tyr Pro Ser Asp
            420                 425                 430 atc gcc gtg gag tgg gag agc aat ggg cag ccg gag aac aac tac aag    1344
Ile Ala Val Glu Trp Glu Ser Asn Gly Gln Pro Glu Asn Asn Tyr Lys
        435                 440                 445 acc acg cct ccc gtg ctg gac tcc gac ggc tcc ttc ttc ctc tat agc    1392
Thr Thr Pro Pro Val Leu Asp Ser Asp Gly Ser Phe Phe Leu Tyr Ser
    450                 455                 460 aag ctc acc gtg gac aag agc agg tgg cag cag ggg aac gtc ttc tca    1440
Lys Leu Thr Val Asp Lys Ser Arg Trp Gln Gln Gly Asn Val Phe Ser
465                 470                 475                 480 tgc tcc gtg atg cat gag gct ctg cac aac cac tac acg cag aag agc    1488
Cys Ser Val Met His Glu Ala Leu His Asn His Tyr Thr Gln Lys Ser
                485                 490                 495 ctc tcc ctg tct ccg ggt aaa taa                                    1512
Leu Ser Leu Ser Pro Gly Lys
                500
```

<210> SEQ ID NO 28
<211> LENGTH: 503
<212> TYPE: PRT
<213> ORGANISM: Artificial Sequence
<220> FEATURE:
<223> OTHER INFORMATION: Fc-fused mouse Siglec-15 peptide

<400> SEQUENCE: 28

```
Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
            20                  25                  30

Asn Thr Glu Ala His Ser Ala Pro Ala Gln Arg Trp Ser Met Gln Val
        35                  40                  45

Pro Ala Glu Val Asn Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Ser Gly Arg Tyr Phe Cys Arg Val
    130                 135                 140

Glu Phe Thr Gly Asp Ala His Asp Arg Tyr Glu Ser Arg His Gly Val
145                 150                 155                 160

Arg Leu Arg Val Thr Ala Ala Pro Arg Ile Val Asn Ile Ser Val Leu
                165                 170                 175

Pro Gly Pro Ala His Ala Phe Arg Ala Leu Cys Thr Ala Glu Gly Glu
            180                 185                 190

Pro Pro Pro Ala Leu Ala Trp Ser Gly Pro Ala Pro Gly Asn Ser Ser
        195                 200                 205
```

```
Ala Ala Leu Gln Gly Gln Gly His Gly Tyr Gln Val Thr Ala Glu Leu
    210                 215                 220
Pro Ala Leu Thr Arg Asp Gly Arg Tyr Thr Cys Thr Ala Ala Asn Ser
225                 230                 235                 240
Leu Gly Arg Ala Glu Ala Ser Val Tyr Leu Phe Arg Phe His Gly Ala
                245                 250                 255
Pro Gly Asp Pro Ala Phe Leu Tyr Lys Val Val Asp Ile Gln Ala Glu
            260                 265                 270
Pro Lys Ser Cys Asp Lys Thr His Thr Cys Pro Pro Cys Pro Ala Pro
        275                 280                 285
Glu Leu Leu Gly Gly Pro Ser Val Phe Leu Phe Pro Pro Lys Pro Lys
    290                 295                 300
Asp Thr Leu Met Ile Ser Arg Thr Pro Glu Val Thr Cys Val Val Val
305                 310                 315                 320
Asp Val Ser His Glu Asp Pro Glu Val Lys Phe Asn Trp Tyr Val Asp
                325                 330                 335
Gly Val Glu Val His Asn Ala Lys Thr Lys Pro Arg Glu Glu Gln Tyr
            340                 345                 350
Asn Ser Thr Tyr Arg Val Val Ser Val Leu Thr Val Leu His Gln Asp
        355                 360                 365
Trp Leu Asn Gly Lys Glu Tyr Lys Cys Lys Val Ser Asn Lys Ala Leu
    370                 375                 380
Pro Ala Pro Ile Glu Lys Thr Ile Ser Lys Ala Lys Gly Gln Pro Arg
385                 390                 395                 400
Glu Pro Gln Val Tyr Thr Leu Pro Pro Ser Arg Glu Glu Met Thr Lys
                405                 410                 415
Asn Gln Val Ser Leu Thr Cys Leu Val Lys Gly Phe Tyr Pro Ser Asp
            420                 425                 430
Ile Ala Val Glu Trp Glu Ser Asn Gly Gln Pro Glu Asn Asn Tyr Lys
        435                 440                 445
Thr Thr Pro Pro Val Leu Asp Ser Asp Gly Ser Phe Phe Leu Tyr Ser
    450                 455                 460
Lys Leu Thr Val Asp Lys Ser Arg Trp Gln Gln Gly Asn Val Phe Ser
465                 470                 475                 480
Cys Ser Val Met His Glu Ala Leu His Asn His Tyr Thr Gln Lys Ser
                485                 490                 495
Leu Ser Leu Ser Pro Gly Lys
            500

<210> SEQ ID NO 29
<211> LENGTH: 35
<212> TYPE: DNA
<213> ORGANISM: Artificial Sequence
<220> FEATURE:
<223> OTHER INFORMATION: PCR primer of human Siglec-15 cDNA

<400> SEQUENCE: 29
attaagcttc accatggaaa agtccatctg gctgc                              35

<210> SEQ ID NO 30
<211> LENGTH: 30
<212> TYPE: DNA
<213> ORGANISM: Artificial Sequence
<220> FEATURE:
<223> OTHER INFORMATION: PCR primer of human Siglec-15 cDNA

<400> SEQUENCE: 30
agtggatcct cacggtgagc acatggtggc                                    30
```

```
<210> SEQ ID NO 31
<211> LENGTH: 20
<212> TYPE: DNA
<213> ORGANISM: Artificial Sequence
<220> FEATURE:
<223> OTHER INFORMATION: PCR primer of human cathepsin K cDNA

<400> SEQUENCE: 31
ccgcagtaat gacacccttt                                           20

<210> SEQ ID NO 32
<211> LENGTH: 20
<212> TYPE: DNA
<213> ORGANISM: Artificial Sequence
<220> FEATURE:
<223> OTHER INFORMATION: PCR primer of human cathepsin K cDNA

<400> SEQUENCE: 32
aaggcattgg tcatgtagcc                                           20

<210> SEQ ID NO 33
<211> LENGTH: 28
<212> TYPE: DNA
<213> ORGANISM: Artificial Sequence
<220> FEATURE:
<223> OTHER INFORMATION: Detection probe of human catheprin K cDNA

<400> SEQUENCE: 33
tcagggtcag tgtggttcct gttgggct                                  28

<210> SEQ ID NO 34
<211> LENGTH: 20
<212> TYPE: DNA
<213> ORGANISM: Artificial Sequence
<220> FEATURE:
<223> OTHER INFORMATION: PCR primer of human TRAP cDNA

<400> SEQUENCE: 34
ctgtcctggc tcaagaaaca                                           20

<210> SEQ ID NO 35
<211> LENGTH: 20
<212> TYPE: DNA
<213> ORGANISM: Artificial Sequence
<220> FEATURE:
<223> OTHER INFORMATION: PCR primer of human TRAP cDNA

<400> SEQUENCE: 35
ccatagtgga agcgcagata                                           20

<210> SEQ ID NO 36
<211> LENGTH: 28
<212> TYPE: DNA
<213> ORGANISM: Artificial Sequence
<220> FEATURE:
<223> OTHER INFORMATION: Detection probe of human TRAP cDNA

<400> SEQUENCE: 36
tgagaatggc gtgggctacg tgctgagt                                  28

<210> SEQ ID NO 37
<211> LENGTH: 20
<212> TYPE: DNA
<213> ORGANISM: Artificial Sequence
<220> FEATURE:
<223> OTHER INFORMATION: PCR primer of human Siglec-15 cDNA
```

-continued

<400> SEQUENCE: 37
cagccaccaa catccatttc                                               20

<210> SEQ ID NO 38
<211> LENGTH: 20
<212> TYPE: DNA
<213> ORGANISM: Artificial Sequence
<220> FEATURE:
<223> OTHER INFORMATION: PCR primer of human Soglec-15 cDNA

<400> SEQUENCE: 38
cgctcaagct aatgcgtgta                                               20

<210> SEQ ID NO 39
<211> LENGTH: 28
<212> TYPE: DNA
<213> ORGANISM: Artificial Sequence
<220> FEATURE:
<223> OTHER INFORMATION: Detection probe of human Siglec-15 cDNA

<400> SEQUENCE: 39
aagaacaaag gccagtgcga ggcttggc                                      28

<210> SEQ ID NO 40
<211> LENGTH: 22
<212> TYPE: DNA
<213> ORGANISM: Artificial Sequence
<220> FEATURE:
<223> OTHER INFORMATION: PCR primer of human L32 ribosomal protein cDNA

<400> SEQUENCE: 40
gagatcgctc acaatgtttc ct                                            22

<210> SEQ ID NO 41
<211> LENGTH: 22
<212> TYPE: DNA
<213> ORGANISM: Artificial Sequence
<220> FEATURE:
<223> OTHER INFORMATION: PCR primer of human L32 ribosomal protein cDNA

<400> SEQUENCE: 41
gatgccagat ggcagttttt ac                                            22

<210> SEQ ID NO 42
<211> LENGTH: 27
<212> TYPE: DNA
<213> ORGANISM: Artificial Sequence
<220> FEATURE:
<223> OTHER INFORMATION: Detection probe of human L32 ribosomal protein
      cDNA

<400> SEQUENCE: 42
accgcaaagc catcgtggaa agagctg                                       27

<210> SEQ ID NO 43
<211> LENGTH: 780
<212> TYPE: DNA
<213> ORGANISM: Homo sapiens
<220> FEATURE:
<221> NAME/KEY: CDR
<222> LOCATION: (1)..(780)
<220> FEATURE:
<221> NAME/KEY: CDS
<222> LOCATION: (1)..(780)

```
<400> SEQUENCE: 43 atg gaa aag tcc atc tgg ctg ctg gcc tgc ttg gcg tgg gtt ctc ccg      48
Met Glu Lys Ser Ile Trp Leu Leu Ala Cys Leu Ala Trp Val Leu Pro
1               5                   10                  15 aca ggc tca ttt gtg aga act aaa ata gat act acg gag aac ttg ctc      96
Thr Gly Ser Phe Val Arg Thr Lys Ile Asp Thr Thr Glu Asn Leu Leu
            20                  25                  30 aac aca gag gtg cac agc tcg cca gcg cag cgc tgg tcc atg cag gtg     144
Asn Thr Glu Val His Ser Ser Pro Ala Gln Arg Trp Ser Met Gln Val
        35                  40                  45 cca ccc gag gtg agc gcg gag gca ggc gac gcg gca gtg ctg ccc tgc     192
Pro Pro Glu Val Ser Ala Glu Ala Gly Asp Ala Ala Val Leu Pro Cys
50                  55                  60 acc ttc acg cac ccg cac cgc cac tac gac ggg ccg ctg acg gcc atc     240
Thr Phe Thr His Pro His Arg His Tyr Asp Gly Pro Leu Thr Ala Ile
65                  70                  75                  80 tgg cgc gcg ggc gag ccc tat gcg ggc ccg cag gtg ttc cgc tgc gct     288
Trp Arg Ala Gly Glu Pro Tyr Ala Gly Pro Gln Val Phe Arg Cys Ala
                85                  90                  95 gcg gcg cgg ggc agc gag ctc tgc cag acg gcg ctg agc ctg cac ggc     336
Ala Ala Arg Gly Ser Glu Leu Cys Gln Thr Ala Leu Ser Leu His Gly
            100                 105                 110 cgc ttc cgg ctg ctg ggc aac ccg cgc aac gac ctc tcg ctg cgc         384
Arg Phe Arg Leu Leu Gly Asn Pro Arg Arg Asn Asp Leu Ser Leu Arg
        115                 120                 125 gtc gag cgc ctc gcc ctg gct gac gac cgc cgc tac ttc tgc cgc gtc     432
Val Glu Arg Leu Ala Leu Ala Asp Asp Arg Arg Tyr Phe Cys Arg Val
130                 135                 140 gag ttc gcc ggc gac gtc cat gac cgc tac gag agc cgc cac ggc gtc     480
Glu Phe Ala Gly Asp Val His Asp Arg Tyr Glu Ser Arg His Gly Val
145                 150                 155                 160 cgg ctg cac gtg aca gcc gcg ccg cgg atc gtc aac atc tcg gtg ctg     528
Arg Leu His Val Thr Ala Ala Pro Arg Ile Val Asn Ile Ser Val Leu
                165                 170                 175 ccc agt ccg gct cac gcc ttc cgc gcg ctc tgc act gcc gaa ggg gag     576
Pro Ser Pro Ala His Ala Phe Arg Ala Leu Cys Thr Ala Glu Gly Glu
            180                 185                 190 ccg ccg ccc gcc ctc gcc tgg tcc ggc ccg gcc ctg ggc aac agc ttg     624
Pro Pro Pro Ala Leu Ala Trp Ser Gly Pro Ala Leu Gly Asn Ser Leu
        195                 200                 205 gca gcc gtg cgg agc ccg cgt gag ggt cac ggc cac cta gtg acc gcc     672
Ala Ala Val Arg Ser Pro Arg Glu Gly His Gly His Leu Val Thr Ala
210                 215                 220 gaa ctg ccc gca ctg acc cat gac ggc cgc tac acg tgt acg gcc gcc     720
Glu Leu Pro Ala Leu Thr His Asp Gly Arg Tyr Thr Cys Thr Ala Ala
225                 230                 235                 240 aac agc ctg ggc cgc tcc gag gcc agc gtc tac ctg ttc cgc ttc cat     768
Asn Ser Leu Gly Arg Ser Glu Ala Ser Val Tyr Leu Phe Arg Phe His
                245                 250                 255 ggc gcc agc ggg                                                     780
Gly Ala Ser Gly
            260

<210> SEQ ID NO 44
<211> LENGTH: 260
<212> TYPE: PRT
<213> ORGANISM: Homo sapiens
```

<400> SEQUENCE: 44

```
Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
        210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly
            260
```

<210> SEQ ID NO 45
<211> LENGTH: 56
<212> TYPE: DNA
<213> ORGANISM: Artificial Sequence
<220> FEATURE:
<223> OTHER INFORMATION: PCR primer of soluble human Siglec-15 cDNA

<400> SEQUENCE: 45
ggggacaagt ttgtacaaaa aagcaggctt caccatggaa aagtccatct ggctgc      56

<210> SEQ ID NO 46
<211> LENGTH: 52
<212> TYPE: DNA
<213> ORGANISM: Artificial Sequence
<220> FEATURE:
<223> OTHER INFORMATION: PCR primer of soluble human Siglec-15 cDNA

<400> SEQUENCE: 46
ggggaccact ttgtacaaga aagctgggtc cccgctggcg ccatggaagc gg          52

```
<210> SEQ ID NO 47
<211> LENGTH: 897
<212> TYPE: DNA
<213> ORGANISM: Artificial Sequence
<220> FEATURE:
<223> OTHER INFORMATION: His-tagged human Siglec-15 cDNA
<220> FEATURE:
<221> NAME/KEY: CDS
<222> LOCATION: (1)..(897)

<400> SEQUENCE: 47
```

| | | | | | | | | | | | | | | | | |
|---|---|---|---|---|---|---|---|---|---|---|---|---|---|---|---|---|
| atg | aag | tcc | atc | tgg | ctg | ctg | gcc | tgc | ttg | gcg | tgg | gtt | ctc | ccg | | 48 |
| Met | Glu | Lys | Ser | Ile | Trp | Leu | Leu | Ala | Cys | Leu | Ala | Trp | Val | Leu | Pro | |
| 1 | | | | 5 | | | | | 10 | | | | | 15 | | |
| aca | ggc | tca | ttt | gtg | aga | act | aaa | ata | gat | act | acg | gag | aac | ttg | ctc | 96 |
| Thr | Gly | Ser | Phe | Val | Arg | Thr | Lys | Ile | Asp | Thr | Thr | Glu | Asn | Leu | Leu | |
| | | | 20 | | | | | 25 | | | | | 30 | | | |
| aac | aca | gag | gtg | cac | agc | tcg | cca | gcg | cag | cgc | tgg | tcc | atg | cag | gtg | 144 |
| Asn | Thr | Glu | Val | His | Ser | Ser | Pro | Ala | Gln | Arg | Trp | Ser | Met | Gln | Val | |
| | | 35 | | | | | 40 | | | | | 45 | | | | |
| cca | ccc | gag | gtg | agc | gcg | gag | gca | ggc | gac | gcg | gca | gtg | ctg | ccc | tgc | 192 |
| Pro | Pro | Glu | Val | Ser | Ala | Glu | Ala | Gly | Asp | Ala | Ala | Val | Leu | Pro | Cys | |
| | 50 | | | | | 55 | | | | | 60 | | | | | |
| acc | ttc | acg | cac | ccg | cac | cgc | cac | tac | gac | ggg | ccg | ctg | acg | gcc | atc | 240 |
| Thr | Phe | Thr | His | Pro | His | Arg | His | Tyr | Asp | Gly | Pro | Leu | Thr | Ala | Ile | |
| 65 | | | | | 70 | | | | | 75 | | | | | 80 | |
| tgg | cgc | gcg | ggc | gag | ccc | tat | gcg | ggc | ccg | cag | gtg | ttc | cgc | tgc | gct | 288 |
| Trp | Arg | Ala | Gly | Glu | Pro | Tyr | Ala | Gly | Pro | Gln | Val | Phe | Arg | Cys | Ala | |
| | | | | 85 | | | | | 90 | | | | | 95 | | |
| gcg | gcg | cgg | ggc | agc | gag | ctc | tgc | cag | acg | gcg | ctg | agc | ctg | cac | ggc | 336 |
| Ala | Ala | Arg | Gly | Ser | Glu | Leu | Cys | Gln | Thr | Ala | Leu | Ser | Leu | His | Gly | |
| | | | 100 | | | | | 105 | | | | | 110 | | | |
| cgc | ttc | cgg | ctg | ctg | ggc | aac | ccg | cgc | cgc | aac | gac | ctc | tcg | ctg | cgc | 384 |
| Arg | Phe | Arg | Leu | Leu | Gly | Asn | Pro | Arg | Arg | Asn | Asp | Leu | Ser | Leu | Arg | |
| | | 115 | | | | | 120 | | | | | 125 | | | | |
| gtc | gag | cgc | ctc | gcc | ctg | gct | gac | gac | cgc | cgc | tac | ttc | tgc | cgc | gtc | 432 |
| Val | Glu | Arg | Leu | Ala | Leu | Ala | Asp | Asp | Arg | Arg | Tyr | Phe | Cys | Arg | Val | |
| | 130 | | | | | 135 | | | | | 140 | | | | | |
| gag | ttc | gcc | ggc | gac | gtc | cat | gac | cgc | tac | gag | agc | cgc | cac | ggc | gtc | 480 |
| Glu | Phe | Ala | Gly | Asp | Val | His | Asp | Arg | Tyr | Glu | Ser | Arg | His | Gly | Val | |
| 145 | | | | | 150 | | | | | 155 | | | | | 160 | |
| cgg | ctg | cac | gtg | aca | gcc | gcg | ccg | cgg | atc | gtc | aac | atc | tcg | gtg | ctg | 528 |
| Arg | Leu | His | Val | Thr | Ala | Ala | Pro | Arg | Ile | Val | Asn | Ile | Ser | Val | Leu | |
| | | | | 165 | | | | | 170 | | | | | 175 | | |
| ccc | agt | ccg | gct | cac | gcc | ttc | cgc | gcg | ctc | tgc | act | gcc | gaa | ggg | gag | 576 |
| Pro | Ser | Pro | Ala | His | Ala | Phe | Arg | Ala | Leu | Cys | Thr | Ala | Glu | Gly | Glu | |
| | | | 180 | | | | | 185 | | | | | 190 | | | |
| ccg | ccc | ccc | gcc | ctc | gcc | tgg | tcc | ggc | ccg | gcc | ctg | ggc | aac | agc | ttg | 624 |
| Pro | Pro | Pro | Ala | Leu | Ala | Trp | Ser | Gly | Pro | Ala | Leu | Gly | Asn | Ser | Leu | |
| | | 195 | | | | | 200 | | | | | 205 | | | | |
| gca | gcc | gtg | cgg | agc | ccg | cgt | gag | ggt | cac | ggc | cac | cta | gtg | acc | gcc | 672 |
| Ala | Ala | Val | Arg | Ser | Pro | Arg | Glu | Gly | His | Gly | His | Leu | Val | Thr | Ala | |
| | 210 | | | | | 215 | | | | | 220 | | | | | |
| gaa | ctg | ccc | gca | ctg | acc | cat | gac | ggc | cgc | tac | acg | tgt | acg | gcc | gcc | 720 |
| Glu | Leu | Pro | Ala | Leu | Thr | His | Asp | Gly | Arg | Tyr | Thr | Cys | Thr | Ala | Ala | |
| 225 | | | | | 230 | | | | | 235 | | | | | 240 | |
| aac | agc | ctg | ggc | cgc | tcc | gag | gcc | agc | gtc | tac | ctg | ttc | cgc | ttc | cat | 768 |
| Asn | Ser | Leu | Gly | Arg | Ser | Glu | Ala | Ser | Val | Tyr | Leu | Phe | Arg | Phe | His | |
| | | | | 245 | | | | | 250 | | | | | 255 | | |
| ggc | gcc | agc | ggg | gac | cca | gct | ttc | ttg | tac | aaa | gtg | gtt | gat | atc | gaa | 816 |
| Gly | Ala | Ser | Gly | Asp | Pro | Ala | Phe | Leu | Tyr | Lys | Val | Val | Asp | Ile | Glu | |
| | | | 260 | | | | | 265 | | | | | 270 | | | |

```
ggt cgt ggg ggt aag cct atc cct aac cct ctc ctc ggt ctc gat tct      864
Gly Arg Gly Gly Lys Pro Ile Pro Asn Pro Leu Leu Gly Leu Asp Ser
            275                 280                 285 acg cgt acc ggt cat cat cac cat cac cat tga                           897
Thr Arg Thr Gly His His His His His His
        290                 295
```

<210> SEQ ID NO 48
<211> LENGTH: 298
<212> TYPE: PRT
<213> ORGANISM: Artificial Sequence
<220> FEATURE:
<223> OTHER INFORMATION: His-tagged human Siglec-15 peptide

<400> SEQUENCE: 48

```
Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Asp Pro Ala Phe Leu Tyr Lys Val Val Asp Ile Glu
            260                 265                 270

Gly Arg Gly Gly Lys Pro Ile Pro Asn Pro Leu Leu Gly Leu Asp Ser
        275                 280                 285

Thr Arg Thr Gly His His His His His His
    290                 295
```

<210> SEQ ID NO 49
<211> LENGTH: 1518
<212> TYPE: DNA
<213> ORGANISM: Artificial Sequence
<220> FEATURE:
<223> OTHER INFORMATION: Fc-fused human Siglec-15 cDNA
<220> FEATURE:
<221> NAME/KEY: CDS
<222> LOCATION: (1)..(1518)

<400> SEQUENCE: 49

| | | | | | | | | | | | | | | | | |
|---|---|---|---|---|---|---|---|---|---|---|---|---|---|---|---|---|
| atg | aaa | aag | tcc | atc | tgg | ctg | ctg | gcc | tgc | ttg | gcg | tgg | gtt | ctc | ccg | 48 |
| Met | Glu | Lys | Ser | Ile | Trp | Leu | Leu | Ala | Cys | Leu | Ala | Trp | Val | Leu | Pro | |
| 1 | | | | 5 | | | | | 10 | | | | | 15 | | |
| aca | ggc | tca | ttt | gtg | aga | act | aaa | ata | gat | act | acg | gag | aac | ttg | ctc | 96 |
| Thr | Gly | Ser | Phe | Val | Arg | Thr | Lys | Ile | Asp | Thr | Thr | Glu | Asn | Leu | Leu | |
| | | | 20 | | | | | 25 | | | | | 30 | | | |
| aac | aca | gag | gtg | cac | agc | tcg | cca | gcg | cag | cgc | tgg | tcc | atg | cag | gtg | 144 |
| Asn | Thr | Glu | Val | His | Ser | Ser | Pro | Ala | Gln | Arg | Trp | Ser | Met | Gln | Val | |
| | | 35 | | | | | 40 | | | | | 45 | | | | |
| cca | ccc | gag | gtg | agc | gcg | gag | gca | ggc | gac | gcg | gca | gtg | ctg | ccc | tgc | 192 |
| Pro | Pro | Glu | Val | Ser | Ala | Glu | Ala | Gly | Asp | Ala | Ala | Val | Leu | Pro | Cys | |
| | 50 | | | | | 55 | | | | | 60 | | | | | |
| acc | ttc | acg | cac | ccg | cac | cgc | cac | tac | gac | ggg | ccg | ctg | acg | gcc | atc | 240 |
| Thr | Phe | Thr | His | Pro | His | Arg | His | Tyr | Asp | Gly | Pro | Leu | Thr | Ala | Ile | |
| 65 | | | | | 70 | | | | | 75 | | | | | 80 | |
| tgg | cgc | gcg | ggc | gag | ccc | tat | gcg | ggc | ccg | cag | gtg | ttc | cgc | tgc | gct | 288 |
| Trp | Arg | Ala | Gly | Glu | Pro | Tyr | Ala | Gly | Pro | Gln | Val | Phe | Arg | Cys | Ala | |
| | | | | 85 | | | | | 90 | | | | | 95 | | |
| gcg | gcg | cgg | ggc | agc | gag | ctc | tgc | cag | acg | gcg | ctg | agc | ctg | cac | ggc | 336 |
| Ala | Ala | Arg | Gly | Ser | Glu | Leu | Cys | Gln | Thr | Ala | Leu | Ser | Leu | His | Gly | |
| | | | 100 | | | | | 105 | | | | | 110 | | | |
| cgc | ttc | cgg | ctg | ctg | ggc | aac | ccg | cgc | aac | gac | ctc | tcg | ctg | cgc | | 384 |
| Arg | Phe | Arg | Leu | Leu | Gly | Asn | Pro | Arg | Arg | Asn | Asp | Leu | Ser | Leu | Arg | |
| | | 115 | | | | | 120 | | | | | 125 | | | | |
| gtc | gag | cgc | ctc | gcc | ctg | gct | gac | gac | gcc | cgc | tac | ttc | tgc | cgc | gtc | 432 |
| Val | Glu | Arg | Leu | Ala | Leu | Ala | Asp | Asp | Arg | Arg | Tyr | Phe | Cys | Arg | Val | |
| | 130 | | | | | 135 | | | | | 140 | | | | | |
| gag | ttc | gcc | ggc | gac | gtc | cat | gac | cgc | tac | gag | agc | cgc | cac | ggc | gtc | 480 |
| Glu | Phe | Ala | Gly | Asp | Val | His | Asp | Arg | Tyr | Glu | Ser | Arg | His | Gly | Val | |
| 145 | | | | | 150 | | | | | 155 | | | | | 160 | |
| cgg | ctg | cac | gtg | aca | gcc | gcg | ccg | cgg | atc | gtc | aac | atc | tcg | gtg | ctg | 528 |
| Arg | Leu | His | Val | Thr | Ala | Ala | Pro | Arg | Ile | Val | Asn | Ile | Ser | Val | Leu | |
| | | | 165 | | | | | 170 | | | | | 175 | | | |
| ccc | agt | ccg | gct | cac | gcc | ttc | cgc | gcg | ctc | tgc | act | gcc | gaa | ggg | gag | 576 |
| Pro | Ser | Pro | Ala | His | Ala | Phe | Arg | Ala | Leu | Cys | Thr | Ala | Glu | Gly | Glu | |
| | | 180 | | | | | 185 | | | | | 190 | | | | |
| ccg | ccg | ccc | gcc | ctc | gcc | tgg | tcc | ggc | ccg | gcc | ctg | ggc | aac | agc | ttg | 624 |
| Pro | Pro | Pro | Ala | Leu | Ala | Trp | Ser | Gly | Pro | Ala | Leu | Gly | Asn | Ser | Leu | |
| | 195 | | | | | 200 | | | | | 205 | | | | | |
| gca | gcc | gtg | cgg | agc | ccg | cgt | gag | ggt | cac | ggc | cac | cta | gtg | acc | gcc | 672 |
| Ala | Ala | Val | Arg | Ser | Pro | Arg | Glu | Gly | His | Gly | His | Leu | Val | Thr | Ala | |
| 210 | | | | | 215 | | | | | 220 | | | | | | |
| gaa | ctg | ccc | gca | ctg | acc | cat | gac | ggc | cgc | tac | acg | tgt | acg | gcc | gcc | 720 |
| Glu | Leu | Pro | Ala | Leu | Thr | His | Asp | Gly | Arg | Tyr | Thr | Cys | Thr | Ala | Ala | |
| 225 | | | | | 230 | | | | | 235 | | | | | 240 | |
| aac | agc | ctg | ggc | cgc | tcc | gag | gcc | agc | gtc | tac | ctg | ttc | cgc | ttc | cat | 768 |
| Asn | Ser | Leu | Gly | Arg | Ser | Glu | Ala | Ser | Val | Tyr | Leu | Phe | Arg | Phe | His | |
| | | | 245 | | | | | 250 | | | | | 255 | | | |
| ggc | gcc | agc | ggg | gac | cca | gct | ttc | ttg | tac | aaa | gtg | gtt | gat | atc | cag | 816 |
| Gly | Ala | Ser | Gly | Asp | Pro | Ala | Phe | Leu | Tyr | Lys | Val | Val | Asp | Ile | Gln | |
| | | 260 | | | | | 265 | | | | | 270 | | | | |
| gca | gag | ccc | aaa | tct | tgt | gac | aaa | act | cac | aca | tgc | cca | ccg | tgc | cca | 864 |
| Ala | Glu | Pro | Lys | Ser | Cys | Asp | Lys | Thr | His | Thr | Cys | Pro | Pro | Cys | Pro | |
| | 275 | | | | | 280 | | | | | 285 | | | | | |

| | | |
|---|---|---|
| gca cct gaa ctc ctg ggg gga ccg tca gtc ttc ctc ttc ccc cca aaa<br>Ala Pro Glu Leu Leu Gly Gly Pro Ser Val Phe Leu Phe Pro Pro Lys<br>290                           295                     300 | | 912 |
| ccc aag gac acc ctc atg atc tcc cgg acc cct gag gtc aca tgc gtg<br>Pro Lys Asp Thr Leu Met Ile Ser Arg Thr Pro Glu Val Thr Cys Val<br>305                       310                       315                 320 | | 960 |
| gtg gtg gac gtg agc cac gaa gac cct gag gtc aag ttc aac tgg tac<br>Val Val Asp Val Ser His Glu Asp Pro Glu Val Lys Phe Asn Trp Tyr<br>                       325                     330                     335 | | 1008 |
| gtg gac ggc gtg gag gtg cat aat gcc aag aca aag ccg cgg gag gag<br>Val Asp Gly Val Glu Val His Asn Ala Lys Thr Lys Pro Arg Glu Glu<br>              340                     345                     350 | | 1056 |
| cag tac aac agc acg tac cgt gtg gtc agc gtc ctc acc gtc ctg cac<br>Gln Tyr Asn Ser Thr Tyr Arg Val Val Ser Val Leu Thr Val Leu His<br>355                           360                     365 | | 1104 |
| cag gac tgg ctg aat ggc aag gag tac aag tgc aag gtc tcc aac aaa<br>Gln Asp Trp Leu Asn Gly Lys Glu Tyr Lys Cys Lys Val Ser Asn Lys<br>   370                      375                     380 | | 1152 |
| gcc ctc cca gcc ccc atc gag aaa acc atc tcc aaa gcc aaa ggg cag<br>Ala Leu Pro Ala Pro Ile Glu Lys Thr Ile Ser Lys Ala Lys Gly Gln<br>385                           390                     395                 400 | | 1200 |
| ccc cga gaa cca cag gtg tac acc ctg ccc cca tcc cgg gag gag atg<br>Pro Arg Glu Pro Gln Val Tyr Thr Leu Pro Pro Ser Arg Glu Glu Met<br>                       405                     410                     415 | | 1248 |
| acc aag aac cag gtc agc ctg acc tgc ctg gtc aaa ggc ttc tat ccc<br>Thr Lys Asn Gln Val Ser Leu Thr Cys Leu Val Lys Gly Phe Tyr Pro<br>              420                     425                     430 | | 1296 |
| agc gac atc gcc gtg gag tgg gag agc aat ggg cag ccg gag aac aac<br>Ser Asp Ile Ala Val Glu Trp Glu Ser Asn Gly Gln Pro Glu Asn Asn<br>              435                     440                     445 | | 1344 |
| tac aag acc acg cct ccc gtg ctg gac tcc gac ggc tcc ttc ttc ctc<br>Tyr Lys Thr Thr Pro Pro Val Leu Asp Ser Asp Gly Ser Phe Phe Leu<br>450                           455                     460 | | 1392 |
| tat agc aag ctc acc gtg gac aag agc agg tgg cag cag ggg aac gtc<br>Tyr Ser Lys Leu Thr Val Asp Lys Ser Arg Trp Gln Gln Gly Asn Val<br>465                           470                     475                 480 | | 1440 |
| ttc tca tgc tcc gtg atg cat gag gct ctg cac aac cac tac acg cag<br>Phe Ser Cys Ser Val Met His Glu Ala Leu His Asn His Tyr Thr Gln<br>                       485                     490                     495 | | 1488 |
| aag agc ctc tcc ctg tct ccg ggt aaa taa<br>Lys Ser Leu Ser Leu Ser Pro Gly Lys<br>500                           505 | | 1518 |

```
<210> SEQ ID NO 50
<211> LENGTH: 505
<212> TYPE: PRT
<213> ORGANISM: Artificial Sequence
<220> FEATURE:
<223> OTHER INFORMATION: Fc-fused human Siglec-15 peptide

<400> SEQUENCE: 50
```

Met Glu Lys Ser Ile Trp Leu Leu Ala Cys Leu Ala Trp Val Leu Pro
1                 5                   10                  15

Thr Gly Ser Phe Val Arg Thr Lys Ile Asp Thr Thr Glu Asn Leu Leu
              20                     25                     30

Asn Thr Glu Val His Ser Ser Pro Ala Gln Arg Trp Ser Met Gln Val
        35                     40                     45

Pro Pro Glu Val Ser Ala Glu Ala Gly Asp Ala Ala Val Leu Pro Cys
   50                     55                     60

Thr Phe Thr His Pro His Arg His Tyr Asp Gly Pro Leu Thr Ala Ile
65                  70                   75                   80

```
Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Asp Pro Ala Phe Leu Tyr Lys Val Val Asp Ile Gln
            260                 265                 270

Ala Glu Pro Lys Ser Cys Asp Lys Thr His Thr Cys Pro Pro Cys Pro
        275                 280                 285

Ala Pro Glu Leu Leu Gly Gly Pro Ser Val Phe Leu Phe Pro Pro Lys
    290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
    370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480
```

```
-continued

Phe Ser Cys Ser Val Met His Glu Ala Leu His Asn His Tyr Thr Gln
            485                 490                 495

Lys Ser Leu Ser Leu Ser Pro Gly Lys
            500             505
```